(12) United States Patent
Phillips et al.

(10) Patent No.: US 6,313,265 B1
(45) Date of Patent: Nov. 6, 2001

(54) NEURITE OUTGROWTH-PROMOTING POLYPEPTIDES CONTAINING FIBRONECTIN TYPE III REPEATS AND METHODS OF USE

(75) Inventors: Greg Phillips, Del Mar; Bruce A. Cunningham; Kathryn L. Crossin, both of San Diego, all of CA (US)

(73) Assignee: The Scripps Research Institute, La Jolla, CA (US)

( * ) Notice: Subject to any disclaimer, the term of this patent is extended or adjusted under 35 U.S.C. 154(b) by 0 days.

(21) Appl. No.: 08/506,296

(22) Filed: Jul. 24, 1995

(51) Int. Cl.$^7$ .................................................. C07K 14/47
(52) U.S. Cl. ........................................... 530/350; 530/395
(58) Field of Search ................................... 530/350, 395; 435/69.7

(56) References Cited

U.S. PATENT DOCUMENTS 5,591,432 * 1/1997 Bronson et al. .
5,872,225 * 2/1999 Lemmon .

FOREIGN PATENT DOCUMENTS

WO 95/13291  5/1915  (WO) .

OTHER PUBLICATIONS

Appel, et al., *J. Neurosci.*, 13: 4764–4775 (1993).
Burgoon, et al., *J. Cell Biol.*, 112: 1017–1029 (1991).
Frei, et al., *J. Cell Biol.*, 118: 177–194 (1992).
Grumet, et al., *Proc. Natl. Acad. Sci., USA*, 81: 7989–7993 (1984).
Grumet, et al., *J. Cell Biol.*, 6: 1399–1412 (1991).
Grumet, et al., *J. Neurosci. Res.*, 31:1–13 (1992).
Hlavin, et al., *Genomics*, 11: 416–423 (1991).
Kadmon, et al., *J. Cell Biol.*, 110: 193–208 (1990).
Moos, et al., *Nature*, 334: 701–703 (1988).
Reid, et al., *J. Mol. Neurosci.*, 3: 127–135 (1992).

* cited by examiner

*Primary Examiner*—Gary L. Kunz
*Assistant Examiner*—Stephen Gucker
(74) *Attorney, Agent, or Firm*—Thomas Fitting; Emily Holmes

(57) ABSTRACT

The present invention relates to polypeptides that promote neurite outgrowth. The polypeptides contain fibronectin Type III repeats derived from a family of cell adhesion molecules characterized by having 6 immunoglobulin domains and 5 fibronectin Type III repeats. The polypeptides of this invention correspond to F80, 3-5 and 4-5 regions of the cell adhesion family members chicken Ng-CAM, chicken Nr-CAM, mouse L1CAM, human L1CAM and homologs thereof. Methods of promoting neurite outgrowth in both diagnostic and therapeutic applications are also described as are methods of making the disclosed polypeptides and devices for using thereof.

6 Claims, 40 Drawing Sheets

Chicken Ng-CAM and fragments

```
             10          20          30          40          50          61
                                                                         >
GAATTCCGGC  AGCCGAGCGG  GGAGCGGTGA  GAGCAGGCGC  GCAGCTGCCC  GTCCCGCC  ATG GCT
                                                                      MET Ala 70          79          88          97         106         115
CTG CCC ATG GTC GGC CTC CTC CTG CTC CTC TTG CTG GGG GGG CCC GGA GCC GCC
Leu Pro MET Val Gly Leu Leu Leu Leu Leu Leu Leu Gly Gly Pro Gly Ala Ala 124         133         142         151         160         169
ATC ACC ATT CCC CCG GAG TAT GGT GCG CAC GAT TTC CTG CAG CCC CCC GAG CTG
Ile Thr Ile Pro Pro Glu Tyr Gly Ala His Asp Phe Leu Gln Pro Pro Glu Leu 178         187         196         205         214         223
ACG GAG GAA CCC CCG GAA CAA CTC GTG GTC TTC CCC AGT GAT GAC ATC GTC CTC
Thr Glu Glu Pro Pro Glu Gln Leu Val Val Phe Pro Ser Asp Asp Ile Val Leu 232         241         250         259         268         277
AAA TGC GTG GCC ACC GGG AAC CCC CCC GTC CAG TAC CGA TGG AGC CGT GAG GAT
Lys Cys Val Ala Thr Gly Asn Pro Pro Val Gln Tyr Arg Trp Ser Arg Glu Asp 286         295         304         313         322         331
CAG CCC TTC GTC CCC GAG GAG CAC GGG GGG GTC TCG GTG GTC CCC GGA TCG GGG
Gln Pro Phe Val Pro Glu Glu His Gly Gly Val Ser Val Val Pro Gly Ser Gly 340         349         358         367         376         385
ACT TTG GTC ATC AAC GCC ACG TTG GCC GCG CGG CTC CAG GGG CGC TTC CGC TGC
Thr Leu Val Ile Asn Ala Thr Leu Ala Ala Arg Leu Gln Gly Arg Phe Arg Cys 394         403         412         421         430         439
TTC GCC ACC AAC GCG TTG GGC ACC GCT GTG TCT CCC GAG GCC AAC GTC ATC GCC
Phe Ala Thr Asn Ala Leu Gly Thr Ala Val Ser Pro Glu Ala Asn Val Ile Ala 448         457         466         475         484         493
GAG AAC ACT CCG CAG TGG CCG AAG GAG AAG GTG ACC CCG GTG GAG GTG GAG GAG
Glu Asn Thr Pro Gln Trp Pro Lys Glu Lys Val Thr Pro Val Glu Val Glu Glu 502         511         520         529         538         547
GGG GAC CCC GTG GTG CTG CCC TGT GAC CCC CCC GAG AGC GCT GTT CCC CCT AAA
Gly Asp Pro Val Val Leu Pro Cys Asp Pro Pro Glu Ser Ala Val Pro Pro Lys 556         565         574         583         592         601
```

FIG. 1A

```
ATC TAT TGG CTC AAC AGC GAC ATC GTT CAC ATC GCT CAG GAC GAG AGG GTC TCT
Ile Tyr Trp Leu Asn Ser Asp Ile Val His Ile Ala Gln Asp Glu Arg Val Ser
     610         619         628         637         646         655

ATG GGG CAG GAT GGG AAC CTC TAC TTC TCC AAC GCC ATG GTG GGC GAC AGC CAC
MET Gly Gln Asp Gly Asn Leu Tyr Phe Ser Asn Ala MET Val Gly Asp Ser His
     664         673         682         691         700         709

CCC GAC TAC ATC TGC CAC GCT CAC TTC CTC GGC CCC CGC ACC ATC ATC CAG AAG
Pro Asp Tyr Ile Cys His Ala His Phe Leu Gly Pro Arg Thr Ile Ile Gln Lys
     718         727         736         745         754         763

GAG CCC CTC GAC CTC CGC GTG GCC CCC AGT AAT GCG GTT CGG TCC CGC CGC CCC
Glu Pro Leu Asp Leu Arg Val Ala Pro Ser Asn Ala Val Arg Ser Arg Arg Pro
     772         781         790         799         808         817

CGC CTG CTG CTG CCC CGC GAC CCC CAA ACG ACC ACC ATC GCC CTC CGG GGG GGC
Arg Leu Leu Leu Pro Arg Asp Pro Gln Thr Thr Thr Ile Ala Leu Arg Gly Gly
     826         835         844         853         862         871

AGC GTC GTG TTG GAG TGC ATC GCT GAG GGG CTC CCC ACT CCA TGG GTC CGA TGG
Ser Val Val Leu Glu Cys Ile Ala Glu Gly Leu Pro Thr Pro Trp Val Arg Trp
     880         889         898         907         916         925

CGG CGG CTG AAC GGC CCC CTC CTC CCG GGC GGC GTT GGA AAC TTC AAC AAA ACG
Arg Arg Leu Asn Gly Pro Leu Leu Pro Gly Gly Val Gly Asn Phe Asn Lys Thr
     934         943         952         961         970         979

CTG CGG CTG TGG GGG GTG ACG GAG AGC GAC GAC GGG GAG TAC GAA TGT GTG GCT
Leu Arg Leu Trp Gly Val Thr Glu Ser Asp Asp Gly Glu Tyr Glu Cys Val Ala
     988         997        1006        1015        1024        1033

GAG AAC GGG AGG GGG ACG GCC AGG GGG ACC CAC AGC GTC ACC GTG GAG GCG GCC
Glu Asn Gly Arg Gly Thr Ala Arg Gly Thr His Ser Val Thr Val Glu Ala Ala
    1042        1051        1060        1069        1078        1087

CCA TAT TGG GTG CGG CGG CCA CAG AGT GGG GTC TTC GGG CCG GGG GAG ACG GCG
Pro Tyr Trp Val Arg Arg Pro Gln Ser Gly Val Phe Gly Pro Gly Glu Thr Ala
    1096        1105        1114        1123        1132        1141

AGG CTG GAC TGC GAG GTG GGG GGG AAA CCC CGA CCC CAA ATC CAA TGG AGC ATC
Arg Leu Asp Cys Glu Val Gly Gly Lys Pro Arg Pro Gln Ile Gln Trp Ser Ile
    1150        1159        1168        1177        1186        1195

AAT GGG GTC CCC ATC GAG GCT GCC GGG GCG GAG CGG CGG TGG CTG CGG GGC GGC
```

FIG. 1B

```
Asn Gly Val Pro Ile Glu Ala Ala Gly Ala Glu Arg Arg Trp Leu Arg Gly Gly
    1204        1213        1222        1231        1240        1249
GCT TTG GTG CTT CCG GAG CTG CGG CCG AAC GAC AGC GCG GTG CTG CAG TGC GAG
Ala Leu Val Leu Pro Glu Leu Arg Pro Asn Asp Ser Ala Val Leu Gln Cys Glu
    1258        1267        1276        1285        1294        1303
GCG AGG AAC CGC CAC GGC CCC CTA TTG GCC AAC GCC TTC CTG CAC GTC GTG GAG
Ala Arg Asn Arg His Gly Pro Leu Leu Ala Asn Ala Phe Leu His Val Val Glu
    1312        1321        1330        1339        1348        1357
CTG CCC CTC CGA ATG CTG ACG GCG GAT GAG CAG CGC TAC GAA GTG GTG GAA AAC
Leu Pro Leu Arg MET Leu Thr Ala Asp Glu Gln Arg Tyr Glu Val Val Glu Asn
    1366        1375        1384        1393        1402        1411
CAA ACA GTG TTT CTG CAC TGC AGA ACC TTC GGG GCC CCC GCG CCA AAC GTC GAG
Gln Thr Val Phe Leu His Cys Arg Thr Phe Gly Ala Pro Ala Pro Asn Val Glu
    1420        1429        1438        1447        1456        1465
TGG CTG ACC CCC ACT TTG GAG CCG GCT CTG CAG GAC GAC CGA TCC TTC GTG TTC
Trp Leu Thr Pro Thr Leu Glu Pro Ala Leu Gln Asp Asp Arg Ser Phe Val Phe
    1474        1483        1492        1501        1510        1519
ACC AAT GGG AGC CTT CGC GTG AGT GCG GTG CGG GGG GGG GAC GGG GGG GTC TAC
Thr Asn Gly Ser Leu Arg Val Ser Ala Val Arg Gly Gly Asp Gly Gly Val Tyr
    1528        1537        1546        1555        1564        1573
ACC TGC ATG GCC CAA AAC GCC CAC AGC AAC GGC AGC CTC ACG GCG CTC CTG GAG
Thr Cys MET Ala Gln Asn Ala His Ser Asn Gly Ser Leu Thr Ala Leu Leu Glu
    1582        1591        1600        1609        1618        1627
GTC AGA GCC CCC ACC CGA ATT TCG GCC CCC CCC CGA AGC GCC ACC GCC AAA AAA
Val Arg Ala Pro Thr Arg Ile Ser Ala Pro Pro Arg Ser Ala Thr Ala Lys Lys
    1636        1645        1654        1663        1672        1681
GGG GAG ACG GTG ACC TTT CAC TGC GGG GCG ACC TTT GAC CCC GCC GTG ACC CCC
Gly Glu Thr Val Thr Phe His Cys Gly Ala Thr Phe Asp Pro Ala Val Thr Pro
    1690        1699        1708        1717        1726        1735
GGG GAG CTG CGA TGG CTG CGG GGG GGG CAG CCG CTG CCC GAC GAC CCC CGG TAT
Gly Glu Leu Arg Trp Leu Arg Gly Gly Gln Pro Leu Pro Asp Asp Pro Arg Tyr
    1744        1753        1762        1771        1780        1789
TCG GTG GCG GCG GAG ATG ACG GTG TCC AAC GTG GAC TAT GGG GAC GAG GGG ACC
Ser Val Ala Ala Glu MET Thr Val Ser Asn Val Asp Tyr Gly Asp Glu Gly Thr
```

FIG. 1C

|  |  |  |  |  |  |
|---|---|---|---|---|---|
| 1798 | 1807 | 1816 | 1825 | 1834 | 1843 |

ATT CAG TGC CGC GCC TCC ACC CCT CTC GAC TCC GCG GAG GCC GAA GCG CAG CTC
Ile Gln Cys Arg Ala Ser Thr Pro Leu Asp Ser Ala Glu Ala Glu Ala Gln Leu

|  |  |  |  |  |  |
|---|---|---|---|---|---|
| 1852 | 1861 | 1870 | 1879 | 1888 | 1897 |

AGA GTC GTG GGC CGC CCC CCA TCC CGG GAC CTC CAA GTG ATG GAG GTG GAC GAA
Arg Val Val Gly Arg Pro Pro Ser Arg Asp Leu Gln Val MET Glu Val Asp Glu

|  |  |  |  |  |  |
|---|---|---|---|---|---|
| 1906 | 1915 | 1924 | 1933 | 1942 | 1951 |

CAC CGC GTG CGC CTC AGC TGG ACC CCG GGG GAC GAC CAT AAC AGC CCC ATA GAG
His Arg Val Arg Leu Ser Trp Thr Pro Gly Asp Asp His Asn Ser Pro Ile Glu

|  |  |  |  |  |  |
|---|---|---|---|---|---|
| 1960 | 1969 | 1978 | 1987 | 1996 | 2005 |

AAG TTC GTG GTG GAG GAG GAG GAG GAG AGA GAG GAT CTT CAG CGG GGT TTC GGA
Lys Phe Val Val Glu Glu Glu Glu Glu Arg Glu Asp Leu Gln Arg Gly Phe Gly

|  |  |  |  |  |  |
|---|---|---|---|---|---|
| 2014 | 2023 | 2032 | 2041 | 2050 | 2059 |

GCG GCT GAC GTT CCG GGG CAG CCG TGG ACG CCC CCC CTC CCG CTG TCC CCA TAC
Ala Ala Asp Val Pro Gly Gln Pro Trp Thr Pro Pro Leu Pro Leu Ser Pro Tyr

|  |  |  |  |  |  |
|---|---|---|---|---|---|
| 2068 | 2077 | 2086 | 2095 | 2104 | 2113 |

GGG CGG TTC CCG TTC CGG GTG GTG GCC GTT AAC GCC TAC GGG AGG GGG GAG CAC
Gly Arg Phe Pro Phe Arg Val Val Ala Val Asn Ala Tyr Gly Arg Gly Glu His

|  |  |  |  |  |  |
|---|---|---|---|---|---|
| 2122 | 2131 | 2140 | 2149 | 2158 | 2167 |

CAC GCC CCC AGC GCC CCC ATC GAG ACC CCC CCC GCG GCT CCG GAG CGC AAC CCG
His Ala Pro Ser Ala Pro Ile Glu Thr Pro Pro Ala Ala Pro Glu Arg Asn Pro

|  |  |  |  |  |  |
|---|---|---|---|---|---|
| 2176 | 2185 | 2194 | 2203 | 2212 | 2221 |

GGG GGG GTC CAT GGG GAG GGC AAT GAG ACC GGC AAC CTC GTC ATC ACC TGG GAG
Gly Gly Val His Gly Glu Gly Asn Glu Thr Gly Asn Leu Val Ile Thr Trp Glu

|  |  |  |  |  |  |
|---|---|---|---|---|---|
| 2230 | 2239 | 2248 | 2257 | 2266 | 2275 |

CCC CTC CCC CCC CAG GCC TGG AAC GCC CCC TGG GCG CGG TAC CGC GTG CAG TGG
Pro Leu Pro Pro Gln Ala Trp Asn Ala Pro Trp Ala Arg Tyr Arg Val Gln Trp

|  |  |  |  |  |  |
|---|---|---|---|---|---|
| 2284 | 2293 | 2302 | 2311 | 2320 | 2329 |

CGG CCA TTG GAG GAG CCC GGC GGG GGC CCT TCG GGG GGG TTC CCG TGG GCC
Arg Pro Leu Glu Glu Pro Gly Gly Gly Gly Pro Ser Gly Gly Phe Pro Trp Ala

|  |  |  |  |  |  |
|---|---|---|---|---|---|
| 2338 | 2347 | 2356 | 2365 | 2374 | 2383 |

GAA AGC ACC GTG GAC GCC CCC CCC GTG GTG GTG GGG GGG CTC CCC CCG TTC AGC
Glu Ser Thr Val Asp Ala Pro Pro Val Val Val Gly Gly Leu Pro Pro Phe Ser

|  |  |  |  |  |  |
|---|---|---|---|---|---|
| 2392 | 2401 | 2410 | 2419 | 2428 | 2437 |

FIG. 1D

```
CCC TTC CAG ATC CGC GTC CAG GCC GTG AAC GGA GCC GGG AAG GGA CCG GAA GCG
Pro Phe Gln Ile Arg Val Gln Ala Val Asn Gly Ala Gly Lys Gly Pro Glu Ala 2446         2455         2464         2473         2482         2491
ACC CCC GGC GTG GGG CAC AGC GGG GAG GAC CTG CCG TTG GTT TAC CCT GAG AAT
Thr Pro Gly Val Gly His Ser Gly Glu Asp Leu Pro Leu Val Tyr Pro Glu Asn
                                                                      |
                                                                 Fn3-5 begins 2500         2509         2518         2527         2536         2545
GTG GGG GTG GAA CTG CTG AAC AGC AGC ACC GTG CGC GTG AGA TGG ACT TTG GGG
Val Gly Val Glu Leu Leu Asn Ser Ser Thr Val Arg Val Arg Trp Thr Leu Gly 2554         2563         2572         2581         2590         2599
GGG GGG CCC AAA GAG CTG CGG GGG CGT CTG AGG GGC TTC CGG GTG CTG TAT TGG
Gly Gly Pro Lys Glu Leu Arg Gly Arg Leu Arg Gly Phe Arg Val Leu Tyr Trp 2608         2617         2626         2635         2644         2653
CGT TTG GGA TGG GTG GGG GAG CGC AGT CGC CGT CAA GCC CCC CCC GAC CCC CCC
Arg Leu Gly Trp Val Gly Glu Arg Ser Arg Arg Gln Ala Pro Pro Asp Pro Pro
                                                    |
                                                F80 begins 2662         2671         2680         2689         2698         2707
CAA ATC CCC CAA AGC CCG GCT GAA GAC CCC CCC CCA TTT CCC CCC GTG GCT CTG
Gln Ile Pro Gln Ser Pro Ala Glu Asp Pro Pro Pro Phe Pro Pro Val Ala Leu 2716         2725         2734         2743         2752         2761
ACA GTG GGG GGG GAC GCG CGG GGG GCG CTG CTG GGG GGG CTG CGG CCC TGG AGC
Thr Val Gly Gly Asp Ala Arg Gly Ala Leu Leu Gly Gly Leu Arg Pro Trp Ser 2770         2779         2788         2797         2806         2815
CGT TAT CAG CTG CGG GTG TTG GTC TTC AAC GGG AGG GGG GAC GGC CCC CCC AGC
Arg Tyr Gln Leu Arg Val Leu Val Phe Asn Gly Arg Gly Asp Gly Pro Pro Ser 2824         2833         2842         2851         2860         2869
GAA CCC ATC GCC TTC GAG ACC CCC GAG GGA GTT CCC GGC CCC CCC GAG GAG CTC
Glu Pro Ile Ala Phe Glu Thr Pro Glu Gly Val Pro Gly Pro Pro Glu Glu Leu
                                                |
                                           Fn4-5 begins 2878         2887         2896         2905         2914         2923
CGC GTG GAG CGG TTG GAC GAC ACC GCC CTC TCC GTA GTT GAA CGC CGC ACG TTT
Arg Val Glu Arg Leu Asp Asp Thr Ala Leu Ser Val Val Glu Arg Arg Thr Phe
```

FIG. 1E

|      |      |      |      |      |      |      |      |      |      |      |      |      |      |      |      |      |      |
|------|------|------|------|------|------|------|------|------|------|------|------|------|------|------|------|------|------|
| 2932 | | | 2941 | | | 2950 | | | 2959 | | | 2968 | | | 2977 | | |
| AAA  | CGG  | AGT  | ATC  | ACG  | GGA  | TAT  | GTG  | TTG  | AGA  | TAC  | CAG  | CAG  | GTG  | GAG  | CCG  | GGC  | TCG  |
| Lys  | Arg  | Ser  | Ile  | Thr  | Gly  | Tyr  | Val  | Leu  | Arg  | Tyr  | Gln  | Gln  | Val  | Glu  | Pro  | Gly  | Ser  |
| 2986 | | | 2995 | | | 3004 | | | 3013 | | | 3022 | | | 3031 | | |
| GCC  | CTC  | CCA  | GGA  | GGC  | TCC  | GTA  | CTC  | CGG  | GAC  | CCT  | CAA  | TGC  | GAC  | CTA  | AGG  | GGG  | CTG  |
| Ala  | Leu  | Pro  | Gly  | Gly  | Ser  | Val  | Leu  | Arg  | Asp  | Pro  | Gln  | Cys  | Asp  | Leu  | Arg  | Gly  | Leu  |
| 3040 | | | 3049 | | | 3058 | | | 3067 | | | 3076 | | | 3085 | | |
| AAT  | GCG  | CGC  | TCC  | CGA  | TAC  | CGG  | CTG  | GCG  | CTG  | CCG  | AGC  | ACG  | CCT  | CGG  | GAG  | CGC  | CCC  |
| Asn  | Ala  | Arg  | Ser  | Arg  | Tyr  | Arg  | Leu  | Ala  | Leu  | Pro  | Ser  | Thr  | Pro  | Arg  | Glu  | Arg  | Pro  |
| 3094 | | | 3103 | | | 3112 | | | 3121 | | | 3130 | | | 3139 | | |
| GCC  | CTG  | CAG  | ACG  | GTG  | GGG  | AGC  | ACG  | AAA  | CCG  | GAA  | CCG  | CCC  | TCC  | CCG  | CTT  | TGG  | AGC  |
| Ala  | Leu  | Gln  | Thr  | Val  | Gly  | Ser  | Thr  | Lys  | Pro  | Glu  | Pro  | Pro  | Ser  | Pro  | Leu  | Trp  | Ser  |
| 3148 | | | 3157 | | | 3166 | | | 3175 | | | 3184 | | | 3193 | | |
| CGT  | TTT  | GGT  | GTC  | GGA  | GGT  | CGG  | GGA  | GGA  | TTT  | CAC  | GGT  | GCT  | GCT  | GTG  | GAG  | TTT  | GGT  |
| Arg  | Phe  | Gly  | Val  | Gly  | Gly  | Arg  | Gly  | Gly  | Phe  | His  | Gly  | Ala  | Ala  | Val  | Glu  | Phe  | Gly  |
| 3202 | | | 3211 | | | 3220 | | | 3229 | | | 3238 | | | 3247 | | |
| GCA  | GCC  | CAG  | GAG  | GAC  | GAC  | GTG  | GAG  | TTC  | GAG  | GTC  | CAA  | TTC  | ATG  | AAT  | AAA  | AGC  | ACG  |
| Ala  | Ala  | Gln  | Glu  | Asp  | Asp  | Val  | Glu  | Phe  | Glu  | Val  | Gln  | Phe  | MET  | Asn  | Lys  | Ser  | Thr  |
| 3256 | | | 3265 | | | 3274 | | | 3283 | | | 3292 | | | 3301 | | |
| GAT  | GAG  | CCG  | TGG  | CGC  | ACT  | TCG  | GGC  | CGC  | GCC  | AAC  | TCC  | TCT  | TTA  | AGG  | CGG  | TAC  | CGT  |
| Asp  | Glu  | Pro  | Trp  | Arg  | Thr  | Ser  | Gly  | Arg  | Ala  | Asn  | Ser  | Ser  | Leu  | Arg  | Arg  | Tyr  | Arg  |
| 3310 | | | 3319 | | | 3328 | | | 3337 | | | 3346 | | | 3355 | | |
| CTG  | GAG  | GGG  | CTG  | CGG  | CCC  | GGC  | ACC  | GCC  | TAC  | CGA  | GTC  | CAA  | TTC  | GTG  | GGC  | CGG  | AAC  |
| Leu  | Glu  | Gly  | Leu  | Arg  | Pro  | Gly  | Thr  | Ala  | Tyr  | Arg  | Val  | Gln  | Phe  | Val  | Gly  | Arg  | Asn  |
| 3364 | | | 3373 | | | 3382 | | | 3391 | | | 3400 | | | 3409 | | |
| CGC  | TCC  | GGG  | GAA  | AAC  | GTG  | GCC  | TTC  | TGG  | GAG  | AGC  | GAA  | GTG  | CAA  | ACC  | AAC  | GGC  | ACC  |
| Arg  | Ser  | Gly  | Glu  | Asn  | Val  | Ala  | Phe  | Trp  | Glu  | Ser  | Glu  | Val  | Gln  | Thr  | Asn  | Gly  | Thr  |
| 3418 | | | 3427 | | | 3436 | | | 3445 | | | 3454 | | | 3463 | | |
| GTG  | GTG  | CCG  | CAG  | CCT  | GGT  | GGG  | GGG  | GTT  | TGC  | ACC  | AAG  | GGG  | TGG  | TTC  | ATC  | GGC  | TTC  |
| Val  | Val  | Pro  | Gln  | Pro  | Gly  | Gly  | Gly  | Val  | Cys  | Thr  | Lys  | Gly  | Trp  | Phe  | Ile  | Gly  | Phe  |

Fn3-5 ends
Fn4-5 ends

|      |      |      |      |      |      |
|------|------|------|------|------|------|
| 3472 | 3481 | 3490 | 3499 | 3508 | 3517 |

FIG. 1F

```
GTC AGC TCC GTG GTG CTC CTT CTC CTC ATC CTC CTC ATC CTC TGC TTC ATC AAA
Val Ser Ser Val Val Leu Leu Leu Leu Ile Leu Leu Ile Leu Cys Phe Ile Lys 3526        3535        3544        3553        3562        3571

CGC AGC AAG GGG GGC AAG TAT TCG GTG AAG GAC AAG GAG GAC ACG CAG GTG GAC
Arg Ser Lys Gly Gly Lys Tyr Ser Val Lys Asp Lys Glu Asp Thr Gln Val Asp 3580        3589        3598        3607        3616        3625

TCT GAG GCG CGG CCC ATG AAG GAT GAG ACC TTT GGG GAG TAC AGG TCG TTG GAG
Ser Glu Ala Arg Pro MET Lys Asp Glu Thr Phe Gly Glu Tyr Arg Ser Leu Glu 3634        3643        3652        3661        3670        3679

AGC GAA GCG GAG AAG GGT TCG GCT TCG GGT TCC GGT GCC GGT TCC GGT GTG GGT
Ser Glu Ala Glu Lys Gly Ser Ala Ser Gly Ser Gly Ala Gly Ser Gly Val Gly 3688        3697        3706        3715        3724        3733

TCT CCG GGT CGG GGT CCG TGC GCG GCG GGC AGC GAA GAC AGC CTG GCG GGG TAC
Ser Pro Gly Arg Gly Pro Cys Ala Ala Gly Ser Glu Asp Ser Leu Ala Gly Tyr 3742        3751        3760        3769        3778        3787

GGA GGC AGC GGG GAT GTG CAG TTC AAT GAG GAT GGA TCC TTC ATC GGG CAG TAC
Gly Gly Ser Gly Asp Val Gln Phe Asn Glu Asp Gly Ser Phe Ile Gly Gln Tyr 3796        3805        3814        3823        3832        3841

CGC GGA CCC GGA GCC GGA CCC GGC AGC TCC GGC CCT GCC AGC CCC TGT GCT GGG
Arg Gly Pro Gly Ala Gly Pro Gly Ser Ser Gly Pro Ala Ser Pro Cys Ala Gly 3850        3859        3869        3879        3889        3899        3909
                  ─────>
                  ─────
CCC CCC CTG GAT TAA ATGGGGGGGA ATGGGGTGGG GGATACCCAT AGGGGGAGCC CTGGAGTGGT
Pro Pro Leu Asp  .
              |
            F80 ends 3919        3929        3939        3949        3959        3969        3979

GGGAACCATA CGGGGTCCCC CGTGGCCATG GAGGGGGGGG GTTCATACGG TGGTAATGGG GGGCACGGGG

3989

GGATAGGAAT TC
```

FIG. 1G

Ng-CAM F80

APPDPPQIPQSPAEDPPPFPPVALTVGGDARGALLGGLRPWSRYQLRVLVFN

GRGDGPPSEPIAFETPEGVPGPPEELRVERLDDTALSVVERRTFKRSITGYVLRYQQVEP

GSALPGGSVLRDPQCDLRGLNARSRYRLALPSTPRERPALQTVGSTKPEPPSPLWSR

FGVGGRGGFHGAAVEFGAAQEDDVEFEVQFMNKSTDEPWRTSGRANSSLRRYR

LEGLRPGTAYRVQFVGRNRSGENVAFWESEVQTNGTVVPQPGGGVCTKGWFIGF

VSSVVLLLLILLILCFIKRSKGGKYSVKDKEDTQVDSEARPMKDETFGEYRSLE

SEAEKGSASGSGAGSGVGSPGRGPCAAGSEDSLAGYGGSGDVQFNEDGSFIGQY

RGPGAGPGSSGPASPCAGPPLD

FIG. 2

Sequence of Human L1 and Fragment Constructs

```
                 10                  20              29              38              47
              >
CGCCGGGAAA G  ATG GTC GTG GCG CTG CGG TAC GTG TGG CCT CTC CTC CTC TGC
              MET Val Val Ala Leu Arg Tyr Val Trp Pro Leu Leu Leu Cys 56            65            74            83            92           101

AGC CCC TGC CTG CTT ATC CAG ATC CCC GAG GAA TAT GAA GGA CAC CAT GTG ATG
Ser Pro Cys Leu Leu Ile Gln Ile Pro Glu Glu Tyr Glu Gly His His Val MET 110           119           128           137           146           155

GAG CCA CCT GTC ATC ACG GAA CAG TCT CCA CGG CGC CTG GTT GTC TTC CCC ACA
Glu Pro Pro Val Ile Thr Glu Gln Ser Pro Arg Arg Leu Val Val Phe Pro Thr 164           173           182           191           200           209

GAT GAC ATC AGC CTC AAG TGT GAG GCC AGT GGC AAG CCC GAA GTG CAG TTC CGC
Asp Asp Ile Ser Leu Lys Cys Glu Ala Ser Gly Lys Pro Glu Val Gln Phe Arg 218           227           236           245           254           263

TGG ACG AGG GAT GGT GTC CAC TTC AAA CCC AAG GAA GAG CTG GGT GTG ACC GTG
Trp Thr Arg Asp Gly Val His Phe Lys Pro Lys Glu Glu Leu Gly Val Thr Val 272           281           290           299           308           317

TAC CAG TCG CCC CAC TCT GGC TCC TTC ACC ATC ACG GGC AAC AAC AGC AAC TTT
Tyr Gln Ser Pro His Ser Gly Ser Phe Thr Ile Thr Gly Asn Asn Ser Asn Phe 326           335           344           353           362           371

GCT CAG AGG TTC CAG GGC ATC TAC CGC TGC TTT GCC AGC AAT AAG CTG GGC ACC
Ala Gln Arg Phe Gln Gly Ile Tyr Arg Cys Phe Ala Ser Asn Lys Leu Gly Thr 380           389           398           407           416           425

GCC ATG TCC CAT GAG ATC CGG CTC ATG GCC GAG GGT GCC CCC AAG TGG CCA AAG
Ala MET Ser His Glu Ile Arg Leu MET Ala Glu Gly Ala Pro Lys Trp Pro Lys 434           443           452           461           470           479

GAG ACA GTG AAG CCC GTG GAG GTG GAG GAA GGG GAG TCA GTG GTT CTG CCT TGC
Glu Thr Val Lys Pro Val Glu Val Glu Glu Gly Glu Ser Val Val Leu Pro Cys 488           497           506           515           524           533

AAC CCT CCC CCA AGT GCA GAG CCT CTC CGG ATC TAC TGG ATG AAC AGC AAG ATC
Asn Pro Pro Pro Ser Ala Glu Pro Leu Arg Ile Tyr Trp MET Asn Ser Lys Ile 542           551           560           569           578           587
```

FIG. 4A

| | | | | | | | | | | | | | | | |
|---|---|---|---|---|---|---|---|---|---|---|---|---|---|---|---|
| TTG | CAC | ATC | AAG | CAG | GAC | GAG | CGG | GTG | ACG | ATG | GGC | CAG | AAC | GGC | AAC | CTC | TAC |
| Leu | His | Ile | Lys | Gln | Asp | Glu | Arg | Val | Thr | MET | Gly | Gln | Asn | Gly | Asn | Leu | Tyr |

596   605   614   623   632   641

TTT GCC AAT GTG CTC ACC TCC GAC AAC CAC TCA GAC TAC ATC TGC CAC GCC CAC
Phe Ala Asn Val Leu Thr Ser Asp Asn His Ser Asp Tyr Ile Cys His Ala His 650   659   668   677   686   695

TTC CCA GGC ACC AGG ACC ATC ATT CAG AAG GAA CCC ATT GAC CTC CGG GTC AAG
Phe Pro Gly Thr Arg Thr Ile Ile Gln Lys Glu Pro Ile Asp Leu Arg Val Lys 704   713   722   731   740   749

GCC ACC AAC AGC ATG ATT GAC AGG AAG CCG CGC CTG CTC TTC CCC ACC AAC TCC
Ala Thr Asn Ser MET Ile Asp Arg Lys Pro Arg Leu Leu Phe Pro Thr Asn Ser 758   767   776   785   794   803

AGC AGC CAC CTG GTG GCC TTG CAG GGG CAG CCA TTG GTC CTG GAG TGC ATC GCC
Ser Ser His Leu Val Ala Leu Gln Gly Gln Pro Leu Val Leu Glu Cys Ile Ala 812   821   830   839   848   857

GAG GGC TTT CCC ACG CCC ACC ATC AAA TGG CTG CGC CCC AGT GGC CCC ATG CCA
Glu Gly Phe Pro Thr Pro Thr Ile Lys Trp Leu Arg Pro Ser Gly Pro MET Pro 866   875   884   893   902   911

GCC GAC CGT GTC ACC TAC CAG AAC CAC AAC AAG ACC CTG CAG CTG CTG AAA GTG
Ala Asp Arg Val Thr Tyr Gln Asn His Asn Lys Thr Leu Gln Leu Leu Lys Val 920   929   938   947   956   965

GGC GAG GAG GAT GAT GGC GAG TAC CGC TGC CTG GCC GAG AAC TCA CTG GGC AGT
Gly Glu Glu Asp Asp Gly Glu Tyr Arg Cys Leu Ala Glu Asn Ser Leu Gly Ser 974   983   992   1001   1010   1019

GCC CGG CAT GCG TAC TAT GTC ACC GTG GAG GCT GCC CCG TAC TGG CTG CAC AAG
Ala Arg His Ala Tyr Tyr Val Thr Val Glu Ala Ala Pro Tyr Trp Leu His Lys 1028   1037   1046   1055   1064   1073

CCC CAG AGC CAT CTA TAT GGG CCA GGA GAG ACT GCC CGC CTG GAC TGC CAA GTC
Pro Gln Ser His Leu Tyr Gly Pro Gly Glu Thr Ala Arg Leu Asp Cys Gln Val 1082   1091   1100   1109   1118   1127

CAG GGC AGG CCC CAA CCA GAG GTC ACC TGG AGA ATC AAC GGG ATC CCT GTG GAG
Gln Gly Arg Pro Gln Pro Glu Val Thr Trp Arg Ile Asn Gly Ile Pro Val Glu 1136   1145   1154   1163   1172   1181

GAG CTG GCC AAA GAC CAG AAG TAC CGG ATT CAG CGT GGC GCC CTG ATC CTG AGC

FIG. 4B

```
       Glu Leu Ala Lys Asp Gln Lys Tyr Arg Ile Gln Arg Gly Ala Leu Ile Leu Ser
       1190          1199          1208          1217          1226          1235
       ___ ___ ___ ___ ___ ___ ___ ___ ___ ___ ___ ___ ___ ___ ___ ___ ___ ___
       AAC GTG CAG CCC AGT GAC ACA ATG GTG ACC CAA TGT GAG GCC CGC AAC CGG CAC
       Asn Val Gln Pro Ser Asp Thr MET Val Thr Gln Cys Glu Ala Arg Asn Arg His
       1244          1253          1262          1271          1280          1289
       ___ ___ ___ ___ ___ ___ ___ ___ ___ ___ ___ ___ ___ ___ ___ ___ ___ ___
       GGG CTC TTG CTG GCC AAT GCC TAC ATC TAC GTT GTC CAG CTG CCA GCC AAG ATC
       Gly Leu Leu Leu Ala Asn Ala Tyr Ile Tyr Val Val Gln Leu Pro Ala Lys Ile
       1298          1307          1316          1325          1334          1343
       ___ ___ ___ ___ ___ ___ ___ ___ ___ ___ ___ ___ ___ ___ ___ ___ ___ ___
       CTG ACT GCG GAC AAT CAG ACG TAC ATG GCT GTC CAG GGC AGC ACT GCC TAC CTT
       Leu Thr Ala Asp Asn Gln Thr Tyr MET Ala Val Gln Gly Ser Thr Ala Tyr Leu
       1352          1361          1370          1379          1388          1397
       ___ ___ ___ ___ ___ ___ ___ ___ ___ ___ ___ ___ ___ ___ ___ ___ ___ ___
       CTG TGC AAG GCC TTC GGA GCG CCT GTG CCC AGT GTT CAG TGG CTG GAC GAG GAT
       Leu Cys Lys Ala Phe Gly Ala Pro Val Pro Ser Val Gln Trp Leu Asp Glu Asp
       1406          1415          1424          1433          1442          1451
       ___ ___ ___ ___ ___ ___ ___ ___ ___ ___ ___ ___ ___ ___ ___ ___ ___ ___
       GGG ACA ACA GTG CTT CAG GAC GAA CGC TTC TTC CCC TAT GCC AAT GGG ACC CTG
       Gly Thr Thr Val Leu Gln Asp Glu Arg Phe Phe Pro Tyr Ala Asn Gly Thr Leu
       1460          1469          1478          1487          1496          1505
       ___ ___ ___ ___ ___ ___ ___ ___ ___ ___ ___ ___ ___ ___ ___ ___ ___ ___
       GGC ATT CGA GAC CTC CAG GCC AAT GAC ACC GGA CGC TAC TTC TGC CTG GCT GCC
       Gly Ile Arg Asp Leu Gln Ala Asn Asp Thr Gly Arg Tyr Phe Cys Leu Ala Ala
       1514          1523          1532          1541          1550          1559
       ___ ___ ___ ___ ___ ___ ___ ___ ___ ___ ___ ___ ___ ___ ___ ___ ___ ___
       AAT GAC CAA AAC AAT GTT ACC ATC ATG GCT AAC CTG AAG GTT AAA GAT GCA ACT
       Asn Asp Gln Asn Asn Val Thr Ile MET Ala Asn Leu Lys Val Lys Asp Ala Thr
       1568          1577          1586          1595          1604          1613
       ___ ___ ___ ___ ___ ___ ___ ___ ___ ___ ___ ___ ___ ___ ___ ___ ___ ___
       CAG ATC ACT CAG GGG CCC CGC AGC ACA ATC GAG AAG AAA GGT TCC AGG GTG ACC
       Gln Ile Thr Gln Gly Pro Arg Ser Thr Ile Glu Lys Lys Gly Ser Arg Val Thr
       1622          1631          1640          1649          1658          1667
       ___ ___ ___ ___ ___ ___ ___ ___ ___ ___ ___ ___ ___ ___ ___ ___ ___ ___
       TTC ACG TGC CAG GCC TCC TTT GAC CCC TCC TTG CAG CCC AGC ATC ACC TGG CGT
       Phe Thr Cys Gln Ala Ser Phe Asp Pro Ser Leu Gln Pro Ser Ile Thr Trp Arg
       1676          1685          1694          1703          1712          1721
       ___ ___ ___ ___ ___ ___ ___ ___ ___ ___ ___ ___ ___ ___ ___ ___ ___ ___
       GGG GAC GGT CGA GAC CTC CAG GAG CTT GGG GAC AGT GAC AAG TAC TTC ATA GAG
       Gly Asp Gly Arg Asp Leu Gln Glu Leu Gly Asp Ser Asp Lys Tyr Phe Ile Glu
       1730          1739          1748          1757          1766          1775
       ___ ___ ___ ___ ___ ___ ___ ___ ___ ___ ___ ___ ___ ___ ___ ___ ___ ___
       GAT GGG CGC CTG GTC ATC CAC AGC CTG GAC TAC AGC GAC CAG GGC AAC TAC AGC
       Asp Gly Arg Leu Val Ile His Ser Leu Asp Tyr Ser Asp Gln Gly Asn Tyr Ser
```

FIG. 4C

| 1784 | | 1793 | | 1802 | | 1811 | | 1820 | | 1829 | | |
|---|---|---|---|---|---|---|---|---|---|---|---|---|
| TGC | GTG | GCC | AGT | ACC | GAA | CTG | GAT | GTG | GTG | GAG | AGT | AGG | GCA | CAG | CTC | TTG | GTG |
| Cys | Val | Ala | Ser | Thr | Glu | Leu | Asp | Val | Val | Glu | Ser | Arg | Ala | Gln | Leu | Leu | Val |

1838        1847        1856        1865        1874        1883

GTG GGG AGC CCT GGG CCG GTG CCA CGG CTG GTG CTG TCC GAC CTG CAC CTG CTG
Val Gly Ser Pro Gly Pro Val Pro Arg Leu Val Leu Ser Asp Leu His Leu Leu 1892        1901        1910        1919        1928        1937

ACG CAG AGC CAG GTG CGC GTG TCC TGG AGT CCT GCA GAA GAC CAC AAT GCC CCC
Thr Gln Ser Gln Val Arg Val Ser Trp Ser Pro Ala Glu Asp His Asn Ala Pro 1946        1955        1964        1973        1982        1991

ATT GAG AAA TAT GAC ATT GAA TTT GAG GAC AAG GAA ATG GCG CCT GAA AAA TGG
Ile Glu Lys Tyr Asp Ile Glu Phe Glu Asp Lys Glu MET Ala Pro Glu Lys Trp 2000        2009        2018        2027        2036        2045

TAC AGT CTG GGC AAG GTT CCA GGG AAC CAG ACC TCT ACC ACC CTC AAG CTG TCG
Tyr Ser Leu Gly Lys Val Pro Gly Asn Gln Thr Ser Thr Thr Leu Lys Leu Ser 2054        2063        2072        2081        2090        2099

CCC TAT GTC CAC TAC ACC TTT AGG GTT ACT GCC ATA AAC AAA TAT GGC CCC GGG
Pro Tyr Val His Tyr Thr Phe Arg Val Thr Ala Ile Asn Lys Tyr Gly Pro Gly 2108        2117        2126        2135        2144        2153

GAG CCC AGC CCG GTC TCT GAG ACT GTG GTC ACA CCT GAG GCA GCC CCA GAG AAG
Glu Pro Ser Pro Val Ser Glu Thr Val Val Thr Pro Glu Ala Ala Pro Glu Lys 2162        2171        2180        2189        2198        2207

AAC CCT GTG GAT GTG AAG GGG GAA GGA AAT GAG ACC ACC AAT ATG GTC ATC ACG
Asn Pro Val Asp Val Lys Gly Glu Gly Asn Glu Thr Thr Asn MET Val Ile Thr 2216        2225        2234        2243        2252        2261

TGG AAG CCG CTC CGG TGG ATG GAC TGG AAC GCC CCC CAG GTT CAG TAC CGC GTG
Trp Lys Pro Leu Arg Trp MET Asp Trp Asn Ala Pro Gln Val Gln Tyr Arg Val 2270        2279        2288        2297        2306        2315

CAG TGG CGC CCT CAG GGG ACA CGA GGG CCC TGG CAG GAG CAG ATT GTC AGC GAC
Gln Trp Arg Pro Gln Gly Thr Arg Gly Pro Trp Gln Glu Gln Ile Val Ser Asp 2324        2333        2342        2351        2360        2369

CCC TTC CTG GTG GTG TCC AAC ACG TCC ACC TTC GTG CCC TAT GAG ATC AAA GTC
Pro Phe Leu Val Val Ser Asn Thr Ser Thr Phe Val Pro Tyr Glu Ile Lys Val 2378        2387        2396        2405        2414        2423

FIG. 4D

| | | | | | | | | | | | | | | | |
|---|---|---|---|---|---|---|---|---|---|---|---|---|---|---|---|
| CAG | GCC | GTC | AAC | AGC | CAG | GGC | AAG | GGA | CCA | GAG | CCC | CAG | GTC | ACT | ATC | GGC | TAC |
| Gln | Ala | Val | Asn | Ser | Gln | Gly | Lys | Gly | Pro | Glu | Pro | Gln | Val | Thr | Ile | Gly | Tyr |

2432　　　　2441　　　　2450　　　　2459　　　　2468　　　　2477

| TCT | GGA | GAG | GAC | TAC | CCC | CAG | GCA | ATC | CCT | GAG | CTG | GAA | GGC | ATT | GAA | ATC | CTC |
|---|---|---|---|---|---|---|---|---|---|---|---|---|---|---|---|---|---|
| Ser | Gly | Glu | Asp | Tyr | Pro | Gln | Ala | Ile | Pro | Glu | Leu | Glu | Gly | Ile | Glu | Ile | Leu |

Fn3-5 begins (under Glu at position 2522)

2486　　　　2495　　　　2504　　　　2513　　　　2522　　　　2531

| AAC | TCA | AGT | GCC | GTG | CTG | GTC | AAG | TGG | CGG | CCG | GTG | GAC | CTG | GCC | CAG | GTC | AAG |
|---|---|---|---|---|---|---|---|---|---|---|---|---|---|---|---|---|---|
| Asn | Ser | Ser | Ala | Val | Leu | Val | Lys | Trp | Arg | Pro | Val | Asp | Leu | Ala | Gln | Val | Lys |

2540　　　　2549　　　　2558　　　　2567　　　　2576　　　　2585

| GGC | CAC | CTC | CGC | GGA | TAC | AAT | GTG | ACG | TAC | TGG | AGG | GAG | GGC | AGT | CAG | AGG | AAG |
|---|---|---|---|---|---|---|---|---|---|---|---|---|---|---|---|---|---|
| Gly | His | Leu | Arg | Gly | Tyr | Asn | Val | Thr | Tyr | Trp | Arg | Glu | Gly | Ser | Gln | Arg | Lys |

2594　　　　2603　　　　2612　　　　2621　　　　2630　　　　2639

| CAC | AGC | AAG | AGA | CAT | ATC | CAC | AAA | GAC | CAT | GTG | GTG | GTG | CCC | GCC | AAC | ACC | ACC |
|---|---|---|---|---|---|---|---|---|---|---|---|---|---|---|---|---|---|
| His | Ser | Lys | Arg | His | Ile | His | Lys | Asp | His | Val | Val | Val | Pro | Ala | Asn | Thr | Thr |

F80 begins (under CAT at position 2621)

2648　　　　2657　　　　2666　　　　2675　　　　2684　　　　2693

| AGT | GTC | ATC | CTC | AGT | GGC | TTG | CGG | CCC | TAT | AGC | TCC | TAC | CAC | CTG | GAG | GTG | CAG |
|---|---|---|---|---|---|---|---|---|---|---|---|---|---|---|---|---|---|
| Ser | Val | Ile | Leu | Ser | Gly | Leu | Arg | Pro | Tyr | Ser | Ser | Tyr | His | Leu | Glu | Val | Gln |

2702　　　　2711　　　　2720　　　　2729　　　　2738　　　　2747

| GCC | TTT | AAC | GGG | CGA | GGA | TCG | GGG | CCC | GCC | AGC | GAG | TTC | ACC | TTC | AGC | ACC | CCA |
|---|---|---|---|---|---|---|---|---|---|---|---|---|---|---|---|---|---|
| Ala | Phe | Asn | Gly | Arg | Gly | Ser | Gly | Pro | Ala | Ser | Glu | Phe | Thr | Phe | Ser | Thr | Pro |

2756　　　　2765　　　　2774　　　　2783　　　　2792　　　　2801

| GAG | GGA | GTG | CCT | GGC | CAC | CCC | GAG | GCG | TTG | CAC | CTG | GAG | TGC | CAG | TCG | AAC | ACC |
|---|---|---|---|---|---|---|---|---|---|---|---|---|---|---|---|---|---|
| Glu | Gly | Val | Pro | Gly | His | Pro | Glu | Ala | Leu | His | Leu | Glu | Cys | Gln | Ser | Asn | Thr |

Fn4-5 begins (under CCT at position 2765)

2810　　　　2819　　　　2828　　　　2837　　　　2846　　　　2855

| AGC | CTG | CTG | CTG | CGC | TGG | CAG | CCC | CCA | CTC | AGC | CAC | AAC | GGC | GTG | CTC | ACC | GGC |
|---|---|---|---|---|---|---|---|---|---|---|---|---|---|---|---|---|---|
| Ser | Leu | Leu | Leu | Arg | Trp | Gln | Pro | Pro | Leu | Ser | His | Asn | Gly | Val | Leu | Thr | Gly |

| | | | | | | | | | | | | | | | | |
|---|---|---|---|---|---|---|---|---|---|---|---|---|---|---|---|---|
| TAC | GTG | CTC | TCC | TAC | CAC | CCC | CTG | GAT | GAG | GGG | GGC | AAG | GGG | CAA | CTG | TCC | TTC |
| Tyr | Val | Leu | Ser | Tyr | His | Pro | Leu | Asp | Glu | Gly | Gly | Lys | Gly | Gln | Leu | Ser | Phe |

2918　　　　2927　　　　2936　　　　2945　　　　2954　　　　2963

| AAC | CTT | CGG | GAC | CCC | GAA | CTT | CGG | ACA | CAC | AAC | CTG | ACC | GAT | CTC | AGC | CCC | CAC |
|---|---|---|---|---|---|---|---|---|---|---|---|---|---|---|---|---|---|
| Asn | Leu | Arg | Asp | Pro | Glu | Leu | Arg | Thr | His | Asn | Leu | Thr | Asp | Leu | Ser | Pro | His |

2972　　　　2981　　　　2990　　　　2999　　　　3008　　　　3017

| CTG | CGG | TAC | CGC | TTC | CAG | CTT | CAG | GCC | ACC | ACC | AAA | GAG | GGC | CCT | GGT | GAA | GCC |
|---|---|---|---|---|---|---|---|---|---|---|---|---|---|---|---|---|---|
| Leu | Arg | Tyr | Arg | Phe | Gln | Leu | Gln | Ala | Thr | Thr | Lys | Glu | Gly | Pro | Gly | Glu | Ala |

3026　　　　3035　　　　3044　　　　3053　　　　3062　　　　3071

| ATC | GTA | CGG | GAA | GGA | GGC | ACT | ATG | GCC | TTG | TCT | GGG | ATC | TCA | GAT | TTT | GGC | AAC |
|---|---|---|---|---|---|---|---|---|---|---|---|---|---|---|---|---|---|
| Ile | Val | Arg | Glu | Gly | Gly | Thr | MET | Ala | Leu | Ser | Gly | Ile | Ser | Asp | Phe | Gly | Asn |

3080　　　　3089　　　　3098　　　　3107　　　　3116　　　　3125

| ATC | TCA | GCC | ACA | GCG | GGT | GAA | AAC | TAC | AGT | GTC | GTC | TCC | TGG | GTC | CCC | AAG | GAG |
|---|---|---|---|---|---|---|---|---|---|---|---|---|---|---|---|---|---|
| Ile | Ser | Ala | Thr | Ala | Gly | Glu | Asn | Tyr | Ser | Val | Val | Ser | Trp | Val | Pro | Lys | Glu |

3134　　　　3143　　　　3152　　　　3161　　　　3170　　　　3179

| GGC | CAG | TGC | AAC | TTC | AGG | TTC | CAT | ATC | TTG | TTC | AAA | GCC | TTG | GGA | GAA | GAG | AAG |
|---|---|---|---|---|---|---|---|---|---|---|---|---|---|---|---|---|---|
| Gly | Gln | Cys | Asn | Phe | Arg | Phe | His | Ile | Leu | Phe | Lys | Ala | Leu | Gly | Glu | Glu | Lys |

3188　　　　3197　　　　3206　　　　3215　　　　3224　　　　3233

| GGT | GGG | GCT | TCC | CTT | TCG | CCA | CAG | TAT | GTC | AGC | TAC | AAC | CAG | AGC | TCC | TAC | ACG |
|---|---|---|---|---|---|---|---|---|---|---|---|---|---|---|---|---|---|
| Gly | Gly | Ala | Ser | Leu | Ser | Pro | Gln | Tyr | Val | Ser | Tyr | Asn | Gln | Ser | Ser | Tyr | Thr |

3242　　　　3251　　　　3260　　　　3269　　　　3278　　　　3287

| CAG | TGG | GAC | CTG | CAG | CCT | GAC | ACT | GAC | TAC | GAG | ATC | CAC | TTG | TTT | AAG | GAG | AGG |
|---|---|---|---|---|---|---|---|---|---|---|---|---|---|---|---|---|---|
| Gln | Trp | Asp | Leu | Gln | Pro | Asp | Thr | Asp | Tyr | Glu | Ile | His | Leu | Phe | Lys | Glu | Arg |

3296　　　　3305　　　　3314　　　　3323　　　　3332　　　　3341

| ATG | TTC | CGG | CAC | CAA | ATG | GCT | GTG | AAG | ACC | AAT | GGC | ACA | GGC | CGC | GTG | AGG | CTC |
|---|---|---|---|---|---|---|---|---|---|---|---|---|---|---|---|---|---|
| MET | Phe | Arg | His | Gln | MET | Ala | Val | Lys | Thr | Asn | Gly | Thr | Gly | Arg | Val | Arg | Leu |

3350　　　　3359　　　　3368　　　　3377　　　　3386　　　　3395

| CCT | CCT | GCT | GGC | TTC | GCC | ACT | GAG | GGC | TGG | TTC | ATC | GGC | TTT | GTG | AGT | GCC | ATC |
|---|---|---|---|---|---|---|---|---|---|---|---|---|---|---|---|---|---|
| Pro | Pro | Ala | Gly | Phe | Ala | Thr | Glu | Gly | Trp | Phe | Ile | Gly | Phe | Val | Ser | Ala | Ile |

|
　　　　　　　　　　　　　　　　　　　Fn3-5 and Fn4-5 ends 3404　　　　3413　　　　3422　　　　3431　　　　3440　　　　3449

| ATC | CTC | CTG | CTC | CTC | GTC | CTG | CTC | ATC | CTC | TGC | TTC | ATC | AAG | CGC | AGC | AAG | GGC |
|---|---|---|---|---|---|---|---|---|---|---|---|---|---|---|---|---|---|
| Ile | Leu | Leu | Leu | Leu | Val | Leu | Leu | Ile | Leu | Cys | Phe | Ile | Lys | Arg | Ser | Lys | Gly |

FIG. 4F

```
3458         3467        3476        3485        3494        3503
GGC AAA TAC TCA GTG AAG GAT AAG GAG GAC ACC CAG GTG GAC TCT GAG GCC CGA
Gly Lys Tyr Ser Val Lys Asp Lys Glu Asp Thr Gln Val Asp Ser Glu Ala Arg 3512         3521        3530        3539        3548        3557
CCG ATG AAA GAT GAG ACC TTC GGC GAG TAC AGT GAC AAC GAG GAG AAG GCC TTT
Pro MET Lys Asp Glu Thr Phe Gly Glu Tyr Ser Asp Asn Glu Glu Lys Ala Phe 3566         3575        3584        3593        3602        3611
GGC AGC AGC CAG CCA TCG CTC AAC GGG GAC ATC AAG CCC CTG GGC AGT GAC GAC
Gly Ser Ser Gln Pro Ser Leu Asn Gly Asp Ile Lys Pro Leu Gly Ser Asp Asp 3620         3629        3638        3647        3656        3665
AGC CTG GCC GAT TAT GGG GGC AGC GTG GAT GTT CAG TTC AAC GAG GAT GGT TCG
Ser Leu Ala Asp Tyr Gly Gly Ser Val Asp Val Gln Phe Asn Glu Asp Gly Ser 3674         3683        3692        3701        3710        3719
TTC ATT GGC CAG TAC AGT GGC AAG AAG GAG AAG GAG GCG GCA GGG GGC AAT GAC
Phe Ile Gly Gln Tyr Ser Gly Lys Lys Glu Lys Glu Ala Ala Gly Gly Asn Asp 3728         3737        3746        3755        3764        3773      3783
                                                              ─────>
AGC TCA GGG GCC ACT TCC CCC ATC AAC CCT GCC GTG GCC CTA GAA TAG TGGAGTCCAG
Ser Ser Gly Ala Thr Ser Pro Ile Asn Pro Ala Val Ala Leu Glu  .

3793        3803        3813        3823        3833        3843        3853
GACAGGAGAT GCTGTGCCCC TGGCCTTGGG ATCCAGGCCC CTCCCTCTCC AGCAGGCCCA TGGGAGGCTG 3863        3873        3883
GAG TTGGGGC AGAGGAGAAC TTGCTGCCTC GGATC
```

FIG. 4G

Mouse L1 and fragments

|  | 9 | 18 | 27 | 36 | 45 | 54 |

> ATG GTC GTG ATG CTG CGG TAC GTG TGG CCT CTC CTC CTC TGC AGC CCC TGC CTG
> MET Val Val MET Leu Arg Tyr Val Trp Pro Leu Leu Leu Cys Ser Pro Cys Leu

|  | 63 | 72 | 81 | 90 | 99 | 108 |

CTC ATA CAG ATT CCA GAC GAA TAT AAA GGA CAC CAT GTG CTA GAG CCA CCT GTC
Leu Ile Gln Ile Pro Asp Glu Tyr Lys Gly His His Val Leu Glu Pro Pro Val

|  | 117 | 126 | 135 | 144 | 153 | 162 |

ATC ACG GAA CAG TCT CCA CGG CGC CTG GTT GTC TTC CCA ACA GAT GAC ATA AGC
Ile Thr Glu Gln Ser Pro Arg Arg Leu Val Val Phe Pro Thr Asp Asp Ile Ser

|  | 171 | 180 | 189 | 198 | 207 | 216 |

CTG AAA TGT GAA GCC AGA GGC AGA CCC CAA GTG GAG TTC CGC TGG ACG AAA GAT
Leu Lys Cys Glu Ala Arg Gly Arg Pro Gln Val Glu Phe Arg Trp Thr Lys Asp

|  | 225 | 234 | 243 | 252 | 261 | 270 |

GGC ATC CAC TTC AAA CCC AAG GAA GAA TTG GGT GTA GTG GTG CAT GAG GCA CCC
Gly Ile His Phe Lys Pro Lys Glu Glu Leu Gly Val Val Val His Glu Ala Pro

|  | 279 | 288 | 297 | 306 | 315 | 324 |

TAT TCT GGC TCC TTC ACC ATC GAA GGC AAC AAC AGC TTT GCC CAG AGG TTT CAG
Tyr Ser Gly Ser Phe Thr Ile Glu Gly Asn Asn Ser Phe Ala Gln Arg Phe Gln

|  | 333 | 342 | 351 | 360 | 369 | 378 |

GGC ATC TAT CGC TGC TAT GCC AGC AAT AAG CTA GGA ACT GCC ATG TCG CAT GAG
Gly Ile Tyr Arg Cys Tyr Ala Ser Asn Lys Leu Gly Thr Ala MET Ser His Glu

|  | 387 | 396 | 405 | 414 | 423 | 432 |

ATC CAG CTC GTG GCC GAG GGT GCC CCC AAG TGG CCG AAG GAG ACT GTA AAA CCT
Ile Gln Leu Val Ala Glu Gly Ala Pro Lys Trp Pro Lys Glu Thr Val Lys Pro

|  | 441 | 450 | 459 | 468 | 477 | 486 |

GTG GAA GTG GAG GAA GGA GAA TCA GTA GTT CTG CCT TGC AAC CCT CCA CCC AGT
Val Glu Val Glu Glu Gly Glu Ser Val Val Leu Pro Cys Asn Pro Pro Pro Ser

|  | 495 | 504 | 513 | 522 | 531 | 540 |

GCA GCC CCA CCT AGG ATC TAC TGG ATG AAC AGC AAG ATT TTC GAC ATC AAA CAA
Ala Ala Pro Pro Arg Ile Tyr Trp MET Asn Ser Lys Ile Phe Asp Ile Lys Gln

|  | 549 | 558 | 567 | 576 | 585 | 594 |

FIG. 5A

```
GAT GAG CGG GTG TCC ATG GGC CAG AAT GGA GAC CTA TAT TTT GCC AAT GTG CTT
Asp Glu Arg Val Ser MET Gly Gln Asn Gly Asp Leu Tyr Phe Ala Asn Val Leu
        603         612         621         630         639         648

ACC TCA GAC AAT CAT TCA GAC TAC ATC TGC AAT GCC CAC TTC CCT GGT ACC CGG
Thr Ser Asp Asn His Ser Asp Tyr Ile Cys Asn Ala His Phe Pro Gly Thr Arg
        657         666         675         684         693         702

ACC ATC ATT CAA AAG GAA CCT ATT GAC CTC CGG GTC AAG CCC ACC AAC AGC ATG
Thr Ile Ile Gln Lys Glu Pro Ile Asp Leu Arg Val Lys Pro Thr Asn Ser MET
        711         720         729         738         747         756

ATT GAC CGG AAG CCA CGT CTG CTC TTT CCC ACA AAC TCC AGC AGC CGC CTG GTA
Ile Asp Arg Lys Pro Arg Leu Leu Phe Pro Thr Asn Ser Ser Ser Arg Leu Val
        765         774         783         792         801         810

GCC TTG CAG GGC CAG TCA TTG ATC CTG GAG TGC ATT GCT GAG GGA TTC CCT ACA
Ala Leu Gln Gly Gln Ser Leu Ile Leu Glu Cys Ile Ala Glu Gly Phe Pro Thr
        819         828         837         846         855         864

CCC ACC ATC AAG TGG CTG CAC CCC AGT GAC CCA ATG CCA ACA GAC CGT GTT ATC
Pro Thr Ile Lys Trp Leu His Pro Ser Asp Pro MET Pro Thr Asp Arg Val Ile
        873         882         891         900         909         918

TAC CAA AAC CAC AAC AAG ACC CTG CAA CTA CTC AAT GTG GGC GAA GAG GAC GAT
Tyr Gln Asn His Asn Lys Thr Leu Gln Leu Leu Asn Val Gly Glu Glu Asp Asp
        927         936         945         954         963         972

GGC GAG TAT ACC TGC CTT GCT GAG AAC TCG CTG GGC AGT GCC CGG CAT GCC TAC
Gly Glu Tyr Thr Cys Leu Ala Glu Asn Ser Leu Gly Ser Ala Arg His Ala Tyr
        981         990         999        1008        1017        1026

TAT GTT ACT GTG GAA GCT GCC CCA TAT TGG CTG CAG AAG CCC CAG AGC CAT TTG
Tyr Val Thr Val Glu Ala Ala Pro Tyr Trp Leu Gln Lys Pro Gln Ser His Leu
       1035        1044        1053        1062        1071        1080

TAT GGT CCA GGA GAG ACT GCC CGC CTA GAC TGC CAA GTC CAG GGC AGG CCC CAA
Tyr Gly Pro Gly Glu Thr Ala Arg Leu Asp Cys Gln Val Gln Gly Arg Pro Gln
       1089        1098        1107        1116        1125        1134

CCA GAG ATC ACT TGG AGA ATC AAC GGA ATG TCT ATG GAG ACG GTG AAC AAG GAC
Pro Glu Ile Thr Trp Arg Ile Asn Gly MET Ser MET Glu Thr Val Asn Lys Asp
       1143        1152        1161        1170        1179        1188

CAG AAG TAC CGG ATT GAG CAG GGG TCT CTG ATC TTG AGT AAC GTG CAG CCA ACT
```

FIG. 5B

```
    Gln Lys Tyr Arg Ile Glu Gln Gly Ser Leu Ile Leu Ser Asn Val Gln Pro Thr 1197         1206          1215         1224         1233          1242
    GAC ACA ATG GTG ACC CAG TGT GAA GCC CGC AAC CAG CAT GGG CTC CTG CTA GCC
    Asp Thr MET Val Thr Gln Cys Glu Ala Arg Asn Gln His Gly Leu Leu Leu Ala 1251         1260          1269         1278         1287          1296
    AAT GCC TAC ATT TAT GTT GTC CAG CTG CCA GCC AGG ATC CTA ACA AAA GAC AAT
    Asn Ala Tyr Ile Tyr Val Val Gln Leu Pro Ala Arg Ile Leu Thr Lys Asp Asn 1305         1314          1323         1332         1341          1350
    CAG ACA TAC ATG GCA GTT GAG GGC AGT ACT GCT TAC TTG CTG TGC AAA GCC TTT
    Gln Thr Tyr MET Ala Val Glu Gly Ser Thr Ala Tyr Leu Leu Cys Lys Ala Phe 1359         1368          1377         1386         1395          1404
    GGA GCT CCT GTT CCC AGT GTC CAG TGG CTG GAT GAA GAA GGA ACC ACA GTG CTT
    Gly Ala Pro Val Pro Ser Val Gln Trp Leu Asp Glu Glu Gly Thr Thr Val Leu 1413         1422          1431         1440         1449          1458
    CAG GAT GAA CGA TTT TTC CCC TAT GCC AAT GGA ACG CTG AGC ATC AGA GAC CTC
    Gln Asp Glu Arg Phe Phe Pro Tyr Ala Asn Gly Thr Leu Ser Ile Arg Asp Leu 1467         1476          1485         1494         1503          1512
    CAG GCC AAT GAC ACT GGA CGC TAT TTC TGC CAG GCT GCC AAT GAC CAG AAC AAT
    Gln Ala Asn Asp Thr Gly Arg Tyr Phe Cys Gln Ala Ala Asn Asp Gln Asn Asn 1521         1530          1539         1548         1557          1566
    GTG ACC ATT TTG GCT AAC CTA CAG GTT AAA GAA GCA ACC CAG ATC ACA CAG GGG
    Val Thr Ile Leu Ala Asn Leu Gln Val Lys Glu Ala Thr Gln Ile Thr Gln Gly 1575         1584          1593         1602         1611          1620
    CCC CGG AGC GCA ATT GAG AAG AAA GGT GCA AGG GTG ACA TTC ACG TGC CAG GCC
    Pro Arg Ser Ala Ile Glu Lys Lys Gly Ala Arg Val Thr Phe Thr Cys Gln Ala 1629         1638          1647         1656         1665          1674
    TCC TTT GAC CCC TCT TTG CAG GCC AGC ATC ACT TGG CGT GGA GAT GGG AGA GAC
    Ser Phe Asp Pro Ser Leu Gln Ala Ser Ile Thr Trp Arg Gly Asp Gly Arg Asp 1683         1692          1701         1710         1719          1728
    CTA CAG GAA CGT GGG GAC AGT GAC AAG TAT TTC ATA GAA GAT GGG AAA CTA GTC
    Leu Gln Glu Arg Gly Asp Ser Asp Lys Tyr Phe Ile Glu Asp Gly Lys Leu Val 1737         1746          1755         1764         1773          1782
    ATC CAG AGC CTG GAC TAC AGT GAC CAG GGC AAC TAC AGT TGT GTG GCC AGC ACT
    Ile Gln Ser Leu Asp Tyr Ser Asp Gln Gly Asn Tyr Ser Cys Val Ala Ser Thr
```

FIG. 5C

|  |  |  |  |  |  |
|---|---|---|---|---|---|
| 1791 | 1800 | 1809 | 1818 | 1827 | 1836 |

GAA CTG GAT GAG GTG GAG AGC AGG GCA CAG CTC TTA GTG GTG GGG AGC CCT GGG
Glu Leu Asp Glu Val Glu Ser Arg Ala Gln Leu Leu Val Val Gly Ser Pro Gly

|  |  |  |  |  |  |
|---|---|---|---|---|---|
| 1845 | 1854 | 1863 | 1872 | 1881 | 1890 |

CCA GTG CCT CAC CTG GAG CTG TCC GAC CGC CAC CTG CTG AAG CAG AGC CAG GTG
Pro Val Pro His Leu Glu Leu Ser Asp Arg His Leu Leu Lys Gln Ser Gln Val

|  |  |  |  |  |  |
|---|---|---|---|---|---|
| 1899 | 1908 | 1917 | 1926 | 1935 | 1944 |

CAC TTG TCT TGG AGC CCT GCT GAA GAC CAC AAC TCT CCC ATT GAG AAG TAT GAC
His Leu Ser Trp Ser Pro Ala Glu Asp His Asn Ser Pro Ile Glu Lys Tyr Asp

|  |  |  |  |  |  |
|---|---|---|---|---|---|
| 1953 | 1962 | 1971 | 1980 | 1989 | 1998 |

ATT GAA TTT GAG GAC AAG GAA ATG GCT CCT GAG AAA TGG TTC AGT CTG GGC AAG
Ile Glu Phe Glu Asp Lys Glu MET Ala Pro Glu Lys Trp Phe Ser Leu Gly Lys

|  |  |  |  |  |  |
|---|---|---|---|---|---|
| 2007 | 2016 | 2025 | 2034 | 2043 | 2052 |

GTG CCA GGA AAT CAG ACC TCT ACT ACC CTC AAG CTG TCC CCC TAT GTC CAC TAC
Val Pro Gly Asn Gln Thr Ser Thr Thr Leu Lys Leu Ser Pro Tyr Val His Tyr

|  |  |  |  |  |  |
|---|---|---|---|---|---|
| 2061 | 2070 | 2079 | 2088 | 2097 | 2106 |

ACC TTT CGG GTC ACT GCC ATT AAC AAA TAT GGT CCT GGA GAA CCC AGC CCT GTC
Thr Phe Arg Val Thr Ala Ile Asn Lys Tyr Gly Pro Gly Glu Pro Ser Pro Val

|  |  |  |  |  |  |
|---|---|---|---|---|---|
| 2115 | 2124 | 2133 | 2142 | 2151 | 2160 |

TCT GAG AGT GTG GTC ACA CCT GAG GCA GCC CCA GAG AAG AAC CCT GTG GAT GTG
Ser Glu Ser Val Val Thr Pro Glu Ala Ala Pro Glu Lys Asn Pro Val Asp Val

|  |  |  |  |  |  |
|---|---|---|---|---|---|
| 2169 | 2178 | 2187 | 2196 | 2205 | 2214 |

AGA GGG GAA GGG AAT GAG ACC AAC AAT ATG GTC ATC ACA TGG AAG CCC CTT CGG
Arg Gly Glu Gly Asn Glu Thr Asn Asn MET Val Ile Thr Trp Lys Pro Leu Arg

|  |  |  |  |  |  |
|---|---|---|---|---|---|
| 2223 | 2232 | 2241 | 2250 | 2259 | 2268 |

TGG ATG GAT TGG AAT GCC CCC CAG ATT CAG TAC CGT GTA CAG TGG CGT CCA CAG
Trp MET Asp Trp Asn Ala Pro Gln Ile Gln Tyr Arg Val Gln Trp Arg Pro Gln

|  |  |  |  |  |  |
|---|---|---|---|---|---|
| 2277 | 2286 | 2295 | 2304 | 2313 | 2322 |

GGC AAG CAG GAG ACC TGG AGG AAA CAG ACC GTG AGC GAC CCT TTC CTG GTG GTG
Gly Lys Gln Glu Thr Trp Arg Lys Gln Thr Val Ser Asp Pro Phe Leu Val Val

|  |  |  |  |  |  |
|---|---|---|---|---|---|
| 2331 | 2340 | 2349 | 2358 | 2367 | 2376 |

TCT AAC ACT TCC ACA TTT GTG CCT TAT GAG ATC AAA GTC CAG GCA GTG AAC AAC
Ser Asn Thr Ser Thr Phe Val Pro Tyr Glu Ile Lys Val Gln Ala Val Asn Asn

|  |  |  |  |  |  |
|---|---|---|---|---|---|
| 2385 | 2394 | 2403 | 2412 | 2421 | 2430 |

FIG. 5D

```
CAG GGC AAG GGC CCT GAG CCC CAG GTC ACC ATT GGC TAT TCA GGG GAA GAC TAC
Gln Gly Lys Gly Pro Glu Pro Gln Val Thr Ile Gly Tyr Ser Gly Glu Asp Tyr
        2439      2448      2457      2466      2475      2484

CCC CAG GTG AGC CCT GAA CTT GAA GAC ATC ACA ATC TTC AAC TCA AGT ACT GTG
Pro Gln Val Ser Pro Glu Leu Glu Asp Ile Thr Ile Phe Asn Ser Ser Thr Val
                            |
                         Fn3-5 begins
        2493      2502      2511      2520      2529      2538

CTT GTC AGG TGG AGG CCT GTG GAC TTG GCC CAG GTT AAG GGC CAC CTC AAG GGA
Leu Val Arg Trp Arg Pro Val Asp Leu Ala Gln Val Lys Gly His Leu Lys Gly
        2547      2556      2565      2574      2583      2592

TAC AAT GTA ACA TAC TGG TGG AAG GGC AGC CAG AGA AAG CAC AGC AAG AGG CAT
Tyr Asn Val Thr Tyr Trp Trp Lys Gly Ser Gln Arg Lys His Ser Lys Arg His
                                                                    |
                                                                F80 begins
        2601      2610      2619      2628      2637      2646

ATC CAC AAA AGC CAC ATA GTG GTA CCT GCA AAT ACC ACC AGT GCC ATC CTC AGT
Ile His Lys Ser His Ile Val Val Pro Ala Asn Thr Thr Ser Ala Ile Leu Ser
        2655      2664      2673      2682      2691      2700

GGT TTG CGC CCT TAC AGC TCT TAC CAT GTG GAG GTA CAG GCC TTT AAT GGG CGG
Gly Leu Arg Pro Tyr Ser Ser Tyr His Val Glu Val Gln Ala Phe Asn Gly Arg
        2709      2718      2727      2736      2745      2754

GGC TTG GGG CCT GCG AGT GAA TGG ACC TTC AGC ACC CCA GAG GGA GTG CCT GGC
Gly Leu Gly Pro Ala Ser Glu Trp Thr Phe Ser Thr Pro Glu Gly Val Pro Gly
                                                                |
                                                            Fn4-5 begins
        2763      2772      2781      2790      2799      2808

CAC CCT GAG GCA TTA CAC CTG GAG TGT CAG TCG GAC ACT AGT CTA CTG CAC
His Pro Glu Ala Leu His Leu Glu Cys Gln Ser Asp Thr Ser Leu Leu Leu His
        2817      2826      2835      2844      2853      2862

TGG CAG CCA CCA CTC AGC CAC AAT GGA GTG CTC ACT GGC TAC CTG CTC TCT TAC
Trp Gln Pro Pro Leu Ser His Asn Gly Val Leu Thr Gly Tyr Leu Leu Ser Tyr
        2871      2880      2889      2898      2907      2916

CAT CCC GTG GAA GGG GAA AGC AAA GAG CAG TTG TTC TTC AAC CTT TCG GAC CCA
His Pro Val Glu Gly Glu Ser Lys Glu Gln Leu Phe Phe Asn Leu Ser Asp Pro
        2925      2934      2943      2952      2961      2970
```

FIG. 5E

| | | | | | | | | | | | | | | | | | |
|---|---|---|---|---|---|---|---|---|---|---|---|---|---|---|---|---|---|
| GAA | CTC | CGG | ACT | CAT | AAT | CTG | ACC | AAC | CTC | AAC | CCT | GAT | CTA | CAG | TAC | CGC | TTC |
| Glu | Leu | Arg | Thr | His | Asn | Leu | Thr | Asn | Leu | Asn | Pro | Asp | Leu | Gln | Tyr | Arg | Phe |

2979        2988        2997        3006        3015        3024

| CAG | CTT | CAG | GCC | ACC | ACC | CAA | CAG | GGG | GGT | CCT | GGT | GAG | GCC | ATC | GTG | CGT | GAA |
|---|---|---|---|---|---|---|---|---|---|---|---|---|---|---|---|---|---|
| Gln | Leu | Gln | Ala | Thr | Thr | Gln | Gln | Gly | Gly | Pro | Gly | Glu | Ala | Ile | Val | Arg | Glu |

3033        3042        3051        3060        3069        3078

| GGA | GGC | ACC | ATG | GCC | CTG | TTT | GGC | AAG | CCA | GAT | TTT | GGC | AAC | ATC | TCA | GCC | ACA |
|---|---|---|---|---|---|---|---|---|---|---|---|---|---|---|---|---|---|
| Gly | Gly | Thr | MET | Ala | Leu | Phe | Gly | Lys | Pro | Asp | Phe | Gly | Asn | Ile | Ser | Ala | Thr |

3087        3096        3105        3114        3123        3132

| GCA | GGT | GAA | AAC | TAC | AGC | GTG | GTC | TCC | TGG | GTC | CCT | CGG | AAG | GGC | CAG | TGC | AAT |
|---|---|---|---|---|---|---|---|---|---|---|---|---|---|---|---|---|---|
| Ala | Gly | Glu | Asn | Tyr | Ser | Val | Val | Ser | Trp | Val | Pro | Arg | Lys | Gly | Gln | Cys | Asn |

3141        3150        3159        3168        3177        3186

| TTC | AGG | TTC | CAT | ATC | TTG | TTC | AAA | GCC | TTA | CCA | GAA | GGG | AAA | GTG | AGC | CCT | GAT |
|---|---|---|---|---|---|---|---|---|---|---|---|---|---|---|---|---|---|
| Phe | Arg | Phe | His | Ile | Leu | Phe | Lys | Ala | Leu | Pro | Glu | Gly | Lys | Val | Ser | Pro | Asp |

3195        3204        3213        3222        3231        3240

| CAC | CAG | CCT | CAG | CCT | CAG | TAT | GTC | AGC | TAC | AAT | CAG | AGC | TCC | TAC | ACA | CAA | TGG |
|---|---|---|---|---|---|---|---|---|---|---|---|---|---|---|---|---|---|
| His | Gln | Pro | Gln | Pro | Gln | Tyr | Val | Ser | Tyr | Asn | Gln | Ser | Ser | Tyr | Thr | Gln | Trp |

3249        3258        3267        3276        3285        3294

| AAC | CTA | CAG | CCT | GAC | ACC | AAA | TAT | GAG | ATC | CAC | CTG | ATA | AAG | GAG | AAG | GTC | CTC |
|---|---|---|---|---|---|---|---|---|---|---|---|---|---|---|---|---|---|
| Asn | Leu | Gln | Pro | Asp | Thr | Lys | Tyr | Glu | Ile | His | Leu | Ile | Lys | Glu | Lys | Val | Leu |

3303        3312        3321        3330        3339        3348

| CTG | CAC | CAT | CTG | GAT | GTG | AAG | ACT | AAT | GGA | ACT | GGC | CCT | GTG | CGA | GTT | TCT | ACT |
|---|---|---|---|---|---|---|---|---|---|---|---|---|---|---|---|---|---|
| Leu | His | His | Leu | Asp | Val | Lys | Thr | Asn | Gly | Thr | Gly | Pro | Val | Arg | Val | Ser | Thr |

3357        3366        3375        3384        3393        3402

| ACA | GGG | AGC | TTT | GCC | TCC | GAG | GGC | TGG | TTC | ATC | GCC | TTT | GTC | AGC | GCT | ATC | ATT |
|---|---|---|---|---|---|---|---|---|---|---|---|---|---|---|---|---|---|
| Thr | Gly | Ser | Phe | Ala | Ser | Glu | Gly | Trp | Phe | Ile | Ala | Phe | Val | Ser | Ala | Ile | Ile |

|
Fn3-5, Fn4-5 ends 3411        3420        3429        3438        3447        3456

| CTC | TTG | CTC | CTC | ATC | CTG | CTC | ATC | CTC | TGC | TTC | ATC | AAA | CGC | AGC | AAG | GGT | GGC |
|---|---|---|---|---|---|---|---|---|---|---|---|---|---|---|---|---|---|
| Leu | Leu | Leu | Leu | Ile | Leu | Leu | Ile | Leu | Cys | Phe | Ile | Lys | Arg | Ser | Lys | Gly | Gly |

3465        3474        3483        3492        3501        3510

| AAA | TAC | TCA | GTG | AAG | GAC | AAG | GAG | GAC | ACT | CAG | GTA | GAT | TCC | GAG | GCC | CGG | CCC |
|---|---|---|---|---|---|---|---|---|---|---|---|---|---|---|---|---|---|
| Lys | Tyr | Ser | Val | Lys | Asp | Lys | Glu | Asp | Thr | Gln | Val | Asp | Ser | Glu | Ala | Arg | Pro |

3519        3528        3537        3546        3555        3564

| ATG | AAA | GAC | GAG | ACC | TTC | GGC | GAG | TAC | AGG | TCC | CTG | GAG | AGT | GAC | AAT | GAA | GAG |
|---|---|---|---|---|---|---|---|---|---|---|---|---|---|---|---|---|---|

FIG. 5F

```
MET Lys Asp Glu Thr Phe Gly Glu Tyr Arg Ser Leu Glu Ser Asp Asn Glu Glu
         3573        3582        3591        3600        3609        3618
    ___ ___ ___ ___ ___ ___ ___ ___ ___ ___ ___ ___ ___ ___ ___ ___ ___ ___
    AAG GCC TTT GGC AGC AGC CAG CCA TCT CTC AAC GGA GAC ATC AAA CCC CTA GGC
    Lys Ala Phe Gly Ser Ser Gln Pro Ser Leu Asn Gly Asp Ile Lys Pro Leu Gly 3627        3636        3645        3654        3663        3672
    ___ ___ ___ ___ ___ ___ ___ ___ ___ ___ ___ ___ ___ ___ ___ ___ ___ ___
    AGT GAT GAC AGC CTG GCT GAT TAT GGG GGC AGT GTG GAC GTC CAG TTC AAT GAG
    Ser Asp Asp Ser Leu Ala Asp Tyr Gly Gly Ser Val Asp Val Gln Phe Asn Glu 3681        3690        3699        3708        3717        3726
    ___ ___ ___ ___ ___ ___ ___ ___ ___ ___ ___ ___ ___ ___ ___ ___ ___ ___
    GAT GGC TCT TTC ATC GGC CAG TAC AGT GGC AAG AAA GAG AAG GAG GCA GCA GGA
    Asp Gly Ser Phe Ile Gly Gln Tyr Ser Gly Lys Lys Glu Lys Glu Ala Ala Gly 3735        3744        3753        3762        3771        3780
    ___ ___ ___ ___ ___ ___ ___ ___ ___ ___ ___ ___ ___ ___ ___ ___ ___ ___
    GGC AAT GAC AGT TCA GGG GCT ACC TCT CCT ATC AAT CCT GCA GTA GCC CTA GAA
    Gly Asn Asp Ser Ser Gly Ala Thr Ser Pro Ile Asn Pro Ala Val Ala Leu Glu
                                                                         |
                                                                        F80
                                                                        ends

─→
TAG
 .
```

FIG. 5G

Ng-CAM Fn3-5

NVGVELLNSSTVRVRWTLGGGPKELRGRLRGFRVLYWRLGWVGERSRRQAP

PDPPQIPQSPAEDPPPFPPVALTVGGDARGALLGGLRPWSRYQLRVLVFN

GRGDGPPSEPIAFETPEGVPGPPEELRVERLDDTALSVVERRTFKRSITGYVLRYQQVEP

GSALPGGSVLRDPQCDLRGLNARSRYRLALPSTPRERPALQTVGSTKPEPPSPLWSR

FGVGGRGGFHGAAVEFGAAQEDDVEFEVQFMNKSTDEPWRTSGRANSSLRRYR

LEGLRPGTAYRVQFVGRNRSGENVAFWESEVQTNGTVVPQPGGGVCTKGW

NG3-5.PEP

FIG. 6

Ng-CAM Fn4-5

PGPPEELRVERLDDTALSVVERRTFKRSITGYVLRYQQVEPGSALPGGSVL

RDPQCDLRGLNARSRYRLALPSTPRERPALQTVGSTKPEPPSPLWSRFGV

GGRGGFHGAAVEFGAAQEDDVEFEVQFMNKSTDEPWRTSGRANSSLRRYR

LEGLRPGTAYRVQFVGRNRSGENVAFWESEVQTNGTVVPQPGGGVCTKGW

NG4-5.PEP

FIG. 7

HUMAN L1 F80

IHKDHVVVPANTTSVILSGLRPYSSYHLEVQAFNGRGSGPASEFTFSTPEGVPGHPEALHLECQSNTSLL
LRWQPPLSHNGVLTGYVLSYHPLDEGGKGQLSFNLRDPELRTHNLTDLSPHLRYRFQLQATTKEGPGEAI
VREGGTMALSGISDFGNISATAGENYSVVSWVPKEGQCNFRFHILFKALGEEKGGASLSPQYVSYNQSSY
TQWDLQPDTDYEIHLFKERMFRHQMAVKTNGTGRVRLPPAGFATEGWFIGFVSAIILLLLVLLILCFIKR
SKGGKYSVKDKEDTQVDSEARPMKDETFGEYSDNEEKAFGSSQPSLNGDIKPLGSDDSLADYGGSVDVQF
NEDGSFIGQYSGKKEKEAAGGNDSSGATSPINPAVALEXWSPGQEMLCPWPWDPGPSLSSRPMGGWSWGR
GELAASD

FIG. 8

HUMAN L1 Fn3-5

LEGIEILNSSAVLVKWRPVDLAQVKGHLRGYNVTYWREGSQRKHSKRHIHKDHVVVPANTTSVILSGLRP
YSSYHLEVQAFNGRGSGPASEFTFSTPEGVPGHPEALHLECQSNTSLLLRWQPPLSHNGVLTGYVLSYHP
LDEGGKGQLSFNLRDPELRTHNLTDLSPHLRYRFQLQATTKEGPGEAIVREGGTMALSGISDFGNISATA
GENYSVVSWVPKEGQCNFRFHILFKALGEEKGGASLSPQYVSYNQSSYTQWDLQPDTDYEIHLFKERMFR
HQMAVKTNGTGRVRLPPAGFATEG

FIG. 9

HUMAN L1 Fn4-5

PGHPEALHLECQSNTSLLLRWQPPLSHNGVLTGYVLSYHPLDEGGKGQLSFNLRDPELRTHNLTDLSPHL
RYRFQLQATTKEGPGEAIVREGGTMALSGISDFGNISATAGENYSVVSWVPKEGQCNFRFHILFKALGEE
KGGASLSPQYVSYNQSSYTQWDLQPDTDYEIHLFKERMFRHQMAVKTNGTGRVRLPPAGFATEG

FIG. 10

Mouse L1 F80

HIHKSHIVVPANTTSAILSGLRPYSSYHVEVQAFNGRGLGPASEWTFSTPEGVPGHPE
ALHLECQSDTSLLLHWQPPLSHNGVLTGYLLSYHPVEGESKEQLFFNLSDPELRTHNL
TNLNPDLQYRFQLQATTQQGGPGQAIVREGGTMALFGKPDFGNISATAGENYSVVSW
VPRKGQCNFRFHILFKALPEGKVSPDHQPQPQYVSYNQSSYTQWNLQPDTKYEIHLIK
EKVLLHHLDVKTNGTGPVRVSTTGSFASEGWFIAFVSAIILLLLILLILCFIKRSKGGKYSV
KDKEDTQVDSEARPMKDETFGEYRSLESDNEEKAFGSSQPSLNGDIKPLGSDDSLAD
YGGSVDVQFNEDGSFIGQYSGKKEKEAAGGNDSSGATSPINPAVALE m/1F80.pep

FIG. 11

Mouse L1 Fn3-5

LEDITIFNSSTVLVRWRPVDLAQVKGHLKGYNVTYWWKGSQRKHSKRHIHKSHIVVPA
NTTSAILSGLRPYSSYHVEVQAFNGRGLGPASEWTFSTPEGVPGHPEALHLECQSDT
SLLLHWQPPLSHNGVLTGYLLSYHPVEGESKEQLFFNLSDPELRTHNLTNLNPDLQYR
FQLQATTQQGGPGQAIVREGGTMALFGKPDFGNISATAGENYSVVSWVPRKGQCNF
RFHILFKALPEGKVSPDHQPQPQYVSYNQSSYTQWNLQPDTKYEIHLIKEKVLLHHLDV
KTNGTGPVRVSTTGSFASEGW m/13-5.pep

FIG. 12

Mouse L1 Fn4-5

PGHPEALHLECQSDTSLLLHWQPPLSHNGVLTGYLLSYHPVEGESKEQLFFNLSDPEL

RTHNLTNLNPDLQYRFQLQATTQQGGPGQAIVREGGTMALFGKPDFGNISATAGENY

SVVSWVPRKGQCNFRFHILFKALPEGKVSPDHQPQPQYVSYNQSSYTQWNLQPDTK

YEIHLIKEKVLLHHLDVKTNGTGPVRVSTTGSFASEGW ml/14-5.pep

FIG. 13

Nr-CAM F80

VEKKILTFRGNKTFGMLPGLEPYSSYKLNVRVVNGKGEGPASPDKVFKTPEGVPSPPS

FLKITNPTLDSLTLEWGSPTHPNGVLTSYILKFQPINNTHELGPLVEIRIPANESSLILKNL

NYSTRYKFYFNAQTSVGSGSQITEEAVTIMDEVQPLYPRIRNVTTAAAETYANISWEYE

GPDHANFYVEYGVAGSKEDWKKEIVNGSRSFFVLKGLTPGTAYKVRVGAEGLSGFRS

SEDLFETGPAMASRQVDIATQGWFIGLMCAVALLILILLIVCFIRRNKGGKYPVKEKEDA

HADPEIQPMKEDDGTFGEYSDAEDHKPLKKGSRTPSDRTVKKEDSDDSLVDYGEGVN

GQFNEDGSFIGQYSGKKEKEPAEGNESSEAPSPVNAMNSFV nrF80.pep

FIG. 14

Nr-CAM Fn3-5

NVQVHVINSTLAKVHWDPVPLKSVRGHLQGYKVYYWKVQSLSRRSKRHVEKKILTFR

GNKTFGMLPGLEPYSSYKLNVRVVNGKGEGPASPDKVFKTPEGVPSPPSFLKITNPTL

DSLTLEWGSPTHPNGVLTSYILKFQPINNTHELGPLVEIRIPANESSLILKNLNYSTRYKF

YFNAQTSVGSGSQITEEAVTIMDEVQPLYPRIRNVTTAAAETYANISWEYEGPDHANFY

VEYGVAGSKEDWKKEIVNGSRSFFVLKGLTPGTAYKVRVGAEGLSGFRSSEDLFETG

PAMASRQVDIATQGW nr3-5.pep

FIG. 15

Nr-CAM Fn4-5

PSPPSFLKITNPTLDSLTLEWGSPTHPNGVLTSYILKFQPINNTHELGPLVEIRIPANESS

LILKNLNYSTRYKFYFNAQTSVGSGSQITEEAVTIMDEVQPLYPRIRNVTTAAAETYANI

SWEYEGPDHANFYVEYGVAGSKEDWKKEIVNGSRSFFVLKGLTPGTAYKVRVGAEGL

SGFRSSEDLFETGPAMASRQVDIATQGW nr4-5.pep

FIG. 16

Ng-CAM F80GST

MSPILGYWKIKGLVQPTRLLLEYLEEKYEEHLYERDEGDKWRNKKFELGLEFPNLPYYI

DGDVKLTQSMAIIRYIADKHNMLGGCPKERAEISMLEGAVLDIRYGVSRIAYSKDFETLK

VDFLSKLPEMLKMFEDRLCHKTYLNGDHVTHPDFMLYDALDVVLYMDPMCLDAFPKL

VCFKKRIEAIPQIDKYLKSSKYIAWPLQGWQATFGGGDHPPKSDLVPRGSAPPDPPQIP

QSPAEDPPPFPPVALTVGGDARGALLGGLRPWSRYQLRVLVFNGRGDGPPSEPIAFE

TPEGVPGPPEELRVERLDDTALSVVERRTFKRSITGYVLRYQQVEPGSALPGGSVLRD

PQCDLRGLNARSRYRLALPSTPRERPALQTVGSTKPEPPSPLWSRFGVGGRGGFHG

AAVEFGAAQEDDVEFEVQFMNKSTDEPWRTSGRANSSLRRYRLEGLRPGTAYRVQF

VGRNRSGENVAFWESEVQTNGTVVPQPGGGVCTKGWFIGFVSSVVLLLLILLILCFIKR

SKGGKYSVKDKEDTQVDSEARPMKDETFGEYRSLESEAEKGSASGSGAGSGVGSPG

RGPCAAGSEDSLAGYGGSGDVQFNEDGSFIGQYRGPGAGPGSSGPASPCAGPPLDP

RNSRVDSSGRI

NGF80.GST

FIG. 17

Ng-CAM 3-5GST

MSPILGYWKIKGLVQPTRLLLEYLEEKYEEHLYERDEGDKWRNKKFELGLEFPNLPYYI

DGDVKLTQSMAIIRYIADKHNMLGGCPKERAEISMLEGAVLDIRYGVSRIAYSKDFETLK

VDFLSKLPEMLKMFEDRLCHKTYLNGDHVTHPDFMLYDALDVVLYMDPMCLDAFPKL

VCFKKRIEAIPQIDKYLKSSKYIAWPLQGWQATFGGGDHPPKSDLVPRGSN

VGVELLNSSTVRVRWTLGGGPKELRGRLRGFRVLYWRLGWVGERSRRQAP

PDPPQIPQSPAEDPPPFPPVALTVGGDARGALLGGLRPWSRYQLRVLVFN

GRGDGPPSEPIAFETPEGVPGPPEELRVERLDDTALSVVERRTFKRSITGYVLRYQQVEP

GSALPGGSVLRDPQCDLRGLNARSRYRLALPSTPRERPALQTVGSTKPEPPSPLWSR

FGVGGRGGFHGAAVEFGAAQEDDVEFEVQFMNKSTDEPWRTSGRANSSLRRYR

LEGLRPGTAYRVQFVGRNRSGENVAFWESEVQTNGTVVPQPGGGVCTKGW

PGIPGSTRAAAS

NG3-5.GST

FIG. 18

Ng-CAM 4-5GST

MSPILGYWKIKGLVQPTRLLLEYLEEKYEEHLYERDEGDKWRNKKFELGLEFPNLPYYI

DGDVKLTQSMAIIRYIADKHNMLGGCPKERAEISMLEGAVLDIRYGVSRIAYSKDFETLK

VDFLSKLPEMLKMFEDRLCHKTYLNGDHVTHPDFMLYDALDVVLYMDPMCLDAFPKL

VCFKKRIEAIPQIDKYLKSSKYIAWPLQGWQATFGGGDHPPKSDLVPRGSP

GPPEELRVERLDDTALSVVERRTFKRSITGYVLRYQQVEPGSALPGGSVL

RDPQCDLRGLNARSRYRLALPSTPRERPALQTVGSTKPEPPSPLWSRFGV

GGRGGFHGAAVEFGAAQEDDVEFEVQFMNKSTDEPWRTSGRANSSLRRYR

LEGLRPGTAYRVQFVGRNRSGENVAFWESEVQTNGTVVPQPGGGVCTKGW

PGIPGSTRAAAS

NG4-5.GST

FIG. 19

HUMAN L1 F80GST

MSPILGYWKIKGLVQPTRLLLEYLEEKYEEHLYERDEGDKWRNKKFELGLEFPNLPYYIDGDVKLTQSMA
IIRYIADKHNMLGGCPKERAEISMLEGAVLDIRYGVSRIAYSKDFETLKVDFLSKLPEMLKMFEDRLCHK
TYLNGDHVTHPDFMLYDALDVVLYMDPMCLDAFPKLVCFKKRIEAIPQIDKYLKSSKYIAWPLQGWQATF
GGGDHPPKSDLVPRGSIHKDHVVVPANTTSVILSGLRPYSSYHLEVQAFNGRGSGPASEFTFSTPEGVPG
HPEALHLECQSNTSLLLRWQPPLSHNGVLTGYVLSYHPLDEGGKGQLSFNLRDPELRTHNLTDLSPHLRY
RFQLQATTKEGPGEAIVREGGTMALSGISDFGNISATAGENYSVVSWVPKEGQCNFRFHILFKALGEEKG
GASLSPQYVSYNQSSYTQWDLQPDTDYEIHLFKERMFRHQMAVKTNGTGRVRLPPAGFATEGWFIGFVSA
IILLLLVLLILCFIKRSKGGKYSVKDKEDTQVDSEARPMKDETFGEYSDNEEKAFGSSQPSLNGDIKPLG
SDDSLADYGGSVDVQFNEDGSFIGQYSGKKEKEAAGGNDSSGATSPINPAVALEXWSPGQEMLCPWPWDP
GPSLSSRPMGGWSWGRGELAASDPRNSRVDSSGRI

FIG. 20

HUMAN L1 Fn3-5GST

MSPILGYWKIKGLVQPTRLLLEYLEEKYEEHLYERDEGDKWRNKKFELGLEFPNLPYYIDGDVKLTQSMA
IIRYIADKHNMLGGCPKERAEISMLEGAVLDIRYGVSRIAYSKDFETLKVDFLSKLPEMLKMFEDRLCHK
TYLNGDHVTHPDFMLYDALDVVLYMDPMCLDAFPKLVCFKKRIEAIPQIDKYLKSSKYIAWPLQGWQATF
GGGDHPPKSDLVPRGSLEGIEILNSSAVLVKWRPVDLAQVKGHLRGYNVTYWREGSQRKHSKRHIHKDHV
VVPANTTSVILSGLRPYSSYHLEVQAFNGRGSGPASEFTFSTPEGVPGHPEALHLECQSNTSLLLRWQPP
LSHNGVLTGYVLSYHPLDEGGKGQLSFNLRDPELRTHNLTDLSPHLRYRFQLQATTKEGPGEAIVREGGT
MALSGISDFGNISATAGENYSVVSWVPKEGQCNFRFHILFKALGEEKGGASLSPQYVSYNQSSYTQWDLQ
PDTDYEIHLFKERMFRHQMAVKTNGTGRVRLPPAGFATEGPGIPGSTRAAAS

FIG. 21

HUMAN L1 Fn4-5GST

MSPILGYWKIKGLVQPTRLLLEYLEEKYEEHLYERDEGDKWRNKKFELGLEFPNLPYYIDGDVKLTQSMA
IIRYIADKHNMLGGCPKERAEISMLEGAVLDIRYGVSRIAYSKDFETLKVDFLSKLPEMLKMFEDRLCHK
TYLNGDHVTHPDFMLYDALDVVLYMDPMCLDAFPKLVCFKKRIEAIPQIDKYLKSSKYIAWPLQGWQATF
GGGDHPPKSDLVPRGSPGHPEALHLECQSNTSLLLRWQPPLSHNGVLTGYVLSYHPLDEGGKGQLSFNLR
DPELRTHNLTDLSPHLRYRFQLQATTKEGPGEAIVREGGTMALSGISDFGNISATAGENYSVVSWVPKEG
QCNFRFHILFKALGEEKGGASLSPQYVSYNQSSYTQWDLQPDTDYEIHLFKERMFRHQMAVKTNGTGRVR
LPPAGFATEGPGIPGSTRAAAS

FIG. 22

Mouse L1 F80GST

MSPILGYWKIKGLVQPTRLLLEYLEEKYEEHLYERDEGDKWRNKKFELGLEFPNLPYYI
DGDVKLTQSMAIIRYIADKHNMLGGCPKERAEISMLEGAVLDIRYGVSRIAYSKDFETLK
VDFLSKLPEMLKMFEDRLCHKTYLNGDHVTHPDFMLYDALDVVLYMDPMCLDAFPKL
VCFKKRIEAIPQIDKYLKSSKYIAWPLQGWQATFGGGDHPPKSDLVPRGSHIHKSHIVV
PANTTSAILSGLRPYSSYHVEVQAFNGRGLGPASEWTFSTPEGVPGHPEALHLECQS
DTSLLLHWQPPLSHNGVLTGYLLSYHPVEGESKEQLFFNLSDPELRTHNLTNLNPDLQ
YRFQLQATTQQGGPGQAIVREGGTMALFGKPDFGNISATAGENYSVVSWVPRKGQCN
FRFHILFKALPEGKVSPDHQPQPQYVSYNQSSYTQWNLQPDTKYEIHLIKEKVLLHHLD
VKTNGTGPVRVSTTGSFASEGWFIAFVSAIILLLLILLILCFIKRSKGGKYSVKDKEDTQV
DSEARPMKDETFGEYRSLESDNEEKAFGSSQPSLNGDIKPLGSDDSLADYGGSVDVQ
FNEDGSFIGQYSGKKEKEAAGGNDSSGATSPINPAVALEPRNSRVDSSGRI m/1F80.gst

FIG. 23

Mouse L1 Fn3-5GST

MSPILGYWKIKGLVQPTRLLLEYLEEKYEEHLYERDEGDKWRNKKFELGLEFPNLPYYI
DGDVKLTQSMAIIRYIADKHNMLGGCPKERAEISMLEGAVLDIRYGVSRIAYSKDFETLK
VDFLSKLPEMLKMFEDRLCHKTYLNGDHVTHPDFMLYDALDVVLYMDPMCLDAFPKL
VCFKKRIEAIPQIDKYLKSSKYIAWPLQGWQATFGGGDHPPKSDLVPRGSLEDITIFNSS
TVLVRWRPVDLAQVKGHLKGYNVTYWWKGSQRKHSKRHIHKSHIVVPANTTSAILSGL
RPYSSYHVEVQAFNGRGLGPASEWTFSTPEGVPGHPEALHLECQSDTSLLLHWQPPL
SHNGVLTGYLLSYHPVEGESKEQLFFNLSDPELRTHNLTNLNPDLQYRFQLQATTQQG
GPGQAIVREGGTMALFGKPDFGNISATAGENYSVVSWVPRKGQCNFRFHILFKALPE
GKVSPDHQPQPQYVSYNQSSYTQWNLQPDTKYEIHLIKEKVLLHHLDVKTNGTGPVR
VSTTGSFASEGWPGIPGSTRAAAS

M/13-5.gst

FIG. 24

Mouse L1 Fn4-5GST

MSPILGYWKIKGLVQPTRLLLEYLEEKYEEHLYERDEGDKWRNKKFELGLEFPNLPYYI

DGDVKLTQSMAIIRYIADKHNMLGGCPKERAEISMLEGAVLDIRYGVSRIAYSKDFETLK

VDFLSKLPEMLKMFEDRLCHKTYLNGDHVTHPDFMLYDALDVVLYMDPMCLDAFPKL

VCFKKRIEAIPQIDKYLKSSKYIAWPLQGWQATFGGGDHPPKSDLVPRGSPGHPEALH

LECQSDTSLLLHWQPPLSHNGVLTGYLLSYHPVEGESKEQLFFNLSDPELRTHNLTNL

NPDLQYRFQLQATTQQGGPGQAIVREGGTMALFGKPDFGNISATAGENYSVVSWVP

RKGQCNFRFHILFKALPEGKVSPDHQPQPQYVSYNQSSYTQWNLQPDTKYEIHLIKEKVL

LHHLDVKTNGTGPVRVSTTGSFASEGWPGIPGSTRAAAS m/14-5.gst

FIG. 25

Nr-CAM F80GST

MSPILGYWKIKGLVQPTRLLLEYLEEKYEEHLYERDEGDKWRNKKFELGLEFPNLPYYI

DGDVKLTQSMAIIRYIADKHNMLGGCPKERAEISMLEGAVLDIRYGVSRIAYSKDFETLK

VDFLSKLPEMLKMFEDRLCHKTYLNGDHVTHPDFMLYDALDVVLYMDPMCLDAFPKL

VCFKKRIEAIPQIDKYLKSSKYIAWPLQGWQATFGGGDHPPKSDLVPRGSVEKKILTFR

GNKTFGMLPGLEPYSSYKLNVRVVNGKGEGPASPDKVFKTPEGVPSPPSFLKITNPTL

DSLTLEWGSPTHPNGVLTSYILKFQPINNTHELGPLVEIRIPANESSLILKNLNYSTRYKF

YFNAQTSVGSGSQITEEAVTIMDEVQPLYPRIRNVTTAAAETYANISWEYEGPDHANFY

VEYGVAGSKEDWKKEIVNGSRSFFVLKGLTPGTAYKVRVGAEGLSGFRSSEDLFETG

PAMASRQVDIATQGWFIGLMCAVALLILILLIVCFIRRNKGGKYPVKEKEDAHADPEIQP

MKEDDGTFGEYSDAEDHKPLKKGSRTPSDRTVKKEDSDDSLVDYGEGVNGQFNEDG

SFIGQYSGKKEKEPAEGNESSEAPSPVNAMNSFVPRNSRVDSSGRI nrf80.gst

FIG. 26

Nr-CAM Fn3-5GST

MSPILGYWKIKGLVQPTRLLLEYLEEKYEEHLYERDEGDKWRNKKFELGLEFPNLPYYI

DGDVKLTQSMAIIRYIADKHNMLGGCPKERAEISMLEGAVLDIRYGVSRIAYSKDFETLK

VDFLSKLPEMLKMFEDRLCHKTYLNGDHVTHPDFMLYDALDVVLYMDPMCLDAFPKL

VCFKKRIEAIPQIDKYLKSSKYIAWPLQGWQATFGGGDHPPKSDLVPRGSNVQVHVIN

STLAKVHWDPVPLKSVRGHLQGYKVYYWKVQSLSRRSKRHVEKKILTFRGNKTFGML

PGLEPYSSYKLNVRVVNGKGEGPASPDKVFKTPEGVPSPPSFLKITNPTLDSLTLEWG

SPTHPNGVLTSYILKFQPINNTHELGPLVEIRIPANESSLILKNLNYSTRYKFYFNAQTSV

GSGSQITEEAVTIMDEVQPLYPRIRNVTTAAAETYANISWEYEGPDHANFYVEYGVAG

SKEDWKKEIVNGSRSFFVLKGLTPGTAYKVRVGAEGLSGFRSSEDLFETGPAMASRQ

VDIATQGWPGIPGSTRAAAS nr3-5.gst

FIG. 27

Nr-CAM Fn4-5GST

MSPILGYWKIKGLVQPTRLLLEYLEEKYEEHLYERDEGDKWRNKKFELGLEFPNLPYYI

DGDVKLTQSMAIIRYIADKHNMLGGCPKERAEISMLEGAVLDIRYGVSRIAYSKDFETLK

VDFLSKLPEMLKMFEDRLCHKTYLNGDHVTHPDFMLYDALDVVLYMDPMCLDAFPKL

VCFKKRIEAIPQIDKYLKSSKYIAWPLQGWQATFGGGDHPPKSDLVPRGSPSPPSFLKI

TNPTLDSLTLEWGSPTHPNGVLTSYILKFQPINNTHELGPLVEIRIPANESSLILKNLNYS

TRYKFYFNAQTSVGSGSQITEEAVTIMDEVQPLYPRIRNVTTAAAETYANISWEYEGPD

HANFYVEYGVAGSKEDWKKEIVNGSRSFFVLKGLTPGTAYKVRVGAEGLSGFRSSED

LFETGPAMASRQVDIATQGWPGIPGSTRAAS nr4-5.gst

FIG. 28

Chicken Nr-CAM and fragments

```
               10         20         30         41         50         59
                                                 >
CAAGAGTGAT TTACTTAGTA GAGCCTAAAA TC ATG ATG AAA GAG AAG AGC ATA TCT GCA
                                   MET MET Lys Glu Lys Ser Ile Ser Ala 68         77         86         95        104        113
AGC AAA GCT TCC TTG GTT TTC TTT CTG TGC CAA ATG ATT TCT GCA TTG GAT GTA
Ser Lys Ala Ser Leu Val Phe Phe Leu Cys Gln MET Ile Ser Ala Leu Asp Val 122        131        140        149        158        167
CCT CTT GAT TCA AAA CTT CTA GAA GAA TTG TCT CAA CCT CCA ACA ATA ACT CAG
Pro Leu Asp Ser Lys Leu Leu Glu Glu Leu Ser Gln Pro Pro Thr Ile Thr Gln 176        185        194        203        212        221
CAG TCT CCA AAA GAT TAC ATT GTT GAC CCT CGA GAG AAT ATT GTA ATA CAA TGT
Gln Ser Pro Lys Asp Tyr Ile Val Asp Pro Arg Glu Asn Ile Val Ile Gln Cys 230        239        248        257        266        275
GAA GCA AAA GGA AAA CCA CCT CCT AGC TTC TCC TGG ACG CGC AAT GGA ACT CAT
Glu Ala Lys Gly Lys Pro Pro Pro Ser Phe Ser Trp Thr Arg Asn Gly Thr His 284        293        302        311        320        329
TTT GAT ATA GAT AAA GAT GCA CAG GTA ACA ATG AAA CCA AAT TCA GGA ACC CTT
Phe Asp Ile Asp Lys Asp Ala Gln Val Thr MET Lys Pro Asn Ser Gly Thr Leu 338        347        356        365        374        383
GTT GTA AAT ATT ATG AAT GGT GTG AAG GCA GAA GCA TAT GAA GGA GTA TAC CAG
Val Val Asn Ile MET Asn Gly Val Lys Ala Glu Ala Tyr Glu Gly Val Tyr Gln 392        401        410        419        428        437
TGT ACA GCA AGG AAT GAA AGA GGA GCA GCC ATT TCC AAC AAT ATT GTT ATA CGG
Cys Thr Ala Arg Asn Glu Arg Gly Ala Ala Ile Ser Asn Asn Ile Val Ile Arg 446        455        464        473        482        491
CCA TCT AGA TCC CCT TTG TGG ACT AAA GAA AAA CTA GAA CCA AAT CAT GTT CGA
Pro Ser Arg Ser Pro Leu Trp Thr Lys Glu Lys Leu Glu Pro Asn His Val Arg 500        509        518        527        536        545
GAA GGT GAT TCC CTA GTA CTA AAC TGC AGA CCT CCT GTT GGC TTA CCA CCA CCT
```

FIG. 30A

```
Glu Gly Asp Ser Leu Val Leu Asn Cys Arg Pro Pro Val Gly Leu Pro Pro Pro
        554         563         572         581         590         599

ATA ATA TTT TGG ATG GAT AAT GCT TTC CAA AGG CTG CCT CAA AGT GAA AGA GTT
Ile Ile Phe Trp MET Asp Asn Ala Phe Gln Arg Leu Pro Gln Ser Glu Arg Val
        608         617         626         635         644         653

TCT CAA GGT CTC AAT GGA GAC CTT TAT TTT TCT AAT GTA CAA CCA GAG GAC ACC
Ser Gln Gly Leu Asn Gly Asp Leu Tyr Phe Ser Asn Val Gln Pro Glu Asp Thr
        662         671         680         689         698         707

CGT GTG GAC TAT ATC TGC TAC GCG AGA TTT AAT CAC ACA CAA ACT ATA CAG CAG
Arg Val Asp Tyr Ile Cys Tyr Ala Arg Phe Asn His Thr Gln Thr Ile Gln Gln
        716         725         734         743         752         761

AAA CAA CCC ATT TCT GTA AAA GTC TTT TCA ACC AAG CCA GTT ACA GAA AGG CCA
Lys Gln Pro Ile Ser Val Lys Val Phe Ser Thr Lys Pro Val Thr Glu Arg Pro
        770         779         788         797         806         815

CCA GTT CTT CTT ACA CCA ATG GGC AGC ACA AGT AAC AAA GTG GAA CTG AGA GGA
Pro Val Leu Leu Thr Pro MET Gly Ser Thr Ser Asn Lys Val Glu Leu Arg Gly
        824         833         842         851         860         869

AAT GTT CTT TTG TTG GAA TGC ATC GCA GCA GGA TTA CCC ACA CCA GTA ATC CGC
Asn Val Leu Leu Leu Glu Cys Ile Ala Ala Gly Leu Pro Thr Pro Val Ile Arg
        878         887         896         905         914         923

TGG ATT AAA GAG GGT GGT GAA CTG CCA GCC AAC AGA ACG TTT TTT GAA AAT TTT
Trp Ile Lys Glu Gly Gly Glu Leu Pro Ala Asn Arg Thr Phe Phe Glu Asn Phe
        932         941         950         959         968         977

AAG AAA ACT CTC AAG ATT ATA GAC GTC TCT GAA GCT GAC TCT GGG AAC TAC AAA
Lys Lys Thr Leu Lys Ile Ile Asp Val Ser Glu Ala Asp Ser Gly Asn Tyr Lys
        986         995        1004        1013        1022        1031

TGT ACA GCA AGA AAT ACA TTG GGT TCT ACT CAT CAT GTC ATT TCG GTA ACT GTA
Cys Thr Ala Arg Asn Thr Leu Gly Ser Thr His His Val Ile Ser Val Thr Val
       1040        1049        1058        1067        1076        1085

AAA GCT GCC CCA TAC TGG ATA ACA GCA CCC AGG AAC TTA GTA TTG TCT CCT GGA
Lys Ala Ala Pro Tyr Trp Ile Thr Ala Pro Arg Asn Leu Val Leu Ser Pro Gly
       1094        1103        1112        1121        1130        1139

GAA GAT GGG ACA TTG ATC TGC AGA GCT AAT GGC AAC CCA AAA CCT AGC ATA AGC
Glu Asp Gly Thr Leu Ile Cys Arg Ala Asn Gly Asn Pro Lys Pro Ser Ile Ser
```

FIG. 30B

|      | 1148 |     |     | 1157 |     |     | 1166 |     |     | 1175 |     |     | 1184 |     |     | 1193 |     |
|------|------|-----|-----|------|-----|-----|------|-----|-----|------|-----|-----|------|-----|-----|------|-----|
| TGG  | TTA  | ACA | AAT | GGC  | GTT | CCC | ATA  | GCA | ATT | GCC  | CCA | GAA | GAT  | CCT | AGC | AGA  | AAG |
| Trp  | Leu  | Thr | Asn | Gly  | Val | Pro | Ile  | Ala | Ile | Ala  | Pro | Glu | Asp  | Pro | Ser | Arg  | Lys |

|      | 1202 |     |     | 1211 |     |     | 1220 |     |     | 1229 |     |     | 1238 |     |     | 1247 |     |
|------|------|-----|-----|------|-----|-----|------|-----|-----|------|-----|-----|------|-----|-----|------|-----|
| GTA  | GAT  | GGG | GAT | ACC  | ATT | ATT | TTC  | TCA | GCT | GTG  | CAA | GAA | CGG  | TCA | AGT | GCT  | GTT |
| Val  | Asp  | Gly | Asp | Thr  | Ile | Ile | Phe  | Ser | Ala | Val  | Gln | Glu | Arg  | Ser | Ser | Ala  | Val |

|      | 1256 |     |     | 1265 |     |     | 1274 |     |     | 1283 |     |     | 1292 |     |     | 1301 |     |
|------|------|-----|-----|------|-----|-----|------|-----|-----|------|-----|-----|------|-----|-----|------|-----|
| TAT  | CAG  | TGC | AAT | GCT  | TCT | AAT | GAG  | TAT | GGA | TAC  | TTG | CTG | GCA  | AAT | GCA | TTT  | GTG |
| Tyr  | Gln  | Cys | Asn | Ala  | Ser | Asn | Glu  | Tyr | Gly | Tyr  | Leu | Leu | Ala  | Asn | Ala | Phe  | Val |

|      | 1310 |     |     | 1319 |     |     | 1328 |     |     | 1337 |     |     | 1346 |     |     | 1355 |     |
|------|------|-----|-----|------|-----|-----|------|-----|-----|------|-----|-----|------|-----|-----|------|-----|
| AAT  | GTT  | CTT | GCT | GAG  | CCA | CCA | AGG  | ATT | CTA | ACT  | CCT | GCT | AAT  | AAA | CTC | TAT  | CAA |
| Asn  | Val  | Leu | Ala | Glu  | Pro | Pro | Arg  | Ile | Leu | Thr  | Pro | Ala | Asn  | Lys | Leu | Tyr  | Gln |

|      | 1364 |     |     | 1373 |     |     | 1382 |     |     | 1391 |     |     | 1400 |     |     | 1409 |     |
|------|------|-----|-----|------|-----|-----|------|-----|-----|------|-----|-----|------|-----|-----|------|-----|
| GTC  | ATC  | GCA | GAT | AGT  | CCT | GCA | TTA  | ATA | GAC | TGT  | GCT | TAT | TTT  | GGT | TCA | CCT  | AAG |
| Val  | Ile  | Ala | Asp | Ser  | Pro | Ala | Leu  | Ile | Asp | Cys  | Ala | Tyr | Phe  | Gly | Ser | Pro  | Lys |

|      | 1418 |     |     | 1427 |     |     | 1436 |     |     | 1445 |     |     | 1454 |     |     | 1463 |     |
|------|------|-----|-----|------|-----|-----|------|-----|-----|------|-----|-----|------|-----|-----|------|-----|
| CCT  | GAA  | ATC | GAA | TGG  | TTT | AGG | GGA  | GTG | AAA | GGT  | AGC | ATC | TTG  | CGA | GGA | AAT  | GAA |
| Pro  | Glu  | Ile | Glu | Trp  | Phe | Arg | Gly  | Val | Lys | Gly  | Ser | Ile | Leu  | Arg | Gly | Asn  | Glu |

|      | 1472 |     |     | 1481 |     |     | 1490 |     |     | 1499 |     |     | 1508 |     |     | 1517 |     |
|------|------|-----|-----|------|-----|-----|------|-----|-----|------|-----|-----|------|-----|-----|------|-----|
| TAT  | GTT  | TTC | CAT | GAT  | AAT | GGA | ACC  | TTG | GAA | ATT  | CCA | GTG | GCT  | CAG | AAG | GAT  | AGT |
| Tyr  | Val  | Phe | His | Asp  | Asn | Gly | Thr  | Leu | Glu | Ile  | Pro | Val | Ala  | Gln | Lys | Asp  | Ser |

|      | 1526 |     |     | 1535 |     |     | 1544 |     |     | 1553 |     |     | 1562 |     |     | 1571 |     |
|------|------|-----|-----|------|-----|-----|------|-----|-----|------|-----|-----|------|-----|-----|------|-----|
| ACT  | GGC  | ACA | TAC | ACA  | TGT | GTT | GCA  | AGG | AAT | AAA  | TTA | GGG | AAG  | ACG | CAA | AAT  | GAA |
| Thr  | Gly  | Thr | Tyr | Thr  | Cys | Val | Ala  | Arg | Asn | Lys  | Leu | Gly | Lys  | Thr | Gln | Asn  | Glu |

|      | 1580 |     |     | 1589 |     |     | 1598 |     |     | 1607 |     |     | 1616 |     |     | 1625 |     |
|------|------|-----|-----|------|-----|-----|------|-----|-----|------|-----|-----|------|-----|-----|------|-----|
| GTA  | CAA  | CTG | GAA | GTT  | AAA | GAC | CCA  | ACG | ATG | ATA  | ATT | AAA | CAG  | CCA | CAG | TAC  | AAA |
| Val  | Gln  | Leu | Glu | Val  | Lys | Asp | Pro  | Thr | MET | Ile  | Ile | Lys | Gln  | Pro | Gln | Tyr  | Lys |

|      | 1634 |     |     | 1643 |     |     | 1652 |     |     | 1661 |     |     | 1670 |     |     | 1679 |     |
|------|------|-----|-----|------|-----|-----|------|-----|-----|------|-----|-----|------|-----|-----|------|-----|
| GTG  | ATT  | CAG | AGA | TCT  | GCC | CAG | GCT  | TCA | TTT | GAG  | TGT | GTA | ATA  | AAA | CAT | GAT  | CCT |
| Val  | Ile  | Gln | Arg | Ser  | Ala | Gln | Ala  | Ser | Phe | Glu  | Cys | Val | Ile  | Lys | His | Asp  | Pro |

|      | 1688 |     |     | 1697 |     |     | 1706 |     |     | 1715 |     |     | 1724 |     |     | 1733 |     |
|------|------|-----|-----|------|-----|-----|------|-----|-----|------|-----|-----|------|-----|-----|------|-----|
| ACC  | TTA  | ATA | CCA | ACA  | GTT | ATA | TGG  | CTG | AAA | GAC  | AAT | AAT | GAA  | CTA | CCA | GAT  | GAT |
| Thr  | Leu  | Ile | Pro | Thr  | Val | Ile | Trp  | Leu | Lys | Asp  | Asn | Asn | Glu  | Leu | Pro | Asp  | Asp |

|      | 1742 |     |     | 1751 |     |     | 1760 |     |     | 1769 |     |     | 1778 |     |     | 1787 |     |

FIG. 30C

```
GAA AGG TTT CTA GTT GGT AAA GAC AAC TTG ACC ATT ATG AAT GTA ACT GAT AAA
Glu Arg Phe Leu Val Gly Lys Asp Asn Leu Thr Ile MET Asn Val Thr Asp Lys
        1796        1805        1814        1823        1832        1841

GAT GAT GGA ACA TAT ACT TGC ATA GTT AAT ACT ACT CTG GAC AGT GTT TCA GCA
Asp Asp Gly Thr Tyr Thr Cys Ile Val Asn Thr Thr Leu Asp Ser Val Ser Ala
        1850        1859        1868        1877        1886        1895

AGT GCT GTG CTT ACT GTT GTT GCT GCT CCC CCA ACT CCA GCT ATC ATT TAC GCT
Ser Ala Val Leu Thr Val Val Ala Ala Pro Pro Thr Pro Ala Ile Ile Tyr Ala
        1904        1913        1922        1931        1940        1949

CGG CCA AAT CCA CCG CTT GAC TTG GAA TTG ACA GGT CAG CTA GAA AGA AGC ATT
Arg Pro Asn Pro Pro Leu Asp Leu Glu Leu Thr Gly Gln Leu Glu Arg Ser Ile
        1958        1967        1976        1985        1994        2003

GAA CTC TCA TGG GTA CCA GGA GAA GAA AAT AAC AGT CCC ATT ACA AAC TTT GTG
Glu Leu Ser Trp Val Pro Gly Glu Glu Asn Asn Ser Pro Ile Thr Asn Phe Val
        2012        2021        2030        2039        2048        2057

ATT GAG TAT GAA GAT GGA CTA CAT GAG CCA GGG GTA TGG CAT TAC CAG ACG GAA
Ile Glu Tyr Glu Asp Gly Leu His Glu Pro Gly Val Trp His Tyr Gln Thr Glu
        2066        2075        2084        2093        2102        2111

GTT CCT GGA TCT CAT ACA ACT GTA CAG TTG AAG TTG TCT CCG TAT GTC AAC TAC
Val Pro Gly Ser His Thr Thr Val Gln Leu Lys Leu Ser Pro Tyr Val Asn Tyr
        2120        2129        2138        2147        2156        2165

TCA TTC CGT GTG ATT GCT GTC AAT GAA ATT GGT AGA AGT CAG CCA AGT GAA CCA
Ser Phe Arg Val Ile Ala Val Asn Glu Ile Gly Arg Ser Gln Pro Ser Glu Pro
        2174        2183        2192        2201        2210        2219

TCT GAA CAG TAC CTG ACA AAG TCC GCA AAC CCC GAT GAA AAT CCT TCT AAT GTA
Ser Glu Gln Tyr Leu Thr Lys Ser Ala Asn Pro Asp Glu Asn Pro Ser Asn Val
        2228        2237        2246        2255        2264        2273

CAA GGG ATA GGC TCG GAA CCT GAT AAT TTG GTA ATA ACG TGG GAG TCT TTA AAA
Gln Gly Ile Gly Ser Glu Pro Asp Asn Leu Val Ile Thr Trp Glu Ser Leu Lys
        2282        2291        2300        2309        2318        2327

GGC TTT CAG TCT AAT GGA CCA GGA CTC CAA TAT AAA GTC AGC TGG CGC CAG AAG
Gly Phe Gln Ser Asn Gly Pro Gly Leu Gln Tyr Lys Val Ser Trp Arg Gln Lys
        2336        2345        2354        2363        2372        2381

GAT GTT GAT GAT GAA TGG ACG TCC GTT GTA GTT GCA AAC GTG TCT AAA TAT ATT
Asp Val Asp Asp Glu Trp Thr Ser Val Val Val Ala Asn Val Ser Lys Tyr Ile
```

FIG. 30D

|      | 2390 | 2399 | 2408 | 2417 | 2426 | 2435 |
|------|------|------|------|------|------|------|
| GTG  | TCT  | GGT  | ACA  | CCA  | ACT  | TTT  | GTT | CCC | TAT | GAA | ATA | AAA | GTA | CAG | GCT | TTA | AAT |
| Val  | Ser  | Gly  | Thr  | Pro  | Thr  | Phe  | Val | Pro | Tyr | Glu | Ile | Lys | Val | Gln | Ala | Leu | Asn |

```
         2444        2453        2462        2471        2480        2489
GAC CTG GGA TAT GCA CCA GAG CCA TCA GAG GTT ATT GGA CAT TCA GGG GAA GAC
Asp Leu Gly Tyr Ala Pro Glu Pro Ser Glu Val Ile Gly His Ser Gly Glu Asp 2498        2507        2516        2525        2534        2543
TTG CCA ATG GTT GCT CCA GGC AAT GTG CAG GTT CAT GTC ATT AAC AGC ACA TTG
Leu Pro MET Val Ala Pro Gly Asn Val Gln Val His Val Ile Asn Ser Thr Leu
                             |
                             Fn3-5 begins 2552        2561        2570        2579        2588        2597
GCA AAG GTG CAC TGG GAC CCT GTT CCA CTA AAA TCT GTC CGA GGA CAT CTT CAA
Ala Lys Val His Trp Asp Pro Val Pro Leu Lys Ser Val Arg Gly His Leu Gln 2606        2615        2624        2633        2642        2651
GGA TAT AAA GTT TAC TAC TGG AAA GTA CAG AGT CTA TCC AGA AGG AGT AAA CGG
Gly Tyr Lys Val Tyr Tyr Trp Lys Val Gln Ser Leu Ser Arg Arg Ser Lys Arg 2660        2669        2678        2687        2696        2705
CAT GTA GAA AAA AAG ATC TTG ACT TTC AGG GGA AAC AAG ACT TTT GGA ATG TTA
His Val Glu Lys Lys Ile Leu Thr Phe Arg Gly Asn Lys Thr Phe Gly MET Leu
     |
     F80 begins 2714        2723        2732        2741        2750        2759
CCA GGG CTA GAG CCC TAT AGT TCT TAC AAG CTG AAT GTT AGA GTT GTT AAT GGT
Pro Gly Leu Glu Pro Tyr Ser Ser Tyr Lys Leu Asn Val Arg Val Val Asn Gly 2768        2777        2786        2795        2804        2813
AAA GGA GAA GGA CCA GCA AGC CCA GAC AAA GTA TTT AAA ACT CCT GAA GGA GTT
Lys Gly Glu Gly Pro Ala Ser Pro Asp Lys Val Phe Lys Thr Pro Glu Gly Val 2822        2831        2840        2849        2858        2867
CCT AGC CCA CCC TCC TTT TTG AAG ATT ACT AAT CCA ACA CTG GAC TCT CTG ACT
Pro Ser Pro Pro Ser Phe Leu Lys Ile Thr Asn Pro Thr Leu Asp Ser Leu Thr
 |
 Fn4-5 begins
```

FIG. 30E

|      2876       |      2885       |      2894       |      2903       |      2912       |      2921       |
|-----------------|-----------------|-----------------|-----------------|-----------------|-----------------|
| CTG GAG TGG     | GGT TCA CCT     | ACC CAT CCA     | AAT GGT GTT     | TTG ACA TCA     | TAC ATA CTG     |
| Leu Glu Trp     | Gly Ser Pro     | Thr His Pro     | Asn Gly Val     | Leu Thr Ser     | Tyr Ile Leu     |

|      2930       |      2939       |      2948       |      2957       |      2966       |      2975       |
|-----------------|-----------------|-----------------|-----------------|-----------------|-----------------|
| AAG TTT CAG     | CCA ATT AAC     | AAC ACA CAT     | GAA TTA GGT     | CCC TTG GTA     | GAG ATA AGA     |
| Lys Phe Gln     | Pro Ile Asn     | Asn Thr His     | Glu Leu Gly     | Pro Leu Val     | Glu Ile Arg     |

|      2984       |      2993       |      3002       |      3011       |      3020       |      3029       |
|-----------------|-----------------|-----------------|-----------------|-----------------|-----------------|
| ATA CCT GCC     | AAC GAG AGC     | AGC TTG ATA     | TTA AAA AAT     | TTA AAT TAC     | AGC ACA CGA     |
| Ile Pro Ala     | Asn Glu Ser     | Ser Leu Ile     | Leu Lys Asn     | Leu Asn Tyr     | Ser Thr Arg     |

|      3038       |      3047       |      3056       |      3065       |      3074       |      3083       |
|-----------------|-----------------|-----------------|-----------------|-----------------|-----------------|
| TAC AAG TTT     | TAC TTT AAT     | GCA CAA ACA     | TCA GTT GGA     | TCA GGA AGT     | CAG ATA ACT     |
| Tyr Lys Phe     | Tyr Phe Asn     | Ala Gln Thr     | Ser Val Gly     | Ser Gly Ser     | Gln Ile Thr     |

|      3092       |      3101       |      3110       |      3119       |      3128       |      3137       |
|-----------------|-----------------|-----------------|-----------------|-----------------|-----------------|
| GAG GAA GCA     | GTA ACA ATT     | ATG GAT GAA     | GTG CAA CCA     | CTT TAT CCA     | AGG ATC AGA     |
| Glu Glu Ala     | Val Thr Ile     | MET Asp Glu     | Val Gln Pro     | Leu Tyr Pro     | Arg Ile Arg     |

|      3146       |      3155       |      3164       |      3173       |      3182       |      3191       |
|-----------------|-----------------|-----------------|-----------------|-----------------|-----------------|
| AAT GTT ACA     | ACA GCT GCT     | GCT GAG ACC     | TAT GCC AAT     | ATT AGT TGG     | GAG TAT GAG     |
| Asn Val Thr     | Thr Ala Ala     | Ala Glu Thr     | Tyr Ala Asn     | Ile Ser Trp     | Glu Tyr Glu     |

|      3200       |      3209       |      3218       |      3227       |      3236       |      3245       |
|-----------------|-----------------|-----------------|-----------------|-----------------|-----------------|
| GGA CCA GAT     | CAT GCC AAC     | TTT TAT GTT     | GAA TAT GGT     | GTA GCA GGC     | AGC AAA GAA     |
| Gly Pro Asp     | His Ala Asn     | Phe Tyr Val     | Glu Tyr Gly     | Val Ala Gly     | Ser Lys Glu     |

|      3254       |      3263       |      3272       |      3281       |      3290       |      3299       |
|-----------------|-----------------|-----------------|-----------------|-----------------|-----------------|
| GAT TGG AAA     | AAA GAA ATT     | GTA AAT GGT     | TCT CGA AGC     | TTC TTT GTG     | TTA AAG GGT     |
| Asp Trp Lys     | Lys Glu Ile     | Val Asn Gly     | Ser Arg Ser     | Phe Phe Val     | Leu Lys Gly     |

|      3308       |      3317       |      3326       |      3335       |      3344       |      3353       |
|-----------------|-----------------|-----------------|-----------------|-----------------|-----------------|
| TTA ACA CCA     | GGA ACA GCA     | TAT AAA GTC     | CGA GTT GGT     | GCT GAG GGC     | CTG TCT GGT     |
| Leu Thr Pro     | Gly Thr Ala     | Tyr Lys Val     | Arg Val Gly     | Ala Glu Gly     | Leu Ser Gly     |

|      3362       |      3371       |      3380       |      3389       |      3398       |      3407       |
|-----------------|-----------------|-----------------|-----------------|-----------------|-----------------|
| TTT AGG AGT     | TCA GAG GAT     | CTG TTT GAG     | ACA GGT CCA     | GCA ATG GCA     | AGT CGG CAG     |
| Phe Arg Ser     | Ser Glu Asp     | Leu Phe Glu     | Thr Gly Pro     | Ala MET Ala     | Ser Arg Gln     |

|      3416       |      3425       |      3434       |      3443       |      3452       |      3461       |
|-----------------|-----------------|-----------------|-----------------|-----------------|-----------------|
| GTA GAC ATT     | GCT ACT CAA     | GGA TGG TTC     | ATT GGA CTT     | ATG TGT GCT     | GTT GCA CTT     |
| Val Asp Ile     | Ala Thr Gln     | Gly Trp Phe     | Ile Gly Leu     | MET Cys Ala     | Val Ala Leu     |

FIG. 30F

|
Fn3-5 ends
Fn4-5 ends

```
      3470         3479         3488         3497         3506         3515
CTT  ATC  TTG  ATT  TTA  TTG  ATT  GTT  TGC  TTC  ATA  AGG  AGG  AAT  AAA  GGT  GGC  AAA
Leu  Ile  Leu  Ile  Leu  Leu  Ile  Val  Cys  Phe  Ile  Arg  Arg  Asn  Lys  Gly  Gly  Lys 3524         3533         3542         3551         3560         3569
TAT  CCA  GTG  AAG  GAA  AAG  GAG  GAT  GCA  CAT  GCT  GAT  CCA  GAA  ATA  CAG  CCT  ATG
Tyr  Pro  Val  Lys  Glu  Lys  Glu  Asp  Ala  His  Ala  Asp  Pro  Glu  Ile  Gln  Pro  MET 3578         3587         3596         3605         3614         3623
AAG  GAA  GAT  GAT  GGA  ACA  TTT  GGT  GAA  TAC  AGT  GAT  GCA  GAG  GAC  CAT  AAA  CCT
Lys  Glu  Asp  Asp  Gly  Thr  Phe  Gly  Glu  Tyr  Ser  Asp  Ala  Glu  Asp  His  Lys  Pro 3632         3641         3650         3659         3668         3677
CTA  AAA  AAA  GGA  AGT  CGG  ACA  CCG  TCA  GAC  AGA  ACT  GTG  AAA  AAA  GAA  GAC  AGT
Leu  Lys  Lys  Gly  Ser  Arg  Thr  Pro  Ser  Asp  Arg  Thr  Val  Lys  Lys  Glu  Asp  Ser 3686         3695         3704         3713         3722         3731
GAT  GAT  AGT  TTA  GTT  GAC  TAT  GGA  GAA  GGT  GTA  AAT  GGC  CAG  TTC  AAT  GAG  GAT
Asp  Asp  Ser  Leu  Val  Asp  Tyr  Gly  Glu  Gly  Val  Asn  Gly  Gln  Phe  Asn  Glu  Asp 3740         3749         3758         3767         3776         3785
GGC  TCC  TTT  ATT  GGA  CAA  TAC  AGC  GGT  AAA  AAA  GAG  AAA  GAA  CCT  GCA  GAA  GGA
Gly  Ser  Phe  Ile  Gly  Gln  Tyr  Ser  Gly  Lys  Lys  Glu  Lys  Glu  Pro  Ala  Glu  Gly 3794         3803         3812         3821         3830         3839
                                                                              ─────>
AAT  GAA  AGT  TCT  GAG  GCT  CCT  TCT  CCT  GTA  AAT  GCC  ATG  AAT  TCA  TTT  GTG  TAA
Asn  Glu  Ser  Ser  Glu  Ala  Pro  Ser  Pro  Val  Asn  Ala  MET  Asn  Ser  Phe  Val
                                                                              |
                                                                           F80 ends 3849         3859         3869         3879         3889         3899         3909
     TCAAAGAACT  TGATTCCCTT  GTGTTTTCTG  TTTGTTTGCA  CTTGTACATC  CTCCTTCTCG  TACGATGAAC 3919         3929         3939
     ATGCAGGTTA  CAAAGCTCCT  CACCTCAAAG  TATT
```

FIG. 30G

NEURITE OUTGROWTH-PROMOTING POLYPEPTIDES CONTAINING FIBRONECTIN TYPE III REPEATS AND METHODS OF USE

GOVERNMENT SUPPORT

This invention was made with government support under Contract Nos. HD 09635 and HD 16550 by The National Institutes of Health. The government has certain rights in the invention.

TECHNICAL FIELD

The present invention relates to neurite outgrowth-promoting polypeptides containing fibronectin Type III repeats derived from a family of cell adhesion molecules defined by having six immunoglobulin domains and five fibronectin Type III repeats. The invention also relates to in vitro and in vivo methods of using the neurite outgrowth-promoting polypeptides. Methods of making the disclosed polypeptides, derivatives and related compositions, which have a variety of diagnostic and therapeutic applications, are also disclosed.

BACKGROUND

A number of molecules and specified regions thereof have been implicated in the ability to support the sprouting of neurites from a neuronal cell, a process also referred to as neurite outgrowth. This process is essential in neural development and regeneration. As such, understanding the structure, function and expression of molecule or molecules that mediate, separately or in concert the complex molecular and cellular events in regulating neurite outgrowth in the nervous system is of paramount importance for both diagnostic and therapeutic uses.

Cell adhesion molecules, also referred to as CAM's have been shown to mediate cell to cell interaction in the nervous system in processes critical for embryonic development and pattern formation. See, Edelman, et al., *Morphoregulatory Molecules*, John Wiley & Sons, New York (1990). Many of the interactions between neural cells with other neural cells, with support cells such a glia or with the extracellular environment involve cell adhesion molecules, as described by Edelman, *Science*, 219:450–457 (1983).

Several neural cell adhesion molecules have been shown to belong to the immunoglobulin superfamily [Williams et al., *Ann. Rev. Immunol.*, 6:381–405 (1988)] that is characterized by the presence of structural motifs consisting of immunoglobulin-like domains (Ig-like). Many-members of this family are also characterized by the presence of fibronectin type III repeats (Fn type III). Various vertebrate molecules in the Ig family include neural cell adhesion molecule (N-CAM) [Cunningham et al., *Science*, 236:799–806 (1987)], neuron-glia CAM (Ng-CAM) [Burgoon et al., *J. Cell Biol.*, 112:1017–1029 (1991)], L1 [Kadmon et al., *J. Cell Biol.*, 110:193–208 (1990)], Nr-CAM [Grumet et al., *J. Cell Biol.*, 6:1399–1412 (1991)], neurofascin [Volkmer et al., *J. Cell Biol.*, 118:149–161 (1992) and the like. These molecules have all been shown to be involved in cell adhesion.

Invertebrate members that resemble the vertebrate Ig-like molecules in structure and function include fasciclin II [Harrelson, et al., *Science*, 242:700–707 (1988), neuroglian [Bieber et al., *Cell*, 59:447–460 (1989) and the like.

By virtue of the number of domains and amino acid identities among the cell adhesion molecules that are members of the Ig superfamily, subfamilies are grouped based on having the same number of Ig-like domains and Fn type III repeats along with greater amino acid similarity of the members, particularly in their cytoplasmic regions. One such subfamily is characterized by having six Ig-like domains and five Fn type III repeats. Members of this subfamily, referred to as the 6/5 family herein, include chicken Ng-CAM, L1, and chicken Nr-CAM that are all post-translationally cleaved in vivo at comparable sites in the middle of the third Fn type III repeat.

The complete nucleotide and amino acid sequence, along with characterization of the biological activities of some of the 6/5 family members have been described in the literature. Ng-CAM, cloned and sequenced as described by Burgoon et al., *J. Cell Biol.*, 112:1017–1029 (1991), is a membrane glycoprotein of the chicken nervous system that is expressed by neurons and Schwann cells and is involved in neuron-neuron and neuron-glia adhesion. Antibody perturbation studies have indicated that it functions in the fasciculation of neurites and in the migration of neurons along Bergmann glial fibers during cerebellar development [Chuong et al., *J. Cell Biol.*, 104:331–342 (1987) and Hoffman et al., *J. Cell Biol.*, 103:145–158 (1986)]. Ng-CAM promotes cell adhesion both homophilically and heterophilically. The biochemistry and biology of Ng-CAM is reviewed by Grumet, *J. Neurosci. Res.*, 31:1–13 (1992).

The predominant Ng-CAM component detected in chicken brain is a 135 kilodalton (kD) glycoprotein but smaller amounts of a 80 kD glycoprotein and a doublet of 190 and 210 kD (which differ in glycosylation of a single polypeptide) are usually seen as described by Grumet et al., *Proc. Natl. Acad. Sci., USA*, 81:7989–7993 (1984). All of these components are derived from a single gene and a single mRNA that encodes the larger 190/210 kD species, designated herein as Ng-CAM 200 as described by Burgoon et al., *J. Cell Biol.*, 112:1017–1029 (1991). The smaller components are generated by proteolysis yielding the amino-terminal 135 kD extracellular fragment, designated herein as F135, and the 80 kD transmembrane fragment, designated herein as F80.

F135 and F80 each contain structural motifs that could contribute to the adhesive functions of Ng-CAM. The F135 polypeptide contains all six Ig-like domains, which in N-CAM and other members of the N-CAM family have been demonstrated to mediate adhesion. See, Brady-Kalnay et al., *J. Biol. Chem.*, 269:28472–28477 (1994); Cunningham et al., *Proc. Natl. Acad. Sci., USA*, 80:3116–3120 (1983) and Rao et al., *J. Cell Biol.*, 118:937–949 (1992). Furthermore, the amino-terminal segment of F80 includes, within the third Fn type III domain, an Arg-Gly-Asp (RGD) sequence that in fibronectin has been demonstrated to mediate adhesion to integrin receptors as described by Ruoslahti, *Ann. Rev. Biochem.*, 57:375–413 (1988).

The complete nucleotide and amino acid sequences of the Ng-CAM homologous molecules, mouse L1 and human L1, have been respectively described by Moos et al., *Nature*, 334:701–703 (1988) and Hlavin et al., *Genomics*, 11:416:423 (1991). Variants of human L1 arising through alternate splicing of RNA were described by Reid et al., *J. Mol. Neurosci.*, 3:127–135 (1992). The complete nucleotide and encoded amino acid sequence of the other 6/5 family member, Nr-CAM, have been described by Grumet et al., *J. Cell Biol.*, 113:1399–1412 (1991). While these references discuss the relationship of the particular molecule to the other members of the subfamily, no reference describes polypeptides corresponding to Ng-CAM F80 or the Fn type III repeats spanning the third to fifth repeat (Fn3-5) or the fourth to fifth repeat (Fn4-5) as having neurite outgrowth promoting activity.

However, in other published references, both the Ig domains and the FN type III repeats of N-CAM [Frei et al., *J. Cell Biol.*, 118:177–194 (1992)] and of mouse L1 [Appel et al., *J. Neurosci.*, 13:4764–4775 (1993)] have been postulated to promote neurite outgrowth and spreading of neuronal cell bodies. In the latter publication, in contrast to the present invention, the regions of mouse L1 shown to promote neurite outgrowth were the Ig-like domains 1-6 and the Fn type III repeats 1 and 2, not Fn type III repeats 3-5 as shown. Moreover, Appel et al. showed that the Ig domains 1-2 and 5-6 and Fn type III domains 3-5 of mouse L1 supported neuronal attachment and not neurite outgrowth as demonstrated by the present invention for Fn3-5, Fn4-5 and F80.

In an International Publication having Publication Number WO 95/13291 by New York University, Ng-CAM and its functional derivatives have been claimed as having neurite outgrowth-promoting activity. As published, the functional derivatives of Ng-CAM claimed to have neurite activity were the first three Ig-like domains and not the Fn type III repeats of the present invention.

Thus, while it is well known that the intact Ng-CAM protein, like that of intact L1 protein and other members of the 6/5 family as well as other cell adhesion molecules in other subfamilies, promotes both cell adhesion and neurite outgrowth, what was not appreciated before the present invention was that, in members of the 6/5 family, the region of the fibronectin type III repeats between the third and the fifth repeat, but not including the RGD-containing region.

BRIEF SUMMARY OF THE INVENTION

Regions of a family of cellular adhesion molecule (CAM) proteins, including Ng-CAM, Nr-CAM and L1, have now been identified that are responsible for the protein's ability to promote neurite sprouting ("neurite outgrowth"). Understanding which regions of this complex protein are responsible for these various functions is essential to determine how the protein may affect neural development and regeneration. These proteins, and particular synthetic polypeptides containing the pharmacologically active regions that induce neurite outgrowth, are useful in promoting nerve regeneration and repair in peripheral nerve injuries as well as in lesions in the central nervous system (CNS), such as in treatment of spinal cord or peripheral nerve injuries.

In one embodiment, the invention contemplates a method of promoting neurite outgrowth of neuronal cells in a cell culture system. The method comprises contacting neuronal cells capable of extending neurites with the cell culture system comprising a substrate containing a neurite outgrowth-promoting composition, wherein the composition contains a polypeptide that promotes neurite outgrowth and the polypeptide comprises an amino acid residue sequence up to 450 residues in length including fibronectin Type III repeats 4-5, wherein the polypeptide has an amino acid residue sequence that is derived from a member of a family of cell adhesion molecules defined by having six immunoglobulin-like domains and five fibronectin Type III domains-like. Preferred and exemplary of the family are members selected from the group consisting of human L1, mouse L1, chicken Ng-CAM and chicken NR-CAM.

Preferred polypeptides are the F80 polypeptide fragment selected from the group consisting of human L1, mouse L1, chicken Ng-CAM and chicken Nr-CAM. Additional preferred polypeptides consist essentially of fibronectin Type III repeats 3-5 selected from the group consisting of human L1, mouse L1, chicken Ng-CAM and chicken Nr-CAM. Further preferred are polypeptides that consist essentially of fibronectin Type III repeats 4-5 selected from the group consisting of human L1, mouse L1, chicken Ng-CAM and chicken Nr-CAM.

In practicing the method, the neurite outgrowth-promoting composition can be attached to the substrate or present in liquid phase.

Also contemplated is a polypeptide that promotes neurite outgrowth, and compositions containing the polypeptide, wherein the polypeptide has an amino acid residue sequence consisting essentially of fibronectin Type III repeats 4-5, and wherein the polypeptide is derived from a member of a family of cell adhesion molecules defined by having six immunoglobulin domains and five fibronectin Type III domains as defined earlier. The polypeptide is preferably produced by use of an expression an expression vector and the expressed polypeptide is in the form of a fusion polypeptide.

Also contemplated are polynucleotide sequences that encode a polypeptide for use in the present methods and compositions.

The invention further contemplates a neurite outgrowth-promoting apparatus that comprises a bioabsorbable matrix and an effective amount of a pharmacologically active agent capable of inducing neurite outgrowth, wherein the agent comprises a polypeptide that promotes neurite outgrowth as described herein. The matrix can be in the form of a solid support and the pharmacologically active agent can be attached to the substrate. The agent can optionally be incorporated into the bioabsorbable matrix, which can be comprised of a biopolymer of a variety of materials. The matrix can further include a substructure comprising freeze dried sponge, powders, films, flaked or broken films, aggregates, microspheres, fibers, fiber bundles, or a combination, thereof. The solid support can be formulated into a prosthetic device, a porous tissue culture insert, an implant and a suture. The matrix can be adapted for use in tissue culture.

The invention also contemplates a method of promoting neurite outgrowth in a subject which comprises administering to the subject a physiologically tolerable composition containing a therapeutically effective amount of a neurite outgrowth-promoting polypeptide as described herein. The polypeptide can be incorporated into a bioabsorbable matrix, as described above for the apparatus of the invention.

Other embodiments will be readily apparent to one skilled in the art based on the present disclosure.

BRIEF DESCRIPTION OF THE DRAWINGS

FIGS. 1A–1G show the complete nucleotide sequence of the top strand in 5' to 3' direction of Ng-CAM. The nucleotide sequence is listed in the Sequence Listing as SEQ ID NO 3. The encoded Ng-CAM amino acid residue sequence is also indicated under the nucleotide sequence in FIGS. 1A–1G and is also listed in SEQ ID NO 3 with the nucleotide sequence. A separate listing in SEQ ID NO 4 is only of the encoded Ng-CAM amino acid residue sequence. The positions of the respective amino and carboxy terminal ends of each of the Ng-CAM-derived polypeptides, F80, Fn3-5 and Fn4-5, are also indicated, thereby defining the amino acid residue sequences that are found in each polypeptide.

FIG. 2 shows the amino acid residue sequence of the F80 proteolytic fragment (having the same sequence as the non-fusion polypeptide) from Ng-CAM as shown in FIG. 1. The Ng-CAM F80 amino acid sequence is listed as SEQ ID NO 5.

FIG. 3A shows the model of the domain structure of Ng-CAM. The six immunoglobulin-like domains (circles), five fibronectin-type III repeats (open rectangles), transmembrane region (TM, vertical black rectangle), and the phosphorylated cytoplasmic region (P) are shown. Cleavage of the protein occurs in the third fibronectin-type III repeat indicated by the arrow; the single RGD sequence is represented by an asterisk. FIG. 3B is a schematic diagram of the regions of the protein encoded by the cDNA constructs as represented by heavy black lines below the model. Portions of the original cDNA clones indicated by the 900 series of numbers used to create the constructs are indicated by unbroken lines below the construct, with the dashed lines indicating the remainder of each original clone. The signal peptides used in constructs are represented as shaded boxes. Restriction sites used for ligation of the constructs are noted: B, Bal I; X, BstX I; P, Pvu II; D, Hind II; F, Fok I; H, Hph I.

FIGS. 4A–4G show the complete nucleotide sequence of the top strand in 5' to 3' direction of human L1. The nucleotide sequence is listed in the Sequence Listing as SEQ ID NO 13. The encoded human L1 amino acid residue sequence is also indicated under the nucleotide sequence in FIGS. 4A–4G and is also listed in SEQ ID NO 13 with the nucleotide sequence. A separate listing in SEQ ID NO 14 is only of the encoded human L1 amino acid residue sequence. The positions of the respective amino and carboxy terminal ends of each of the human L1-derived polypeptides, F80, Fn3-5 and Fn4-5, are also indicated, thereby defining the amino acid residue sequences that are found in each polypeptide.

FIGS. 5A–5G show the complete nucleotide sequence of the top strand in 5' to 3' direction of mouse L1. The nucleotide sequence is listed in the Sequence Listing as SEQ ID NO 20. The encoded mouse L1 amino acid residue sequence is also indicated under the nucleotide sequence in FIGS. 5A–5G and is also listed in SEQ ID NO 20 with the nucleotide sequence. A separate listing is SEQ ID NO 21 is only of the encoded mouse L1 amino acid residue sequence. The positions of the respective amino and carboxy terminal ends of each of the mouse L1-derived polypeptides, F80, Fn3-5 and Fn4-5, are also indicate, thereby defining the amino acid residue sequences that are found in each polypeptide.

FIG. 6 shows the amino acid residue sequence of the Ng-CAM non-fusion Fn3-5 polypeptide that is also listed as SEQ ID NO 54.

FIG. 7 shows the amino acid residue sequence of the Ng-CAM non-fusion Fn4-5 polypeptide that is also listed as SEQ ID NO 55.

FIG. 8 shows the amino acid residue sequence of the human L1 non-fusion F80 polypeptide that is also listed as SEQ ID NO 56.

FIG. 9 shows the amino acid residue sequence of the human L1 non-fusion Fn3-5 polypeptide that is also listed as SEQ ID NO 57.

FIG. 10 shows the amino acid residue sequence of the human L1 non-fusion Fn4-5 polypeptide that is also listed as SEQ ID NO 58.

FIG. 11 shows the amino acid residue sequence of the mouse L1 non-fusion F80 polypeptide that is also listed as SEQ ID No 59.

FIG. 12 shows the amino acid residue sequence of the mouse L1 non-fusion Fn3-5 polypeptide that is also listed as SEQ ID NO 60.

FIG. 13 shows the amino acid residue sequence of the mouse L1 non-fusion Fn4-5 polypeptide that is also listed as SEQ ID NO 61.

FIG. 14 shows the amino acid residue sequence of the Nr-CAM non-fusion F80 polypeptide that is also listed as SEQ ID NO 62.

FIG. 15 shows the amino acid residue sequence of the Nr-CAM non-fusion Fn3-5 polypeptide that is also listed as SEQ ID NO 63.

FIG. 16 shows the amino acid residue sequence of the Nr-CAM non-fusion Fn4-5 polypeptide that is also listed as SEQ ID NO 64.

FIG. 17 shows the amino acid residue sequence of the Ng-CAM fusion F80 polypeptide that is also listed as SEQ ID NO 65.

FIG. 18 shows the amino acid residue sequence of the Ng-CAM fusion Fn3-5 polypeptide that is also listed as SEQ ID NO 66.

FIG. 19 shows the amino acid residue sequence of the Ng-CAM fusion Fn4-5 polypeptide that is also listed as SEQ ID NO 67.

FIG. 20 shows the amino acid residue sequence of the human L1 fusion F80 polypeptide that is also listed as SEQ ID NO 68.

FIG. 21 shows the amino acid residue sequence of the human L1 fusion Fn3-5 polypeptide that is also listed as SEQ ID NO 69.

FIG. 22 shows the amino acid residue sequence of the human L1 fusion Fn4-5 polypeptide that is also listed as SEQ ID NO 70.

FIG. 23 shows the amino acid residue sequence of the mouse L1 fusion F80 polypeptide that is also listed as SEQ ID NO 71.

FIG. 24 shows the amino acid residue sequence of the mouse L1 fusion Fn3-5 polypeptide that is also listed as SEQ ID NO 72.

FIG. 25 shows the amino acid residue sequence of the mouse L1 fusion Fn4-5 polypeptide that is also listed as SEQ ID NO 73.

FIG. 26 shows the amino acid residue sequence of the chicken Nr-CAM fusion F80 polypeptide that is also listed as SEQ ID NO 74.

FIG. 27 shows the amino acid residue sequence of the chicken Nr-CAM fusion Fn3-5 polypeptide that is also listed as SEQ ID NO 75.

FIG. 28 shows the amino acid residue sequence of the chicken Nr-CAM fusion Fn4-5 polypeptide that is also listed as SEQ ID NO 76.

FIGS. 30A–30G show the complete nucleotide sequence of the top strand in 5' to 3' direction of chicken Nr-CAM.

Figure 3A:
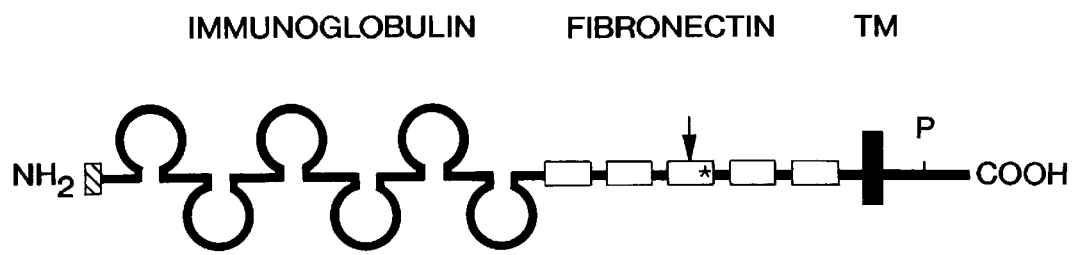
FIGS. 3A and 3B respectively show the structure of Ng-CAM and the Ng-CAM cDNA constructs for encoding the Ng-CAM 200 kilodalton (kD), 135 kD and 80 kD polypeptides.

The nucleotide sequence is listed in the Sequence Listing as SEQ ID NO 27. The encoded chicken Nr-CAM amino acid residue sequence is also indicated under the nucleotide sequence in FIGS. 30A–30G and is also listed in SEQ ID NO 27 with the nucleotide sequence. A separate listing in SEQ ID NO 28 is only of the encoded chicken Nr-CAM amino acid residue sequence. The positions of the respective amino and carboxy terminal ends of each of the chicken Nr-CAM-derived polypeptides, F80, Fn3-5 and Fn4-5, are also indicated, thereby defining the amino acid residue sequences that are found in each polypeptide.

DETAILED DESCRIPTION

A. Definitions

Amino Acid Residue: An amino acid, e.g., one formed upon chemical digestion (hydrolysis) of a polypeptide at its peptide linkages. The amino acid residues identified herein are preferably in the natural "L" isomeric form. However, residues in the "D" isomeric form can be substituted for any L-amino acid residue, as long as the desired functional property is retained by the polypeptide. $NH_2$ refers to the free amino group present at the amino terminus of a polypeptide. COOH refers to the free carboxy group present at the carboxy terminus of a polypeptide. In keeping with standard polypeptide nomenclature, J. Biol. Chem. 243: 3552–59 (1969) and adopted at 37 CFR §1.822(b)(2), abbreviations for amino acid residues are shown in the following Table of Correspondence:

| TABLE OF CORRESPONDENCE | | |
|---|---|---|
| SYMBOL | | |
| 1-Letter | 3-Letter | AMINO ACID |
| Y | Tyr | tyrosine |
| G | Gly | glycine |
| F | Phe | phenylalanine |
| M | Met | methionine |
| A | Ala | alanine |
| S | Ser | serine |
| I | Ile | isoleucine |
| L | Leu | leucine |
| T | Thr | threonine |
| V | Val | valine |
| P | Pro | proline |
| K | Lys | lysine |
| H | His | histidine |
| Q | Gln | glutamine |
| E | Glu | glutamic acid |
| W | Trp | tryptophan |
| R | Arg | arginine |
| D | Asp | aspartic acid |
| N | Asn | asparagine |
| C | Cys | cysteine |
| X | Xaa | unknown or any amino acid |
| B | Asx | aspartic acid or asparagine |
| Z | Glx | glutamic acid or glutamine |

It should be noted that all amino acid residue sequences are represented herein by formulae whose left and right orientation is in the conventional direction of amino-terminus to carboxy-terminus. In addition, the phrase "amino acid residue" is broadly defined to include modified and unusual amino acids, such as those listed in 37 CFR §1.822(b)(4), which disclosures are incorporated by reference herein. Furthermore, it should be noted that a dash (-) at the beginning or end of an amino acid residue sequence indicates either a peptide bond to a further sequence of one or more amino acid residues or a covalent bond to a carboxyl or hydroxyl end group.

Recombinant DNA (rDNA) molecule: A DNA molecule produced by operatively linking two or more DNA segments. Thus, a recombinant DNA molecule is a hybrid DNA molecule comprising at least two nucleotide sequences not normally found together in nature. Recombinant DNA molecules (rDNAs) not having a common biological origin, i.e., evolutionarily different, are said to be "heterologous".

Vector: A rDNA molecule capable of autonomous replication and to which a DNA segment, e.g., a gene or polynucleotide, can be operatively linked so as to bring about replication of the attached segment. Vectors capable of directing the expression of genes encoding for one or more polypeptides are referred to herein as "expression vectors". Particularly preferred vectors according to the present invention allow cloning of cDNA (complementary DNA) from messenger RNA (mRNA) produced using reverse transcriptase.

Receptor: A receptor is a biologically active proteinaceous molecule, such as a protein, glycoprotein, and the like, that can specifically (non-randomly) bind to a different molecule or molecules, generally termed ligand molecules.

Fusion Polypeptide: A polypeptide comprised of at least two polypeptides and a linking sequence which operatively links the polypeptides into one continuous polypeptide. The two or more polypeptides linked in a fusion polypeptide are typically derived from two independent sources, and therefore a fusion polypeptide comprises two or more linked polypeptides not normally found linked in nature. The terms "fusion protein(s)" and "fusion polypeptide(s)" may be used interchangeably herein.

Upstream: In the direction opposite to the direction of DNA transcription, that is, going from 5' to 3' on the non-coding strand, or 3' to 5' on the mRNA.

Downstream: Further along a DNA sequence in the direction of sequence transcription or read-out, that is traveling in a 3'- to 5'-direction along the non-coding strand of the DNA or 5'- to 3'-direction along the RNA transcript.

Cistron: Sequence of nucleotides in a DNA molecule coding for an amino acid residue sequence and including upstream and downstream DNA expression control elements.

Reading Frame: Particular sequence of contiguous nucleotide triplets (codons) employed in translation. The reading frame depends on the location of the translation initiation codon.

Protein, Polypeptide and Peptide: "protein", "polypeptide" and "peptide" are terms used interchangeably herein to designate a series of amino acid residues connected one to the other by peptide bonds between the alpha-amino and carboxy groups of adjacent residues. Where the polypeptide includes an amino acid residue sequence that defines the pharmacologically active fibronectin Type III repeats 4-5, or other active domains, it is referred to herein as a "subject" polypeptide.

Synthetic Peptide: Synthetic peptide refers to a chemically produced polymer or chain of amino acid residues typically linked together by peptide bonds. As used herein, the term is not generally intended to include naturally occurring proteins and fragments thereof.

Conservative Substitution: "conservative substitution" as used herein denotes the replacement of an amino acid residue by another, biologically similar residue. Examples of conservative substitutions include the substitution of one hydrophobic residue such as isoleucine, valine, leucine or methionine for another, or the substitution of one polar residue for another, such as the substitution of arginine for lysine, glutamic for aspartic acid, or glutamine for asparagine, and the like. "Conservative substitution" is also intended to include differential splicing and repeats of various sequences, such as those seen in the various isoforms described herein (e.g. those seen in human, murine and chick CAM proteins). The term "conservative substitution" as used herein also includes the use of a substituted amino acid in place of an unsubstituted parent amino acid provided that described homolog having the substituted polypeptide also stimulates cell attachment and/or neurite outgrowth.

Substantially homologous means that a particular subject sequence or molecule, for example, a mutant sequence, varies from a reference sequence by one or more substitutions, deletions, or additions, the net effect of which does not result in an adverse functional dissimilarity between reference and subject sequences. For purposes of the present invention, amino acid sequences having greater than 75% similarity, preferably greater than 80% similarity, more preferably greater than 90% similarity, equivalent biological activity, and equivalent expression characteristics are considered substantially homologous and are included within the scope of proteins and polypeptides defined by the the present invention. Amino acid sequences having greater than 40 percent similarity are considered substantially similar. For purposes of determining homology or similarity, truncation or internal deletions of the reference sequence should be disregarded, as should subsequent modifications of the molecule, e.g., glycosylation. Sequences having lesser degrees of homology and comparable bioactivity are considered equivalents. Similarly, nucleotide sequences at least 75% homologous to one encoding a bioactive polypeptide disclosed herein (or a portion thereof) are considered substantially homologous.

B. Neurite Outrowth Promoting Polypeptides

Neurite outgrowth-promoting polypeptides of the present invention are polypeptides that include an amino acid residue sequence derived from the fibronectin Type III repeats 4-5 domain of a family of cell adhesion molecules (CAM). It has been discovered that the Type III repeats 4-5 from members of a family of related CAMs all posses the pharmacological activity of promoting neurite outgrowth when present in a variety of polypeptide and fusion protein forms described herein.

Although there are many cell adhesion molecules (CAM) in mamalian systems, the CAM proteins of interest are defined structurally and by homology to be in a family. The CAM family of interest in the present invention contains six immunoglobulin-like domains and five (I–V) fibronectin Type III domains and can be exemplified by the well known proteins chicken Ng-CAM and Nr-CAM, and both human and mouse L1.

Proteins and polypeptides useful as disclosed herein also include polypeptide derivatives that are substantially homologous to a CAM protein domain having the capability to promote neurite outgrowth as defined herein, whether it is derived from human, avian, murine or other mammalian sources.

A preferred polypeptide for use in the methods and compositions of the present invention promotes neurite outgrowth in an biological assay for such activity and comprises an amino acid residue sequence derived from or homologous to the fibronectin Type III repeats 4-5 of a member of the family of cell adhesion molecules (CAM) defined by having six immunoglobulin domains and five fibronectin Type III domains, designated 1-5.

Preferably, a subject polypeptide has the sequence of the fibronectin Type III repeats 4-5 of a CAM selected from the group consisting of human L1, mouse L1, chicken Ng-CAM and chicken Nr-CAM. More preferably, a preferred polypeptide is no longer than 450 amino acid residues in length. A subject polypeptide for use in the present methods and compositions can comprise more than repeats 4-5 of fibronectin and possess the biological activity of promoting neurite growth. In particular, the polypeptide may include additional Type III repeats of the native CAM protein, such as 4-5, 3-5, 2-5 and the like, or may comprise larger portions of the CAM protein, such as the F80 fragment, and the like polypeptides.

In one embodiment, a subject polypeptide is a F80 polypeptide fragment selected from the group consisting of human L1 (SEQ ID NO 56), mouse L1 (SEQ ID NO 59), chicken Ng-CAM (SEQ ID NO 5) and chicken Nr-CAM (SEQ ID NO 62).

In another embodiment, a subject polypeptide consists essentially of fibronectin Type III repeats 3-5 selected from the group consisting of human L1 (SEQ ID NO 57), mouse L1 (SEQ ID NO 60), chicken Ng-CAM (SEQ ID NO 54) and chicken Nr-CAM (SEQ ID NO 63).

In still another embodiment, a subject polypeptide consists essentially of fibronectin Type III repeats 4-5 selected from the group consisting of human L1 (SEQ ID NO 58), mouse L1 (SEQ ID NO 61), chicken Ng-CAM (SEQ ID NO 55) and chicken Nr-CAM (SEQ ID NO 64).

It is to be understood that a polypeptide useful in the methods and compositions of the present invention can be produced in a variety of manners, and the invention need not be limited to any particular mode of preparation.

For example the polypeptide can prepared from a biochemically purified protein isolated from a cell or tissue source, such as brain.

Alternatively, the gene encoding a CAM protein of this invention can be isolated or synthesized and used for the expression of the polypeptide, as described herein. In this manner, the polypeptide can be synthesized substantially free of other proteins of mammalian origin by use of a prokaryotic host expression system or a non-mammalian eukaryotic host expression system.

In addition, the polypeptide can be synthesized by well known solid phase methods for polypeptide synthesis.

An instant polypeptide can incorporate a variety of changes, such as insertions, deletions, and substitutions of amino acid residues which are either conservative or nonconservative, as long as the resulting polypeptide molecule exhibits the desired properties of its ability to stimulate neurite outgrowth. Methods for determining this activity are well known, and include the assay methods described in the Examples.

When a polypeptide of the present invention incorporates conservative substitutions as discussed herein, the substituted amino acid residues are preferably replaced by another, biologically similar amino acid residue such that the resulting polypeptide has an amino acid residue sequence that is similar to (i.e., is at least 50% homologous to) the parent amino acid sequences. Still another aspect of a polypeptide incorporating conservative substitutions occurs when using a non-native "substituted" amino acid residue to replace an unsubstituted parent amino acid residue. Examples of substituted amino acids may be found at 37 C.F.R. §1.822(b)(4), which species are incorporated herein by reference.

A subject polypeptide includes any analog, fragment or chemical derivative of a polypeptide whose amino acid residue sequence is shown herein so long as the polypeptide is capable of stimulating neurite outgrowth. Therefore, a polypeptide of the present invention can be subject to various changes, substitutions, insertions, and deletions, where such changes provide for certain advantages in its use. In this regard, a polypeptide of this invention corresponds to, rather than is identical to, one or more of the preferred polypeptides identified herein.

The term "analog" includes any polypeptide having an amino acid residue sequence substantially identical to a sequence specifically shown herein in which one or more residues have been conservatively substituted with a functionally similar residue and which displays the within-described abilities. The phrase "conservative substitution" also includes the use of a chemically derivatized residue in place of a non-derivatized residue provided that such polypeptide displays the requisite inhibition activity. "Chemical derivative" refers to a subject polypeptide having one or more residues chemically derivatized by reaction of a functional side group. Such derivatized molecules include, for example, those molecules in which free amino groups have been derivatized to form amine hydrochlorides, p-toluene sulfonyl groups, carbobenzoxy groups, t-butyloxycarbonyl groups, chloroacetyl groups or formyl groups. Free carboxyl groups may be derivatized to form salts, methyl and ethyl esters or other types of esters or hydrazides. Free hydroxyl groups may be derivatized to form O-acyl or O-alkyl derivatives. The imidazole nitrogen of histidine may be derivatized to form N-im-benzylhistidine.

Also included as chemical derivatives are those peptides which contain one or more naturally occurring amino acid derivatives of the twenty standard amino acids. Examples: 4-hydroxyproline may be substituted for proline; 5-hydroxylysine may be substituted for lysine; 3-methylhistidine may be substituted for histidine; homoserine may be substituted for serine; and ornithine may be substituted for lysine. Polypeptides of the present invention also include any polypeptide having one or more additions and/or deletions or residues relative to the sequence of a polypeptide whose sequence is shown herein, so long as the requisite activity is maintained.

When a polypeptide of the present invention has a sequence that is not identical to the sequence of a polypeptide disclosed herein, it is typically because one or more conservative or non-conservative substitutions have been made, usually no more than about 30 number percent, and preferably no more than 10 number percent of the amino acid residues are substituted. Additional residues may also be added at either terminus of a claimed polypeptide for the purpose of providing a "linker" by which the polypeptides of this invention can be conveniently affixed to a second polypeptide to form a fusion protein, to a label or solid matrix, or to carrier.

Amino acid residue linkers are usually at least one residue and can be 40 or more residues, more often 1 to 10 residues. Typical amino acid residues used for linking are tyrosine, cysteine, lysine, glutamic and aspartic acid, or the like. In addition, a subject polypeptide can differ, unless otherwise specified, from the natural sequence of the CAM protein from which it was derived by the sequence being modified by terminal-$NH_2$ acylation, e.g., acetylation, or thioglycolic acid amidation, by terminal-carboxlyamidation, e.g., with ammonia, methylamine, and the like terminal modifications. Terminal modifications are useful, as is well known, to reduce susceptibility by proteinase digestion, and therefore serve to prolong half life of the polypeptides in solutions, particularly biological fluids where proteases may be present. In this regard, polypeptide cyclization is also a useful terminal modification.

Any peptide of the present invention may also be used in the form of a pharmaceutically acceptable salt. Suitable acids which are capable of forming salts with the peptides of the present invention include inorganic acids such as hydrochloric acid, hydrobromic acid, perchloric acid, nitric acid, thiocyanic acid, sulfuric acid, phosphoric acetic acid, propionic acid, glycolic acid, lactic acid, pyruvic acid, oxalic acid, malonic acid, succinic acid, maleic acid, fumaric acid, anthranilic acid, cinnamic acid, naphthalene sulfonic acid, sulfanilic acid or the like.

Suitable bases capable of forming salts with the peptides of the present invention include inorganic bases such as sodium hydroxide, ammonium hydroxide, potassium hydroxide and the like; and organic bases such as mono-, di- and tri-alkyl and aryl amines (e.g. triethylamine, diisopropyl amine, methyl amine, dimethyl amine and the like) and optionally substituted ethanolamines (e.g. ethanolamine, diethanolamine and the like).

A polypeptide of the present invention can be synthesized by any of the synthetic techniques known to those skilled in the art. A summary of some of the techniques available can be found in J. M. Stuard and J. D. Young, *Solid Phase Peptide Synthesis,* W. H. Freeman, Co., San Francisco (1969); J. Meinhofer, *Hormonal Proteins and Peptides* Vol. 2, pp. 46, Academic Press (New York) 1983; E. Schroder and K. Kubke, *The Peptides* (Vol. 1), Academic Press (New York), 1965 for classical solution synthesis, and U.S. Pat. No. 4,631,211, the disclosures of which are incorporated herein by reference. Appropriate protective groups usable in the aforementioned syntheses are described in the above texts and in J. F. W. McOmie, *Protective Groups in Organic Chemistry,* Plenum Press, New York, 1973, which is incorporated herein by reference.

An instant polypeptide can also be synthesized by recombinant DNA techniques. Such recombinant techniques are favored especially when the desired polypeptide is relatively long such as for a fusion protein. When recombinant DNA techniques are employed to prepare an instant polypeptide (see Examples hereinbelow), a DNA segment encoding the desired polypeptide is incorporated into a preselected vector that is subsequently expressed in a suitable host. The expressed polypeptide is then purified by a routine method such as gel electrophoresis, immunosorbent chromatography, and the like biochemical isolation methods.

C. Fusion Proteins

Due to the relatively large size of a subject polypeptide that includes the fibronectin Type III repeats 4-5, it is preferred that the polypeptides of the present invention be produced by recombinant DNA methods, and particularly in the form of a fusion protein for reasons of synthesis and purification.

In addition, the use of recombinant DNA expression methods in the design and expression of fusion proteins that contain a subject polypeptide makes it particularly convenient to expiditiously prepare, express and evaluate additional fusion protein constructs having altered polypeptide structures for the preparation of homologs and variants of the polypeptides disclosed herein.

The preparation of fusion proteins is generally well known and can involve the fusion of a subject polypeptide to any of a variety of "carrier" proteins, which are selected for reasons of ease of expression, stability in the expression host, structural compatibility with fusions to forein polypeptides and suitability for subsequent purification from the expression host. A fusion protein may include "linker" amino acid residues which facilitate fusion between the carrier protein and the subject polypeptide.

The glutathione-S-trasnferase (GST) fusion protein system commercially available as described herein is a preferred choice because the GST fusion protein can be purified rapidly by binding to glutathione-agarose beads, washed and easily released from the beads in mild buffers. In addition, where the nucleotide sequences that encode a subject polypeptide are inserted into the particularly preferred pGEX expression vector system (Pharmacia), the portion of the fusion protein representing the GST protein can be cleaved with thrombin and the engineered polypeptide can generally be recovered free of the GST protein following fusion protein purification on the agaraose beads. See, for example, Ausubel et al., *Current Protocols in Molecular Biology*, John Wiley & Sons, 1990, New York. Other systems for cleavage may be utilized and therefore the GST system need not be considered as limiting. Insofar as the cleavage of a fusion protein that produces a subject polypeptide may not occur adjacent to the first amino acid residue of a subject polypeptide, the resulting purified polypeptide may include additional amino acid residues derived from the fusion protein.

Fusion proteins may also be expressed in insect cells using a baculovirus expression system. Fusion protein expression in insect cells can be achieved by infecting the insect host cell with a baculovirus engineered to express selected polypeptides using methods known to those skilled in the art of baculovirus expression systems. For example, a fusion protein can be constructed by operably linking nucleotide sequences that encode a subject polypeptide to the regulatory regions of the viral polyhedrin protein as described by Jasny (*Science*, 238:1653, 1987). Following infection with the recombinant baculovirus, cultured insect cells, or the live insects themselves, can produce the fusion protein in amounts as great as 20 to 50% of total protein production. When live insects are used, catepillars are preferred as hosts for large scale production.

Thus, in one embodiment, the invention contemplates methods and compositions in which a subject polypeptide of this invention is in the form of a fusion polypeptide, or in the form of the purified subject polypeptide produced by wxpression and cleavage of the fusion protein, and their methods of synthesis are described in the Examples.

D. Nucleic Acid Molecules and Vectors

1. Nucleic Acid Molecules

The present invention describes a variety of novel and useful nucleic acid molecules.

A nucleic acid molecule of the present invention includes a nucleotide sequence that encodes a subject polypeptide as described herein, and is useful for the expression of a subject polypeptide as described herein. A nucleic acid molecule of this invention may be be in the form of an isolated oligonucleotide, or can be provided in the form of an expression vector, as described herein.

In one embodiment, a nucleic acid molecule according to the present invention has a sequence identified herein, or a nucleotide sequence substantially homologous thereto. In another variation, a nucleic acid molecule according to the present invention encodes a protein homologous to the protein identified herein.

In addition, in view of the well known redundancy of the genetic code, the invention contemplates a nucleic acid molecule having any nucleic acid sequence based on the genetic code so long as the nucleic acid encodes a subject polypeptide.

In preferred embodiments, a nucleic acid molecule according to the present invention encodes a chimeric protein or polypeptide, a fusion protein or polypeptide, or a conjugate, wherein the amino acid sequence encoded by said nucleic acid molecule corresponds to a polypeptide of this invention. In preferred embodiments, a nucleic acid that encodes a subject polypeptide is described in the Examples, or encodes a subject polypeptide described in the Examples.

As noted hereinabove, proteins and polypeptides of the present invention may be synthesized (or otherwise modified) using recombinant techniques. Albeit DNA constructs are described herein as exemplary, it is expressly to be understood that RNA molecules are also contemplated for use as disclosed herein. For example, a protein or polypeptide of the present invention may be prepared and expressed as described in the Examples hereinbelow.

When recombinant techniques are employed to prepare a polypeptide of the present invention, a nucleic acid (e.g., DNA) molecule or segment encoding the polypeptide is preferably used. A preferred DNA molecule contemplated by the present invention is operatively linked to a vector that is subsequently expressed in a suitable host. The molecule is "operatively linked" to the vector as used herein when it is ligated (covalently bound) thereto, according to common usage. The present invention also encompasses RNA molecules equivalent to the instantly-disclosed DNA molecules.

Whenever an RNA molecule encoding a polypeptide of the present invention is used, the RNA molecule including the polypeptide coding molecule is transcribed into complementary DNA (cDNA) via a reverse transcriptase. The cDNA molecule can then be used as described herein to generate a subject polypeptide.

Insofar as nucleic acids can be produced in a variety of forms, both single and double stranded and as both DNA or RNA, the term "polynucleotide" is meant to indicate a nucleic acid in any of the before-mentioned forms wherein the nucleotide sequence encodes a subject polypeptide or is complementary to a sequence that encodes a subject polypeptide.

In a preferred aspect of the invention, a DNA nucleotide sequence (molecule) encoding at least one of the amino acid residue sequences of a polypeptide as described herein is operatively linked to a larger DNA molecule. The resultant DNA molecule is then transformed or transfected into a suitable host and expressed therein.

A nucleic acid molecule encoding an amino acid residue sequence according to the present invention can be provided with start and stop codons, or one or both of the start and stop codons can be provided by a larger nucleic acid molecule (e.g., a vector) operatively linked to the nucleic acid molecule so that only the corresponding polypeptide is generated. Alternatively, a nucleic acid sequence encoding additional amino acid residues can be provided at the 3' and/or 5' ends of the nucleic acid molecule so that a larger polypeptide is expressed having an amino acid residue sequence at either or both of its N-terminal and C-terminal ends in addition to an amino acid residue sequence of (or derived from) the pharmacologically active polypeptide.

DNA segments (i.e., synthetic oligonucleotides) that encode a polypeptide or fusion protein of the invention can easily be synthesized by chemical techniques, for example, the phosphotriester method of Matteucci, et al., (*J. Am. Chem. Soc.*, 103:3185–3191, 1981) or via using automated synthesis methods. In addition, larger DNA segments can readily be prepared by well known methods, such as synthesis of a group of oligonucleotides that define the DNA segment, followed by hybridization and ligation of oligonucleotides to build the complete segment.

Of course, by chemically synthesizing the coding sequence, any desired modifications can be made simply by substituting the appropriate bases for those encoding the native amino acid residue sequence. Furthermore, DNA segments consisting essentially of structural genes encoding a claimed polypeptide can be obtained from recombinant DNA molecules containing a gene that defines a disclosed CAM protein, and can be subsequently modified, as by site directed mutagenesis, to introduce the desired substitutions.

A nucleic acid molecule according to the present invention may be produced by enzymatic techniques. Thus, restriction enzymes which cleave nucleic acid molecules at predefined recognition sequences can be used to isolate nucleic acid fragments from larger nucleic acid molecules containing the desired nucleic acid molecules such as the DNA (or RNA) that codes for a claimed polypeptide. Typically, DNA fragments produced in this manner will have cohesive, "overhanging" termini, in which single-stranded nucleic acid sequences extend beyond the double-stranded portion of the molecule. The presence of such cohesive termini is generally preferred over blunt-ended DNA molecules. The isolated fragments containing the desired coding sequence can then be ligated (cloned) into a suitable vector for amplification and expression.

Using PCR, it is possible to synthesize useful polypeptide-encoding polynucleotide sequences which may then be operatively linked to a vector and used to transform or transfect an appropriate cell and expressed therein. Particularly preferred methods for producing large quantities of recombinant polypeptides and proteins of the present invention rely on the use of preselected oligonucleotides as primers in a polymerase chain reaction (PCR) to form PCR reaction products for use in preparing expression vectors.

2. Vectors

Expression of recombinant polypeptides and proteins of this invention is accomplished through the use of expression vectors into which the nucleotide sequences encoding a subject polypeptide have been inserted. The expression vectors may be constructed utilizing any of the well-known vector construction techniques.

The choice of vector to which a nucleotide segment of the present invention is operatively linked depends directly, as is well known in the art, on the functional properties desired, e.g., protein expression, and the host cell to be transformed or transfected, these being limitations inherent in the art of constructing recombinant DNA molecules. However, a vector contemplated by the present invention is at least capable of directing the replication, and preferably also expression, of the beneficial protein structural gene included in DNA segments to which it is operatively linked.

Thus, the present invention contemplates a vector that can be operatively linked to a nucleic acid molecule of the present invention to provide a recombinant DNA molecule that encodes and expresses a polypeptide sequence identified herein. The recombinant molecule can be used to transform or transfect suitable host cells so that the host cells express the desired polypeptide.

In many preferred embodiments, the vector also contains a selectable marker. One example of a selectable marker is antibiotic resistance. A plasmid encoding ampicillin or tetracycline resistance (or both) may be used such that a population of cells that express the gene(s) of choice may be ascertained by growing the transfectants in selection medium. Examples of vectors including such markers are pUC18, pUC19, pKK233-2, and pKK388-1 (Clontech, Palo Alto, Calif.).

In various embodiments, the translatable nucleotide sequence may be incorporated into a plasmid with an appropriate controllable transcriptional promoter, translational control sequences, and a polylinker to simplify insertion of the translatable nucleotide sequence in the correct orientation, and may be expressed in the host cells. Useful host cells include eukaryotic insect cells, such as *Spodoptera frugiperda,* or prokaryotic cells, such as *Escherichia coli.* As described in the Examples herein, prokaryotic cells are particularly preferred. Preferably, there are 5' control sequences defining a promoter for initiating transcription and a ribosome binding site operatively linked at the 5' terminus of the upstream translatable DNA sequence. Examples of useful expression vectors including promoters such as tac, trc, or $P_L$, for example, include pTrc99A (Pharmacia, Piscataway, N.J.), pKK223-3 (Clontech), and PET 3d (Novagen).

Prokaryotic gene fusion vectors, which have the ability to express cloned genes as fusion proteins, are also useful according to the present invention. For example, protein A vectors pRIT2T or pEZZ18 (Pharmacia) use protein A as the fusion partner and IgG Sepharose 6FF for affinity purification. Phagemid EZZ18 (Pharmacia) allows for the secretion of fusion proteins from *E. coli* into the surrounding culture medium.

Another useful protein fusion and purification system is one available from New England Biolabs (Beverly, Mass.), which uses pMAL vectors. In this system, the cloned gene is inserted into a pMAL vector downstream from the malE gene, which encodes maltose-binding protein (MBP). This results in the expression of an MBP-fusion protein. (See, e.g., Guan, et al., Gene, 67:21–30, 1987). The technique uses the strong $P_{tac}$ promoter and the translation initiation signals of MBP to express large amounts of the fusion protein. The fusion protein is then purified by a one-step affinity purification for MBP (Kellerman and Ferenci, *Meth. Enzymol.,* 90:459–463, 1982). Also see Riggs, et al. (eds.), *Current Protocols in Molecular Biology,* Greene Assoc./Wiley Interscience, NY (1990) and the manufacturer's instructions accompanying the pMAL kit.

A particularly useful system for cloning and expression is the GST gene fusion system (Pharmacia, Piscataway, N.J.), use of which is described in the Examples herein. Useful prokaryotic gene fusion vectors include pGEX-1λT, pGEX-2T, pGEX-3X, pGEX-4T-1, pGEX-4T-2, pGEX-4T-3, pGEX-5X-1, pGEX-5X-2, pGEX-5X-3, and pGEX-2TK; and useful protein A vectors include pRIT2T or pEZZ18 (Pharmacia, Piscataway, N.J.). Kits for cloning and expression are also commercially available and include the GST Gene Fusion System available from Pharmacia (Piscataway, N.J.).

Exemplary cloning and expression vector systems for use according to the within-described methods include those described in the Examples herein. For example, the pGEX system is particularly useful according to the within-disclosed methods.

Successfully transformed or transfected cells, i.e., cells that contain a rDNA molecule of the present invention, can be identified by well known techniques. For example, cells resulting from the introduction of an rDNA of the present invention can be subjected to assays for detecting the presence of specific rDNA using a nucleic acid hybridization method such as that described by Southern, *J. Mol. Biol.,* 98:503 (1975) or Berent et al., *Biotech.,* 3:208 (1985).

In addition to directly assaying for the presence of rDNA, successful transformation or transfection can be confirmed by well known immunological methods for the presence of expressed protein. For example, cells successfully transformed or transfected with an expression vector produce proteins which then can be assayed directly by immunological methods or for the presence of the function of the expressed protein.

It will be understood that this invention, although described herein in terms of various preferred embodiments, should not be construed as limited to the host cells, expression vectors and expression vectors systems exemplified. Other expression vector systems, well known to one of ordinary skill in the art and described by Kaufman, et al., in *Current Protocols in Molecular Biology,* Ausubel et al., eds., Unit 16, New York (1990), are contemplated for preparing recombinant polypeptides and proteins for use in this invention.

Expression vectors compatible with eukaryotic cells, preferably those compatible with mammalian cells, can also be used to form a recombinant DNA molecule as described above. Eukaryotic cell expression vectors are well known in the art and are available from several commercial sources. Typically, such vectors are provided with convenient restriction sites for insertion of the desired DNA molecule. Typical of such vectors are PSVL, pSVK3 and pKSV-10 (Pharmacia), pBPV-1pML2d (International Biotechnologies, Inc.), pXT1 and pSG5 (Stratagene, La Jolla, Calif.) and pTDT1 (ATCC, #31255). Other useful vectors include the pREP series vectors and pEBVhis, which are available from Invitrogen (San Diego, Calif.); vectors pTDT1 (ATCC #31255), pCP1 (ATCC #37351) and pJ4W (ATCC #37720), available from the American Type Culture Collection (ATCC); and other, similar expression vectors. A preferred drug resistance marker for use in vectors compatible with eukaryotic cells is the neomycin phosphotransferase (neo) gene. (Southern et al., *J. Mol. Appl. Genet.,* 1:327–341, 1982).

3. Transformation/Transfection of Hosts

The present invention also relates to host cells transformed or transfected with a recombinant DNA molecule of the present invention. The host cell can be either prokaryotic or eukaryotic. Preferred prokaryotic host cells are strains of *E. coli,* e.g., the *E. coli* strain NM522 available from Stratagene (La Jolla, Calif.). Preferred eukaryotic host cells include but are not limited to insect, yeast and mammalian cells, preferably vertebrate cells such as those from mouse, rat, monkey or human fibroblastic cell line. Preferred eukaryotic host cells also include mouse L1 cells, Chinese hamster ovary (CHO) cells, such as those available from the ATCC as CCL61, and NIH Swiss mouse embryo cells NIH/3T3 available from the ATCC as CRL 1658. Preferred insect cells include lepidoptera cells, preferably SP9 cells available from Pharminegen, Inc. (San Diego, Calif.).

Transformation or transfection of appropriate cell hosts with a recombinant DNA molecule of the present invention is accomplished by well known methods that typically depend on the type of vector used. With regard to transformation of prokaryotic host cells, see, for example, Maniatis et al., *Molecular Cloning, A Laboratory Manual,* Cold Spring Harbor Laboratory, Cold Spring Harbor, N.Y. (1982).

Successfully transformed or transfected cells, i.e., those containing a recombinant DNA molecule of the present invention, can be identified by well known techniques. For example, transformed or transfected cells can be cloned to produce monoclonal colonies. Cells from those colonies can be harvested, lysed and their DNA content examined for the presence of the desired DNA molecule using a method such as that described by Southern, *J. Mol. Biol.,* 98:503 (1975).

In addition to directly assaying for the presence of the desired DNA molecule, successful transformation or transfection can be confirmed by well known methods for detection of the expressed protein when the DNA directs expression of the polypeptides of the present invention, such as measuring the capability for inducing neurite outgrowth by the present methods. Samples of cells suspected of being transformed or transfected are harvested and assayed for biological activity.

In addition to the transformed or transfected host cells themselves, also contemplated by the present invention are cultures of those cells. Nutrient media useful for culturing transformed or transfected host cells are well known in the art and can be obtained from several commercial sources. In embodiments wherein the host cell is mammalian a "serum-free" medium is preferably used.

Methods for recovering an expressed protein from a culture are well known in the art. For instance, gel filtration, gel chromatography, ultrafiltration, electrophoresis, ion exchange, affinity chromatography and related techniques can be used to isolate the expressed proteins found in the culture. In addition, immunochemical methods, such as immunoaffinity, immunoadsorption, and the like, can be performed using well known methods, as exemplified by the methods described herein.

E. Methods for Promoting Neurite Outgrowth

The discovery that regions of the CAM family proteins described herein can promote neurite outgrowth, and the accompanying identification of pharmacologically active polypeptides, provides agents for use in improving nerve regeneration or promoting nerve survival, in treating peripheral nerve injury and spinal cord injury, and in stimulation of growth of endogenous, implanted or transplanted CNS tissue.

The present invention therefore also provides a method of promoting regeneration of an injured or severed nerve or nerve tissue, or promoting neurite outgrowth in neuronal cells under a variety of neurological conditions requiring neuronal cell outgrowth. The method comprises contacting a neuronal cell capable of extending neurites, or an injured or severed nerve, with a cell culture system comprising a substrate containing a neurite outgrowth-promoting polypeptide of this invention in an amount effective to promote neurite outgrowth. The method may be carried out in vitro or in vivo.

The polypeptide used in the present method can by any of the subject polypeptides described herein.

Any of a variety of mammalian neuronal cells can be treated by the present method in the cell culture system, including neuronal cells from brain, CNS, peripheral nerves and the like. In addition, the cells can be from any of a variety of mammalian species, including human, mouse, chicken, and any other mammalian species, including the agricultural stock and non-domesticated mammals.

In selecting a particular subject polypeptide for use in the methods, any of the polypeptides described herein can be utilized to promote neurite outgrowth, irrespective of the species of neuronal cell and species of CAM protein from which a subject polypeptide is derived. However, it is preferred to use a human CAM protein to induce neurite outgrowth on a human neuronal cell, and the like species selectivity. Thus, in preferred embodiments, the method uses mouse neuronal cells and a polypeptide derived from a mouse CAM protein, or human neuronal cells and a polypeptide derived from a human CAM protein, or chicken neuronal cells and a polypeptide derived from a chicken CAM protein, etc.

The neurite outgrowth-promoting composition can be attached to the substrate, can be contacted in the liquid phase or in a collagen gel phase. The composition may contain the subject polypeptide in the form of a fusion protein as described herein. The method may be practiced using the subject polypeptide in any of the various apparati format described herein.

The methods can optionally be practiced in combination with contacting the neuronal cells or nerves with other agents capable of promoting neuron survivals growth, differentiation or regeneration.

1. Cell Culture Methods for Promoting Neurite Outgrowth

In one embodiment, the invention contemplates in vitro methods and kits for culturing neuronal cells under conditions where the subject polypeptides are used to promote neurite outgrowth, and can include methods for detecting the presence and amount of stimulation of neurite outgrowth in the cultured neuronal cells. Various proteins and polypeptides disclosed herein are useful according to the within-disclosed methods and may be included in the kits that are also described herein.

Appropriate cells are prepared for use in a neurite outgrowth assay. For example, a preparation of dorsal root ganglia cells is described in the Examples. Before beginning the assay, the cells may be resuspended, added to substrate-coated dishes, and placed under predetermined assay conditions for a preselected period of time. After the attachment and growth period, the dishes may be rinsed to remove unbound cells, fixed, and viewed—e.g., by phase contrast microscopy.

Preferably, a plurality of cells are analyzed for each substrate. Cells are then "judged" based on predetermined criteria. For example, cells may be considered neurite-bearing if the length of the processes are greater than one cell diameter. The percent of cells that are sprouting neurites is preferably determined, as is the average neurite length. A particularly preferred neurite outgrowth assay method is disclosed in the Examples.

The proteins and polypeptides of the present invention are therefore useful in a variety of applications relating to cell and tissue cultures.

For example, in one embodiment, a method of promoting neurite outgrowth of neuronal cells in a cell culture system comprises the steps of (1) introducing neuronal cells into tissue culturing conditions comprising a culture medium; and (2) introducing a polypeptide of the present invention having neurite outgrowth-promoting activity into the culture medium in an amount effective to promote neurite outgrowth stimulating conditions in the culture.

In another embodiment, a method of promoting neurite outgrowth of neuronal cells in a cell culture system comprises the steps of (1) immobilizing on the substrate a polypeptide of the present invention having neurite outgrowth-promoting activity; and (2) contacting neuronal cells with the substrate under tissue culturing conditions.

The invention also discloses compositions comprising polypeptides exhibiting a neurite outgrowth-promoting in substantially pure form. In various embodiments, the polypeptides are derived from segments of a CAM protein in the disclosed family having the fibronectin Type III repeats 4-5, which family members include hL1, mL1, Ng-Cam, Nr-CAM, and the like family members.

In another embodiment, a composition according to the present invention comprises a subject polypeptide in substantially pure form and attached to a solid support or substrate. The solid support may be a prosthetic device, implant, or suturing device designed to have a surface in contact with neuronal cells or the like; further, it may be designed to lessen the likelihood of immune system rejection, wherein said surface of said device is coated with a subject polypeptide or other material designed to ameliorate rejection.

2. In vivo Methods for Promoting Neurite Outgrowth

The various proteins and polypeptides disclosed herein are also useful in a variety of therapeutic applications as described herein.

The present therapeutic methods are useful in treating peripheral nerve damage associated with physical or surgical trauma, infarction, bacterial or viral infection, toxin exposure, degenerative disease, malignant disease that affects peripheral or central neurons, or in surgical or transplantation methods in which new neuronal cells from brain, spinal cord or dorsal root ganglia are introduced and require stimulation of neurite outgrowth from the implant and innervation into the recipient tissue. Such diseases further include but are not limited to CNS lesions, gliosis, Parkinson's disease, Alzheimer's disease, neuronal degeneration, and the like. The present methods are also useful for treating any disorder which induces a gliotic response or inflammation.

In treating nerve injury, contacting a therapeutic composition of this invention with the injured nerve soon after injury is particularly important for accelerating the rate and extent of recovery.

Thus the invention contemplates a method of promoting neurite outgrowth in a subject, or in selected tissues thereof, comprising administering to the subject or the tissue a physiologically tolerable composition containing a therapeutically effective amount of a neurite outgrowth-promoting polypeptide of the present invention.

In preferred methods, a human patient is the subject, and the administered polypeptide comprises fibronectin Type III repeats 4-5 of human cell adhesion molecule L1 (hL1).

In one embodiment, a severed or damaged nerve may be repaired or regenerated by surgically entubating the nerve in an entubalation device in which an effective amount of a neurite outgrowth-promoting polypeptide of this invention can be applied to the nerve.

In a related embodiment, a polypeptide of the invention can be impregnated into an implantable delivery device such as a cellulose bridge, suture, sling prosthesis or related delivery apparatus. Such a device can optionally be covered with glia, as described by Silver, et al, *Science* 220:1067–1069, (1983), which reference is hereby incorporated by reference.

The composition containing the neurite outgrowth-promoting polypeptide may be incorporated or impregnated into a bioabsorbable matrix, with the matrix being administered in the form of a suspension of matrix, a gel or a solid support. In addition, the matrix may be comprised of a biopolymer.

A suitable biopolymer for the present invention can include one or more macromolecules selected from the group consisting of collagen, elastin, fibronectin, vitronectin, laminin, polyglycolic acid, hyaluronic acid, chondroitin sulfate, dermatan sulfate, heparin sulfate, heparin, fibrin, cellulose, gelatin, polylysine, echinonectin, entactin, thrombospondin, uvomorulin, biglycan, decorin, and dextran. The formulation of these macromolecules into a biopolymer is well known in the art.

In constructing the matrix, it may be useful for the matrix to further include a substructure for purposes of administration and/or stability. Suitable substructures include freeze dried sponge, powders, films, flaked or broken films, aggregates, microspheres, fibers, fiber bundles, or a combination thereof.

In addition, the matrix may be attached to a solid support for administration purposes. Suitable supports depend upon the specific use and can include a prosthetic device, a porous tissue culture insert, an implant, a suture, and the like.

Therapeutic compositions of the present invention may include a physiologically tolerable carrier together with at least one species of neurite outgrowth-promoting polypeptide of this invention as described herein, dispersed therein as an active ingredient. In a preferred embodiment, the therapeutic composition is not immunogenic when administered to a human patient for therapeutic purposes.

For the sake of simplicity, the active agent of the therapeutic compositions described herein shall be referred to as a "neurite outgrowth-promoting polypeptide". It should be appreciated that this term is intended to encompass a variety of polypeptides including fusion proteins, synthetic polypeptides, and fragments of naturally ocurring proteins, as well as derivatives thereof, as described herein.

As used herein, the terms "pharmaceutically acceptable", "physiologically tolerable" and grammatical variations thereof, as they refer to compositions, carriers, diluents and reagents, are used interchangeably and represent that the materials are capable of administration upon a mammal or human without the production of undesirable physiological effects such as nausea, dizziness, gastric upset and the like.

The preparation of a pharmacological composition that contains active ingredients dispersed therein is well understood in the art. Typically such compositions are prepared as sterile compositions either as liquid solutions or suspensions, aqueous or non-aqueous, however, suspensions in liquid prior to use can also be prepared.

The active ingredient can be mixed with excipients which are pharmaceutically acceptable and compatible with the active ingredient and in amounts suitable for use in the therapeutic methods described herein. Suitable excipients are, for example, water, saline, dextrose, glycerol, ethanol or the like and combinations thereof. In addition, if desired, the composition can contain minor amounts of auxiliary substances such as wetting or emulsifying agents, pH buffering agents and the like which enhance the effectiveness of the active ingredient.

A therapeutic composition of the present invention can include pharmaceutically acceptable salts of the components therein. Pharmaceutically acceptable salts include the acid addition salts (formed with the free amino groups of the polypeptide) that are formed with inorganic acids such as, for example, hydrochloric or phosphoric acids, or such organic acids as acetic, tartaric, mandelic and the like. Salts formed with the free carboxyl groups can also be derived from inorganic bases such as, for example, sodium, potassium, ammonium, calcium or ferric hydroxides, and such organic bases as isopropylamine, trimethylamine, 2-ethylamino ethanol, histidine, procaine and the like.

Physiologically tolerable carriers are well known in the art. Exemplary of liquid carriers are sterile aqueous solutions that contain no materials in addition to the active ingredients and water, or contain a buffer such as sodium phosphate at physiological pH value, physiological saline or both, such as phosphate-buffered saline. Still further, aqueous carriers can contain more than one buffer salt, as well as salts such as sodium and potassium chlorides, dextrose, propylene glycol, polyethylene glycol and other solutes.

Liquid compositions can also contain liquid phases in addition to and to the exclusion of water. Exemplary of such additional liquid phases are glycerin, vegetable oils such as cottonseed oil, organic esters such as ethyl oleate, and water-oil emulsions.

A therapeutic composition contains a polypeptide of the present invention, typically an amount of at least 0.1 weight percent of polypeptide per weight of total therapeutic composition. A weight percent is a ratio by weight of polypeptide to total composition. Thus, for example, 0.1 weight percent is 0.1 grams of polypeptide per 100 grams of total composition.

A therapeutically effective amount of a neurite outgrowth-promoting polypeptide-containing composition, or beneficial compound therein, is a predetermined amount calculated to achieve the desired effect, i.e., to effectively promote neurite outgrowth of targeted neuronal cells. In addition, an effective amount can be measured by improvements in one or more symptoms occurring in a patient.

Effective amounts can be measured by improvements in neuronal or ganglion cell survival, axonal regrowth, and connectivity following axotomy using well known methods. See, e.g., Bray, et al., "Neuronal and Nonneuronal Influences on Retinal Ganglion Cell Survival, Axonal Regrowth, and Connectivity After Axotomy", *Ann. N.Y. Acad. Sci.*, pp. 214–228 (1991). Improvements in neuronal regeneration in the CNS and PNS are also indicators of the effectiveness of treatment with the disclosed compounds and compositions, as are improvements in nerve fiber regeneration following traumatic lesions. (See, e.g., Cadelli, et al., *Exp. Neurol.* 115: 189–192 (1992), and Schwab, *Phil. Trans. R. Soc. Lond.* 331: 303–306 (1991).)

Thus, the dosage ranges for the administration of a polypeptide of the invention are those large enough to produce the desired effect in which the condition to be treated is ameliorated. The dosage should not be so large as to cause adverse side effects. Generally, the dosage will vary with the age, condition, and sex of the patient, and the extent of the disease in the patient, and can be determined by one of skill in the art. The dosage can be adjusted by the individual physician in the event of any complication.

The compositions are administered in a manner compatible with the dosage formulation, and in a therapeutically effective amount. A therapeutic amount of a polypeptide composition of this invention is an amount sufficient to produce the desired result, and can vary widely depending upon the disease condition and the potency of the therapeutic compound. The quantity to be administered depends on the subject to be treated, the capacity of the subject's system to utilize the active ingredient, and the degree of therapeutic effect desired. Precise amounts of active ingredient required to be administered depend on the judgment of the practitioner and are peculiar to each individual. However, suitable dosage ranges for systemic application are disclosed herein and depend on the conditions of administration. Suitable regimes for administration are also variable, but are typified by an initial administration followed by repeated doses at one or more hour intervals by a subsequent administration.

A therapeutically effective amount of a polypeptide of this invention is typically an amount such that when it is administered in a physiologically tolerable composition, it is sufficient to achieve a plasma or local concentration of from about 0.1 to 1,000 micromolar (uM), preferably about 1 to 100 uM.

Alternatively, the dosage can be metered in terms of the body weight of the patient to be treated. In this case, a typical dosage of a therapeutic composition is formulated to deliver a pharmacologically active polypeptide of this invention is amount of about 0.1 microgram (ug) to 100 ug per kilogram (kg) body weight, or more preferably about 1 to 50 ug/kg.

Furthermore, certain utilities of the present invention involve local administration of a pharmacologically active polypeptide to a site of lesion, and therefore is best expressed in unit dosage form. Such local administration is typically by topical or local administration of a liquid or gel composition containing about 1 to 1000 micrograms (ug) of active polypeptide per milliliter (ml) of composition, preferably about 5 to 500 ug/ml, and more preferably about 10 to 100 ug/ml.

Thus a therapeutic composition can be administered via a solid, semi-solid (gel) or liquid composition, each providing particular advantages for the route of administration.

A polypeptide of the invention can be administered parenterally by injection or by gradual infusion over time. For example, a polypeptide of the invention can be administered topically, locally, perilesionally, perineuronally, intracranially, intravenously, intrathecally, intramuscularly, subcutaneously, intracavity, transdermally, dermally, or via an implanted device, and they may also be delivered by peristaltic means. In general, local, prerilesional, intrathecal, perineuronal, or intra-CNS administration is preferred.

The therapeutic compositions containing a polypeptide of this invention are conventionally administered intravenously, as by injection of a unit dose, for example. The term "unit dose" when used in reference to a therapeutic composition of the present invention refers to physically discrete units suitable as unitary dosage for the subject, each unit containing a predetermined quantity of active material calculated to produce the desired therapeutic effect in association with the required diluent; i.e., carrier, or vehicle.

Alternatively, continuous intravenous infusion sufficient to maintain therapeutically effective concentrations in the blood are contemplated. Therapeutically effective blood concentrations of a polypeptide of the present invention are in the range of about 0.01 uM to about 100 uM, preferably about 1 uM to about 10 uM.

The terms "therapeutically effective" or "effective", as used herein, may be used interchangeably and refer to an amount of a therapeutic composition of the present invention—e.g., one containing a neurite outgrowth-promoting polypeptide of this invention. For example, a therapeutically effective amount of a neurite outgrowth-promoting polypeptide-containing composition, or beneficial compound therein, is a predetermined amount calculated to achieve the desired effect, i.e., to effectively promote neurite outgrowth of neurons in an individual to whom the composition is administered.

The polypeptides of the present invention are typically administered as a pharmaceutical composition in the form of a solution, gel or suspension. However, therapeutic compositions of the present invention may also be formulated for therapeutic administration as a tablet, pill, capsule, aerosol, sustained release formulation or powder.

It is further contemplated that the various polypeptides as described herein can be used therapeutically in a variety of applications. For example, as described above, a variety of useful compositions and formats, including bioabsorbable materials or matrices may be used in conjunction with the polypeptides of the present invention to coat the interior of tubes used to connect severed neurons; they may be added directly to suture materials or incorporated in bioabsorbable materials in and on sutures; further, they may be utilized on/in implants and prosthetic devices, either alone or in conjunction with other bioabsorbable and supporting materials.

Thus in one embodiment, a pharmacologically active polypeptide of this invention can be incorporated into a bioabsorbable matrix, which matrix can be formulated into a variety of mediums, including a semi-solid gel, a liquid permeable but porous insoluble matrix, or a porous biopolymer as described further herein.

A variety of useful compositions, including bioabsorbable materials (e.g., collagen qels) may be used in conjunction with a polypeptide of the present invention in a variety of therapeutic applications. For example, a neurite outgrowth-promoting polypeptide can be used to coat the interior of tubes used to connect severed neurons; they may be added directly to suture materials or incorporated in bioabsorbable materials in and on sutures; further, they may be utilized on/in implants. and prosthetic devices, either alone or in conjunction with other bioabsorbable and supporting materials.

F. Apparatus

The invention also contemplates a variety of apparati for use in practicing the methods of the invention, both in vitro and in vivo. As described in above for practicing the methods, the subject polypeptide can be incorporated into a bioabsorbable matrix which is formulated in a variety of solid and semi-solid formats which can comprise a apparatus for administering the active polypepitde.

Thus, the invention contemplates a neurite outgrowth-promoting apparatus that comprises a bioabsorbable matrix combined with an effective amount of a pharmacologically active agent capable of inducing neurite outgrowth of neuronal cells. The agent is a composition containing any one or more of the subject polypeptides of this invention in an amount effective to induce neurite outgrowth as defined herein.

The apparatus can be formulated in a variety of configurations for adminstration purposes as described herein for the methods of treatment, and include combining the matrix with a solid support into a prosthetic device, a porous tissue culture insert, an implant, a suture, an entubation apparatus and the like.

Solid supports (also described as solid surfaces or solid substrates) useful according to the present invention include supports made of glass, plastic, nitrocellulose, cross-linked dextrans (e.g., SEPHADEX; Pharmacia, Piscataway, N.J.), agarose in its derivatized and/or cross-linked form, polyvinyl chloride, polystyrene, cross-linked polyacrylamide, nitrocellulose- or nylon-based webs such as sheets, strips or paddles, tubes, plates, the wells of a microtiter plate such as those made from polystyrene or polyvinylchloride, and the like, and may take the form of a planar surface or microspheres to name a few variations.

Useful solid support materials in this regard include the derivatized cross-linked dextran available under the trademark SEPHADEX from Pharmacia Fine Chemicals (Piscataway, N.J.), agarose in its derivatized and/or cross-linked form, polystyrene beads about 1 micron to about 5 millimeters in diameter (available from Abbott Laboratories of North Chicago, Ill.), polyvinyl chloride, polystyrene, cross-linked polyacrylamide, nitrocellulose- or nylon-based webs such as sheets, strips or paddles, tubes, plates, the wells of a microtiter plate such as those made from polystyrene or polyvinylchloride, and the like.

In another embodiment, the invention discloses a method of preparing substrates (solid support) for the attachment of cells thereto useful for promoting neurite outgrowth, comprising providing a composition containing a polypeptide exhibiting neurite outgrowth-promoting activity of this invention and treating by coating or impregnating a matrix in or on the solid substrate with said polypeptide-containing composition. In various disclosed embodiments, the solid support or substrate may comprise glass, agarose, a synthetic resin material (e.g., nitrocellulose, polyester, polyethylene, and the like), long-chain polysaccharides, and other similar substances. The solid support can be formulated, as described herein, in a variety of administration formats for both in vitro or in vivo use, and the specific format need not be considered as limiting to the invention.

EXAMPLES

The following examples relating to this invention are illustrative and should not, of course, be construed as specifically limiting the invention. Moreover, such variations of the invention, now known or later developed, which would be within the purview of one skilled in the art are to be considered to fall within the scope of the present invention hereinafter.

1. Preparation of Expression Vectors Containing DNA Inserts for Expressing Polypeptides and Fusion Polypeptides Members of the cell adhesion molecule (CAM) family having six extracellular immunoglobulin-like domains and five extracellular fibronectin type III (Fn type III) repeat domains are multidomain proteins which have several different functions in vivo. These functions comprise cell attachment and neurite outgrowth. In order to associate the various functions of members of this family, referred to herein as the 6/5 family, with specific domains and fragments thereof, recombinant protein fragments of various members of the 6/5 family were made. Members of the 6/5 family include chicken Ng-CAM, chicken Nr-CAM, mouse L1 (mL1), human L1 (hL1) and the like. All of these cell surface glycoproteins also are similar to each other in amino acid sequence, particularly in their cytoplasmic regions. All members of this family are also post-translationally cleaved in vivo; Ng-CAM, Nr-CAM and L1 are cleaved at comparable sites in the middle of the third Fn type III repeat generating two fragments of approximately 135–140 kilodaltons (kD) and 80 (kD), the latter fragment comprising the carboxy end of the molecule containing a portion of the third Fn repeat, all of the fourth and fifth repeats along with the transmembrane and cytoplasmic domains.

As presented in the following examples, the expressed recombinant polypeptides and fusion polypeptides prepared below were used in assays to evaluate their effectiveness in promoting neurite outgrowth of cells.

A. Preparation of DNA Inserts Encoding Polypeptides Containing 6/5-Derived Fibronectin Type III Repeats 1. DNA Inserts for Expression of Non-fusion Polypeptides a. Chicken Ng-CAM The Ng-CAM construct for encoding the F80 fragment was prepared using cDNA clones for chicken Ng-CAM prepared as described herein and by Burgoon et al., *J. Cell Biol.*, 112:1017–1029 (1991). The F80 polypeptide along with the other Ng-CAM-derived polypeptide fragments of Fn type III repeats 3-5 and 4-5 (abbreviated as Fn3-5 and Fn4-5, respectively) were generated by polymerase chain reaction (PCR) amplification of Ng-CAM cDNA, the procedure for which is described below.

In the manuscript by Burgoon et al., the isolation of cDNA clones encoding the entire amino acid residue sequence of chicken Ng-CAM was described. Briefly, cDNA libraries were constructed in λgt11 from total RNA or poly (A)+ RNA isolated from 9- to 14- day embryonic chicken brains. cDNA was synthesized by the RNAse H method described by Gubler et al. *Gene*, 25:263–269 (1983), using oligo (dT) or synthetic oligonucleotides as primers. After methylation with EcoR I methylase and S-adenosyl methionine, the cDNA was ligated to EcoR I linkers, and then ligated to EcoR I-digested λgt11 DNA and packaged using Gigapack Plus (Stratagene, La Jolla, Calif.). Sixteen cDNA libraries were prepared in this way while several other libraries were prepared from RNA that had been extensively denatured by incubation at 65° C. and treated with Actinomycin D and methyl mercuric hydroxide.

The resultant libraries were screened with polyclonal antibodies against denatured Ng-CAM protein that recognize polypeptide components of 210, 190, 135 and 80 kD as described by the above referenced Burgoon et al. manuscript and available from the present inventors. Such antibodies are readily generated by isolating the cell adhesion molecule from brain tissue from a preselected species, such as chicken. The isolated proteins can be used in either native or denatured form as immunogens for the generation of either polyclonal or monoclonal antibodies. In addition, polypeptide sequences from selected regions of a known amino acid residue sequence of a cell adhesion molecule can be synthesized, coupled to haptens and used as immunogens for preparation of either polyclonal sera or monoclonal antibodies, procedures that are well known to one of ordinary skill in the art.

Positive clones identified as λN902 and λN925 were isolated to homogeneity and the inserts were excised from λgt11 arms by restriction with EcoR I endonuclease. Isolated cDNA inserts were then radioisotopically labeled and used to screen λgt11 libraries to obtain overlapping clones. The resultant cDNA inserts were then subcloned into M13mp18 and M13mp19 vectors (BRL, Gaithersburg, Md.) and sequenced by the dideoxynucleotide chain-termination method using Sequenase (United States Biochemical Corp., Cleveland, Ohio).

Clone λN903 was isolated using PCR as described by Burgoon et al. with primers based on the amino acid sequence of a CNBr peptide. Restriction fragments of the three clones obtained above were then used to screen different libraries, including new libraries generated with oligonucleotides corresponding to specific Ng-CAM sequences. As a result, 14 cDNA clones were obtained and sequenced to provide the complete DNA sequence.

A reanalysis of the Ng-CAM sequence revealed a double frame shift in the sequence as originally reported in the manuscript by Burgoon et al. Correction of the frame shifts add one amino acid to the reported sequence and changes the reported amino acid sequence only over the segment of residues 54–72 from ISPSSPRSTGGSRWSPDRH (SEQ ID NO 1) to DQPFVPEEHGGVSVVPGSGT (SEQ ID NO 2). In addition, the nucleotide at the reported position 464 is "G" instead of "A", changing the translated amino residue at that position from a lysine to a glutamic acid. These corrections were entered in the Genbank/EMBL database on Jun. 1, 1994 (EMBL/GenBank accession number X56969).] The corrected nucleotide sequence of 3991 bp of the top strand of Ng-CAM cDNA listed in the 5' to 3' direction and the entire encoded Ng-CAM amino acid sequence are both shown in FIGS. 1A–1G and listed as SEQ ID NOs 3 and 4, respectively. The amino and carboxy terminal ends of the Fn type III repeats 3-5, 4-5 and F80 Ng-CAM fragments are also indicated spanning different regions in the FIGS. 1E–1G.

The cDNA sequence was determined to be continuous across the junction between the predominant 135 kD and less prevalent 80 kD components. The deduced amino acid residue sequence of these two components indicated that they were derived from the same mRNA and were generated from a larger species by proteolytic cleavage. The cleavage site between the 135 kD fragment and the 80 kD fragment, as determined in the Ng-CAM precursor amino acid residue sequence shown in FIGS. 1A–1G, occurs between amino acid residue positions 860 and 861 as shown in FIG. 1E. The cleavage site indicates the carboxy end of the 135 kD fragment and the amino terminal end of the 80 kD fragment as shown in FIG. 1E. The encoded amino acid residue sequence of the F80 polypeptide fragment is shown in FIG. 2 and listed in SEQ ID NO 5.

Figure 3B:
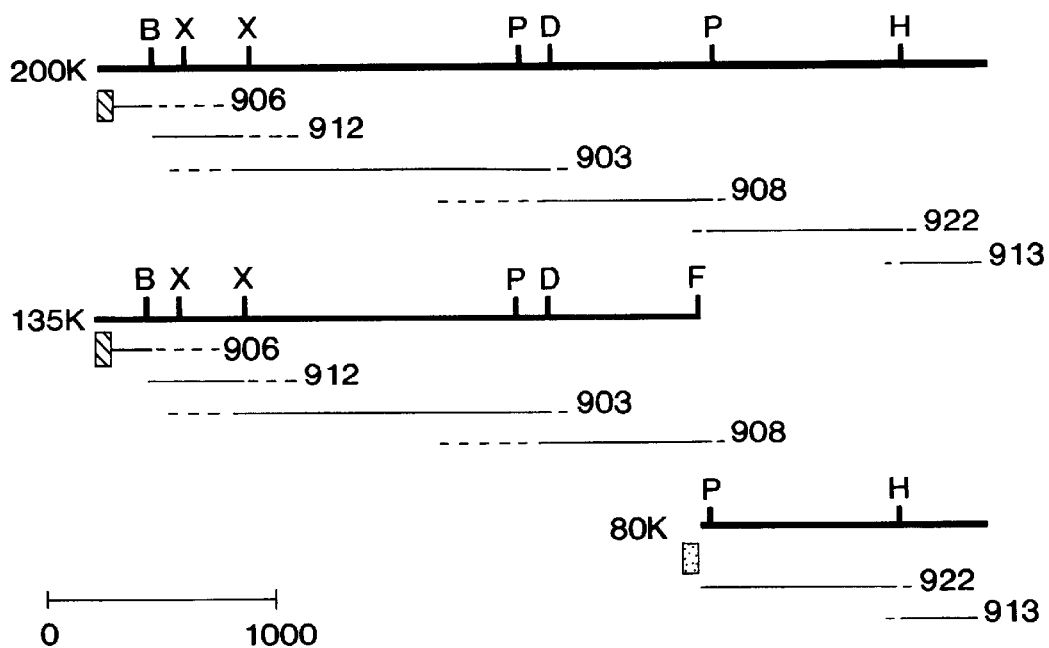

In order to generate Ng-CAM DNA fragments that encoded that F80 fragment as well as the 135 kD fragment and a 200 kD component containing both the 80 kD and 135 kD components, shown in relation to the schematic of the entire Ng-CAM protein in FIG. 3A, the following cloning manipulations of the isolated cDNA clones were performed as described below. Schematics of the Ng-CAM 200 kD, 135 kD and 80 kD polypeptides are shown in FIG. 3B. The relative positions of the λgtII cDNA clones 906, 912, 903, 908, 922, and 913 used in preparing the three DNA inserts that encoded the 200, 135 and 80 kD fragments are also indicated in FIG. 3B.

The λgtII clones indicated above were subcloned into the M13mp18 vector and linked together as shown in FIG. 3B. For the F80 construct, clone 922 was digested with Hph I and ligated to the Hph I site of clone 913. The EcoR I fragment of the 922-913 clone was treated with mung bean nuclease to generate blunt ends and ligated to a cDNA fragment encoding a signal peptide (714), from the Ng-CAM related CAM, Nr-CAM, as described by Grumet et al., *J. Cell Biol.*, 113:1399–1412 (1991). Clone 714 was digested with Fok I and treated with Klenow to generate blunt ends. The resulting 630 base pair (bp) fragment was digested with Sal I (pBS polylinker site) and the 360 bp Fok I/Sal I fragment was then ligated at the 5' end of the blunt-ended 922-913 fragment, into the Sal I/Sma I-digested Bluescript SK vector (Stratagene).

The 714-922-913 construct was excised from Bluescript, ligated to Bgl II linkers (New England Biolabs, Beverly, Mass.), and the Bgl II digested insert was then ligated into the BamH I site of PSVK3 (Pharmacia LKB Biotechnology, Alameda, Calif.), directly behind the SV40 early promoter, for expression in mammalian cells as described in Example 2. This 80 kD-encoding construct was prepared from CDNA clones which lacked the nucleotide sequence for expressing the first six amino acid residues of the 80 kD component, but in all other respects is expressed at the cell surface as the intact 80 kD component.

For preparing the construct encoding the Ng-CAM 200 kD polypeptide, the EcoR I fragment of the 922-913 clone prepared above was digested with Pvu II and ligated to the 856 bp Pvu II/Pvu II fragment of the λgtII clone 908. The Hind II/Hind III fragment from the 908-922-913 clone was blunt-ended with Klenow and ligated as the last step into the Ng-CAM 200 construct. For the 5' end of this construct, the Hind III (M13 polylinker site)/Bal I fragment of clone 906 and the EcoR I (M13 polylinker site)/Bal I fragment of clone 912 were ligated together. The resulting 906-912 clone was digested with EcoR I and partially digested with BstX I. The 630 bp EcoR I/BstX I fragment was ligated to the 2273 bp EcoR I/BstX I fragment of clone 903. The 906-912-903 clone was digested with Hind II and the vector-containing fragment was ligated to the blunt-ended Hind II/Hind III fragment of clone 908-922-913. From this final clone, the entire EcoR I fragment was ligated into the EcoR I site of the pSVK3 vector behind the SV40 early promoter.

For preparing the F135 construct, the 760 bp Fok I/Fok I fragment from the 200 kD-encoding clone in PSVK3 prepared above was treated with Klenow to generate blunt ends and ligated to Xba I linkers (New England Biolabs), containing an AMBER stop codon in frame at the 3' end. This fragment was digested with Hind II/Xba I and the 525 bp fragment was ligated into the Hind II/Xba I (vector polylinker site) sites of the 200 kD-encoding clone which had been recloned into the EcoR I site of pRSETB (Invitrogen Corporation, San Diego, Calif.). The EcoR I/Xba I (pSVK3 polylinker sites) fragment of this clone was treated with Klenow to generate blunt ends and ligated in the + orientation into the Sma I site of the pcDNA1neo vector (Invitrogen), directly behind the CMV promoter. The Fok I site in the Ng-CAM sequence used to add the stop codon was four amino acid residues amino terminal from the beginning of the F80 sequence. The F135 component terminated at this site may represent a slightly shorter form of the component, although attempts to characterize the carboxyl end of the native chicken F135 component have not clearly identified its carboxyl terminal residues (see Burgoon et al., *J. Cell Biol.*, 112:1017–1029 (1991). The correct orientation and order of the fragments in each of the final constructs were confirmed by restriction analysis and sequence analysis across the ligation junctions.

The DNA inserts for the bacterial expression of the non-fusion Fn type III repeats 3-5 and 4-5 polypeptides of Ng-CAM, respectively referred to as Fn3-5 and Fn4-5, are generated by PCR using a 5' primer corresponding to the amino terminal boundary of either the third or fourth Fn type III repeat and a common 3' primer corresponding to a region just before the transmembrane domain. In both cases the 5' primers include Nco I restriction sites for insertion into the ATG initiation site of the pET 3d bacterial expression vector (Novagen, Madison, Wis.). One additional triplet codon, GGC, is also amplified into the product encoding a glycine residue. As a result, the products contain two extra amino acids, methionine (M) and glycine (G), at the amino terminus. The 3' primer common for amplifying both Fn3-5 and Fn4-5 includes a BamH I site and a stop codon to prevent expression of additional amino acids encoded by vector sequences.

For all the primers specified in the Examples for generating F80, Fn3-5 and Fn4-5 polypeptides from 6/5 family homologs, a-portion of the primer nucleotide sequence is designed from the template cDNA sequence to allow for adequate priming while the additional nucleotides are designed to introduce restriction sites into the amplified products to provide for ligation into expression vectors. Primers are similarly designed to facilitate amplification of the nucleotide sequence encoding Fn3-5 and Fn4-5 and ligation into the mammalian expression vector pSVK3 (Pharmacia LKB Biotechnology, Piscataway, N.J.) for expression in mammalian cells.

The 5' and 3' PCR primers for amplifying the DNA fragments to be ligated into pET 3d are listed in 5' to 3' direction as follows: 5' primer for Fn3-5: 5'CAAC-CATGGGCAATGTGGGGGTG3' (SEQ ID NO 6); 5' primer for Fn4-5: 5'CAGCCATGGGCCCCGGCCCCCCC3' (SEQ ID NO 7); and 3' primer for both Fn3-5 and Fn4-5: 5'AAAG-GATCCCTACCACCCCTTGGT3' (SEQ ID NO 8).

The Ng-CAN F80-encoding fragment is similarly amplified as described above with the respective 5' and 3' primer pairs, both written in the 5' to 3' direction, 5'CAAC-CATGGGCGCCCCCCCCGAC3' (SEQ ID NO 9) and 5'AAAGGATCCCTATTAATCCAGGGG3' (SEQ ID NO 10).

The polynucleotide primers for use in the PCR amplifications are prepared using any suitable method, such as, for example, the phosphotriester or phosphodiester methods. (See Narang et al., *Meth. Enzymol.*, 68:90 (1979); U.S. Pat. No. 4,356,270; and Brown et al., *Meth. Enzymol.*, 68:109 (1979), the disclosures of which are incorporated by reference herein.) All primers and synthetic polynucleotides described herein are synthesized on an Applied Biosystems DNA synthesizer, model 381A, following the manufacturer's instructions.

PCR amplification to obtain the Fn3-5, Fn4-5 and F80 DNA products is separately performed for each product in a 100 μl reaction containing approximately 100 nanograms (ng) of the chicken Ng-CAM 200 cDNA template prepared above, 100 ng of the fragment—(i.e., polypeptide)—specific 3' primer, 100 ng of the fragment-specific 5' primer, 200 mM of a mixture of dNTP's, 50 mM KCl, 10 mM Tris-HCl (pH 8.3), 1.5 mM $MgCl_2$, 0.001% gelatin and 2.5 units of *Thermus aquaticus* (Taq) DNA polymerase (Perkins Elmer Cetus, Norwalk, Calif.). The reaction mixture is overlaid with mineral oil and subjected to 30 cycles of amplification. Each amplification cycle includes denaturation at 93° C. for 1 minute, annealing at 48° C. for 1 minute and polynucleotide synthesis by primer extension (elongation) at 72° C. for 2 minutes. The amplified products are then extracted twice with phenol/chloroform, once with chloroform, ethanol precipitated and are stored at −70° C. in 10 mM Tris-HCl, pH 7.5, and 1 mM ethylenediaminetetraacetic acid (EDTA).

The resultant amplified DNA fragments of 980 bp for Fn3-5,635 bp for Fn4-5 and 1241 bp for F80 are then electrophoresed, excised and purified from a 1.5% agarose gel, followed by digestion with Nco I and BamH I, and directionally ligated into the corresponding sites in the pET 3d vector as described in Example 1B to prepare expression vector constructs.

For the F80, Fn3-5 and Fn4-5 fragments of Ng-CAM and the homologous proteins, human L1, mouse L1, chicken Nr-CAM and the like, PCR primers are designed as described above for amplification and subsequent ligation into mammalian expression vector systems. Products similarly amplified for insertion into mammalian specific constructs such as pSVK3 as described above are then digested for ligation thereof.

In addition to the methods of cloning and PCR amplification of fragments as described herein, the F80, Fn3-5 and Fn4-5 fragments of the 6/5 homolog family are also generated by producing sequential polynucleotide oligomers for each of the complete polypeptide fragments where the oligomers are subsequently annealed to create a linear arrangement of overlapping fragments into which 5' and 3' linkers for ligating are inserted for facilitating ligation into similarly digested expression vectors.

b. Human L1

Constructs for encoding the complete human L1 cell adhesion molecule (hL1) along with constructs for encoding the hL1 homologs to the Ng-CAM F80, Fn3-5 and Fn4-5 fragments are also be made for ligation into the pET 3d vector (Novagen) for bacterial expression of the respective polypeptides.

The cloning of human L1 cDNA has been described by Reid et al., *J. Mol. Neurosci.*, 3:127–135 (1992). The nucleotide sequence has been shown to predict a 1253 amino acid residue protein having a signal sequence, transmembrane segment, RGD sequence, potential glycosylation and phosphorylation sites along with six immunoglobulin-like domains and five Fn type III domains. The nucleotide and deduced amino acid sequence identities between human and mouse L1 are respectively 85% and 87% while the amino acid identity between human L1 and Ng-CAM is only 45%.

To clone human L1 cDNA, a probe for human L1 is initially prepared by reverse transcription of human brain poly (A)+ RNA followed by PCR amplification referred to as RT-PCR. Mouse L1 cytoplasmic primers, having the sequences 5'TGGCAAATACTCAGTGAA3' (SEQ ID NO 11) and 5CCTTCTCTTCATTGTCAC3' (SEQ ID NO 12) that has correspondence to the top strand of the complete human L1 nucleotide sequence shown in FIGS. 4A–4G (SEQ ID NO 13), are used for both cDNA synthesis and amplification to produce a 104 bp PCR product. FIGS. 4A–4G also show the encoded amino acid residue sequence of human L1 (SEQ ID Nos 13 and 14) along with the fragments F80, Fn3-5 and Fn4-5 that correspond to those present in Ng-CAM as described above.

The RT-PCR protocol is based on the one-step protocol described by Goblet et al., Nuc. Acids Res., 17:2144 (1989). Briefly, 2 μg poly (A)+ RNA and 300 ng of each primer in 66 μl water are incubated at 65° C. for 15 minutes and cooled on ice. Then, 33 μl of 3× RT-PCR reagent mix [3× PCR buffer, 150 mM KCl, 30 mM Tris-HCl (pH 8.3), 4.5 mM $MgCl_2$, 0.03% (w/v) gelatin, 600 μM dNTPs, 200 units M-MLV reverse transcriptase; 4 units RNasin-(Promega, Madison, Wis.), 2.5 units Taq polymerase (Perkins Elmer Cetus)] is added and the reaction is incubated at 37° C. for 30 minutes, followed by 40 cycles of 94° C. for 1 minute, 40° C. for 2 minutes, and 72° C. for 2 minutes.

The product is then isolated, sequenced, and then used to to screen a human Kelly neuroblastoma λgt10 cDNA library (Clontech, Palo Alto, Calif.) and a fetal brain λgt10 cDNA library (Clontech) to obtain overlapping L1 cDNA clones.

Bacteriophage lambda cDNA inserts obtained above are then subcloned into pBluescript SK+ (Stratagene) and sequenced manually by dideoxy chain-termination with Sequenase (United States Biochemical Corp.) or by dye-termination or dye-labeled primer automated sequencing (model 373A, ABI, Foster City, Calif.) as recommended by the manufacturers. The entire human L1 sequence is then determined by sequencing both strands of the cDNAs, the sequence of which is shown in FIGS. 4A–4G and listed in SEQ ID NO 13.

The human L1 CAM-derived F80-, Fn3-5- and Fn4-5-encoding fragments are obtained by through PCR amplification with specified pairs of primers on the human L1 cDNA template prepared above. Primers for the 5' end of F80 human L1 as well as Fn3-5 and Fn4-5 include Nco I restriction sites for insertion into the ATG initiation site of the pET 3d vector as described above for Ng-CAM. One additional amino acid residue to the primer introduced methionine is glycine encoded by GGC also present in the primer but not on the template cDNA. As a result, the PCR products have two additional amino acids at the amino terminus. The common primer at the 3' end of Fn5 as well as the F80 primer and designed to incorporate a BamH I restriction site for directional cloning and a stop codon to prevent expression of additional amino acids encoded by vector sequences. The primers listed in the 5' to 3' direction are as follows: 5' primer for Fn3-5: 5'CAACCATGGGC-CTGGAAGGCATTG3' (SEQ ID NO 15); 5' primer for Fn4-5: 5'CAGCCATGGGCCCTGGCCACCCC3' (SEQ ID NO 16); and 3' primer for both Fn3-5 and Fn4-5: 5'AAAG-GATCCCTACCAGCCCTCAGT3' (SEQ ID NO 17). The 5' and 3' primers for the F80 fragment have the respective sequences 5'GCGGGATCCCATATCCACAAA3' (SEQ ID NO 18) and 5'AAAGGATCCCTACTATTCTAGGGC3' (SEQ ID NO 19).

The PCR amplifications are performed as described above for Ng-CAM as are the subsequent procedures for purification of fragments of 937 bp for Fn3-5, 636 bp for Fn4-5 and 1191 bp for F80 that are excised from an agarose gel. The resultant fragments are subsequently digested with the restriction enzymes Nco I and BamH I for directional ligation into a similarly digested pET 3d expression vector as described in Example 1B.

c. Mouse L1

The cloning of the cDNA encoding mouse L1 was first described by Tacke et al., *Neurosci. Lett.*, 82:89–94 (1987).

For use in obtaining neurite outgrowth-promoting polypeptide fragments of this invention, cDNA clones encoding the entire coding region of mouse L1 is similarly obtained from a λgt11 library of an 8 day old mouse brain poly (A)+ RNA that is constructed using oligo (dT) priming as described for preparing chicken Ng-CAM cDNA and as described in the manuscript by Tacke et al. Additional clones are obtained from a λgt10 library that is constructed with the same mouse brain cDNA as the previous library by hybridization with the first probe and with additional oligonucleotide probes derived from amino acid residue sequences of the amino terminal end of the 80 kD and 140 kD proteolytic fragments of L1. Chicken λgt11 cDNA libraries are also commercially available (Clontech). Sequencing of overlapping clones obtained from screening the libraries is performed as described for Ng-CAM above.

The complete nucleotide sequence of mouse L1 as described by Moos et al., Nature, 334:701–703 (1988) is approximately 5100 nucleotides with an open reading frame of 3783 amino acid residues. The precursor and mature mouse L1 proteins respectively contain 1260 and 1241 amino acids.

The top strand of the mouse L1 cDNA nucleotide sequence that encodes the complete mouse L1 protein of 1260 amino acids is shown in FIGS. 5A–5G and is listed in SEQ ID NO 20. The encoded amino acid residue sequence is listed in SEQ ID NO 20 with the nucleotide sequence and separately in SEQ ID NO 21. The amino and carboxy terminal ends of the Fn type III repeats 3-5, 4-5 and F80 mouse L1 fragments are also indicated in FIGS. 5E–5G.

The DNA inserts for the bacterial expression of the non-fusion Fn type III repeats 3-5 and 4-5, along with the polypeptide corresponding to the F80 fragment of Ng-CAM also referred to as F80 for mouse L1, are generated by PCR as described in Example 1A1)a for Ng-CAM. The primers are designed to incorporate the Nco I and BamH I restriction sites respectively into the amplified 5' and 3' ends of the fragments for subsequent ligation into pET 3d as previously described.

The 5' and 3' PCR primers for amplifying the above DNA fragments are listed in the 5' to 3' direction as follows: 5' primer for Fn3-5: 5'CAACCATGGGCCTTGAAGACATC3' (SEQ ID NO 22); 5' primer for Fn4-5: 5'CAGCCATGGGCCCTGGCCACCCT3' (SEQ ID NO 23); 3' primer for both Fn3-5 and Fn4-5: 5'AAAGGATCCCTACCAGCCCTCGGA3' (SEQ ID NO 24); 5' primer for F80: 5'CAACCATGGGCCATATCCACAAA3' (SEQ ID NO 25); and 3' primer for F80: 5'AAAGGATCCCTACTATTGTAGGGC3' (SEQ ID NO 26).

The resultant PCR amplification products from the three separate reactions performed with the primers listed above for each of the three polypeptide fragments are then digested with Nco I and BamH I as described in Example 1B.

d. Chicken Nr-CAM

The cloning of the cDNA encoding chicken Nr-CAM was first described by Grumet et al., J. Cell Biol., 113:1399–1412 (1991). For use in obtaining neurite outgrowth-promoting polypeptide fragments of this invention, cDNA clones encoding the entire coding region of chicken Nr-CAM is similarly obtained from a λgt11 library of total RNA or poly (A)+ RNA isolated from 9 to 14 day old embryonic chicken brains by the RNase H method using oligo (dT) priming or synthetic oligonucleotides as primers as described for preparing chicken Ng-CAM cDNA. Chicken λgt11 cDNA libraries are also commercially available (Clontech).

The libraries are first screened with polyclonal antibodies against denatured Ng-CAM protein that recognize all the components of Ng-CAM as described for cloning of Ng-CAN. cDNA inserts, radioactively labeled with random primers as described by Feinberg et al., Anal. Biochem., 137:266–267 (1984), are used to screen the above libraries to obtain overlapping clones. Sequencing is performed as described for Ng-CAM above.

The complete nucleotide sequence of chicken Nr-CAM as described by Grumet et al., J. Cell Biol., 113:1399–1412 (1991) is available from EMBL/Genbank/DDBJ under the accession number X58482. The longest encoded open reading frame is 1268 amino acid residues.

The top strand of the chicken Nr-CAM cDNA nucleotide sequence that encodes the complete protein sequence is shown in FIGS. 30A–30G and is listed in SEQ ID NO 27. The encoded amino acid residue sequence is listed in SEQ ID NO 27 with the nucleotide sequence and separately in SEQ ID NO 28. The amino and carboxy terminal ends of the Fn type III repeats 3-5, 4-5 and F80 chicken Nr-CAM fragments are also indicated in FIGS. 30E–30G.

The DNA inserts for the bacterial expression of the non-fusion Fn type III repeats 3-5 and 4-5, along with the polypeptide corresponding to the F80 fragment of Ng-CAM also referred to as F80 for chicken Nr-CAM, are generated by PCR as described in Example 1A1)a for Ng-CAM. The primers are designed to incorporate the Nco I and BamH I restriction sites respectively into the amplified 5' and 3' ends of the fragments for subsequent ligation into pET 3d as previously described.

The 5' and 3' PCR primers for amplifying the above DNA fragments are listed in the 5' to 3' direction as follows: 5' primer for Fn3-5: 5'CAACCATGGGCAATGTGCAGGTT3' (SEQ ID NO 29); 5' primer for Fn4-5: 5'CAGCCATGGGCCCTAGCCCACCC3' (SEQ ID NO 30); 3' primer for both Fn3-5 and Fn4-5: 5'AAAGGATCCCTACCATCCTTGAGT3' (SEQ ID NO 31); 5' primer for F80: 5'CAACCATGGGCGTAGAAAAAAG3' (SEQ ID NO 32); and 3' primer for F80: 5'AAAGGATCCCTATTACACAAATGA3' (SEQ ID NO 33).

The resultant PCR amplification products from the three separate reactions performed with the primers listed above for each of the three polypeptide fragments are then digested with Nco I and BamH I as described in Example 1B.

2) DNA Inserts for Expression of Fusion Polypeptides a. Chicken Ng-CAM cDNA constructs for expressing fusion proteins were modifications of the constructs prepared above for production of non-fusion polypeptides for each of the 6/5 family homologs and for transfection to produce surface expressed polypeptides. For preparing fusion polypeptides in bacteria, the preferred vectors are the pGEX vectors available from Pharmacia as the vectors allow for the production of fusion proteins with glutathione-S-transferase (GST). This facet allows for rapid purification of fusion proteins by binding to glutathione-agarose beads and for subsequent purification of the corresponding non-fusion protein by cleavage with thrombin or activated Factor Xa.

For the F80 construct, the 922-913 insert from Bluescript was excised with EcoR I, treated with Klenow to generate blunt ends, and ligated into the Sma I site of the bacterial expression vector pGEX2T (Pharmacia). For the F135 construct from which the F135 kD fusion polypeptide was expressed and used as a control in neurite outgrowth assays as described below, the signal peptide-encoding segment at the 5' region was replaced with a short PCR product beginning at the amino terminus of the mature protein. A PCR product from the nucleotide region 119–685 of the Ng-CAM sequence (FIGS. 1A–1G) and containing an EcoR I site at the 5' end was digested with EcoR I and partially digested at nucleotide position 630 with BstX I, yielding a 516 bp fragment. The resultant EcoR I/BstX I fragment was ligated to the BstX I site of the 3359 bp fragment from the EcoR I/BstX I digest of the Ng-CAM 200 construct in pSVK3. The resulting ligation product was ligated into the EcoR I site of PGEX1λT (Pharmacia).

For the F135 pGEX construct, the 516 bp EcoR I/BstX I PCR fragment from above was ligated into the EcoR I/BstX I sites of the F135 construct in pSVK3 PCR-F135 digested at its 3' end only with Xba I, blunt-ended with Klenow, and ligated to EcoR I linkers. Upon excision by EcoR I digestion, the entire PCR-F135 insert was ligated into the EcoR I site of pGEX1λT for expression of the F135 polypeptide as a fusion protein with GST.

Fusion proteins spanning Fn type III repeats 3-5 and 4-5 of Ng-CAM were generated by PCR on the same template as described for non-fusion Ng-CAM constructs using a 5' primer corresponding to the amino terminal boundary of either the third or fourth Fn type III repeat and a common 3' primer corresponding to a region just before the transmembrane domain. In both cases the 5' primer contained a BamH I restriction site and the 3' primer contained an EcoR I restriction site. The 5' and 3' PCR primers written in the 5' to 3' direction used were as follows: 5' primer for Fn3-5: 5'GCGGGATCCAATGTGGGGGTGGAACTGCTG3' (SEQ ID NO 34); 5' primer for Fn4-5: 5'GCGGGATCCCCCGGCCCCCCCGAGGAGCTC3' (SEQ ID NO 35); and 3' primer for both Fn3-5 and Fn4-5: 5'GCGGAATTCCCACCCCTTGGTGCAAACCCC3' (SEQ ID NO 36). The PCR amplification was performed as described in 1A1)a for amplifying non-fusion constructs of Ng-CAM.

DNA fragments of 980 base pairs for Fn3-5 and 635 base pairs for Fn4-5 were amplified from Ng-CAM cDNA, excised and purified from a 1.5% agarose gel, digested with BamH I/EcoR I, and cloned into the BamH I/EcoR I sites of pGEX4T2 (Pharmacia) for expression of Ng-CAM fusion polypeptides as described in Example 2.

In a similar procedure, the Ng-CAM F80 construct is amplified for production of a DNA insert for ligation into the GST fusion expression vector pGEX. For the reaction performed as previously described, the 5' primer contains a BamH I restriction site and the 3' primer contains an EcoR I restriction site. The 5' and 3' PCR primers written in the 5' to 3' direction used are as follows: 5' primer: 5'GCGGGATCCGCCCCCCCGACCCCCCCCAAA3' (SEQ ID NO 37); and 3' primer: 5'GCGGAATTCTTAATCCAGGGGGGGCCCAGC3' (SEQ ID NO 38). The PCR amplification is performed as described in 1A1)a for amplifying non-fusion constructs of Ng-CAM. The resultant PCR products are then digested as described above for insertion into a similarly digested pGEX-based vector for expression of Ng-CAM F80-GST fusion polypeptides.

b. Human L1

Fusion proteins of human L1 that span regions homologous to FN repeats 3-5 and 4-5 as well as the F80 fragment of chicken Ng-CAM are amplified from human L1 cDNA in a similar approach as the non-fusion human L1 constructs prepared above. The primers for amplifying the specified fragments are as described above for Ng-CAM fusion constructs with the exception of the human L1-specific priming sequences.

The 5' and 3' PCR primers written in the 5' to 3' direction used are as follows: 5' primer for Fn3-5: 5'GCGGGATCCCTGGAAGGCATTGAAATC3' (SEQ ID NO 39); 5' primer for Fn4-5: 5'GCGGGATCCCCTGGCCACCCCGAGGCG3' (SEQ ID NO 40); and 3' primer for both Fn3-5 and Fn4-5: 5'GCGGAATTCCCAGCCCTCAGTGGCGAA3' (SEQ ID NO 41). The PCR amplification is performed as described in Example 1A1)a for amplifying non-fusion constructs of Ng-CAM.

DNA fragments of 932 bp for the third through fifth repeat and 631 bp for the fourth through fifth repeat are amplified, excised and purified from an agarose gel, digested with BamH I/EcoR I, and cloned into the BamH I/EcoR I sites of pGEX4T2 as described in Example 1B for expression of human L1 fusion polypeptides.

In a similar procedure, the human L1 F80 construct is amplified for production of a DNA insert for ligation into the GST fusion expression vector pGEX. For the reaction performed as previously described, the 5' primer contains a BamH I restriction site and the 3' primer contains an EcoR I restriction site. The 5' and 3' PCR primers written in the 5' to 3' direction used are as follows: 5' primer: 5'GCGGGATCCCATATCCACAAAGACCAT3' (SEQ ID NO 42); and 3' primer: 5'GCGGAATTCCTATTCTAGGGCCACGGC3' (SEQ ID NO 43). The PCR amplification is performed as described in Example 1A1)a for amplifying non-fusion constructs of Ng-CAM. The resultant PCR products are then digested as described above for insertion into a similarly digested pGEX-based vector for expression of human L1 F80-GST fusion polypeptides.

c. Mouse L1

Fusion proteins of mouse L1 that span regions homologous to FN repeats 3-5 and 4-5 as well as the F80 fragment of chicken Ng-CAM are amplified from mouse L1 cDNA in a similar approach to that of the non-fusion mouse L1 constructs prepared above. The primers for amplifying the specified fragments are as described above for Ng-CAM fusion constructs with the exception of the mouse L1-specific priming sequences.

The 5' and 3' PCR primers written in the 5' to 3' direction used are as follows: 5' primer for Fn3-5: 5'GCGGGATCCCTTGAAGACATCACAATC3' (SEQ ID NO 44); 5' primer for Fn4-5: 5'GCGGGATCCCCTGGCCACCCTGAGGCA3' (SEQ ID NO 45); and 3' primer for both Fn3-5 and Fn4-5: 5'GCGGAATTCCCAGCCCTCGGAGGCAAA3' (SEQ ID NO 46). The PCR amplification is performed as described in Example 1A1)a for amplifying non-fusion constructs of Ng-CAM.

The resultant DNA fragments are then purified as previously described, digested with BamH I/EcoR I, and cloned into the BamH I/EcoR I sites of pGEX4T2 as described in Example 1B for subsequent expression of recombinant mouse L1 polypeptides.

In a similar procedure, the mouse L1 F80 construct is amplified for production of a DNA insert for ligation into the GST fusion expression vector pGEX. For the reaction performed as previously described, the 5' primer contains a BamH I restriction site and the 3' primer contains an EcoR I restriction site. The 5' and 3' PCR primers written in the 5' to 3' direction used are as follows: 5' primer: 5'GCGGGATCCCATATCCACAAAAGCCAC3' (SEQ ID NO 47); and 3' primer: 5'GCGGAATTCCTATTGTAGGGCTACTGC3' (SEQ ID NO 48). The PCR amplification is performed as described in Example 1A1)a for amplifying non-fusion constructs of Ng-CAM. The resultant PCR products are then digested as described above for insertion into a similarly digested pGEX-based vector for expression of mouse L1 F80-GST fusion polypeptides.

d. Chicken Nr-CAM

Fusion proteins of chicken Nr-CAM that span regions homologous to FN repeats 3-5 and 4-5 as well as the F80 fragment of chicken Ng-CAM are amplified from chicken Nr-CAM cDNA in a similar approach to that of the non-fusion chicken Nr-CAM constructs prepared above. The primers for amplifying the specified fragments are as described above for Ng-CAM fusion constructs with the exception of the chicken Nr-CAM-specific priming sequences.

The 5' and 3' PCR primers written in the 5' to 3' direction used are as follows: 5' primer for Fn3-5: 5'GCGGGATC-CAATGTGCAGGTTCATGTC3' (SEQ ID NO 49); 5' primer for Fn4-5: 5'GCGGGATCCCCTAGCCCACCCTC-CTTT3' (SEQ ID NO 50); and 3' primer for both Fn3-5 and Fn4-5: 5'GCGGAATTCCCATCCTTGAGTAGCAAT3' (SEQ ID NO 51). The PCR amplification is performed as described in Example 1A1)a for amplifying non-fusion constructs of Ng-CAM.

The resultant DNA fragments are then purified as previously described, digested with BamH I/EcoR I, and cloned into the BamH I/EcoR I sites of pGEX4T2 as described in Example 1B for subsequent expression of recombinant chicken Nr-CAM polypeptides.

In a similar procedure, the chicken Nr-CAM F80 construct is amplified for production of a DNA insert for ligation into the GST fusion expression vector pGEX. For the reaction performed as previously described, the 5' primer contains a BamH I restriction site and the 3' primer contains an EcoR I restriction site. The 5' and 3' PCR primers written in the 5' to 3' direction used are as follows: 5' primer: 5'GCGGGATCCGTAGAAAAAAAGATCTTG3' (SEQ ID NO 52); and 3' primer: 5'GCGGAATTCTTACACAAAT-GAATTCAT3' (SEQ ID NO 53). The PCR amplification is performed as described in Example 1A1)a for amplifying non-fusion constructs of Ng-CAM. The resultant PCR products are then digested as described above for insertion into a similarly digested pGEX-based vector for expression of chicken Nr-CAM F80-GST fusion polypeptides.

B. Preparation of DNA Expression Vectors With DNA Inserts Encoding Polypeptides Containing 6/5-Derived Fibronectin Type III Repeats 1) Subcloning of Non-Fusion Polypeptide-Encoding DNA Constructs Expression of the DNA constructs encoding the F80, Fn3-5 and Fn4-5 non-fusion polypeptides derived from the 6/5 family of homologous cell adhesion molecules is accomplished by subcloning the DNA constructs prepared in Example 1A1)a into a suitable expression vector. As described above, the DNA constructs encoding the Ng-CAM F135 polypeptide as well the F80 construct obtained through cloning of cDNA fragments were subcloned into the mammalian expression vector pSVK3 for subsequent expression in mammalian cells. The cloned F80 construct was first digested with Bgl II and ligated into the BamH I site of pSVK3 directly behind the SV40 early promoter. The F135 fragment was subcloned as described in Example 1A1)a.

The PCR amplified DNA constructs encoding the non-fusion F80, Fn3-5 and Fn4-5 poly eptides from Ng-CAM, human L1, mouse L1 and chicken Nr-CAM are separately purified as described in Example 1A1) and digested with Nco I and BamH I to create cohesive termini that allows for directional ligation into a similarly digested pET 3d (Novagen) vector. The restriction digestions are performed according to manufacturer's instructions. The double-digested PCR products are then purified and subcloned as described below for subcloning of DNA constructs for producing fusion proteins. The separate pET 3d expression vectors containing the various DNA constructs prepared in Example 1A1) are then transfected into bacterial hosts as described in Example 2 for expression of non-fusion polypeptides.

2) Subcloning of Fusion Polypeptide-Encoding DNA Constructs

When the DNA constructs prepared above for encoding the 6/5-derived polypeptides as fusion proteins are separately inserted into the pGEX vectors in the same translational frame as the DNA encoding the glutathione-S-transferase (GST) protein domain, fusion proteins consisting of the carboxy-terminal portions of GST fused to the various encoded 6/5-derived fibronectin type III domain-containing polypeptides are expressed. The PGEX plasmids are designed for inducible, high-level intracellular expression of genes or gene fragments as fusions with *Schistosoma japonicum* glutathione S-transferase (GST) [Smith, et al., *Gene*, 67:31 (1988)]. GST provides a means for the purification of the expressed fusion proteins from bacterial lysates by affinity chromatography using glutathione-Sepharose 4B. Elution from the glutathione-Sepharose 4B using reduced glutathione provides very mild elution conditions for the release of the GST fusion protein from the affinity matrix, thereby minimizing effects on functional activity of the fusion protein.

The multiple cloning sites of the pGEX vectors provide for the unidirectional insertion of cDNA inserts. The primary differences between the various PGEX vectors used in this invention are the restriction sites and the reading frame of the restriction sites present in the multiple cloning site. The DNA constructs prepared in Example 1A2) were designed to provide for in-frame translation with GST.

Some preferred pGEX-based vectors for use in expressing polypeptides of this invention in bacteria include pGEX2T, pGEX3X vectors (Pharmacia) [Prieto, et al., *J. Cell Biol.*, 119:663–678 (1992) and Prieto, et al., *Proc. Natl. Acad. Sci.*, *USA*, 90:10154–10158 (1993)], pGEX1λT and pGEX4T2 vector (Pharmacia).

The Ng-CAM F80 cDNA construct along with the Fn3-5 and Fn4-5 PCR products prepared in Example 1A2)a were separately subcloned in the appropriate restriction sites of pGEX-based vectors. For the F80 cloned construct excised from Bluescript, the isolated fragment was treated with Klenow to generate blunt ends and ligated into the Sma I site of pGEX2T. The PCR amplified Ng-CAM Fn3-5 and Fn4-5 products were separately digested with BamH I/EcoR I and subcloned into a similarly digested pGEX4T2 expression vector. The ligations resulted in the in-frame constructs for expression of the Ng-CAM fusion proteins.

For restriction endonuclease digestion of the DNA inserts, the DNA was separately digested at 37° C. with the specified restriction enzymes according to manufacturer's instructions. The resulting digested fragments have cohesive termini adapted for ligation. Double-digested fragments were directionally ligated.

The digest DNA inserts were separately purified by extracting the solution with a mixture of phenol and chloroform followed by ethanol precipitation. The purified digests were then separately ligated into comparably digested expression vectors by mixing approximately three moles of the DNA fragments per mole of the pGEX expression vector in the presence of T4 DNA ligase using the manufacturer's recommended conditions.

The Ng-CAM F80-encoding amplified DNA construct along with the F80-, Fn3-5- and Fn4-5-encoding amplified DNA constructs from human L1, mouse L1 and chicken Nr-CAM prepared in Example 1A2) are separately ligated into pGEX4T2 as described above for Ng-CAM Fn3-5 and Fn4-5-encoding amplified DNA constructs to produce separate expression vectors for expression of the various polypeptides as fusion proteins with GST.

2. Expression and Purification of Non-Fusion and Fusion Polypeptides

A. Mammalian Expression

The Ng-CAM F135 and F80 cloned DNA constructs subcloned into pSVK3 and pCDNA1neo as described in Example 1B1) were transfected into mouse L-M (TK⁻) cells (CCL1.3; American Type Tissue Culture Collection, Rockville, Md.) using calcium phosphate precipitation of the DNA. The Ng-CAM F80 eukaryotic expression constructs in the pSVK3 vector were cotransfected into the above L-cells with the selectable marker vector, pSV2neo. Clones were selected using G418 (Gibco Laboratories, Grand Island, N.Y.) at 500 µg/ml (244 µg/ml active). Clones resistant to G418 were cloned by limiting dilution up to three times and selected by immunofluorescent staining with anti-Ng-CAM antibodies.

Five clones expressing F135 and four expressing F80 were isolated. Each cell line expressed proteins on the cell surface as detected by immunofluorescence and the expressed proteins were of the expected sizes as indicated by immunoblots. The F135 transfectants showed a more diffuse staining pattern in the Golgi in addition to cell surface staining in contrast to that of F80 that showed a predominantly cell surface localization. The antibodies showed no reactivity with untransfected L-cells or with L-cells transfected with the neomycin vector only.

A 135 kD component was detected in F135-encoding DNA transfected cells. Lower molecular weight components were observed that reacted with the anti-Ng-CAM antibodies indicating that they may be proteolytic products. Although F80 was recognized on transfected cells by immunofluorescence with the Ng-CAM antibodies, it was not recognized well in immunoblots with these antibodies. In contrast, this component was recognized very well by rabbit antibodies to the cytoplasmic portion of Ng-CAM. These rabbit antibodies also reacted with a 180 kD component in untransfected L-cells indicating that there is a molecule in L-cells immunologically related to the cytoplasmic domain of Ng-CAM; this molecule was not recognized, however, by any antibodies that react with the extracellular portion of Ng-CAM.

In vivo, Ng-CAM is cleaved proteolytically to give F135 and F80. The media from F135-encoding DNA transfected cells ($3 \times 10^7$ cells) contained some F135 in the media. Although F135 was found in the media of the F135-encoding DNA transfected cells, a significant amount of the protein remained attached to the cells as revealed by immunoblots and immunofluorescence. The F135 polypeptide has no transmembrane region and because the F135 transfected L-cells contain no F80, the F135 must be anchored to the cell via another molecule.

In order to obtain isolated. Ng-CAM F80 expressed from mammalian cells, the clone expressing the polypeptide is expanded followed by lysis in 1% NP-40 in 50 mM Tris-HCl at pH 7.4 containing 150 mM NaCl and 1 mM PMSF. The cells are lysed and the resultant lysate is applied onto an rabbit anti-Ng-CAM cytoplasmic portion affinity column according to procedures well known to one of ordinary skill in the art. Antibodies raised against cytoplasmic portions of Ng-CAM were obtained by immunizing rabbits at four-week intervals with 200 µg protein in PBS/Freund's Adjuvant as described by Brackenbury et al., *J. Biol. Chem.*, 252:6835–6840 (1977). Rabbits were bled after the third injection and Fab' prepared. The bound expressed F80 polypeptide is thereafter eluted and isolated for use in neurite outgrowth assays as described in Example 3.

B. Bacterial Expression of Non-Fusion Polypeptides

For expression of F80, Fn3-5 and Fn4-5 non-fusion polypeptides from 6/5 family-derived DNA inserts subcloned into the pET 3d vector as described above, the expression vectors are separately transfected into *E. coli*, strain BL21(DE3) or BL21pLys. For production of the recombinant non-fusion polypeptides, three liter cultures of bacteria in exponential phase containing these constructs are induced with 1 mM isopropyl-beta-D-1-thiogalactopyranoside (IPTG) for 4 hours at 37° C. The induced bacteria are then lysed with a French press and the cell supernatant is clarified by centrifugation. The expressed endogenous and recombinant proteins are then purified from the bacterial lysate by ammonium sulfate precipitation (40–70%), chromatography on DEAE cellulose (DE52, Whatman), in 20–50 mM Tris, pH 8.0 buffer (elution with gradients of 0–1 M NaCl), and gel filtration over Sephacryl S100 HR (Pharmacia) in 20–50 mM Tris-HCl, pH 8.0.

Expression of the non-fusion polypeptides in the pET 3d vector system results in the introduction of two additional amino acid residues, methionine (M) and glycine (G), to the amino terminal end of the expressed polypeptides. This is due to the 5' primers used for amplifying the DNA constructs that include nucleotide sequences for the Nco I restriction site to allow directional ligation into the ATG initiation site of the vector. The primer nucleotides ATG and GGC respectively encode the methionine and glycine residues.

Neither of these residues effect the neurite outgrowth-promoting activity of the resultant expressed polypeptide fragments. As such, the amino acid residue sequence of each of the expressed non-fusion polypeptides produced by pET 3d expression vectors is not presented with the two additional amino acid residues at the amino terminus.

Therefore, the following figures in which the amino acid residue sequence for each of F80, Fn3-5 and Fn4-5 non-fusion polypeptides from the 6/5 homologs, chicken Ng-CAM, human L1, mouse L1 and chicken Nr-CAM, show the expressed polypeptide sequence. For each of the amino acid residue sequences, a corresponding SEQ ID NO has been assigned indicating the position of such in the Sequence Listing.

For chicken Ng-CAM, the amino acid residue sequence of the expressed polypeptides, F80, Fn3-5 and Fn4-5, are respectively shown in FIGS. 2 (SEQ ID NO 5), 6 (SEQ ID NO 54) and 7 (SEQ ID NO 55).

For human L1, the amino acid residue sequence of the expressed polypeptides, F80, Fn3-5 and Fn4-5 are respectively shown in FIGS. 8 (SEQ ID NO 56), 9 (SEQ ID NO 57) and 10 (SEQ ID NO 58).

For mouse L1, the amino acid residue sequence of the expressed polypeptides, F80, Fn3-5 and Fn4-5 are respectively shown in FIGS. 11 (SEQ ID NO 59), 12 (SEQ ID NO 60) and 13 (SEQ ID NO 61).

For chicken Nr-CAM, the amino acid residue sequence of the expressed polypeptides, F80, Fn3-5 and Fn4-5 are respectively shown in FIGS. 14 (SEQ ID NO 62), 15 (SEQ ID NO 63) and 16 (SEQ ID NO 64).

The isolated recombinant F80, Fn3-5 and Fn4-5 non-fusion polypeptides listed above are then used in neurite outgrowth assays as described in Example 3.

C. Bacterial Expression of Fusion Polypeptides

In order to express GST fusion proteins for the Ng-CAM-derived F135, F80, Fn3-5 and Fn4-5 polypeptides, the pGEX-based plasmids prepared in Example 1B2) were transfected into *E. coli* strain NM522 cells (Stratagene, La Jolla, Calif.) according to the manufacturer's specifications and selected with ampicillin.

NM522 colonies containing the pGEX vector construct which expresses an Fn3-5:GST or Fn4-5 fusion protein was selected by plating the transformation mixture in L-broth cultures containing 50 μg/ml ampicillin, referred to as LA-broth, (Maniatis, *Molecular Cloning: A Laboratory Manual,* Cold Spring Harbor Laboratory, Cold Spring Harbor, N.Y. (1982)) and as described by Prieto et al., *J. Cell Biol.,* 119:663–678 (1992).

The cultures were used to inoculate 900 ml of LA-broth which were then further incubated for 3–4 hours at 25° C. with agitation until reaching an optical density of 1.0 at 650 nm. The culture was then treated with IPTG added at a final concentration of 0.1 mM and the cultures were incubated for an additional 20 hours. The bacterial cells were then harvested by centrifugation and the pellet was resuspended in 50 ml of L-buffer consisting of 50 mM Tris-HCl at pH 7.5, 25% sucrose, 0.5% NP-40 and 5 mM $MgCl_2$.

The cells were then lysed by three cycles of freeze-thawing followed by sonication. The resulting lysate was centrifuged and the resulting supernatant was collected for subsequent application onto glutathione-Sepharose 4B beads. The beads were then incubated at 4° C. for 1 hour with gentle rotation. The fusion proteins bound to the glutathione-Sepharose 4B beads were then washed extensively with a washing buffer (20 mM Tris-HCl, pH 7.5 and 1 mM dithiothreitol) to remove unbound bacterial debris.

The beads were then washed extensively with 20 mM Tris-HCl, pH 7.5, 1mM DTT and eluted with 50 mM Tris-HCl, pH 8, containing 1 mM reduced glutathione. The eluate was dialyzed against distilled water and lyophilized. The lyophilized fusion proteins of each polypeptide fragment were then separately dissolved in sterile phosphate buffered saline (PBS), the protein concentration determined, and aliquots of the protein stored at −70° C.

The molecular weight and purity of the eluted proteins was determined by sodium dodecyl sulfate-polyacrylamide gel electrophoresis (SDS-PAGE). Since the GST was not cleaved from the fusion protein during purification, the molecular weight of the fusion protein includes 26,000 kD of the GST protein. The separated proteins were visualized by staining the proteins with Coomassie Blue and the apparent molecular weight ($M_r$) determined by comparison to protein molecular weight standards.

To isolate expressed polypeptides without GST, proteolytic cleavage of the fusion protein is performed while the fusion proteins are still attached to the glutathione beads following the procedure described by Prieto et al., *J. Cell Biol.,* 119:663–678 (1992). The resultant purified polypeptides have the same amino acid residue sequence as for expressed non-fusion polypeptides as described above.

SDS-PAGE of the F135 fusion protein yielded a major protein of 140 kD and several minor components at approximately 100 kD. The F80 fusion protein, the amino acid sequence of which is shown in FIG. 17 (SEQ ID NO 65) yielded a major component at approximately 70 kD, corresponding to the predicted size of the glutathione-S-transferase segment plus the Ng-CAM insert, and several small components. All of these components immunoblotted with anti-Ng-CAM antibodies. Expression of the Fn3-5 construct yielded a protein product having the amino acid residue sequence shown in FIG. 18 (SEQ ID NO 66) of approximately 70 kD with some degradation products of 40 kD. The Fn4-5 construct yielded a product having the amino acid residue sequence shown in FIG. 19 (SEQ ID NO 67) of approximately 60 kD with degradation products of 35 kD.

For human L1, the amino acid residue sequence of the expressed fusion polypeptides, F80, Fn3-5 and Fn4-5, are respectively shown in FIGS. 20 (SEQ ID NO 68), 21 (SEQ ID NO 69) and 22 (SEQ ID NO 70).

For mouse L1, the amino acid residue sequence of the expressed fusion polypeptides, F80, Fn3-5 and Fn4-5, are respectively shown in FIGS. 23 (SEQ ID NO 71), 24 (SEQ ID NO 72) and 25 (SEQ ID NO 73).

For chicken Nr-CAM, the amino acid residue sequence of the expressed fusion polypeptides, F80, Fn3-5 and Fn4-5 are respectively shown in FIGS. 26 (SEQ ID NO 74), 27 (SEQ ID NO 75) and 28 (SEQ ID NO 76).

The isolated recombinant F80, Fn3-5 and Fn4-5 fusion polypeptides listed above are then used in neurite outgrowth assays as described in Example 3.

3. Neurite Outgrowth Assays with Expressed Polypeptides and Fusion Polypeptides

For neurite outgrowth assays with the non-fusion and fusion polypeptides produced in this invention as described in Example 2, all steps were carried out in a 3.5 cm bacteriological culture dish (Falcon 1008) that was separately spotted in a circular dot pattern with 2 μl of Ng-CAM fusion polypeptides, F136, F80, Fn3-5 and Fn4-5 at a concentration of 5 μmol/ml. Plates were incubated for 60 minutes at room temperature. The solutions were aspirated, and the dishes washed twice and blocked for 60 minutes at room temperature with 250 μl PBS/2% BSA. The blocking solution was aspirated and cells were added as described below and incubated for 60 minutes at 37° C.

Dorsal root ganglia were dissected from day six chicken embryos and placed in Hank's balanced salt solution (HBSS). The ganglia were placed in calcium, magnesium-free Hank's Balanced Salt Solution (CMF-HBSS) and incubated at 37° C. for ten minutes. The ganglia were transferred to 0.08% trypsin in CMF-HBSS and incubated at 37° C. for 20 minutes. An equal volume of DMEM/F12, 10% FCS, 20 ng/ml NGF, 10 μg/ml gentamicin (10% medium), was added. The ganglia were pelleted and resuspended in 2 ml of 10% medium and triturated with a fire polished Pasteur pipette for 15 strokes. The single cell suspension was washed once with 10% medium, and preplated in a 10 cm tissue culture dish for one hour at 37° C., 5% $CO_2$. After one hour, the medium containing a cell population enriched for DRG neurons was removed and the cells were pelleted and washed two times with DMEM/F12, 1% FCS, 20 ng/ml NGF, 10 μg/ml gentamicin (1% medium). Cells were resuspended at a density of $2 \times 10^4$ cells/ml in 1% medium and 300 μl of-cell suspension was added to the center of the prepared bacteriological plates. The plates were placed in a humidified chamber and incubated at 37° C., 5% $CO_2$ for 15 hours. After the growth period, the. cells were fixed with 1% glutaraldehyde and the number of cells that sprouted neurites were counted and neurite length was measured by phase contrast microscopy.

Figure 29A:
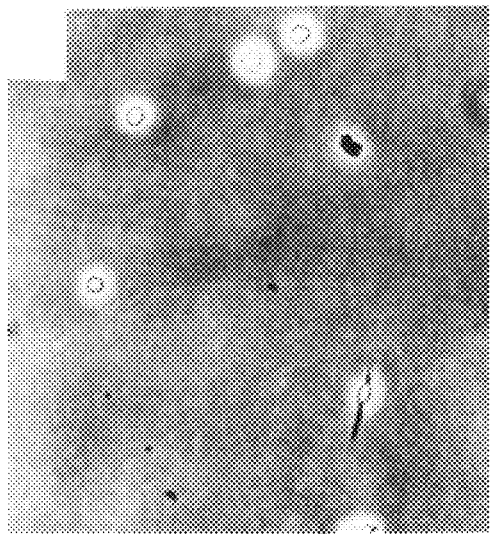
FIGS. 29A–29D are photographs showing the effect of neurite outgrowth of dorsal root ganglia neurites on Ng-CAM F135, F80 and Fn3-5 fusion proteins. Phase-contrast photographs of dissociated dorsal root ganglia cells from E8 chick embryos cultured on surfaces coated with Ng-CAM F135 (FIG. 29A), F80 (FIG. 29B), Fn3-5 (FIG. 29C) fusion proteins or GST alone as a control (FIG. 29D). Cells were cultured for 15 hours in plastic dishes precoated with equimolar amounts of F135 or F80 fusion protein, fixed with glutaraldehyde and photographed. The assays and results are discussed in Example 3. Bar=50 μm.
Figure 29B:
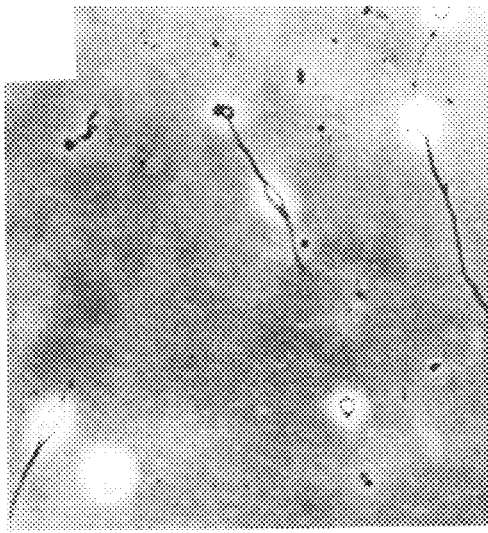

Since Ng-CAM has been previously shown to promote neurite outgrowth as discussed in the Background, to assess the regions of Ng-CAM responsible for this activity, F135 and F80-GST fusion proteins were used as substrates for culturing chick dorsal root ganglia cells (FIGS. 29A–D) over a 15 hour time period. Although both substrates supported neuronal attachment in long-term culture, only the F80-fusion protein promoted extensive neurite outgrowth as shown in FIG. 29B. In contrast, the F135 had little effect on DRG neurite outgrowth (FIG. 29A). When neurite outgrowth was tested on substrates coated with various concentrations of F135 and F80, F80 supported neurite outgrowth at coating at concentrations as low as 0.2 mg/ml whereas F135 did not support neurite outgrowth even when coated at concentrations as high as 1.5 mg/ml.

Figure 29C:
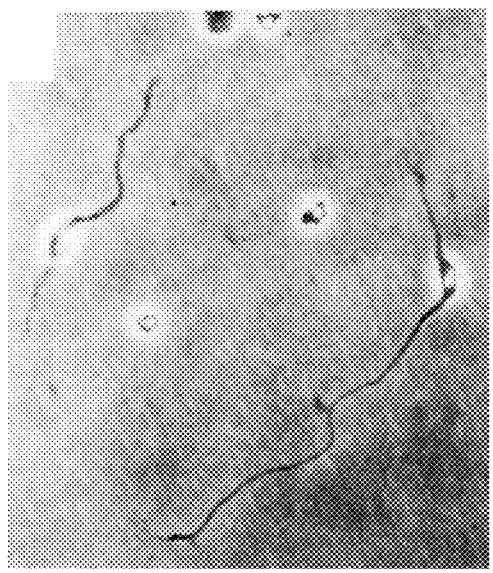
Figure 29D:
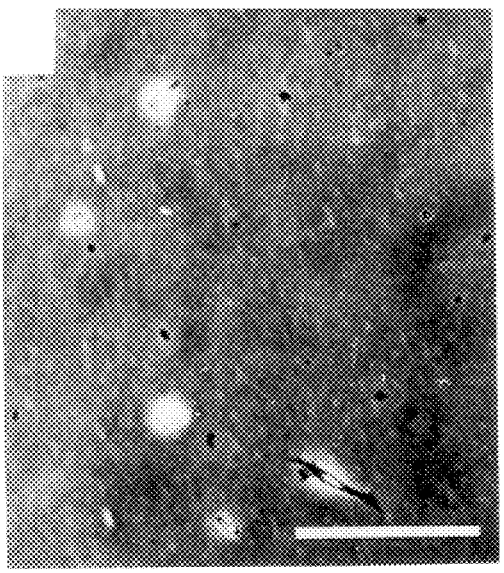

To control for the possibility that the transmembrane domain present in F80 affected neurite outgrowth due to hydrophobic effects, fusion proteins corresponding to the three type III Fn repeats, Fn3-5 and Fn4-5 in F80 were prepared as described in Example 2. Both of these fusion proteins supported neurite outgrowth comparable to F80. The response to Fn3-5 is shown in FIG. 29C compared with the outgrowth observed on GST alone (FIG. 29D).

These results indicate that the neurite outgrowth-promoting activity of Ng-CAM resides in the fibronectin type III domains. In accord with the finding that the Fn type III repeats 4-5 supported neurite outgrowth, a peptide having the single letter amino acid residue sequence FNGRDG-PPSEPIAC (SEQ ID NO 77) corresponding to the RGD-containing region of Fn III in the third domain did not inhibit outgrowth. This suggests that while the third Fn type III repeat domain may contribute to the neurite outgrowth-promoting activity, the RGD-containing region is not essential.

The results presented here localize the ability of Ng-CAM to promote neurite outgrowth to the F80 region and to the FN type III repeats 3-5 and 4-5 of NG-CAM. Localization of the major portion of the neurite promoting activity of Ng-CAM to the F80 region in the present study suggests that post-translational cleavage segregates cell binding activity from the ability of Ng-CAM expressing cells to promote outgrowth. The activity was localized to the extracellular Fn type III repeats of F80, including Fn3-5 and Fn4-5 and apparently neither cleavage within the third Fn type III repeat nor the presence of the RGD sequence in third repeat is essential for the activity. However, all three polypeptide fragments of Ng-CAM, the F80, Fn3-5 and Fn4-5 support neurite outgrowth of chicken dorsal root ganglion cells in culture. Because the F80 segment neither binds to itself nor to F135, neuronal molecules other than Ng-CAM itself are likely to be involved in the ability of Ng-CAM to promote neurite outgrowth.

For measuring the outgrowth of neurites from plating on fusion or non-fusion polypeptides derived from human L1, substrates for neurite outgrowth assays are prepared by coating non-tissue culture treated polystyrene dishes with solutions containing 0.5–5.0 $\mu$M of the human L1-derived fusion or non-fusion proteins-produced in Example 2 in PBS for 30 minutes. The dishes are then blocked with 2% BSA in PBS for 1 hour.

The human neuroblastoma cell line SK-N-SH is used for the neurite outgrowth assays on human L1-derived polypeptides. The cells are grown in DMEM with 10% FCS, passaged the night before the assay and seeded at a density of 1:2. The cells are harvested in calcium-magnesium free Hank's balanced salt solution (CMF-HBSS) with 20 mM Hepes buffer and 5 mM EDNA added. The cells are washed in DMEM containing 1% FCS three times, and resuspended to a density of 5×10$^4$ cells/ml in DMEM 1% FCS. The cells are then added to the coated plates and incubated at 37° C., 5% CO2, for 15 hours and are then analyzed for neurite outgrowth.

The percentage of cells that sprout neurites longer than one cells diameter are determined as well as the total length of neurites for each neurite bearing cells. These values are compared to non-specific coated substrates such as glutathione-S-transferase if measuring the effectiveness of fusion proteins or with poly-lysine if measuring the effectiveness of non-fusion polypeptides. The values for human L1 coated substrates are judged as significant from control values using the student's T test.

Comparable assays with the mouse L1 and chicken Nr-CAM expressed polypeptides are performed as described herein. The in vitro assay systems as described are not limited by evaluating neurite outgrowth of one species of cells on the corresponding cell adhesion protein species, i.e, syngenic species. Thus, neurite outgrowth assays are performed where a potential neurite-promoting cell population from one species is plated on fusion or non-fusion polypeptides from another species.

4. Implantation of Tubes Containing Expressed Non-Fusion Polypeptides Derived from the 6/5 Family of Cell Adhesion Molecules To analyze the ability of F80, Fn3-5 and Fn4-5 non-fusion polypeptides to promote regeneration in animals, and as a therapeutic model, the polypeptides from Ng-CAM, human L1, mouse L1 and chicken Nr-CAM are separately incorporated into silicone tubes. As described previously by LeBeau, et al., *J. Neurocytol.*, 17:161–172 (1988), the proximal and distal stumps of severed rat sciatic nerves are sutured into the openings of silicone tubes. The insides of the tubes are filled with a saline solution containing 1–100 $\mu$g/ml of expressed non-fusion polypeptides prepared as described in Example 2. Albumin and the F135 polypeptide serves as a control protein. At various intervals following the initial surgery, the ability of the various polypeptides to promote recovery of neuromuscular function is assessed in the live animals by measuring evoked muscle action potentials in the gastrocnemius muscles, as described by Archibald, et al., *J. Comp. Neurol.*, 306:685–696 (1991). The nerves are then surgically removed from the rats, fixed and analyzed by microscopy for nerve regrowth along with the rate of the regeneration process and recovery of neuromuscular function.

5. Implantation of Tissue Guides Impregnated With Expressed Non-Fusion Polypeptides Derived from the 6/5 Family of Cell Adhesion Molecules As another method to analyze the ability of the polypeptides described in Example 4 to promote regeneration in animals, and as a therapeutic model, the polypeptides are separately incorporated into collagen based nerve guides as conduits for peripheral nerve regeneration. The collagen guides are impregnated with a saline solution containing 1–100 $\mu$g/ml of expressed polypeptides or a control protein (such as albumin). At various intervals following initial surgery, the ability of the Ng-CAM to promote recovery of neuromuscular function is assessed in the live animals by measuring evoked muscle action potentials in the gastrocnemius muscles. The nerves are then surgically removed from-the rats, fixed and analyzed by microscopy for nerve regrowth, the rate of the regeneration processes and the recovery of neuromuscular function.

The foregoing specification, including the specific embodiments and examples, is intended to be illustrative of the present invention and is not to be taken as limiting. Numerous other variations and modifications can be effected without departing from the true spirit and scope of the present invention.

What is claimed is:

1. A synthesized polypeptide that promotes neurite outgrowth, wherein the polypeptide is a Type III repeat derived from Ng-CAM and wherein the polypeptide consists of the amino acid residue sequence selected from the group consisting of SEQ ID NO 54, 55, 66, and 67.

2. The synthesized polypeptide of claim 1 wherein the polypeptide is a recombinant expressed polypeptide.

3. A synthesized polypeptide that promotes neurite outgrowth, wherein the polypeptide is a Type III repeat derived from L1 and wherein the polypeptide consists of the amino acid residue sequence selected from the group consisting of SEQ ID NO 57, 58, 61, 69, 70, 72, and 73.

4. The synthesized polypeptide of claim 3 wherein the polypeptide is a recombinant expressed polypeptide.

5. A synthesized polypeptide that promotes neurite outgrowth, wherein the polypeptide is a Type III repeat derived from Nr-CAM and wherein the polypeptide consists of the amino acid residue sequence selected from the group consisting of SEQ ID NO 63, 64, 75, and 76.

6. The synthesized polypeptide of claim 5 wherein the polypeptide is a recombinant expressed polypeptide.

* * * * *

SEQUENCE LISTING (1) GENERAL INFORMATION:

(iii) NUMBER OF SEQUENCES: 77

(2) INFORMATION FOR SEQ ID NO:1:

(i) SEQUENCE CHARACTERISTICS:
      (A) LENGTH: 19 amino acids
      (B) TYPE: amino acid
      (D) TOPOLOGY: linear (ii) MOLECULE TYPE: peptide (v) FRAGMENT TYPE: internal (xi) SEQUENCE DESCRIPTION: SEQ ID NO:1:

```
Ile Ser Pro Ser Ser Pro Arg Ser Thr Gly Gly Ser Arg Trp Ser Pro
1               5                   10                  15

Asp Arg His
```

(2) INFORMATION FOR SEQ ID NO:2:

(i) SEQUENCE CHARACTERISTICS:
      (A) LENGTH: 20 amino acids
      (B) TYPE: amino acid
      (D) TOPOLOGY: linear (ii) MOLECULE TYPE: peptide (v) FRAGMENT TYPE: internal (xi) SEQUENCE DESCRIPTION: SEQ ID NO:2:

```
Asp Gln Pro Phe Val Pro Glu Glu His Gly Gly Val Ser Val Val Pro
1               5                   10                  15

Gly Ser Gly Thr
            20
```

(2) INFORMATION FOR SEQ ID NO:3:

(i) SEQUENCE CHARACTERISTICS:
      (A) LENGTH: 3991 base pairs
      (B) TYPE: nucleic acid
      (C) STRANDEDNESS: double
      (D) TOPOLOGY: linear (ii) MOLECULE TYPE: cDNA (iii) HYPOTHETICAL: NO (iv) ANTI-SENSE: NO (ix) FEATURE:
      (A) NAME/KEY: CDS
      (B) LOCATION: 59..3859

(xi) SEQUENCE DESCRIPTION: SEQ ID NO:3:

```
GAATTCCGGC AGCCGAGCGG GGAGCGGTGA GAGCAGGCGC GCAGCTGCCC GTCCCGCC                58

ATG GCT CTG CCC ATG GTC GGC CTC CTC CTG CTC CTG TTG CTG GGG GGG               106
Met Ala Leu Pro Met Val Gly Leu Leu Leu Leu Leu Leu Leu Gly Gly
1               5                   10                  15

CCC GGA GCC GCC ATC ACC ATT CCC CCG GAG TAT GGT GCG CAC GAT TTC               154
Pro Gly Ala Ala Ile Thr Ile Pro Pro Glu Tyr Gly Ala His Asp Phe
                20                  25                  30

CTG CAG CCC CCC GAG CTG ACG GAG GAA CCC CCG GAA CAA CTC GTG GTC               202
Leu Gln Pro Pro Glu Leu Thr Glu Glu Pro Pro Glu Gln Leu Val Val
```

```
              35                  40                  45
TTC CCC AGT GAT GAC ATC GTC CTC AAA TGC GTG GCC ACC GGG AAC CCC      250
Phe Pro Ser Asp Asp Ile Val Leu Lys Cys Val Ala Thr Gly Asn Pro
        50                  55                  60

CCC GTC CAG TAC CGA TGG AGC CGT GAG GAT CAG CCC TTC GTC CCC GAG      298
Pro Val Gln Tyr Arg Trp Ser Arg Glu Asp Gln Pro Phe Val Pro Glu
 65                  70                  75                  80

GAG CAC GGG GGG GTC TCG GTG GTC CCC GGA TCG GGG ACT TTG GTC ATC      346
Glu His Gly Gly Val Ser Val Val Pro Gly Ser Gly Thr Leu Val Ile
                 85                  90                  95

AAC GCC ACG TTG GCC GCG CGG CTC CAG GGG CGC TTC CGC TGC TTC GCC      394
Asn Ala Thr Leu Ala Ala Arg Leu Gln Gly Arg Phe Arg Cys Phe Ala
                100                 105                 110

ACC AAC GCG TTG GGC ACC GCT GTG TCT CCC GAG GCC AAC GTC ATC GCC      442
Thr Asn Ala Leu Gly Thr Ala Val Ser Pro Glu Ala Asn Val Ile Ala
            115                 120                 125

GAG AAC ACT CCG CAG TGG CCG AAG GAG AAG GTG ACC CCG GTG GAG GTG      490
Glu Asn Thr Pro Gln Trp Pro Lys Glu Lys Val Thr Pro Val Glu Val
        130                 135                 140

GAG GAG GGG GAC CCC GTG GTG CTG CCC TGT GAC CCC CCC GAG AGC GCT      538
Glu Glu Gly Asp Pro Val Val Leu Pro Cys Asp Pro Pro Glu Ser Ala
145                 150                 155                 160

GTT CCC CCT AAA ATC TAT TGG CTC AAC AGC GAC ATC GTT CAC ATC GCT      586
Val Pro Pro Lys Ile Tyr Trp Leu Asn Ser Asp Ile Val His Ile Ala
                165                 170                 175

CAG GAC GAG AGG GTC TCT ATG GGG CAG GAT GGG AAC CTC TAC TTC TCC      634
Gln Asp Glu Arg Val Ser Met Gly Gln Asp Gly Asn Leu Tyr Phe Ser
                180                 185                 190

AAC GCC ATG GTG GGC GAC AGC CAC CCC GAC TAC ATC TGC CAC GCT CAC      682
Asn Ala Met Val Gly Asp Ser His Pro Asp Tyr Ile Cys His Ala His
            195                 200                 205

TTC CTC GGC CCC CGC ACC ATC ATC CAG AAG GAG CCC CTC GAC CTC CGC      730
Phe Leu Gly Pro Arg Thr Ile Ile Gln Lys Glu Pro Leu Asp Leu Arg
        210                 215                 220

GTG GCC CCC AGT AAT GCG GTT CGG TCC CGC CGC CCC CGC CTG CTG CTG      778
Val Ala Pro Ser Asn Ala Val Arg Ser Arg Arg Pro Arg Leu Leu Leu
225                 230                 235                 240

CCC CGC GAC CCC CAA ACG ACC ACC ATC GCC CTC CGG GGG GGC AGC GTC      826
Pro Arg Asp Pro Gln Thr Thr Thr Ile Ala Leu Arg Gly Gly Ser Val
                245                 250                 255

GTG TTG GAG TGC ATC GCT GAG GGG CTC CCC ACT CCA TGG GTC CGA TGG      874
Val Leu Glu Cys Ile Ala Glu Gly Leu Pro Thr Pro Trp Val Arg Trp
                260                 265                 270

CGG CGG CTG AAC GGC CCC CTC CTC CCG GGC GGT GTT GGA AAC TTC AAC      922
Arg Arg Leu Asn Gly Pro Leu Leu Pro Gly Gly Val Gly Asn Phe Asn
            275                 280                 285

AAA ACG CTG CGG CTG TGG GGG GTG ACG GAG AGC GAC GAC GGG GAG TAC      970
Lys Thr Leu Arg Leu Trp Gly Val Thr Glu Ser Asp Asp Gly Glu Tyr
        290                 295                 300

GAA TGT GTG GCT GAG AAC GGG AGG GGG ACG GCC AGG GGG ACC CAC AGC     1018
Glu Cys Val Ala Glu Asn Gly Arg Gly Thr Ala Arg Gly Thr His Ser
305                 310                 315                 320

GTC ACC GTG GAG GCG GCC CCA TAT TGG GTG CGG CGG CCA CAG AGT GGG     1066
Val Thr Val Glu Ala Ala Pro Tyr Trp Val Arg Arg Pro Gln Ser Gly
                325                 330                 335

GTC TTC GGG CCG GGG GAG ACG GCG AGG CTG GAC TGC GAG GTG GGG GGG     1114
Val Phe Gly Pro Gly Glu Thr Ala Arg Leu Asp Cys Glu Val Gly Gly
                340                 345                 350

AAA CCC CGA CCC CAA ATC CAA TGG AGC ATC AAT GGG GTC CCC ATC GAG     1162
```

```
                  Lys Pro Arg Pro Gln Ile Gln Trp Ser Ile Asn Gly Val Pro Ile Glu
                              355                 360                 365

GCT GCC GGG GCG GAG CGG CGG TGG CTG CGG GGC GGC GCT TTG GTG CTT        1210
Ala Ala Gly Ala Glu Arg Arg Trp Leu Arg Gly Gly Ala Leu Val Leu
            370                 375                 380

CCG GAG CTG CGG CCG AAC GAC AGC GCG GTG CTG CAG TGC GAG GCG AGG        1258
Pro Glu Leu Arg Pro Asn Asp Ser Ala Val Leu Gln Cys Glu Ala Arg
385                 390                 395                 400

AAC CGC CAC GGC CCC CTA TTG GCC AAC GCC TTC CTG CAC GTC GTG GAG        1306
Asn Arg His Gly Pro Leu Leu Ala Asn Ala Phe Leu His Val Val Glu
                405                 410                 415

CTG CCC CTC CGA ATG CTG ACG GCG GAT GAG CAG CGC TAC GAA GTG GTG        1354
Leu Pro Leu Arg Met Leu Thr Ala Asp Glu Gln Arg Tyr Glu Val Val
            420                 425                 430

GAA AAC CAA ACA GTG TTT CTG CAC TGC AGA ACC TTC GGG GCC CCC GCG        1402
Glu Asn Gln Thr Val Phe Leu His Cys Arg Thr Phe Gly Ala Pro Ala
                435                 440                 445

CCA AAC GTC GAG TGG CTG ACC CCC ACT TTG GAG CCG GCT CTG CAG GAC        1450
Pro Asn Val Glu Trp Leu Thr Pro Thr Leu Glu Pro Ala Leu Gln Asp
            450                 455                 460

GAC CGA TCC TTC GTG TTC ACC AAT GGG AGC CTT CGC GTG AGT GCG GTG        1498
Asp Arg Ser Phe Val Phe Thr Asn Gly Ser Leu Arg Val Ser Ala Val
465                 470                 475                 480

CGG GGG GGG GAC GGG GGG GTC TAC ACC TGC ATG GCC CAA AAC GCC CAC        1546
Arg Gly Gly Asp Gly Gly Val Tyr Thr Cys Met Ala Gln Asn Ala His
                485                 490                 495

AGC AAC GGC AGC CTC ACG GCG CTC CTG GAG GTC AGA GCC CCC ACC CGA        1594
Ser Asn Gly Ser Leu Thr Ala Leu Leu Glu Val Arg Ala Pro Thr Arg
            500                 505                 510

ATT TCG GCC CCC CCC CGA AGC GCC ACC GCC AAA AAA GGG GAG ACG GTG        1642
Ile Ser Ala Pro Pro Arg Ser Ala Thr Ala Lys Lys Gly Glu Thr Val
            515                 520                 525

ACC TTT CAC TGC GGG GCG ACC TTT GAC CCC GCC GTG ACC CCC GGG GAG        1690
Thr Phe His Cys Gly Ala Thr Phe Asp Pro Ala Val Thr Pro Gly Glu
            530                 535                 540

CTG CGA TGG CTG CGG GGG GGG CAG CCG CTG CCC GAC GAC CCC CGG TAT        1738
Leu Arg Trp Leu Arg Gly Gly Gln Pro Leu Pro Asp Asp Pro Arg Tyr
545                 550                 555                 560

TCG GTG GCG GCG GAG ATG ACG GTG TCC AAC GTG GAC TAT GGG GAC GAG        1786
Ser Val Ala Ala Glu Met Thr Val Ser Asn Val Asp Tyr Gly Asp Glu
                565                 570                 575

GGG ACC ATT CAG TGC CGC GCC TCC ACC CCT CTC GAC TCC GCG GAG GCC        1834
Gly Thr Ile Gln Cys Arg Ala Ser Thr Pro Leu Asp Ser Ala Glu Ala
            580                 585                 590

GAA GCG CAG CTC AGA GTC GTG GGC CGC CCC CCA TCC CGG GAC CTC CAA        1882
Glu Ala Gln Leu Arg Val Val Gly Arg Pro Pro Ser Arg Asp Leu Gln
            595                 600                 605

GTG ATG GAG GTG GAC GAA CAC CGC GTG CGC CTC AGC TGG ACC CCG GGG        1930
Val Met Glu Val Asp Glu His Arg Val Arg Leu Ser Trp Thr Pro Gly
610                 615                 620

GAC GAC CAT AAC AGC CCC ATA GAG AAG TTC GTG GTG GAG GAG GAG GAG        1978
Asp Asp His Asn Ser Pro Ile Glu Lys Phe Val Val Glu Glu Glu Glu
625                 630                 635                 640

GAG AGA GAG GAT CTT CAG CGG GGT TTC GGA GCG GCT GAC GTT CCG GGG        2026
Glu Arg Glu Asp Leu Gln Arg Gly Phe Gly Ala Ala Asp Val Pro Gly
                645                 650                 655

CAG CCG TGG ACG CCC CCC CTC CCG CTG TCC CCA TAC GGG CGG TTC CCG        2074
Gln Pro Trp Thr Pro Pro Leu Pro Leu Ser Pro Tyr Gly Arg Phe Pro
            660                 665                 670
```

```
TTC CGG GTG GTG GCC GTT AAC GCC TAC GGG AGG GGG GAG CAC CAC GCC      2122
Phe Arg Val Val Ala Val Asn Ala Tyr Gly Arg Gly Glu His His Ala
        675                 680                 685

CCC AGC GCC CCC ATC GAG ACC CCC CCC GCG GCT CCG GAG CGC AAC CCG      2170
Pro Ser Ala Pro Ile Glu Thr Pro Pro Ala Ala Pro Glu Arg Asn Pro
690                 695                 700

GGG GGG GTC CAT GGG GAG GGC AAT GAG ACC GGC AAC CTC GTC ATC ACC      2218
Gly Gly Val His Gly Glu Gly Asn Glu Thr Gly Asn Leu Val Ile Thr
705                 710                 715                 720

TGG GAG CCC CTC CCC CCC CAG GCC TGG AAC GCC CCC TGG GCG CGG TAC      2266
Trp Glu Pro Leu Pro Pro Gln Ala Trp Asn Ala Pro Trp Ala Arg Tyr
                725                 730                 735

CGC GTG CAG TGG CGG CCA TTG GAG GAG CCC GGC GGG GGG GGC CCT TCG      2314
Arg Val Gln Trp Arg Pro Leu Glu Glu Pro Gly Gly Gly Gly Pro Ser
            740                 745                 750

GGG GGG TTC CCG TGG GCC GAA AGC ACC GTG GAC GCC CCC CCC GTG GTG      2362
Gly Gly Phe Pro Trp Ala Glu Ser Thr Val Asp Ala Pro Pro Val Val
        755                 760                 765

GTG GGG GGG CTC CCC CCG TTC AGC CCC TTC CAG ATC CGC GTC CAG GCC      2410
Val Gly Gly Leu Pro Pro Phe Ser Pro Phe Gln Ile Arg Val Gln Ala
770                 775                 780

GTG AAC GGA GCC GGG AAG GGA CCG GAA GCG ACC CCC GGC GTG GGG CAC      2458
Val Asn Gly Ala Gly Lys Gly Pro Glu Ala Thr Pro Gly Val Gly His
785                 790                 795                 800

AGC GGG GAG GAC CTG CCG TTG GTT TAC CCT GAG AAT GTG GGG GTG GAA      2506
Ser Gly Glu Asp Leu Pro Leu Val Tyr Pro Glu Asn Val Gly Val Glu
                805                 810                 815

CTG CTG AAC AGC AGC ACC GTG CGC GTG AGA TGG ACT TTG GGG GGG GGG      2554
Leu Leu Asn Ser Ser Thr Val Arg Val Arg Trp Thr Leu Gly Gly Gly
            820                 825                 830

CCC AAA GAG CTG CGG GGG CGT CTG AGG GGC TTC CGG GTG CTG TAT TGG      2602
Pro Lys Glu Leu Arg Gly Arg Leu Arg Gly Phe Arg Val Leu Tyr Trp
        835                 840                 845

CGT TTG GGA TGG GTG GGG GAG CGC AGT CGC CGT CAA GCC CCC CCC GAC      2650
Arg Leu Gly Trp Val Gly Glu Arg Ser Arg Arg Gln Ala Pro Pro Asp
850                 855                 860

CCC CCC CAA ATC CCC CAA AGC CCG GCT GAA GAC CCC CCC CCA TTT CCC      2698
Pro Pro Gln Ile Pro Gln Ser Pro Ala Glu Asp Pro Pro Pro Phe Pro
865                 870                 875                 880

CCC GTG GCT CTG ACA GTG GGG GGG GAC GCG CGG GGG GCG CTG CTG GGG      2746
Pro Val Ala Leu Thr Val Gly Gly Asp Ala Arg Gly Ala Leu Leu Gly
                885                 890                 895

GGG CTG CGG CCC TGG AGC CGT TAT CAG CTG CGG GTG TTG GTC TTC AAC      2794
Gly Leu Arg Pro Trp Ser Arg Tyr Gln Leu Arg Val Leu Val Phe Asn
            900                 905                 910

GGG AGG GGG GAC GGC CCC CCC AGC GAA CCC ATC GCC TTC GAG ACC CCC      2842
Gly Arg Gly Asp Gly Pro Pro Ser Glu Pro Ile Ala Phe Glu Thr Pro
        915                 920                 925

GAG GGA GTT CCC GGC CCC CCC GAG GAG CTC CGC GTG GAG CGG TTG GAC      2890
Glu Gly Val Pro Gly Pro Pro Glu Glu Leu Arg Val Glu Arg Leu Asp
930                 935                 940

GAC ACC GCC CTC TCC GTA GTT GAA CGC CGC ACG TTT AAA CGG AGT ATC      2938
Asp Thr Ala Leu Ser Val Val Glu Arg Arg Thr Phe Lys Arg Ser Ile
945                 950                 955                 960

ACG GGA TAT GTG TTG AGA TAC CAG CAG GTG GAG CCG GGC TCG GCC CTC      2986
Thr Gly Tyr Val Leu Arg Tyr Gln Gln Val Glu Pro Gly Ser Ala Leu
                965                 970                 975

CCA GGA GGC TCC GTA CTC CGG GAC CCT CAA TGC GAC CTA AGG GGG CTG      3034
Pro Gly Gly Ser Val Leu Arg Asp Pro Gln Cys Asp Leu Arg Gly Leu
            980                 985                 990
```

-continued

```
AAT GCG CGC TCC CGA TAC CGG CTG GCG CTG CCG AGC ACG CCT CGG GAG      3082
Asn Ala Arg Ser Arg Tyr Arg Leu Ala Leu Pro Ser Thr Pro Arg Glu
        995                 1000                1005

CGC CCC GCC CTG CAG ACG GTG GGG AGC ACG AAA CCG GAA CCG CCC TCC      3130
Arg Pro Ala Leu Gln Thr Val Gly Ser Thr Lys Pro Glu Pro Pro Ser
1010                1015                1020

CCG CTT TGG AGC CGT TTT GGT GTC GGA GGT CGG GGA GGA TTT CAC GGT      3178
Pro Leu Trp Ser Arg Phe Gly Val Gly Gly Arg Gly Gly Phe His Gly
1025                1030                1035                1040

GCT GCT GTG GAG TTT GGT GCA GCC CAG GAG GAC GAC GTG GAG TTC GAG      3226
Ala Ala Val Glu Phe Gly Ala Ala Gln Glu Asp Asp Val Glu Phe Glu
                1045                1050                1055

GTC CAA TTC ATG AAT AAA AGC ACG GAT GAG CCG TGG CGC ACT TCG GGC      3274
Val Gln Phe Met Asn Lys Ser Thr Asp Glu Pro Trp Arg Thr Ser Gly
        1060                1065                1070

CGC GCC AAC TCC TCT TTA AGG CGG TAC CGT CTG GAG GGG CTG CGG CCC      3322
Arg Ala Asn Ser Ser Leu Arg Arg Tyr Arg Leu Glu Gly Leu Arg Pro
        1075                1080                1085

GGC ACC GCC TAC CGA GTC CAA TTC GTG GGC CGG AAC CGC TCC GGG GAA      3370
Gly Thr Ala Tyr Arg Val Gln Phe Val Gly Arg Asn Arg Ser Gly Glu
        1090                1095                1100

AAC GTG GCC TTC TGG GAG AGC GAA GTG CAA ACC AAC GGC ACC GTG GTG      3418
Asn Val Ala Phe Trp Glu Ser Glu Val Gln Thr Asn Gly Thr Val Val
1105                1110                1115                1120

CCG CAG CCT GGT GGG GGG GTT TGC ACC AAG GGG TGG TTC ATC GGC TTC      3466
Pro Gln Pro Gly Gly Gly Val Cys Thr Lys Gly Trp Phe Ile Gly Phe
                1125                1130                1135

GTC AGC TCC GTG GTG CTC CTT CTC CTC ATC CTC CTC ATC CTC TGC TTC      3514
Val Ser Ser Val Val Leu Leu Leu Leu Ile Leu Leu Ile Leu Cys Phe
                1140                1145                1150

ATC AAA CGC AGC AAG GGG GGC AAG TAT TCG GTG AAG GAC AAG GAG GAC      3562
Ile Lys Arg Ser Lys Gly Gly Lys Tyr Ser Val Lys Asp Lys Glu Asp
        1155                1160                1165

ACG CAG GTG GAC TCT GAG GCG CGG CCC ATG AAG GAT GAG ACC TTT GGG      3610
Thr Gln Val Asp Ser Glu Ala Arg Pro Met Lys Asp Glu Thr Phe Gly
        1170                1175                1180

GAG TAC AGG TCG TTG GAG AGC GAA GCG GAG AAG GGT TCG GCT TCG GGT      3658
Glu Tyr Arg Ser Leu Glu Ser Glu Ala Glu Lys Gly Ser Ala Ser Gly
1185                1190                1195                1200

TCC GGT GCC GGT TCC GGT GTG GGT TCT CCG GGT CGG GGT CCG TGC GCG      3706
Ser Gly Ala Gly Ser Gly Val Gly Ser Pro Gly Arg Gly Pro Cys Ala
                1205                1210                1215

GCG GGC AGC GAA GAC AGC CTG GCG GGG TAC GGA GGC AGC GGG GAT GTG      3754
Ala Gly Ser Glu Asp Ser Leu Ala Gly Tyr Gly Gly Ser Gly Asp Val
                1220                1225                1230

CAG TTC AAT GAG GAT GGA TCC TTC ATC GGG CAG TAC CGC GGA CCC GGA      3802
Gln Phe Asn Glu Asp Gly Ser Phe Ile Gly Gln Tyr Arg Gly Pro Gly
        1235                1240                1245

GCC GGA CCC GGC AGC TCC GGC CCT GCC AGC CCC TGT GCT GGG CCC CCC      3850
Ala Gly Pro Gly Ser Ser Gly Pro Ala Ser Pro Cys Ala Gly Pro Pro
1250                1255                1260

CTG GAT TAAATGGGGG GGAATGGGGT GGGGGATACC CATAGGGGGA GCCCTGGAGT       3906
Leu Asp
1265

GGTGGGAACC ATACGGGGTC CCCCGTGGCC ATGGAGGGGG GGGGTTCATA CGGTGGTAAT    3966

GGGGGGCACG GGGGGATAGG AATTC                                          3991
```

(2) INFORMATION FOR SEQ ID NO:4:

(i) SEQUENCE CHARACTERISTICS:
    (A) LENGTH: 1266 amino acids
    (B) TYPE: amino acid
    (D) TOPOLOGY: linear (ii) MOLECULE TYPE: protein (xi) SEQUENCE DESCRIPTION: SEQ ID NO:4:

```
Met Ala Leu Pro Met Val Gly Leu Leu Leu Leu Leu Leu Gly Gly
  1               5                  10                  15

Pro Gly Ala Ala Ile Thr Ile Pro Pro Glu Tyr Gly Ala His Asp Phe
             20                  25                  30

Leu Gln Pro Pro Glu Leu Thr Glu Glu Pro Pro Glu Gln Leu Val Val
         35                  40                  45

Phe Pro Ser Asp Asp Ile Val Leu Lys Cys Val Ala Thr Gly Asn Pro
     50                  55                  60

Pro Val Gln Tyr Arg Trp Ser Arg Glu Asp Gln Pro Phe Val Pro Glu
 65                  70                  75                  80

Glu His Gly Gly Val Ser Val Val Pro Gly Ser Gly Thr Leu Val Ile
                 85                  90                  95

Asn Ala Thr Leu Ala Ala Arg Leu Gln Gly Arg Phe Arg Cys Phe Ala
                100                 105                 110

Thr Asn Ala Leu Gly Thr Ala Val Ser Pro Glu Ala Asn Val Ile Ala
            115                 120                 125

Glu Asn Thr Pro Gln Trp Pro Lys Glu Lys Val Thr Pro Val Glu Val
            130                 135                 140

Glu Glu Gly Asp Pro Val Val Leu Pro Cys Asp Pro Pro Glu Ser Ala
145                 150                 155                 160

Val Pro Pro Lys Ile Tyr Trp Leu Asn Ser Asp Ile Val His Ile Ala
                165                 170                 175

Gln Asp Glu Arg Val Ser Met Gly Gln Asp Gly Asn Leu Tyr Phe Ser
                180                 185                 190

Asn Ala Met Val Gly Asp Ser His Pro Asp Tyr Ile Cys His Ala His
            195                 200                 205

Phe Leu Gly Pro Arg Thr Ile Ile Gln Lys Glu Pro Leu Asp Leu Arg
210                 215                 220

Val Ala Pro Ser Asn Ala Val Arg Ser Arg Arg Pro Arg Leu Leu Leu
225                 230                 235                 240

Pro Arg Asp Pro Gln Thr Thr Thr Ile Ala Leu Arg Gly Gly Ser Val
                245                 250                 255

Val Leu Glu Cys Ile Ala Glu Gly Leu Pro Thr Pro Trp Val Arg Trp
            260                 265                 270

Arg Arg Leu Asn Gly Pro Leu Leu Pro Gly Gly Val Gly Asn Phe Asn
                275                 280                 285

Lys Thr Leu Arg Leu Trp Gly Val Thr Glu Ser Asp Asp Gly Glu Tyr
            290                 295                 300

Glu Cys Val Ala Glu Asn Gly Arg Gly Thr Ala Arg Gly Thr His Ser
305                 310                 315                 320

Val Thr Val Glu Ala Ala Pro Tyr Trp Val Arg Arg Pro Gln Ser Gly
                325                 330                 335

Val Phe Gly Pro Gly Glu Thr Ala Arg Leu Asp Cys Glu Val Gly Gly
            340                 345                 350

Lys Pro Arg Pro Gln Ile Gln Trp Ser Ile Asn Gly Val Pro Ile Glu
            355                 360                 365
```

```
Ala Ala Gly Ala Glu Arg Arg Trp Leu Arg Gly Gly Ala Leu Val Leu
    370                 375                 380

Pro Glu Leu Arg Pro Asn Asp Ser Ala Val Leu Gln Cys Glu Ala Arg
385                 390                 395                 400

Asn Arg His Gly Pro Leu Leu Ala Asn Ala Phe Leu His Val Val Glu
                405                 410                 415

Leu Pro Leu Arg Met Leu Thr Ala Asp Glu Gln Arg Tyr Glu Val Val
            420                 425                 430

Glu Asn Gln Thr Val Phe Leu His Cys Arg Thr Phe Gly Ala Pro Ala
        435                 440                 445

Pro Asn Val Glu Trp Leu Thr Pro Thr Leu Glu Pro Ala Leu Gln Asp
    450                 455                 460

Asp Arg Ser Phe Val Phe Thr Asn Gly Ser Leu Arg Val Ser Ala Val
465                 470                 475                 480

Arg Gly Gly Asp Gly Gly Val Tyr Thr Cys Met Ala Gln Asn Ala His
                485                 490                 495

Ser Asn Gly Ser Leu Thr Ala Leu Leu Glu Val Arg Ala Pro Thr Arg
            500                 505                 510

Ile Ser Ala Pro Pro Arg Ser Ala Thr Ala Lys Lys Gly Glu Thr Val
        515                 520                 525

Thr Phe His Cys Gly Ala Thr Phe Asp Pro Ala Val Thr Pro Gly Glu
    530                 535                 540

Leu Arg Trp Leu Arg Gly Gly Gln Pro Leu Pro Asp Asp Pro Arg Tyr
545                 550                 555                 560

Ser Val Ala Ala Glu Met Thr Val Ser Asn Val Asp Tyr Gly Asp Glu
                565                 570                 575

Gly Thr Ile Gln Cys Arg Ala Ser Thr Pro Leu Asp Ser Ala Glu Ala
            580                 585                 590

Glu Ala Gln Leu Arg Val Val Gly Arg Pro Pro Ser Arg Asp Leu Gln
        595                 600                 605

Val Met Glu Val Asp Glu His Arg Val Arg Leu Ser Trp Thr Pro Gly
    610                 615                 620

Asp Asp His Asn Ser Pro Ile Glu Lys Phe Val Val Glu Glu Glu Glu
625                 630                 635                 640

Glu Arg Glu Asp Leu Gln Arg Gly Phe Gly Ala Ala Asp Val Pro Gly
                645                 650                 655

Gln Pro Trp Thr Pro Pro Leu Pro Leu Ser Pro Tyr Gly Arg Phe Pro
            660                 665                 670

Phe Arg Val Val Ala Val Asn Ala Tyr Gly Arg Gly Glu His His Ala
        675                 680                 685

Pro Ser Ala Pro Ile Glu Thr Pro Ala Ala Pro Glu Arg Asn Pro
    690                 695                 700

Gly Gly Val His Gly Glu Gly Asn Glu Thr Gly Asn Leu Val Ile Thr
705                 710                 715                 720

Trp Glu Pro Leu Pro Pro Gln Ala Trp Asn Ala Pro Trp Ala Arg Tyr
                725                 730                 735

Arg Val Gln Trp Arg Pro Leu Glu Glu Pro Gly Gly Gly Pro Ser
            740                 745                 750

Gly Gly Phe Pro Trp Ala Glu Ser Thr Val Asp Ala Pro Pro Val Val
        755                 760                 765

Val Gly Gly Leu Pro Pro Phe Ser Pro Phe Gln Ile Arg Val Gln Ala
    770                 775                 780

Val Asn Gly Ala Gly Lys Gly Pro Glu Ala Thr Pro Gly Val Gly His
```

-continued

```
785                 790                 795                 800

Ser Gly Glu Asp Leu Pro Leu Val Tyr Pro Glu Asn Val Gly Val Glu
                805                 810                 815

Leu Leu Asn Ser Ser Thr Val Arg Val Arg Trp Thr Leu Gly Gly Gly
                820                 825                 830

Pro Lys Glu Leu Arg Gly Arg Leu Arg Gly Phe Arg Val Leu Tyr Trp
                835                 840                 845

Arg Leu Gly Trp Val Gly Glu Arg Ser Arg Arg Gln Ala Pro Pro Asp
            850                 855                 860

Pro Pro Gln Ile Pro Gln Ser Pro Ala Glu Asp Pro Pro Phe Pro
865                 870                 875                 880

Pro Val Ala Leu Thr Val Gly Gly Asp Ala Arg Gly Ala Leu Leu Gly
                885                 890                 895

Gly Leu Arg Pro Trp Ser Arg Tyr Gln Leu Arg Val Leu Val Phe Asn
                900                 905                 910

Gly Arg Gly Asp Gly Pro Pro Ser Glu Pro Ile Ala Phe Glu Thr Pro
                915                 920                 925

Glu Gly Val Pro Gly Pro Pro Glu Glu Leu Arg Val Glu Arg Leu Asp
            930                 935                 940

Asp Thr Ala Leu Ser Val Val Glu Arg Arg Thr Phe Lys Arg Ser Ile
945                 950                 955                 960

Thr Gly Tyr Val Leu Arg Tyr Gln Gln Val Glu Pro Gly Ser Ala Leu
                965                 970                 975

Pro Gly Gly Ser Val Leu Arg Asp Pro Gln Cys Asp Leu Arg Gly Leu
                980                 985                 990

Asn Ala Arg Ser Arg Tyr Arg Leu Ala Leu Pro Ser Thr Pro Arg Glu
            995                 1000                1005

Arg Pro Ala Leu Gln Thr Val Gly Ser Thr Lys Pro Glu Pro Pro Ser
    1010                1015                1020

Pro Leu Trp Ser Arg Phe Gly Val Gly Gly Arg Gly Phe His Gly
1025                1030                1035                1040

Ala Ala Val Glu Phe Gly Ala Gln Glu Asp Asp Val Glu Phe Glu
                1045                1050                1055

Val Gln Phe Met Asn Lys Ser Thr Asp Glu Pro Trp Arg Thr Ser Gly
                1060                1065                1070

Arg Ala Asn Ser Ser Leu Arg Arg Tyr Arg Leu Glu Gly Leu Arg Pro
            1075                1080                1085

Gly Thr Ala Tyr Arg Val Gln Phe Val Gly Arg Asn Arg Ser Gly Glu
            1090                1095                1100

Asn Val Ala Phe Trp Glu Ser Glu Val Gln Thr Asn Gly Thr Val Val
1105                1110                1115                1120

Pro Gln Pro Gly Gly Gly Val Cys Thr Lys Gly Trp Phe Ile Gly Phe
                1125                1130                1135

Val Ser Ser Val Val Leu Leu Leu Leu Ile Leu Leu Ile Leu Cys Phe
                1140                1145                1150

Ile Lys Arg Ser Lys Gly Gly Lys Tyr Ser Val Lys Asp Lys Glu Asp
            1155                1160                1165

Thr Gln Val Asp Ser Glu Ala Arg Pro Met Lys Asp Glu Thr Phe Gly
    1170                1175                1180

Glu Tyr Arg Ser Leu Glu Ser Glu Ala Glu Lys Gly Ser Ala Ser Gly
1185                1190                1195                1200

Ser Gly Ala Gly Ser Gly Val Gly Ser Pro Gly Arg Gly Pro Cys Ala
            1205                1210                1215
```

```
Ala Gly Ser Glu Asp Ser Leu Ala Gly Tyr Gly Gly Ser Gly Asp Val
        1220                1225                1230

Gln Phe Asn Glu Asp Gly Ser Phe Ile Gly Gln Tyr Arg Gly Pro Gly
        1235                1240                1245

Ala Gly Pro Gly Ser Ser Gly Pro Ala Ser Pro Cys Ala Gly Pro Pro
        1250                1255                1260

Leu Asp
1265

(2) INFORMATION FOR SEQ ID NO:5:

(i) SEQUENCE CHARACTERISTICS:
        (A) LENGTH: 406 amino acids
        (B) TYPE: amino acid
        (D) TOPOLOGY: linear (ii) MOLECULE TYPE: protein (v) FRAGMENT TYPE: C-terminal (xi) SEQUENCE DESCRIPTION: SEQ ID NO:5:

Ala Pro Pro Asp Pro Pro Gln Ile Pro Gln Ser Pro Ala Glu Asp Pro
1               5                   10                  15

Pro Pro Phe Pro Pro Val Ala Leu Thr Val Gly Gly Asp Ala Arg Gly
            20                  25                  30

Ala Leu Leu Gly Gly Leu Arg Pro Trp Ser Arg Tyr Gln Leu Arg Val
        35                  40                  45

Leu Val Phe Asn Gly Arg Gly Asp Gly Pro Pro Ser Glu Pro Ile Ala
    50                  55                  60

Phe Glu Thr Pro Glu Gly Val Pro Gly Pro Pro Glu Glu Leu Arg Val
65                  70                  75                  80

Glu Arg Leu Asp Asp Thr Ala Leu Ser Val Val Glu Arg Arg Thr Phe
                85                  90                  95

Lys Arg Ser Ile Thr Gly Tyr Val Leu Arg Tyr Gln Gln Val Glu Pro
            100                 105                 110

Gly Ser Ala Leu Pro Gly Gly Ser Val Leu Arg Asp Pro Gln Cys Asp
        115                 120                 125

Leu Arg Gly Leu Asn Ala Arg Ser Arg Tyr Arg Leu Ala Leu Pro Ser
    130                 135                 140

Thr Pro Arg Glu Arg Pro Ala Leu Gln Thr Val Gly Ser Thr Lys Pro
145                 150                 155                 160

Glu Pro Pro Ser Pro Leu Trp Ser Arg Phe Gly Val Gly Gly Arg Gly
                165                 170                 175

Gly Phe His Gly Ala Ala Val Glu Phe Gly Ala Ala Gln Glu Asp Asp
            180                 185                 190

Val Glu Phe Glu Val Gln Phe Met Asn Lys Ser Thr Asp Glu Pro Trp
        195                 200                 205

Arg Thr Ser Gly Arg Ala Asn Ser Ser Leu Arg Tyr Arg Leu Glu
    210                 215                 220

Gly Leu Arg Pro Gly Thr Ala Tyr Arg Val Gln Phe Val Gly Arg Asn
225                 230                 235                 240

Arg Ser Gly Glu Asn Val Ala Phe Trp Glu Ser Glu Val Gln Thr Asn
                245                 250                 255

Gly Thr Val Val Pro Gln Pro Gly Gly Gly Val Cys Thr Lys Gly Trp
            260                 265                 270

Phe Ile Gly Phe Val Ser Ser Val Val Leu Leu Leu Leu Ile Leu Leu
```

```
            275                 280                 285
Ile Leu Cys Phe Ile Lys Arg Ser Lys Gly Gly Lys Tyr Ser Val Lys
    290                 295                 300

Asp Lys Glu Asp Thr Gln Val Asp Ser Glu Ala Arg Pro Met Lys Asp
305                 310                 315                 320

Glu Thr Phe Gly Glu Tyr Arg Ser Leu Glu Ser Glu Ala Glu Lys Gly
                325                 330                 335

Ser Ala Ser Gly Ser Gly Ala Gly Ser Gly Val Gly Ser Pro Gly Arg
                340                 345                 350

Gly Pro Cys Ala Ala Gly Ser Glu Asp Ser Leu Ala Gly Tyr Gly Gly
            355                 360                 365

Ser Gly Asp Val Gln Phe Asn Glu Asp Gly Ser Phe Ile Gly Gln Tyr
        370                 375                 380

Arg Gly Pro Gly Ala Gly Pro Gly Ser Ser Gly Pro Ala Ser Pro Cys
385                 390                 395                 400

Ala Gly Pro Pro Leu Asp
                405
```

(2) INFORMATION FOR SEQ ID NO:6:

(i) SEQUENCE CHARACTERISTICS:
        (A) LENGTH: 23 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO:6:

CAACCATGGG CAATGTGGGG GTG                                     23

(2) INFORMATION FOR SEQ ID NO:7:

(i) SEQUENCE CHARACTERISTICS:
        (A) LENGTH: 23 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO:7:

CAGCCATGGG CCCCGGCCCC CCC                                     23

(2) INFORMATION FOR SEQ ID NO:8:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO:8:

AAAGGATCCC TACCACCCCT TGGT                    24

(2) INFORMATION FOR SEQ ID NO:9:

(i) SEQUENCE CHARACTERISTICS:
        (A) LENGTH: 23 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO:9:

CAACCATGGG CGCCCCCCCC GAC                     23

(2) INFORMATION FOR SEQ ID NO:10:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO:10:

AAAGGATCCC TATTAATCCA GGGG                    24

(2) INFORMATION FOR SEQ ID NO:11:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO:11:

TGGCAAATAC TCAGTGAA                           18

(2) INFORMATION FOR SEQ ID NO:12:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO:12:

CCTTCTCTTC ATTGTCAC                           18

(2) INFORMATION FOR SEQ ID NO:13:

(i) SEQUENCE CHARACTERISTICS:
        (A) LENGTH: 3888 base pairs
        (B) TYPE: nucleic acid
        (C) STRANDEDNESS: double
        (D) TOPOLOGY: linear (ii) MOLECULE TYPE: cDNA (iii) HYPOTHETICAL: NO (iv) ANTI-SENSE: NO (ix) FEATURE:
        (A) NAME/KEY: CDS
        (B) LOCATION: 12..3773

(xi) SEQUENCE DESCRIPTION: SEQ ID NO:13:

```
CGCCGGGAAA G ATG GTC GTG GCG CTG CGG TAC GTG TGG CCT CTC CTC CTC        50
             Met Val Val Ala Leu Arg Tyr Val Trp Pro Leu Leu Leu
              1               5                  10

TGC AGC CCC TGC CTG CTT ATC CAG ATC CCC GAG GAA TAT GAA GGA CAC         98
Cys Ser Pro Cys Leu Leu Ile Gln Ile Pro Glu Glu Tyr Glu Gly His
         15                  20                  25

CAT GTG ATG GAG CCA CCT GTC ATC ACG GAA CAG TCT CCA CGG CGC CTG        146
His Val Met Glu Pro Pro Val Ile Thr Glu Gln Ser Pro Arg Arg Leu
 30                  35                  40                  45

GTT GTC TTC CCC ACA GAT GAC ATC AGC CTC AAG TGT GAG GCC AGT GGC        194
Val Val Phe Pro Thr Asp Asp Ile Ser Leu Lys Cys Glu Ala Ser Gly
                 50                  55                  60

AAG CCC GAA GTG CAG TTC CGC TGG ACG AGG GAT GGT GTC CAC TTC AAA        242
Lys Pro Glu Val Gln Phe Arg Trp Thr Arg Asp Gly Val His Phe Lys
             65                  70                  75

CCC AAG GAA GAG CTG GGT GTG ACC GTG TAC CAG TCG CCC CAC TCT GGC        290
Pro Lys Glu Glu Leu Gly Val Thr Val Tyr Gln Ser Pro His Ser Gly
         80                  85                  90

TCC TTC ACC ATC ACG GGC AAC AAC AGC AAC TTT GCT CAG AGG TTC CAG        338
Ser Phe Thr Ile Thr Gly Asn Asn Ser Asn Phe Ala Gln Arg Phe Gln
     95                 100                 105

GGC ATC TAC CGC TGC TTT GCC AGC AAT AAG CTG GGC ACC GCC ATG TCC        386
Gly Ile Tyr Arg Cys Phe Ala Ser Asn Lys Leu Gly Thr Ala Met Ser
110                 115                 120                 125

CAT GAG ATC CGG CTC ATG GCC GAG GGT GCC CCC AAG TGG CCA AAG GAG        434
His Glu Ile Arg Leu Met Ala Glu Gly Ala Pro Lys Trp Pro Lys Glu
                130                 135                 140

ACA GTG AAG CCC GTG GAG GTG GAG GAA GGG GAG TCA GTG GTT CTG CCT        482
Thr Val Lys Pro Val Glu Val Glu Glu Gly Glu Ser Val Val Leu Pro
            145                 150                 155

TGC AAC CCT CCC CCA AGT GCA GAG CCT CTC CGG ATC TAC TGG ATG AAC        530
Cys Asn Pro Pro Pro Ser Ala Glu Pro Leu Arg Ile Tyr Trp Met Asn
        160                 165                 170

AGC AAG ATC TTG CAC ATC AAG CAG GAC GAG CGG GTG ACG ATG GGC CAG        578
Ser Lys Ile Leu His Ile Lys Gln Asp Glu Arg Val Thr Met Gly Gln
    175                 180                 185

AAC GGC AAC CTC TAC TTT GCC AAT GTG CTC ACC TCC GAC AAC CAC TCA        626
Asn Gly Asn Leu Tyr Phe Ala Asn Val Leu Thr Ser Asp Asn His Ser
190                 195                 200                 205

GAC TAC ATC TGC CAC GCC CAC TTC CCA GGC ACC AGG ACC ATC ATT CAG        674
Asp Tyr Ile Cys His Ala His Phe Pro Gly Thr Arg Thr Ile Ile Gln
                210                 215                 220

AAG GAA CCC ATT GAC CTC CGG GTC AAG GCC ACC AAC AGC ATG ATT GAC        722
```

-continued

| | | | | | | | | | | | | | | |
|---|---|---|---|---|---|---|---|---|---|---|---|---|---|---|
| Lys | Glu | Pro | Ile | Asp | Leu | Arg | Val | Lys | Ala | Thr | Asn | Ser | Met | Ile | Asp |
| | | 225 | | | | 230 | | | | 235 | | | | | |

```
AGG AAG CCG CGC CTG CTC TTC CCC ACC AAC TCC AGC AGC CAC CTG GTG        770
Arg Lys Pro Arg Leu Leu Phe Pro Thr Asn Ser Ser Ser His Leu Val
        240                 245                 250

GCC TTG CAG GGG CAG CCA TTG GTC CTG GAG TGC ATC GCC GAG GGC TTT        818
Ala Leu Gln Gly Gln Pro Leu Val Leu Glu Cys Ile Ala Glu Gly Phe
        255                 260                 265

CCC ACG CCC ACC ATC AAA TGG CTG CGC CCC AGT GGC CCC ATG CCA GCC        866
Pro Thr Pro Thr Ile Lys Trp Leu Arg Pro Ser Gly Pro Met Pro Ala
270                 275                 280                 285

GAC CGT GTC ACC TAC CAG AAC CAC AAC AAG ACC CTG CAG CTG CTG AAA        914
Asp Arg Val Thr Tyr Gln Asn His Asn Lys Thr Leu Gln Leu Leu Lys
                290                 295                 300

GTG GGC GAG GAG GAT GAT GGC GAG TAC CGC TGC CTG GCC GAG AAC TCA        962
Val Gly Glu Glu Asp Asp Gly Glu Tyr Arg Cys Leu Ala Glu Asn Ser
                305                 310                 315

CTG GGC AGT GCC CGG CAT GCG TAC TAT GTC ACC GTG GAG GCT GCC CCG       1010
Leu Gly Ser Ala Arg His Ala Tyr Tyr Val Thr Val Glu Ala Ala Pro
        320                 325                 330

TAC TGG CTG CAC AAG CCC CAG AGC CAT CTA TAT GGG CCA GGA GAG ACT       1058
Tyr Trp Leu His Lys Pro Gln Ser His Leu Tyr Gly Pro Gly Glu Thr
        335                 340                 345

GCC CGC CTG GAC TGC CAA GTC CAG GGC AGG CCC CAA CCA GAG GTC ACC       1106
Ala Arg Leu Asp Cys Gln Val Gln Gly Arg Pro Gln Pro Glu Val Thr
350                 355                 360                 365

TGG AGA ATC AAC GGG ATC CCT GTG GAG GAG CTG GCC AAA GAC CAG AAG       1154
Trp Arg Ile Asn Gly Ile Pro Val Glu Glu Leu Ala Lys Asp Gln Lys
                370                 375                 380

TAC CGG ATT CAG CGT GGC GCC CTG ATC CTG AGC AAC GTG CAG CCC AGT       1202
Tyr Arg Ile Gln Arg Gly Ala Leu Ile Leu Ser Asn Val Gln Pro Ser
                385                 390                 395

GAC ACA ATG GTG ACC CAA TGT GAG GCC CGC AAC CGG CAC GGG CTC TTG       1250
Asp Thr Met Val Thr Gln Cys Glu Ala Arg Asn Arg His Gly Leu Leu
                400                 405                 410

CTG GCC AAT GCC TAC ATC TAC GTT GTC CAG CTG CCA GCC AAG ATC CTG       1298
Leu Ala Asn Ala Tyr Ile Tyr Val Val Gln Leu Pro Ala Lys Ile Leu
        415                 420                 425

ACT GCG GAC AAT CAG ACG TAC ATG GCT GTC CAG GGC AGC ACT GCC TAC       1346
Thr Ala Asp Asn Gln Thr Tyr Met Ala Val Gln Gly Ser Thr Ala Tyr
430                 435                 440                 445

CTT CTG TGC AAG GCC TTC GGA GCG CCT GTG CCC AGT GTT CAG TGG CTG       1394
Leu Leu Cys Lys Ala Phe Gly Ala Pro Val Pro Ser Val Gln Trp Leu
                450                 455                 460

GAC GAG GAT GGG ACA ACA GTG CTT CAG GAC GAA CGC TTC TTC CCC TAT       1442
Asp Glu Asp Gly Thr Thr Val Leu Gln Asp Glu Arg Phe Phe Pro Tyr
                465                 470                 475

GCC AAT GGG ACC CTG GGC ATT CGA GAC CTC CAG GCC AAT GAC ACC GGA       1490
Ala Asn Gly Thr Leu Gly Ile Arg Asp Leu Gln Ala Asn Asp Thr Gly
        480                 485                 490

CGC TAC TTC TGC CTG GCT GCC AAT GAC CAA AAC AAT GTT ACC ATC ATG       1538
Arg Tyr Phe Cys Leu Ala Ala Asn Asp Gln Asn Asn Val Thr Ile Met
        495                 500                 505

GCT AAC CTG AAG GTT AAA GAT GCA ACT CAG ATC ACT CAG GGG CCC CGC       1586
Ala Asn Leu Lys Val Lys Asp Ala Thr Gln Ile Thr Gln Gly Pro Arg
510                 515                 520                 525

AGC ACA ATC GAG AAG AAA GGT TCC AGG GTG ACC TTC ACG TGC CAG GCC       1634
Ser Thr Ile Glu Lys Lys Gly Ser Arg Val Thr Phe Thr Cys Gln Ala
                530                 535                 540
```

```
TCC TTT GAC CCC TCC TTG CAG CCC AGC ATC ACC TGG CGT GGG GAC GGT    1682
Ser Phe Asp Pro Ser Leu Gln Pro Ser Ile Thr Trp Arg Gly Asp Gly
            545                 550                 555

CGA GAC CTC CAG GAG CTT GGG GAC AGT GAC AAG TAC TTC ATA GAG GAT    1730
Arg Asp Leu Gln Glu Leu Gly Asp Ser Asp Lys Tyr Phe Ile Glu Asp
            560                 565                 570

GGG CGC CTG GTC ATC CAC AGC CTG GAC TAC AGC GAC CAG GGC AAC TAC    1778
Gly Arg Leu Val Ile His Ser Leu Asp Tyr Ser Asp Gln Gly Asn Tyr
575                 580                 585

AGC TGC GTG GCC AGT ACC GAA CTG GAT GTG GTG GAG AGT AGG GCA CAG    1826
Ser Cys Val Ala Ser Thr Glu Leu Asp Val Val Glu Ser Arg Ala Gln
590                 595                 600                 605

CTC TTG GTG GTG GGG AGC CCT GGG CCG GTG CCA CGG CTG GTG CTG TCC    1874
Leu Leu Val Val Gly Ser Pro Gly Pro Val Pro Arg Leu Val Leu Ser
                610                 615                 620

GAC CTG CAC CTG CTG ACG CAG AGC CAG GTG CGC GTG TCC TGG AGT CCT    1922
Asp Leu His Leu Leu Thr Gln Ser Gln Val Arg Val Ser Trp Ser Pro
                625                 630                 635

GCA GAA GAC CAC AAT GCC CCC ATT GAG AAA TAT GAC ATT GAA TTT GAG    1970
Ala Glu Asp His Asn Ala Pro Ile Glu Lys Tyr Asp Ile Glu Phe Glu
                640                 645                 650

GAC AAG GAA ATG GCG CCT GAA AAA TGG TAC AGT CTG GGC AAG GTT CCA    2018
Asp Lys Glu Met Ala Pro Glu Lys Trp Tyr Ser Leu Gly Lys Val Pro
655                 660                 665

GGG AAC CAG ACC TCT ACC ACC CTC AAG CTG TCG CCC TAT GTC CAC TAC    2066
Gly Asn Gln Thr Ser Thr Thr Leu Lys Leu Ser Pro Tyr Val His Tyr
670                 675                 680                 685

ACC TTT AGG GTT ACT GCC ATA AAC AAA TAT GGC CCC GGG GAG CCC AGC    2114
Thr Phe Arg Val Thr Ala Ile Asn Lys Tyr Gly Pro Gly Glu Pro Ser
                690                 695                 700

CCG GTC TCT GAG ACT GTG GTC ACA CCT GAG GCA GCC CCA GAG AAG AAC    2162
Pro Val Ser Glu Thr Val Val Thr Pro Glu Ala Ala Pro Glu Lys Asn
                705                 710                 715

CCT GTG GAT GTG AAG GGG GAA GGA AAT GAG ACC ACC AAT ATG GTC ATC    2210
Pro Val Asp Val Lys Gly Glu Gly Asn Glu Thr Thr Asn Met Val Ile
                720                 725                 730

ACG TGG AAG CCG CTC CGG TGG ATG GAC TGG AAC GCC CCC CAG GTT CAG    2258
Thr Trp Lys Pro Leu Arg Trp Met Asp Trp Asn Ala Pro Gln Val Gln
            735                 740                 745

TAC CGC GTG CAG TGG CGC CCT CAG GGG ACA CGA GGG CCC TGG CAG GAG    2306
Tyr Arg Val Gln Trp Arg Pro Gln Gly Thr Arg Gly Pro Trp Gln Glu
750                 755                 760                 765

CAG ATT GTC AGC GAC CCC TTC CTG GTG GTG TCC AAC ACG TCC ACC TTC    2354
Gln Ile Val Ser Asp Pro Phe Leu Val Val Ser Asn Thr Ser Thr Phe
                770                 775                 780

GTG CCC TAT GAG ATC AAA GTC CAG GCC GTC AAC AGC CAG GGC AAG GGA    2402
Val Pro Tyr Glu Ile Lys Val Gln Ala Val Asn Ser Gln Gly Lys Gly
                785                 790                 795

CCA GAG CCC CAG GTC ACT ATC GGC TAC TCT GGA GAG GAC TAC CCC CAG    2450
Pro Glu Pro Gln Val Thr Ile Gly Tyr Ser Gly Glu Asp Tyr Pro Gln
            800                 805                 810

GCA ATC CCT GAG CTG GAA GGC ATT GAA ATC CTC AAC TCA AGT GCC GTG    2498
Ala Ile Pro Glu Leu Glu Gly Ile Glu Ile Leu Asn Ser Ser Ala Val
815                 820                 825

CTG GTC AAG TGG CGG CCG GTG GAC CTG GCC CAG GTC AAG GGC CAC CTC    2546
Leu Val Lys Trp Arg Pro Val Asp Leu Ala Gln Val Lys Gly His Leu
830                 835                 840                 845

CGC GGA TAC AAT GTG ACG TAC TGG AGG GAG GGC AGT CAG AGG AAG CAC    2594
Arg Gly Tyr Asn Val Thr Tyr Trp Arg Glu Gly Ser Gln Arg Lys His
                850                 855                 860
```

```
AGC AAG AGA CAT ATC CAC AAA GAC CAT GTG GTG GTG CCC GCC AAC ACC    2642
Ser Lys Arg His Ile His Lys Asp His Val Val Val Pro Ala Asn Thr
            865                 870                 875

ACC AGT GTC ATC CTC AGT GGC TTG CGG CCC TAT AGC TCC TAC CAC CTG    2690
Thr Ser Val Ile Leu Ser Gly Leu Arg Pro Tyr Ser Ser Tyr His Leu
            880                 885                 890

GAG GTG CAG GCC TTT AAC GGG CGA GGA TCG GGG CCC GCC AGC GAG TTC    2738
Glu Val Gln Ala Phe Asn Gly Arg Gly Ser Gly Pro Ala Ser Glu Phe
895                 900                 905

ACC TTC AGC ACC CCA GAG GGA GTG CCT GGC CAC CCC GAG GCG TTG CAC    2786
Thr Phe Ser Thr Pro Glu Gly Val Pro Gly His Pro Glu Ala Leu His
910                 915                 920                 925

CTG GAG TGC CAG TCG AAC ACC AGC CTG CTG CTG CGC TGG CAG CCC CCA    2834
Leu Glu Cys Gln Ser Asn Thr Ser Leu Leu Leu Arg Trp Gln Pro Pro
            930                 935                 940

CTC AGC CAC AAC GGC GTG CTC ACC GGC TAC GTG CTC TCC TAC CAC CCC    2882
Leu Ser His Asn Gly Val Leu Thr Gly Tyr Val Leu Ser Tyr His Pro
            945                 950                 955

CTG GAT GAG GGG GGC AAG GGG CAA CTG TCC TTC AAC CTT CGG GAC CCC    2930
Leu Asp Glu Gly Gly Lys Gly Gln Leu Ser Phe Asn Leu Arg Asp Pro
            960                 965                 970

GAA CTT CGG ACA CAC AAC CTG ACC GAT CTC AGC CCC CAC CTG CGG TAC    2978
Glu Leu Arg Thr His Asn Leu Thr Asp Leu Ser Pro His Leu Arg Tyr
975                 980                 985

CGC TTC CAG CTT CAG GCC ACC ACC AAA GAG GGC CCT GGT GAA GCC ATC    3026
Arg Phe Gln Leu Gln Ala Thr Thr Lys Glu Gly Pro Gly Glu Ala Ile
990                 995                 1000                1005

GTA CGG GAA GGA GGC ACT ATG GCC TTG TCT GGG ATC TCA GAT TTT GGC    3074
Val Arg Glu Gly Gly Thr Met Ala Leu Ser Gly Ile Ser Asp Phe Gly
            1010                1015                1020

AAC ATC TCA GCC ACA GCG GGT GAA AAC TAC AGT GTC GTC TCC TGG GTC    3122
Asn Ile Ser Ala Thr Ala Gly Glu Asn Tyr Ser Val Val Ser Trp Val
            1025                1030                1035

CCC AAG GAG GGC CAG TGC AAC TTC AGG TTC CAT ATC TTG TTC AAA GCC    3170
Pro Lys Glu Gly Gln Cys Asn Phe Arg Phe His Ile Leu Phe Lys Ala
            1040                1045                1050

TTG GGA GAA GAG AAG GGT GGG GCT TCC CTT TCG CCA CAG TAT GTC AGC    3218
Leu Gly Glu Glu Lys Gly Gly Ala Ser Leu Ser Pro Gln Tyr Val Ser
            1055                1060                1065

TAC AAC CAG AGC TCC TAC ACG CAG TGG GAC CTG CAG CCT GAC ACT GAC    3266
Tyr Asn Gln Ser Ser Tyr Thr Gln Trp Asp Leu Gln Pro Asp Thr Asp
1070                1075                1080                1085

TAC GAG ATC CAC TTG TTT AAG GAG AGG ATG TTC CGG CAC CAA ATG GCT    3314
Tyr Glu Ile His Leu Phe Lys Glu Arg Met Phe Arg His Gln Met Ala
            1090                1095                1100

GTG AAG ACC AAT GGC ACA GGC CGC GTG AGG CTC CCT CCT GCT GGC TTC    3362
Val Lys Thr Asn Gly Thr Gly Arg Val Arg Leu Pro Pro Ala Gly Phe
            1105                1110                1115

GCC ACT GAG GGC TGG TTC ATC GGC TTT GTG AGT GCC ATC ATC CTC CTG    3410
Ala Thr Glu Gly Trp Phe Ile Gly Phe Val Ser Ala Ile Ile Leu Leu
            1120                1125                1130

CTC CTC GTC CTG CTC ATC CTC TGC TTC ATC AAG CGC AGC AAG GGC GGC    3458
Leu Leu Val Leu Leu Ile Leu Cys Phe Ile Lys Arg Ser Lys Gly Gly
            1135                1140                1145

AAA TAC TCA GTG AAG GAT AAG GAG GAC ACC CAG GTG GAC TCT GAG GCC    3506
Lys Tyr Ser Val Lys Asp Lys Glu Asp Thr Gln Val Asp Ser Glu Ala
1150                1155                1160                1165

CGA CCG ATG AAA GAT GAG ACC TTC GGC GAG TAC AGT GAC AAC GAG GAG    3554
Arg Pro Met Lys Asp Glu Thr Phe Gly Glu Tyr Ser Asp Asn Glu Glu
```

```
                    1170              1175              1180
AAG GCC TTT GGC AGC AGC CAG CCA TCG CTC AAC GGG GAC ATC AAG CCC      3602
Lys Ala Phe Gly Ser Ser Gln Pro Ser Leu Asn Gly Asp Ile Lys Pro
            1185              1190              1195

CTG GGC AGT GAC GAC AGC CTG GCC GAT TAT GGG GGC AGC GTG GAT GTT      3650
Leu Gly Ser Asp Asp Ser Leu Ala Asp Tyr Gly Gly Ser Val Asp Val
        1200              1205              1210

CAG TTC AAC GAG GAT GGT TCG TTC ATT GGC CAG TAC AGT GGC AAG AAG      3698
Gln Phe Asn Glu Asp Gly Ser Phe Ile Gly Gln Tyr Ser Gly Lys Lys
        1215              1220              1225

GAG AAG GAG GCG GCA GGG GGC AAT GAC AGC TCA GGG GCC ACT TCC CCC      3746
Glu Lys Glu Ala Ala Gly Gly Asn Asp Ser Ser Gly Ala Thr Ser Pro
1230              1235              1240              1245

ATC AAC CCT GCC GTG GCC CTA GAA TAGTGGAGTC CAGGACAGGA GATGCTGTGC     3800
Ile Asn Pro Ala Val Ala Leu Glu
                1250

CCCTGGCCTT GGGATCCAGG CCCCTCCCTC TCCAGCAGGC CCATGGGAGG CTGGAGTTGG    3860

GGCAGAGGAG AACTTGCTGC CTCGGATC                                      3888

(2) INFORMATION FOR SEQ ID NO:14:

(i) SEQUENCE CHARACTERISTICS:
        (A) LENGTH: 1253 amino acids
        (B) TYPE: amino acid
        (D) TOPOLOGY: linear (ii) MOLECULE TYPE: protein (xi) SEQUENCE DESCRIPTION: SEQ ID NO:14:

Met Val Val Ala Leu Arg Tyr Val Trp Pro Leu Leu Leu Cys Ser Pro
1               5                  10                  15

Cys Leu Leu Ile Gln Ile Pro Glu Glu Tyr Glu Gly His His Val Met
                20                  25                  30

Glu Pro Pro Val Ile Thr Glu Gln Ser Pro Arg Arg Leu Val Val Phe
            35                  40                  45

Pro Thr Asp Asp Ile Ser Leu Lys Cys Glu Ala Ser Gly Lys Pro Glu
        50                  55                  60

Val Gln Phe Arg Trp Thr Arg Asp Gly Val His Phe Lys Pro Lys Glu
65                  70                  75                  80

Glu Leu Gly Val Thr Val Tyr Gln Ser Pro His Ser Gly Ser Phe Thr
                85                  90                  95

Ile Thr Gly Asn Asn Ser Asn Phe Ala Gln Arg Phe Gln Gly Ile Tyr
                100                 105                 110

Arg Cys Phe Ala Ser Asn Lys Leu Gly Thr Ala Met Ser His Glu Ile
            115                 120                 125

Arg Leu Met Ala Glu Gly Ala Pro Lys Trp Pro Lys Glu Thr Val Lys
        130                 135                 140

Pro Val Glu Val Glu Glu Gly Glu Ser Val Val Leu Pro Cys Asn Pro
145                 150                 155                 160

Pro Pro Ser Ala Glu Pro Leu Arg Ile Tyr Trp Met Asn Ser Lys Ile
                165                 170                 175

Leu His Ile Lys Gln Asp Glu Arg Val Thr Met Gly Gln Asn Gly Asn
            180                 185                 190

Leu Tyr Phe Ala Asn Val Leu Thr Ser Asp Asn His Ser Asp Tyr Ile
        195                 200                 205

Cys His Ala His Phe Pro Gly Thr Arg Thr Ile Ile Gln Lys Glu Pro
    210                 215                 220
```

```
Ile Asp Leu Arg Val Lys Ala Thr Asn Ser Met Ile Asp Arg Lys Pro
225                 230                 235                 240

Arg Leu Leu Phe Pro Thr Asn Ser Ser Ser His Leu Val Ala Leu Gln
            245                 250                 255

Gly Gln Pro Leu Val Leu Glu Cys Ile Ala Glu Gly Phe Pro Thr Pro
        260                 265                 270

Thr Ile Lys Trp Leu Arg Pro Ser Gly Pro Met Pro Ala Asp Arg Val
    275                 280                 285

Thr Tyr Gln Asn His Asn Lys Thr Leu Gln Leu Leu Lys Val Gly Glu
290                 295                 300

Glu Asp Asp Gly Glu Tyr Arg Cys Leu Ala Glu Asn Ser Leu Gly Ser
305                 310                 315                 320

Ala Arg His Ala Tyr Tyr Val Thr Val Glu Ala Ala Pro Tyr Trp Leu
                325                 330                 335

His Lys Pro Gln Ser His Leu Tyr Gly Pro Gly Glu Thr Ala Arg Leu
            340                 345                 350

Asp Cys Gln Val Gln Gly Arg Pro Gln Pro Glu Val Thr Trp Arg Ile
        355                 360                 365

Asn Gly Ile Pro Val Glu Glu Leu Ala Lys Asp Gln Lys Tyr Arg Ile
    370                 375                 380

Gln Arg Gly Ala Leu Ile Leu Ser Asn Val Gln Pro Ser Asp Thr Met
385                 390                 395                 400

Val Thr Gln Cys Glu Ala Arg Asn Arg His Gly Leu Leu Leu Ala Asn
                405                 410                 415

Ala Tyr Ile Tyr Val Val Gln Leu Pro Ala Lys Ile Leu Thr Ala Asp
            420                 425                 430

Asn Gln Thr Tyr Met Ala Val Gln Gly Ser Thr Ala Tyr Leu Leu Cys
        435                 440                 445

Lys Ala Phe Gly Ala Pro Val Pro Ser Val Gln Trp Leu Asp Glu Asp
    450                 455                 460

Gly Thr Thr Val Leu Gln Asp Glu Arg Phe Phe Pro Tyr Ala Asn Gly
465                 470                 475                 480

Thr Leu Gly Ile Arg Asp Leu Gln Ala Asn Asp Thr Gly Arg Tyr Phe
                485                 490                 495

Cys Leu Ala Ala Asn Asp Gln Asn Asn Val Thr Ile Met Ala Asn Leu
            500                 505                 510

Lys Val Lys Asp Ala Thr Gln Ile Thr Gln Gly Pro Arg Ser Thr Ile
        515                 520                 525

Glu Lys Lys Gly Ser Arg Val Thr Phe Thr Cys Gln Ala Ser Phe Asp
    530                 535                 540

Pro Ser Leu Gln Pro Ser Ile Thr Trp Arg Gly Asp Gly Arg Asp Leu
545                 550                 555                 560

Gln Glu Leu Gly Asp Ser Asp Lys Tyr Phe Ile Glu Asp Gly Arg Leu
                565                 570                 575

Val Ile His Ser Leu Asp Tyr Ser Asp Gln Gly Asn Tyr Ser Cys Val
            580                 585                 590

Ala Ser Thr Glu Leu Asp Val Val Glu Ser Arg Ala Gln Leu Leu Val
        595                 600                 605

Val Gly Ser Pro Gly Pro Val Pro Arg Leu Val Leu Ser Asp Leu His
    610                 615                 620

Leu Leu Thr Gln Ser Gln Val Arg Val Ser Trp Ser Pro Ala Glu Asp
625                 630                 635                 640
```

-continued

```
His Asn Ala Pro Ile Glu Lys Tyr Asp Ile Glu Phe Glu Asp Lys Glu
                645                 650                 655

Met Ala Pro Glu Lys Trp Tyr Ser Leu Gly Lys Val Pro Gly Asn Gln
            660                 665                 670

Thr Ser Thr Thr Leu Lys Leu Ser Pro Tyr Val His Tyr Thr Phe Arg
        675                 680                 685

Val Thr Ala Ile Asn Lys Tyr Gly Pro Gly Glu Pro Ser Pro Val Ser
690                 695                 700

Glu Thr Val Val Thr Pro Glu Ala Ala Pro Glu Lys Asn Pro Val Asp
705                 710                 715                 720

Val Lys Gly Glu Gly Asn Glu Thr Thr Asn Met Val Ile Thr Trp Lys
                725                 730                 735

Pro Leu Arg Trp Met Asp Trp Asn Ala Pro Gln Val Gln Tyr Arg Val
            740                 745                 750

Gln Trp Arg Pro Gln Gly Thr Arg Gly Pro Trp Gln Glu Gln Ile Val
        755                 760                 765

Ser Asp Pro Phe Leu Val Val Ser Asn Thr Ser Thr Phe Val Pro Tyr
770                 775                 780

Glu Ile Lys Val Gln Ala Val Asn Ser Gln Gly Lys Gly Pro Glu Pro
785                 790                 795                 800

Gln Val Thr Ile Gly Tyr Ser Gly Glu Asp Tyr Pro Gln Ala Ile Pro
                805                 810                 815

Glu Leu Glu Gly Ile Glu Ile Leu Asn Ser Ser Ala Val Leu Val Lys
            820                 825                 830

Trp Arg Pro Val Asp Leu Ala Gln Val Lys Gly His Leu Arg Gly Tyr
        835                 840                 845

Asn Val Thr Tyr Trp Arg Glu Gly Ser Gln Arg Lys His Ser Lys Arg
850                 855                 860

His Ile His Lys Asp His Val Val Pro Ala Asn Thr Thr Ser Val
865                 870                 875                 880

Ile Leu Ser Gly Leu Arg Pro Tyr Ser Ser Tyr His Leu Glu Val Gln
                885                 890                 895

Ala Phe Asn Gly Arg Gly Ser Gly Pro Ala Ser Glu Phe Thr Phe Ser
            900                 905                 910

Thr Pro Glu Gly Val Pro Gly His Pro Glu Ala Leu His Leu Glu Cys
        915                 920                 925

Gln Ser Asn Thr Ser Leu Leu Leu Arg Trp Gln Pro Pro Leu Ser His
930                 935                 940

Asn Gly Val Leu Thr Gly Tyr Val Leu Ser Tyr His Pro Leu Asp Glu
945                 950                 955                 960

Gly Gly Lys Gly Gln Leu Ser Phe Asn Leu Arg Asp Pro Glu Leu Arg
                965                 970                 975

Thr His Asn Leu Thr Asp Leu Ser Pro His Leu Arg Tyr Arg Phe Gln
            980                 985                 990

Leu Gln Ala Thr Thr Lys Glu Gly Pro Gly Glu Ala Ile Val Arg Glu
        995                 1000                1005

Gly Gly Thr Met Ala Leu Ser Gly Ile Ser Asp Phe Gly Asn Ile Ser
    1010                1015                1020

Ala Thr Ala Gly Glu Asn Tyr Ser Val Val Ser Trp Val Pro Lys Glu
1025                1030                1035                1040

Gly Gln Cys Asn Phe Arg Phe His Ile Leu Phe Lys Ala Leu Gly Glu
                1045                1050                1055

Glu Lys Gly Gly Ala Ser Leu Ser Pro Gln Tyr Val Ser Tyr Asn Gln
```

−continued

```
                1060                1065                1070
Ser Ser Tyr Thr Gln Trp Asp Leu Gln Pro Asp Thr Asp Tyr Glu Ile
                1075                1080                1085

His Leu Phe Lys Glu Arg Met Phe Arg His Gln Met Ala Val Lys Thr
    1090                1095                1100

Asn Gly Thr Gly Arg Val Arg Leu Pro Pro Ala Gly Phe Ala Thr Glu
1105                1110                1115                1120

Gly Trp Phe Ile Gly Phe Val Ser Ala Ile Ile Leu Leu Leu Leu Val
                1125                1130                1135

Leu Leu Ile Leu Cys Phe Ile Lys Arg Ser Lys Gly Gly Lys Tyr Ser
                1140                1145                1150

Val Lys Asp Lys Glu Asp Thr Gln Val Asp Ser Glu Ala Arg Pro Met
        1155                1160                1165

Lys Asp Glu Thr Phe Gly Glu Tyr Ser Asp Asn Glu Glu Lys Ala Phe
    1170                1175                1180

Gly Ser Ser Gln Pro Ser Leu Asn Gly Asp Ile Lys Pro Leu Gly Ser
1185                1190                1195                1200

Asp Asp Ser Leu Ala Asp Tyr Gly Gly Ser Val Asp Val Gln Phe Asn
                1205                1210                1215

Glu Asp Gly Ser Phe Ile Gly Gln Tyr Ser Gly Lys Lys Glu Lys Glu
            1220                1225                1230

Ala Ala Gly Gly Asn Asp Ser Ser Gly Ala Thr Ser Pro Ile Asn Pro
                1235                1240                1245

Ala Val Ala Leu Glu
    1250
```

(2) INFORMATION FOR SEQ ID NO:15:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO:15:

CAACCATGGG CCTGGAAGGC ATTG                                        24

(2) INFORMATION FOR SEQ ID NO:16:

(i) SEQUENCE CHARACTERISTICS:
        (A) LENGTH: 23 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO:16:

CAGCCATGGG CCCTGGCCAC CCC                                          23

(2) INFORMATION FOR SEQ ID NO:17:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO:17:

AAAGGATCCC TACCAGCCCT CAGT                                            24

(2) INFORMATION FOR SEQ ID NO:18:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO:18:

GCGGGATCCC ATATCCACAA A                                               21

(2) INFORMATION FOR SEQ ID NO:19:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO:19:

AAAGGATCCC TACTATTCTA GGGC                                            24

(2) INFORMATION FOR SEQ ID NO:20:

(i) SEQUENCE CHARACTERISTICS:
        (A) LENGTH: 3783 base pairs
        (B) TYPE: nucleic acid
        (C) STRANDEDNESS: double
        (D) TOPOLOGY: linear (ii) MOLECULE TYPE: cDNA (iii) HYPOTHETICAL: NO (iv) ANTI-SENSE: NO (ix) FEATURE:
        (A) NAME/KEY: CDS
        (B) LOCATION: 1..3783

(xi) SEQUENCE DESCRIPTION: SEQ ID NO:20:

ATG GTC GTG ATG CTG CGG TAC GTG TGG CCT CTC CTC CTC TGC AGC CCC      48
Met Val Val Met Leu Arg Tyr Val Trp Pro Leu Leu Leu Cys Ser Pro
 1               5                  10                  15

```
TGC CTG CTC ATA CAG ATT CCA GAC GAA TAT AAA GGA CAC CAT GTG CTA      96
Cys Leu Leu Ile Gln Ile Pro Asp Glu Tyr Lys Gly His His Val Leu
            20                  25                  30

GAG CCA CCT GTC ATC ACG GAA CAG TCT CCA CGG CGC CTG GTT GTC TTC     144
Glu Pro Pro Val Ile Thr Glu Gln Ser Pro Arg Arg Leu Val Val Phe
        35                  40                  45

CCA ACA GAT GAC ATA AGC CTG AAA TGT GAA GCC AGA GGC AGA CCC CAA     192
Pro Thr Asp Asp Ile Ser Leu Lys Cys Glu Ala Arg Gly Arg Pro Gln
    50                  55                  60

GTG GAG TTC CGC TGG ACG AAA GAT GGC ATC CAC TTC AAA CCC AAG GAA     240
Val Glu Phe Arg Trp Thr Lys Asp Gly Ile His Phe Lys Pro Lys Glu
65                  70                  75                  80

GAA TTG GGT GTA GTG GTG CAT GAG GCA CCC TAT TCT GGC TCC TTC ACC     288
Glu Leu Gly Val Val Val His Glu Ala Pro Tyr Ser Gly Ser Phe Thr
                85                  90                  95

ATC GAA GGC AAC AAC AGC TTT GCC CAG AGG TTT CAG GGC ATC TAT CGC     336
Ile Glu Gly Asn Asn Ser Phe Ala Gln Arg Phe Gln Gly Ile Tyr Arg
            100                 105                 110

TGC TAT GCC AGC AAT AAG CTA GGA ACT GCC ATG TCG CAT GAG ATC CAG     384
Cys Tyr Ala Ser Asn Lys Leu Gly Thr Ala Met Ser His Glu Ile Gln
        115                 120                 125

CTC GTG GCC GAG GGT GCC CCC AAG TGG CCG AAG GAG ACT GTA AAA CCT     432
Leu Val Ala Glu Gly Ala Pro Lys Trp Pro Lys Glu Thr Val Lys Pro
    130                 135                 140

GTG GAA GTG GAG GAA GGA GAA TCA GTA GTT CTG CCT TGC AAC CCT CCA     480
Val Glu Val Glu Glu Gly Glu Ser Val Val Leu Pro Cys Asn Pro Pro
145                 150                 155                 160

CCC AGT GCA GCC CCA CCT AGG ATC TAC TGG ATG AAC AGC AAG ATT TTC     528
Pro Ser Ala Ala Pro Pro Arg Ile Tyr Trp Met Asn Ser Lys Ile Phe
                165                 170                 175

GAC ATC AAA CAA GAT GAG CGG GTG TCC ATG GGC CAG AAT GGA GAC CTA     576
Asp Ile Lys Gln Asp Glu Arg Val Ser Met Gly Gln Asn Gly Asp Leu
            180                 185                 190

TAT TTT GCC AAT GTG CTT ACC TCA GAC AAT CAT TCA GAC TAC ATC TGC     624
Tyr Phe Ala Asn Val Leu Thr Ser Asp Asn His Ser Asp Tyr Ile Cys
        195                 200                 205

AAT GCC CAC TTC CCT GGT ACC CGG ACC ATC ATT CAA AAG GAA CCT ATT     672
Asn Ala His Phe Pro Gly Thr Arg Thr Ile Ile Gln Lys Glu Pro Ile
    210                 215                 220

GAC CTC CGG GTC AAG CCC ACC AAC AGC ATG ATT GAC CGG AAG CCA CGT     720
Asp Leu Arg Val Lys Pro Thr Asn Ser Met Ile Asp Arg Lys Pro Arg
225                 230                 235                 240

CTG CTC TTT CCC ACA AAC TCC AGC AGC CGC CTG GTA GCC TTG CAG GGC     768
Leu Leu Phe Pro Thr Asn Ser Ser Ser Arg Leu Val Ala Leu Gln Gly
                245                 250                 255

CAG TCA TTG ATC CTG GAG TGC ATT GCT GAG GGA TTC CCT ACA CCC ACC     816
Gln Ser Leu Ile Leu Glu Cys Ile Ala Glu Gly Phe Pro Thr Pro Thr
            260                 265                 270

ATC AAG TGG CTG CAC CCC AGT GAC CCA ATG CCA ACA GAC CGT GTT ATC     864
Ile Lys Trp Leu His Pro Ser Asp Pro Met Pro Thr Asp Arg Val Ile
        275                 280                 285

TAC CAA AAC CAC AAC AAG ACC CTG CAA CTA CTC AAT GTG GGC GAA GAG     912
Tyr Gln Asn His Asn Lys Thr Leu Gln Leu Leu Asn Val Gly Glu Glu
    290                 295                 300

GAC GAT GGC GAG TAT ACC TGC CTT GCT GAG AAC TCG CTG GGC AGT GCC     960
Asp Asp Gly Glu Tyr Thr Cys Leu Ala Glu Asn Ser Leu Gly Ser Ala
305                 310                 315                 320

CGG CAT GCC TAC TAT GTT ACT GTG GAA GCT GCC CCA TAT TGG CTG CAG    1008
Arg His Ala Tyr Tyr Val Thr Val Glu Ala Ala Pro Tyr Trp Leu Gln
                325                 330                 335
```

```
AAG CCC CAG AGC CAT TTG TAT GGT CCA GGA GAG ACT GCC CGC CTA GAC    1056
Lys Pro Gln Ser His Leu Tyr Gly Pro Gly Glu Thr Ala Arg Leu Asp
            340                 345                 350

TGC CAA GTC CAG GGC AGG CCC CAA CCA GAG ATC ACT TGG AGA ATC AAC    1104
Cys Gln Val Gln Gly Arg Pro Gln Pro Glu Ile Thr Trp Arg Ile Asn
                355                 360                 365

GGA ATG TCT ATG GAG ACG GTG AAC AAG GAC CAG AAG TAC CGG ATT GAG    1152
Gly Met Ser Met Glu Thr Val Asn Lys Asp Gln Lys Tyr Arg Ile Glu
        370                 375                 380

CAG GGG TCT CTG ATC TTG AGT AAC GTG CAG CCA ACT GAC ACA ATG GTG    1200
Gln Gly Ser Leu Ile Leu Ser Asn Val Gln Pro Thr Asp Thr Met Val
385                 390                 395                 400

ACC CAG TGT GAA GCC CGC AAC CAG CAT GGG CTC CTG CTA GCC AAT GCC    1248
Thr Gln Cys Glu Ala Arg Asn Gln His Gly Leu Leu Leu Ala Asn Ala
                405                 410                 415

TAC ATT TAT GTT GTC CAG CTG CCA GCC AGG ATC CTA ACA AAA GAC AAT    1296
Tyr Ile Tyr Val Val Gln Leu Pro Ala Arg Ile Leu Thr Lys Asp Asn
        420                 425                 430

CAG ACA TAC ATG GCA GTT GAG GGC AGT ACT GCT TAC TTG CTG TGC AAA    1344
Gln Thr Tyr Met Ala Val Glu Gly Ser Thr Ala Tyr Leu Leu Cys Lys
            435                 440                 445

GCC TTT GGA GCT CCT GTT CCC AGT GTC CAG TGG CTG GAT GAA GAA GGA    1392
Ala Phe Gly Ala Pro Val Pro Ser Val Gln Trp Leu Asp Glu Glu Gly
    450                 455                 460

ACC ACA GTG CTT CAG GAT GAA CGA TTT TTC CCC TAT GCC AAT GGA ACG    1440
Thr Thr Val Leu Gln Asp Glu Arg Phe Phe Pro Tyr Ala Asn Gly Thr
465                 470                 475                 480

CTG AGC ATC AGA GAC CTC CAG GCC AAT GAC ACT GGA CGC TAT TTC TGC    1488
Leu Ser Ile Arg Asp Leu Gln Ala Asn Asp Thr Gly Arg Tyr Phe Cys
                485                 490                 495

CAG GCT GCC AAT GAC CAG AAC AAT GTG ACC ATT TTG GCT AAC CTA CAG    1536
Gln Ala Ala Asn Asp Gln Asn Asn Val Thr Ile Leu Ala Asn Leu Gln
            500                 505                 510

GTT AAA GAA GCA ACC CAG ATC ACA CAG GGG CCC CGG AGC GCA ATT GAG    1584
Val Lys Glu Ala Thr Gln Ile Thr Gln Gly Pro Arg Ser Ala Ile Glu
        515                 520                 525

AAG AAA GGT GCA AGG GTG ACA TTC ACG TGC CAG GCC TCC TTT GAC CCC    1632
Lys Lys Gly Ala Arg Val Thr Phe Thr Cys Gln Ala Ser Phe Asp Pro
530                 535                 540

TCT TTG CAG GCC AGC ATC ACT TGG CGT GGA GAT GGG AGA GAC CTA CAG    1680
Ser Leu Gln Ala Ser Ile Thr Trp Arg Gly Asp Gly Arg Asp Leu Gln
545                 550                 555                 560

GAA CGT GGG GAC AGT GAC AAG TAT TTC ATA GAA GAT GGG AAA CTA GTC    1728
Glu Arg Gly Asp Ser Asp Lys Tyr Phe Ile Glu Asp Gly Lys Leu Val
                565                 570                 575

ATC CAG AGC CTG GAC TAC AGT GAC CAG GGC AAC TAC AGT TGT GTG GCC    1776
Ile Gln Ser Leu Asp Tyr Ser Asp Gln Gly Asn Tyr Ser Cys Val Ala
            580                 585                 590

AGC ACT GAA CTG GAT GAG GTG GAG AGC AGG GCA CAG CTC TTA GTG GTG    1824
Ser Thr Glu Leu Asp Glu Val Glu Ser Arg Ala Gln Leu Leu Val Val
        595                 600                 605

GGG AGC CCT GGG CCA GTG CCT CAC CTG GAG CTG TCC GAC CGC CAC CTG    1872
Gly Ser Pro Gly Pro Val Pro His Leu Glu Leu Ser Asp Arg His Leu
    610                 615                 620

CTG AAG CAG AGC CAG GTG CAC TTG TCT TGG AGC CCT GCT GAA GAC CAC    1920
Leu Lys Gln Ser Gln Val His Leu Ser Trp Ser Pro Ala Glu Asp His
625                 630                 635                 640

AAC TCT CCC ATT GAG AAG TAT GAC ATT GAA TTT GAG GAC AAG GAA ATG    1968
Asn Ser Pro Ile Glu Lys Tyr Asp Ile Glu Phe Glu Asp Lys Glu Met
```

|  |  |  |  |  |  |  |  |  |  |  |  |  |  |  |  |
|---|---|---|---|---|---|---|---|---|---|---|---|---|---|---|---|
| GCT | CCT | GAG | AAA | TGG | TTC | AGT | CTG | GGC | AAG | GTG | CCA | GGA | AAT | CAG | ACC | 2016 |
| Ala | Pro | Glu | Lys | Trp | Phe | Ser | Leu | Gly | Lys | Val | Pro | Gly | Asn | Gln | Thr |
|  |  |  | 660 |  |  |  | 665 |  |  |  |  | 670 |  |  |  |

```
                     645                    650                     655

GCT CCT GAG AAA TGG TTC AGT CTG GGC AAG GTG CCA GGA AAT CAG ACC             2016
Ala Pro Glu Lys Trp Phe Ser Leu Gly Lys Val Pro Gly Asn Gln Thr
            660                 665                 670

TCT ACT ACC CTC AAG CTG TCC CCC TAT GTC CAC TAC ACC TTT CGG GTC             2064
Ser Thr Thr Leu Lys Leu Ser Pro Tyr Val His Tyr Thr Phe Arg Val
                675                 680                 685

ACT GCC ATT AAC AAA TAT GGT CCT GGA GAA CCC AGC CCT GTC TCT GAG             2112
Thr Ala Ile Asn Lys Tyr Gly Pro Gly Glu Pro Ser Pro Val Ser Glu
        690                 695                 700

AGT GTG GTC ACA CCT GAG GCA GCC CCA GAG AAG AAC CCT GTG GAT GTG             2160
Ser Val Val Thr Pro Glu Ala Ala Pro Glu Lys Asn Pro Val Asp Val
705                 710                 715                 720

AGA GGG GAA GGG AAT GAG ACC AAC AAT ATG GTC ATC ACA TGG AAG CCC             2208
Arg Gly Glu Gly Asn Glu Thr Asn Asn Met Val Ile Thr Trp Lys Pro
                    725                 730                 735

CTT CGG TGG ATG GAT TGG AAT GCC CCC CAG ATT CAG TAC CGT GTA CAG             2256
Leu Arg Trp Met Asp Trp Asn Ala Pro Gln Ile Gln Tyr Arg Val Gln
                740                 745                 750

TGG CGT CCA CAG GGC AAG CAG GAG ACC TGG AGG AAA CAG ACC GTG AGC             2304
Trp Arg Pro Gln Gly Lys Gln Glu Thr Trp Arg Lys Gln Thr Val Ser
            755                 760                 765

GAC CCT TTC CTG GTG GTG TCT AAC ACT TCC ACA TTT GTG CCT TAT GAG             2352
Asp Pro Phe Leu Val Val Ser Asn Thr Ser Thr Phe Val Pro Tyr Glu
        770                 775                 780

ATC AAA GTC CAG GCA GTG AAC AAC CAG GGC AAG GGC CCT GAG CCC CAG             2400
Ile Lys Val Gln Ala Val Asn Asn Gln Gly Lys Gly Pro Glu Pro Gln
785                 790                 795                 800

GTC ACC ATT GGC TAT TCA GGG GAA GAC TAC CCC CAG GTG AGC CCT GAA             2448
Val Thr Ile Gly Tyr Ser Gly Glu Asp Tyr Pro Gln Val Ser Pro Glu
                    805                 810                 815

CTT GAA GAC ATC ACA ATC TTC AAC TCA AGT ACT GTG CTT GTC AGG TGG             2496
Leu Glu Asp Ile Thr Ile Phe Asn Ser Ser Thr Val Leu Val Arg Trp
                820                 825                 830

AGG CCT GTG GAC TTG GCC CAG GTT AAG GGC CAC CTC AAG GGA TAC AAT             2544
Arg Pro Val Asp Leu Ala Gln Val Lys Gly His Leu Lys Gly Tyr Asn
            835                 840                 845

GTA ACA TAC TGG TGG AAG GGC AGC CAG AGA AAG CAC AGC AAG AGG CAT             2592
Val Thr Tyr Trp Trp Lys Gly Ser Gln Arg Lys His Ser Lys Arg His
        850                 855                 860

ATC CAC AAA AGC CAC ATA GTG GTA CCT GCA AAT ACC ACC AGT GCC ATC             2640
Ile His Lys Ser His Ile Val Val Pro Ala Asn Thr Thr Ser Ala Ile
865                 870                 875                 880

CTC AGT GGT TTG CGC CCT TAC AGC TCT TAC CAT GTG GAG GTA CAG GCC             2688
Leu Ser Gly Leu Arg Pro Tyr Ser Ser Tyr His Val Glu Val Gln Ala
                    885                 890                 895

TTT AAT GGG CGG GGC TTG GGG CCT GCG AGT GAA TGG ACC TTC AGC ACC             2736
Phe Asn Gly Arg Gly Leu Gly Pro Ala Ser Glu Trp Thr Phe Ser Thr
                900                 905                 910

CCA GAG GGA GTG CCT GGC CAC CCT GAG GCA TTA CAC CTG GAG TGT CAG             2784
Pro Glu Gly Val Pro Gly His Pro Glu Ala Leu His Leu Glu Cys Gln
            915                 920                 925

TCG GAC ACT AGT CTG CTA CTG CAC TGG CAG CCA CCA CTC AGC CAC AAT             2832
Ser Asp Thr Ser Leu Leu Leu His Trp Gln Pro Pro Leu Ser His Asn
        930                 935                 940

GGA GTG CTC ACT GGC TAC CTG CTC TCT TAC CAT CCC GTG GAA GGG GAA             2880
Gly Val Leu Thr Gly Tyr Leu Leu Ser Tyr His Pro Val Glu Gly Glu
945                 950                 955                 960

AGC AAA GAG CAG TTG TTC TTC AAC CTT TCG GAC CCA GAA CTC CGG ACT             2928
```

```
Ser Lys Glu Gln Leu Phe Phe Asn Leu Ser Asp Pro Glu Leu Arg Thr
            965                 970                 975

CAT AAT CTG ACC AAC CTC AAC CCT GAT CTA CAG TAC CGC TTC CAG CTT       2976
His Asn Leu Thr Asn Leu Asn Pro Asp Leu Gln Tyr Arg Phe Gln Leu
            980                 985                 990

CAG GCC ACC ACC CAA CAG GGG GGT CCT GGT GAG GCC ATC GTG CGT GAA       3024
Gln Ala Thr Thr Gln Gln Gly Gly Pro Gly Glu Ala Ile Val Arg Glu
            995                 1000                1005

GGA GGC ACC ATG GCC CTG TTT GGC AAG CCA GAT TTT GGC AAC ATC TCA       3072
Gly Gly Thr Met Ala Leu Phe Gly Lys Pro Asp Phe Gly Asn Ile Ser
    1010                1015                1020

GCC ACA GCA GGT GAA AAC TAC AGC GTG GTC TCC TGG GTC CCT CGG AAG       3120
Ala Thr Ala Gly Glu Asn Tyr Ser Val Val Ser Trp Val Pro Arg Lys
1025                1030                1035                1040

GGC CAG TGC AAT TTC AGG TTC CAT ATC TTG TTC AAA GCC TTA CCA GAA       3168
Gly Gln Cys Asn Phe Arg Phe His Ile Leu Phe Lys Ala Leu Pro Glu
                1045                1050                1055

GGG AAA GTG AGC CCT GAT CAC CAG CCT CAG CCT CAG TAT GTC AGC TAC       3216
Gly Lys Val Ser Pro Asp His Gln Pro Gln Pro Gln Tyr Val Ser Tyr
            1060                1065                1070

AAT CAG AGC TCC TAC ACA CAA TGG AAC CTA CAG CCT GAC ACC AAA TAT       3264
Asn Gln Ser Ser Tyr Thr Gln Trp Asn Leu Gln Pro Asp Thr Lys Tyr
            1075                1080                1085

GAG ATC CAC CTG ATA AAG GAG AAG GTC CTC CTG CAC CAT CTG GAT GTG       3312
Glu Ile His Leu Ile Lys Glu Lys Val Leu Leu His His Leu Asp Val
            1090                1095                1100

AAG ACT AAT GGA ACT GGC CCT GTG CGA GTT TCT ACT ACA GGG AGC TTT       3360
Lys Thr Asn Gly Thr Gly Pro Val Arg Val Ser Thr Thr Gly Ser Phe
1105                1110                1115                1120

GCC TCC GAG GGC TGG TTC ATC GCC TTT GTC AGC GCT ATC ATT CTC TTG       3408
Ala Ser Glu Gly Trp Phe Ile Ala Phe Val Ser Ala Ile Ile Leu Leu
                1125                1130                1135

CTC CTC ATC CTG CTC ATC CTC TGC TTC ATC AAA CGC AGC AAG GGT GGC       3456
Leu Leu Ile Leu Leu Ile Leu Cys Phe Ile Lys Arg Ser Lys Gly Gly
            1140                1145                1150

AAA TAC TCA GTG AAG GAC AAG GAG GAC ACT CAG GTA GAT TCC GAG GCC       3504
Lys Tyr Ser Val Lys Asp Lys Glu Asp Thr Gln Val Asp Ser Glu Ala
            1155                1160                1165

CGG CCC ATG AAA GAC GAG ACC TTC GGC GAG TAC AGG TCC CTG GAG AGT       3552
Arg Pro Met Lys Asp Glu Thr Phe Gly Glu Tyr Arg Ser Leu Glu Ser
            1170                1175                1180

GAC AAT GAA GAG AAG GCC TTT GGC AGC AGC CAG CCA TCT CTC AAC GGA       3600
Asp Asn Glu Glu Lys Ala Phe Gly Ser Ser Gln Pro Ser Leu Asn Gly
1185                1190                1195                1200

GAC ATC AAA CCC CTA GGC AGT GAT GAC AGC CTG GCT GAT TAT GGG GGC       3648
Asp Ile Lys Pro Leu Gly Ser Asp Asp Ser Leu Ala Asp Tyr Gly Gly
                1205                1210                1215

AGT GTG GAC GTC CAG TTC AAT GAG GAT GGC TCT TTC ATC GGC CAG TAC       3696
Ser Val Asp Val Gln Phe Asn Glu Asp Gly Ser Phe Ile Gly Gln Tyr
                1220                1225                1230

AGT GGC AAG AAA GAG AAG GAG GCA GCA GGA GGC AAT GAC AGT TCA GGG       3744
Ser Gly Lys Lys Glu Lys Glu Ala Ala Gly Gly Asn Asp Ser Ser Gly
            1235                1240                1245

GCT ACC TCT CCT ATC AAT CCT GCA GTA GCC CTA GAA TAG                   3783
Ala Thr Ser Pro Ile Asn Pro Ala Val Ala Leu Glu
            1250                1255                1260
```

(2) INFORMATION FOR SEQ ID NO:21:

(i) SEQUENCE CHARACTERISTICS:

(A) LENGTH: 1260 amino acids
(B) TYPE: amino acid
(D) TOPOLOGY: linear (ii) MOLECULE TYPE: protein (xi) SEQUENCE DESCRIPTION: SEQ ID NO:21:

```
Met Val Val Met Leu Arg Tyr Val Trp Pro Leu Leu Leu Cys Ser Pro
 1               5                  10                  15

Cys Leu Leu Ile Gln Ile Pro Asp Glu Tyr Lys Gly His His Val Leu
             20                  25                  30

Glu Pro Pro Val Ile Thr Glu Gln Ser Pro Arg Arg Leu Val Val Phe
         35                  40                  45

Pro Thr Asp Asp Ile Ser Leu Lys Cys Glu Ala Arg Gly Arg Pro Gln
     50                  55                  60

Val Glu Phe Arg Trp Thr Lys Asp Gly Ile His Phe Lys Pro Lys Glu
 65                  70                  75                  80

Glu Leu Gly Val Val Val His Glu Ala Pro Tyr Ser Gly Ser Phe Thr
                 85                  90                  95

Ile Glu Gly Asn Asn Ser Phe Ala Gln Arg Phe Gln Gly Ile Tyr Arg
            100                 105                 110

Cys Tyr Ala Ser Asn Lys Leu Gly Thr Ala Met Ser His Glu Ile Gln
        115                 120                 125

Leu Val Ala Glu Gly Ala Pro Lys Trp Pro Lys Glu Thr Val Lys Pro
130                 135                 140

Val Glu Val Glu Glu Gly Glu Ser Val Val Leu Pro Cys Asn Pro Pro
145                 150                 155                 160

Pro Ser Ala Ala Pro Arg Ile Tyr Trp Met Asn Ser Lys Ile Phe
                165                 170                 175

Asp Ile Lys Gln Asp Glu Arg Val Ser Met Gly Gln Asn Gly Asp Leu
            180                 185                 190

Tyr Phe Ala Asn Val Leu Thr Ser Asp Asn His Ser Asp Tyr Ile Cys
        195                 200                 205

Asn Ala His Phe Pro Gly Thr Arg Thr Ile Ile Gln Lys Glu Pro Ile
    210                 215                 220

Asp Leu Arg Val Lys Pro Thr Asn Ser Met Ile Asp Arg Lys Pro Arg
225                 230                 235                 240

Leu Leu Phe Pro Thr Asn Ser Ser Arg Leu Val Ala Leu Gln Gly
                245                 250                 255

Gln Ser Leu Ile Leu Glu Cys Ile Ala Glu Gly Phe Pro Thr Pro Thr
            260                 265                 270

Ile Lys Trp Leu His Pro Ser Asp Pro Met Pro Thr Asp Arg Val Ile
        275                 280                 285

Tyr Gln Asn His Asn Lys Thr Leu Gln Leu Leu Asn Val Gly Glu Glu
    290                 295                 300

Asp Asp Gly Glu Tyr Thr Cys Leu Ala Glu Asn Ser Leu Gly Ser Ala
305                 310                 315                 320

Arg His Ala Tyr Tyr Val Thr Val Glu Ala Ala Pro Tyr Trp Leu Gln
                325                 330                 335

Lys Pro Gln Ser His Leu Tyr Gly Pro Gly Glu Thr Ala Arg Leu Asp
            340                 345                 350

Cys Gln Val Gln Gly Arg Pro Gln Pro Glu Ile Thr Trp Arg Ile Asn
        355                 360                 365

Gly Met Ser Met Glu Thr Val Asn Lys Asp Gln Lys Tyr Arg Ile Glu
    370                 375                 380
```

-continued

Gln Gly Ser Leu Ile Leu Ser Asn Val Gln Pro Thr Asp Thr Met Val
385                 390                 395                 400

Thr Gln Cys Glu Ala Arg Asn Gln His Gly Leu Leu Leu Ala Asn Ala
            405                 410                 415

Tyr Ile Tyr Val Val Gln Leu Pro Ala Arg Ile Leu Thr Lys Asp Asn
            420                 425                 430

Gln Thr Tyr Met Ala Val Glu Gly Ser Thr Ala Tyr Leu Leu Cys Lys
            435                 440                 445

Ala Phe Gly Ala Pro Val Pro Ser Val Gln Trp Leu Asp Glu Gly
450                 455                 460

Thr Thr Val Leu Gln Asp Glu Arg Phe Phe Pro Tyr Ala Asn Gly Thr
465                 470                 475                 480

Leu Ser Ile Arg Asp Leu Gln Ala Asn Asp Thr Gly Arg Tyr Phe Cys
            485                 490                 495

Gln Ala Ala Asn Asp Gln Asn Asn Val Thr Ile Leu Ala Asn Leu Gln
            500                 505                 510

Val Lys Glu Ala Thr Gln Ile Thr Gln Gly Pro Arg Ser Ala Ile Glu
        515                 520                 525

Lys Lys Gly Ala Arg Val Thr Phe Thr Cys Gln Ala Ser Phe Asp Pro
530                 535                 540

Ser Leu Gln Ala Ser Ile Thr Trp Arg Gly Asp Gly Arg Asp Leu Gln
545                 550                 555                 560

Glu Arg Gly Asp Ser Asp Lys Tyr Phe Ile Glu Asp Gly Lys Leu Val
                565                 570                 575

Ile Gln Ser Leu Asp Tyr Ser Asp Gln Gly Asn Tyr Ser Cys Val Ala
            580                 585                 590

Ser Thr Glu Leu Asp Glu Val Glu Ser Arg Ala Gln Leu Leu Val Val
        595                 600                 605

Gly Ser Pro Gly Pro Val Pro His Leu Glu Leu Ser Asp Arg His Leu
        610                 615                 620

Leu Lys Gln Ser Gln Val His Leu Ser Trp Ser Pro Ala Glu Asp His
625                 630                 635                 640

Asn Ser Pro Ile Glu Lys Tyr Asp Ile Glu Phe Glu Asp Lys Glu Met
            645                 650                 655

Ala Pro Glu Lys Trp Phe Ser Leu Gly Lys Val Pro Gly Asn Gln Thr
            660                 665                 670

Ser Thr Thr Leu Lys Leu Ser Pro Tyr Val His Tyr Thr Phe Arg Val
            675                 680                 685

Thr Ala Ile Asn Lys Tyr Gly Pro Gly Glu Pro Ser Pro Val Ser Glu
690                 695                 700

Ser Val Val Thr Pro Glu Ala Ala Pro Glu Lys Asn Pro Val Asp Val
705                 710                 715                 720

Arg Gly Glu Gly Asn Glu Thr Asn Asn Met Val Ile Thr Trp Lys Pro
                725                 730                 735

Leu Arg Trp Met Asp Trp Asn Ala Pro Gln Ile Gln Tyr Arg Val Gln
            740                 745                 750

Trp Arg Pro Gln Gly Lys Gln Glu Thr Trp Arg Lys Gln Thr Val Ser
        755                 760                 765

Asp Pro Phe Leu Val Val Ser Asn Thr Ser Thr Phe Val Pro Tyr Glu
        770                 775                 780

Ile Lys Val Gln Ala Val Asn Asn Gln Gly Lys Gly Pro Glu Pro Gln
785                 790                 795                 800

```
Val Thr Ile Gly Tyr Ser Gly Glu Asp Tyr Pro Gln Val Ser Pro Glu
                805                 810                 815

Leu Glu Asp Ile Thr Ile Phe Asn Ser Ser Thr Val Leu Val Arg Trp
            820                 825                 830

Arg Pro Val Asp Leu Ala Gln Val Lys Gly His Leu Lys Gly Tyr Asn
        835                 840                 845

Val Thr Tyr Trp Trp Lys Gly Ser Gln Arg Lys His Ser Lys Arg His
    850                 855                 860

Ile His Lys Ser His Ile Val Pro Ala Asn Thr Thr Ser Ala Ile
865                 870                 875                 880

Leu Ser Gly Leu Arg Pro Tyr Ser Ser Tyr His Val Glu Val Gln Ala
                885                 890                 895

Phe Asn Gly Arg Gly Leu Gly Pro Ala Ser Glu Trp Thr Phe Ser Thr
            900                 905                 910

Pro Glu Gly Val Pro Gly His Pro Glu Ala Leu His Leu Glu Cys Gln
        915                 920                 925

Ser Asp Thr Ser Leu Leu Leu His Trp Gln Pro Pro Leu Ser His Asn
    930                 935                 940

Gly Val Leu Thr Gly Tyr Leu Leu Ser Tyr His Pro Val Glu Gly Glu
945                 950                 955                 960

Ser Lys Glu Gln Leu Phe Phe Asn Leu Ser Asp Pro Glu Leu Arg Thr
                965                 970                 975

His Asn Leu Thr Asn Leu Asn Pro Asp Leu Gln Tyr Arg Phe Gln Leu
            980                 985                 990

Gln Ala Thr Thr Gln Gln Gly Gly Pro Gly Glu Ala Ile Val Arg Glu
        995                 1000                1005

Gly Gly Thr Met Ala Leu Phe Gly Lys Pro Asp Phe Gly Asn Ile Ser
    1010                1015                1020

Ala Thr Ala Gly Glu Asn Tyr Ser Val Val Ser Trp Val Pro Arg Lys
1025                1030                1035                1040

Gly Gln Cys Asn Phe Arg Phe His Ile Leu Phe Lys Ala Leu Pro Glu
                1045                1050                1055

Gly Lys Val Ser Pro Asp His Gln Pro Gln Pro Gln Tyr Val Ser Tyr
            1060                1065                1070

Asn Gln Ser Ser Tyr Thr Gln Trp Asn Leu Gln Pro Asp Thr Lys Tyr
        1075                1080                1085

Glu Ile His Leu Ile Lys Glu Lys Val Leu Leu His His Leu Asp Val
    1090                1095                1100

Lys Thr Asn Gly Thr Gly Pro Val Arg Val Ser Thr Thr Gly Ser Phe
1105                1110                1115                1120

Ala Ser Glu Gly Trp Phe Ile Ala Phe Val Ser Ala Ile Ile Leu Leu
                1125                1130                1135

Leu Leu Ile Leu Leu Ile Leu Cys Phe Ile Lys Arg Ser Lys Gly Gly
            1140                1145                1150

Lys Tyr Ser Val Lys Asp Lys Glu Asp Thr Gln Val Asp Ser Glu Ala
        1155                1160                1165

Arg Pro Met Lys Asp Glu Thr Phe Gly Glu Tyr Arg Ser Leu Glu Ser
    1170                1175                1180

Asp Asn Glu Glu Lys Ala Phe Gly Ser Ser Gln Pro Ser Leu Asn Gly
1185                1190                1195                1200

Asp Ile Lys Pro Leu Gly Ser Asp Asp Ser Leu Ala Asp Tyr Gly Gly
                1205                1210                1215

Ser Val Asp Val Gln Phe Asn Glu Asp Gly Ser Phe Ile Gly Gln Tyr
```

```
                    1220            1225            1230
Ser Gly Lys Lys Glu Lys Glu Ala Ala Gly Gly Asn Asp Ser Ser Gly
            1235            1240            1245

Ala Thr Ser Pro Ile Asn Pro Ala Val Ala Leu Glu
        1250            1255            1260
```

(2) INFORMATION FOR SEQ ID NO:22:

(i) SEQUENCE CHARACTERISTICS:
        (A) LENGTH: 23 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO:22:

CAACCATGGG CCTTGAAGAC ATC                                    23

(2) INFORMATION FOR SEQ ID NO:23:

(i) SEQUENCE CHARACTERISTICS:
        (A) LENGTH: 23 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO:23:

CAGCCATGGG CCCTGGCCAC CCT                                    23

(2) INFORMATION FOR SEQ ID NO:24:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO:24:

AAAGGATCCC TACCAGCCCT CGGA                                  24

(2) INFORMATION FOR SEQ ID NO:25:

(i) SEQUENCE CHARACTERISTICS:
        (A) LENGTH: 23 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO:25:

CAACCATGGG CCATATCCAC AAA                                              23

(2) INFORMATION FOR SEQ ID NO:26:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO:26:

AAAGGATCCC TACTATTGTA GGGC                                             24

(2) INFORMATION FOR SEQ ID NO:27:

(i) SEQUENCE CHARACTERISTICS:
        (A) LENGTH: 3943 base pairs
        (B) TYPE: nucleic acid
        (C) STRANDEDNESS: double
        (D) TOPOLOGY: linear (ii) MOLECULE TYPE: cDNA (iii) HYPOTHETICAL: NO (iv) ANTI-SENSE: NO (ix) FEATURE:
        (A) NAME/KEY: CDS
        (B) LOCATION: 33..3839

(xi) SEQUENCE DESCRIPTION: SEQ ID NO:27:

```
CAAGAGTGAT TTACTTAGTA GAGCCTAAAA TC ATG ATG AAA GAG AAG AGC ATA         53
                                   Met Met Lys Glu Lys Ser Ile
                                    1               5

TCT GCA AGC AAA GCT TCC TTG GTT TTC TTT CTG TGC CAA ATG ATT TCT        101
Ser Ala Ser Lys Ala Ser Leu Val Phe Phe Leu Cys Gln Met Ile Ser
            10                  15                  20

GCA TTG GAT GTA CCT CTT GAT TCA AAA CTT CTA GAA GAA TTG TCT CAA        149
Ala Leu Asp Val Pro Leu Asp Ser Lys Leu Leu Glu Glu Leu Ser Gln
        25                  30                  35

CCT CCA ACA ATA ACT CAG CAG TCT CCA AAA GAT TAC ATT GTT GAC CCT        197
Pro Pro Thr Ile Thr Gln Gln Ser Pro Lys Asp Tyr Ile Val Asp Pro
 40                  45                  50                  55

CGA GAG AAT ATT GTA ATA CAA TGT GAA GCA AAA GGA AAA CCA CCT CCT        245
Arg Glu Asn Ile Val Ile Gln Cys Glu Ala Lys Gly Lys Pro Pro Pro
                 60                  65                  70

AGC TTC TCC TGG ACG CGC AAT GGA ACT CAT TTT GAT ATA GAT AAA GAT        293
Ser Phe Ser Trp Thr Arg Asn Gly Thr His Phe Asp Ile Asp Lys Asp
             75                  80                  85

GCA CAG GTA ACA ATG AAA CCA AAT TCA GGA ACC CTT GTT GTA AAT ATT        341
Ala Gln Val Thr Met Lys Pro Asn Ser Gly Thr Leu Val Val Asn Ile
         90                  95                 100

ATG AAT GGT GTG AAG GCA GAA GCA TAT GAA GGA GTA TAC CAG TGT ACA        389
Met Asn Gly Val Lys Ala Glu Ala Tyr Glu Gly Val Tyr Gln Cys Thr
    105                 110                 115

GCA AGG AAT GAA AGA GGA GCA GCC ATT TCC AAC AAT ATT GTT ATA CGG        437
Ala Arg Asn Glu Arg Gly Ala Ala Ile Ser Asn Asn Ile Val Ile Arg
```

```
                120                  125                  130                  135
CCA TCT AGA TCC CCT TTG TGG ACT AAA GAA AAA CTA GAA CCA AAT CAT        485
Pro Ser Arg Ser Pro Leu Trp Thr Lys Glu Lys Leu Glu Pro Asn His
            140                  145                  150

GTT CGA GAA GGT GAT TCC CTA GTA CTA AAC TGC AGA CCT CCT GTT GGC        533
Val Arg Glu Gly Asp Ser Leu Val Leu Asn Cys Arg Pro Pro Val Gly
            155                  160                  165

TTA CCA CCA CCT ATA ATA TTT TGG ATG GAT AAT GCT TTC CAA AGG CTG        581
Leu Pro Pro Pro Ile Ile Phe Trp Met Asp Asn Ala Phe Gln Arg Leu
            170                  175                  180

CCT CAA AGT GAA AGA GTT TCT CAA GGT CTC AAT GGA GAC CTT TAT TTT        629
Pro Gln Ser Glu Arg Val Ser Gln Gly Leu Asn Gly Asp Leu Tyr Phe
            185                  190                  195

TCT AAT GTA CAA CCA GAG GAC ACC CGT GTG GAC TAT ATC TGC TAC GCG        677
Ser Asn Val Gln Pro Glu Asp Thr Arg Val Asp Tyr Ile Cys Tyr Ala
200                  205                  210                  215

AGA TTT AAT CAC ACA CAA ACT ATA CAG CAG AAA CAA CCC ATT TCT GTA        725
Arg Phe Asn His Thr Gln Thr Ile Gln Gln Lys Gln Pro Ile Ser Val
            220                  225                  230

AAA GTC TTT TCA ACC AAG CCA GTT ACA GAA AGG CCA CCA GTT CTT CTT        773
Lys Val Phe Ser Thr Lys Pro Val Thr Glu Arg Pro Pro Val Leu Leu
            235                  240                  245

ACA CCA ATG GGC AGC ACA AGT AAC AAA GTG GAA CTG AGA GGA AAT GTT        821
Thr Pro Met Gly Ser Thr Ser Asn Lys Val Glu Leu Arg Gly Asn Val
            250                  255                  260

CTT TTG TTG GAA TGC ATC GCA GCA GGA TTA CCC ACA CCA GTA ATC CGC        869
Leu Leu Leu Glu Cys Ile Ala Ala Gly Leu Pro Thr Pro Val Ile Arg
            265                  270                  275

TGG ATT AAA GAG GGT GGT GAA CTG CCA GCC AAC AGA ACG TTT TTT GAA        917
Trp Ile Lys Glu Gly Gly Glu Leu Pro Ala Asn Arg Thr Phe Phe Glu
280                  285                  290                  295

AAT TTT AAG AAA ACT CTC AAG ATT ATA GAC GTC TCT GAA GCT GAC TCT        965
Asn Phe Lys Lys Thr Leu Lys Ile Ile Asp Val Ser Glu Ala Asp Ser
            300                  305                  310

GGG AAC TAC AAA TGT ACA GCA AGA AAT ACA TTG GGT TCT ACT CAT CAT       1013
Gly Asn Tyr Lys Cys Thr Ala Arg Asn Thr Leu Gly Ser Thr His His
            315                  320                  325

GTC ATT TCG GTA ACT GTA AAA GCT GCC CCA TAC TGG ATA ACA GCA CCC       1061
Val Ile Ser Val Thr Val Lys Ala Ala Pro Tyr Trp Ile Thr Ala Pro
            330                  335                  340

AGG AAC TTA GTA TTG TCT CCT GGA GAA GAT GGG ACA TTG ATC TGC AGA       1109
Arg Asn Leu Val Leu Ser Pro Gly Glu Asp Gly Thr Leu Ile Cys Arg
            345                  350                  355

GCT AAT GGC AAC CCA AAA CCT AGC ATA AGC TGG TTA ACA AAT GGC GTT       1157
Ala Asn Gly Asn Pro Lys Pro Ser Ile Ser Trp Leu Thr Asn Gly Val
360                  365                  370                  375

CCC ATA GCA ATT GCC CCA GAA GAT CCT AGC AGA AAG GTA GAT GGG GAT       1205
Pro Ile Ala Ile Ala Pro Glu Asp Pro Ser Arg Lys Val Asp Gly Asp
            380                  385                  390

ACC ATT ATT TTC TCA GCT GTG CAA GAA CGG TCA AGT GCT GTT TAT CAG       1253
Thr Ile Ile Phe Ser Ala Val Gln Glu Arg Ser Ser Ala Val Tyr Gln
            395                  400                  405

TGC AAT GCT TCT AAT GAG TAT GGA TAC TTG CTG GCA AAT GCA TTT GTG       1301
Cys Asn Ala Ser Asn Glu Tyr Gly Tyr Leu Leu Ala Asn Ala Phe Val
            410                  415                  420

AAT GTT CTT GCT GAG CCA CCA AGG ATT CTA ACT CCT GCT AAT AAA CTC       1349
Asn Val Leu Ala Glu Pro Pro Arg Ile Leu Thr Pro Ala Asn Lys Leu
            425                  430                  435

TAT CAA GTC ATC GCA GAT AGT CCT GCA TTA ATA GAC TGT GCT TAT TTT       1397
```

-continued

| | | |
|---|---|---|
| Tyr Gln Val Ile Ala Asp Ser Pro Ala Leu Ile Asp Cys Ala Tyr Phe<br>440                             445                    450                  455 | |
| GGT TCA CCT AAG CCT GAA ATC GAA TGG TTT AGG GGA GTG AAA GGT AGC<br>Gly Ser Pro Lys Pro Glu Ile Glu Trp Phe Arg Gly Val Lys Gly Ser<br>                 460                    465                    470 | 1445 |
| ATC TTG CGA GGA AAT GAA TAT GTT TTC CAT GAT AAT GGA ACC TTG GAA<br>Ile Leu Arg Gly Asn Glu Tyr Val Phe His Asp Asn Gly Thr Leu Glu<br>             475                    480                   485 | 1493 |
| ATT CCA GTG GCT CAG AAG GAT AGT ACT GGC ACA TAC ACA TGT GTT GCA<br>Ile Pro Val Ala Gln Lys Asp Ser Thr Gly Thr Tyr Thr Cys Val Ala<br>        490                    495                    500 | 1541 |
| AGG AAT AAA TTA GGG AAG ACG CAA AAT GAA GTA CAA CTG GAA GTT AAA<br>Arg Asn Lys Leu Gly Lys Thr Gln Asn Glu Val Gln Leu Glu Val Lys<br>505                           510                   515 | 1589 |
| GAC CCA ACG ATG ATA ATT AAA CAG CCA CAG TAC AAA GTG ATT CAG AGA<br>Asp Pro Thr Met Ile Ile Lys Gln Pro Gln Tyr Lys Val Ile Gln Arg<br>520                         525                    530                535 | 1637 |
| TCT GCC CAG GCT TCA TTT GAG TGT GTA ATA AAA CAT GAT CCT ACC TTA<br>Ser Ala Gln Ala Ser Phe Glu Cys Val Ile Lys His Asp Pro Thr Leu<br>             540                    545                   550 | 1685 |
| ATA CCA ACA GTT ATA TGG CTG AAA GAC AAT AAT GAA CTA CCA GAT GAT<br>Ile Pro Thr Val Ile Trp Leu Lys Asp Asn Asn Glu Leu Pro Asp Asp<br>             555                    560                   565 | 1733 |
| GAA AGG TTT CTA GTT GGT AAA GAC AAC TTG ACC ATT ATG AAT GTA ACT<br>Glu Arg Phe Leu Val Gly Lys Asp Asn Leu Thr Ile Met Asn Val Thr<br>        570                    575                   580 | 1781 |
| GAT AAA GAT GAT GGA ACA TAT ACT TGC ATA GTT AAT ACT ACT CTG GAC<br>Asp Lys Asp Asp Gly Thr Tyr Thr Cys Ile Val Asn Thr Thr Leu Asp<br>585                         590                    595 | 1829 |
| AGT GTT TCA GCA AGT GCT GTG CTT ACT GTT GTT GCT GCT CCC CCA ACT<br>Ser Val Ser Ala Ser Ala Val Leu Thr Val Val Ala Ala Pro Pro Thr<br>600                         605                    610                615 | 1877 |
| CCA GCT ATC ATT TAC GCT CGG CCA AAT CCA CCG CTT GAC TTG GAA TTG<br>Pro Ala Ile Ile Tyr Ala Arg Pro Asn Pro Pro Leu Asp Leu Glu Leu<br>             620                    625                   630 | 1925 |
| ACA GGT CAG CTA GAA AGA AGC ATT GAA CTC TCA TGG GTA CCA GGA GAA<br>Thr Gly Gln Leu Glu Arg Ser Ile Glu Leu Ser Trp Val Pro Gly Glu<br>        635                    640                   645 | 1973 |
| GAA AAT AAC AGT CCC ATT ACA AAC TTT GTG ATT GAG TAT GAA GAT GGA<br>Glu Asn Asn Ser Pro Ile Thr Asn Phe Val Ile Glu Tyr Glu Asp Gly<br>             650                    655                   660 | 2021 |
| CTA CAT GAG CCA GGG GTA TGG CAT TAC CAG ACG GAA GTT CCT GGA TCT<br>Leu His Glu Pro Gly Val Trp His Tyr Gln Thr Glu Val Pro Gly Ser<br>        665                    670                   675 | 2069 |
| CAT ACA ACT GTA CAG TTG AAG TTG TCT CCG TAT GTC AAC TAC TCA TTC<br>His Thr Thr Val Gln Leu Lys Leu Ser Pro Tyr Val Asn Tyr Ser Phe<br>680                       685                    690                695 | 2117 |
| CGT GTG ATT GCT GTC AAT GAA ATT GGT AGA AGT CAG CCA AGT GAA CCA<br>Arg Val Ile Ala Val Asn Glu Ile Gly Arg Ser Gln Pro Ser Glu Pro<br>             700                    705                   710 | 2165 |
| TCT GAA CAG TAC CTG ACA AAG TCC GCA AAC CCC GAT GAA AAT CCT TCT<br>Ser Glu Gln Tyr Leu Thr Lys Ser Ala Asn Pro Asp Glu Asn Pro Ser<br>        715                    720                   725 | 2213 |
| AAT GTA CAA GGG ATA GGC TCG GAA CCT GAT AAT TTG GTA ATA ACG TGG<br>Asn Val Gln Gly Ile Gly Ser Glu Pro Asp Asn Leu Val Ile Thr Trp<br>             730                    735                   740 | 2261 |
| GAG TCT TTA AAA GGC TTT CAG TCT AAT GGA CCA GGA CTC CAA TAT AAA<br>Glu Ser Leu Lys Gly Phe Gln Ser Asn Gly Pro Gly Leu Gln Tyr Lys<br>        745                    750                   755 | 2309 |

```
                                                              -continued
GTC AGC TGG CGC CAG AAG GAT GTT GAT GAT GAA TGG ACG TCC GTT GTA    2357
Val Ser Trp Arg Gln Lys Asp Val Asp Asp Glu Trp Thr Ser Val Val
760             765             770             775

GTT GCA AAC GTG TCT AAA TAT ATT GTG TCT GGT ACA CCA ACT TTT GTT    2405
Val Ala Asn Val Ser Lys Tyr Ile Val Ser Gly Thr Pro Thr Phe Val
            780             785             790

CCC TAT GAA ATA AAA GTA CAG GCT TTA AAT GAC CTG GGA TAT GCA CCA    2453
Pro Tyr Glu Ile Lys Val Gln Ala Leu Asn Asp Leu Gly Tyr Ala Pro
        795             800             805

GAG CCA TCA GAG GTT ATT GGA CAT TCA GGG GAA GAC TTG CCA ATG GTT    2501
Glu Pro Ser Glu Val Ile Gly His Ser Gly Glu Asp Leu Pro Met Val
    810             815             820

GCT CCA GGC AAT GTG CAG GTT CAT GTC ATT AAC AGC ACA TTG GCA AAG    2549
Ala Pro Gly Asn Val Gln Val His Val Ile Asn Ser Thr Leu Ala Lys
825             830             835

GTG CAC TGG GAC CCT GTT CCA CTA AAA TCT GTC CGA GGA CAT CTT CAA    2597
Val His Trp Asp Pro Val Pro Leu Lys Ser Val Arg Gly His Leu Gln
840             845             850             855

GGA TAT AAA GTT TAC TAC TGG AAA GTA CAG AGT CTA TCC AGA AGG AGT    2645
Gly Tyr Lys Val Tyr Tyr Trp Lys Val Gln Ser Leu Ser Arg Arg Ser
            860             865             870

AAA CGG CAT GTA GAA AAA AAG ATC TTG ACT TTC AGG GGA AAC AAG ACT    2693
Lys Arg His Val Glu Lys Lys Ile Leu Thr Phe Arg Gly Asn Lys Thr
        875             880             885

TTT GGA ATG TTA CCA GGG CTA GAG CCC TAT AGT TCT TAC AAG CTG AAT    2741
Phe Gly Met Leu Pro Gly Leu Glu Pro Tyr Ser Ser Tyr Lys Leu Asn
    890             895             900

GTT AGA GTT GTT AAT GGT AAA GGA GAA GGA CCA GCA AGC CCA GAC AAA    2789
Val Arg Val Val Asn Gly Lys Gly Glu Gly Pro Ala Ser Pro Asp Lys
905             910             915

GTA TTT AAA ACT CCT GAA GGA GTT CCT AGC CCA CCC TCC TTT TTG AAG    2837
Val Phe Lys Thr Pro Glu Gly Val Pro Ser Pro Pro Ser Phe Leu Lys
920             925             930             935

ATT ACT AAT CCA ACA CTG GAC TCT CTG ACT CTG GAG TGG GGT TCA CCT    2885
Ile Thr Asn Pro Thr Leu Asp Ser Leu Thr Leu Glu Trp Gly Ser Pro
            940             945             950

ACC CAT CCA AAT GGT GTT TTG ACA TCA TAC ATA CTG AAG TTT CAG CCA    2933
Thr His Pro Asn Gly Val Leu Thr Ser Tyr Ile Leu Lys Phe Gln Pro
        955             960             965

ATT AAC AAC ACA CAT GAA TTA GGT CCC TTG GTA GAG ATA AGA ATA CCT    2981
Ile Asn Asn Thr His Glu Leu Gly Pro Leu Val Glu Ile Arg Ile Pro
    970             975             980

GCC AAC GAG AGC AGC TTG ATA TTA AAA AAT TTA AAT TAC AGC ACA CGA    3029
Ala Asn Glu Ser Ser Leu Ile Leu Lys Asn Leu Asn Tyr Ser Thr Arg
985             990             995

TAC AAG TTT TAC TTT AAT GCA CAA ACA TCA GTT GGA TCA GGA AGT CAG    3077
Tyr Lys Phe Tyr Phe Asn Ala Gln Thr Ser Val Gly Ser Gly Ser Gln
1000            1005            1010            1015

ATA ACT GAG GAA GCA GTA ACA ATT ATG GAT GAA GTG CAA CCA CTT TAT    3125
Ile Thr Glu Glu Ala Val Thr Ile Met Asp Glu Val Gln Pro Leu Tyr
            1020            1025            1030

CCA AGG ATC AGA AAT GTT ACA ACA GCT GCT GCT GAG ACC TAT GCC AAT    3173
Pro Arg Ile Arg Asn Val Thr Thr Ala Ala Ala Glu Thr Tyr Ala Asn
        1035            1040            1045

ATT AGT TGG GAG TAT GAG GGA CCA GAT CAT GCC AAC TTT TAT GTT GAA    3221
Ile Ser Trp Glu Tyr Glu Gly Pro Asp His Ala Asn Phe Tyr Val Glu
    1050            1055            1060

TAT GGT GTA GCA GGC AGC AAA GAA GAT TGG AAA AAA GAA ATT GTA AAT    3269
Tyr Gly Val Ala Gly Ser Lys Glu Asp Trp Lys Lys Glu Ile Val Asn
1065            1070            1075
```

| | | |
|---|---|---|
| GGT TCT CGA AGC TTC TTT GTG TTA AAG GGT TTA ACA CCA GGA ACA GCA<br>Gly Ser Arg Ser Phe Phe Val Leu Lys Gly Leu Thr Pro Gly Thr Ala<br>1080                          1085                     1090                        1095 | 3317 |
| TAT AAA GTC CGA GTT GGT GCT GAG GGC CTG TCT GGT TTT AGG AGT TCA<br>Tyr Lys Val Arg Val Gly Ala Glu Gly Leu Ser Gly Phe Arg Ser Ser<br>                           1100                     1105                     1110 | 3365 |
| GAG GAT CTG TTT GAG ACA GGT CCA GCA ATG GCA AGT CGG CAG GTA GAC<br>Glu Asp Leu Phe Glu Thr Gly Pro Ala Met Ala Ser Arg Gln Val Asp<br>                 1115                     1120                     1125 | 3413 |
| ATT GCT ACT CAA GGA TGG TTC ATT GGA CTT ATG TGT GCT GTT GCA CTT<br>Ile Ala Thr Gln Gly Trp Phe Ile Gly Leu Met Cys Ala Val Ala Leu<br>                 1130                     1135                     1140 | 3461 |
| CTT ATC TTG ATT TTA TTG ATT GTT TGC TTC ATA AGG AGG AAT AAA GGT<br>Leu Ile Leu Ile Leu Leu Ile Val Cys Phe Ile Arg Arg Asn Lys Gly<br>                 1145                     1150                     1155 | 3509 |
| GGC AAA TAT CCA GTG AAG GAA AAG GAG GAT GCA CAT GCT GAT CCA GAA<br>Gly Lys Tyr Pro Val Lys Glu Lys Glu Asp Ala His Ala Asp Pro Glu<br>1160                          1165                     1170                     1175 | 3557 |
| ATA CAG CCT ATG AAG GAA GAT GAT GGA ACA TTT GGT GAA TAC AGT GAT<br>Ile Gln Pro Met Lys Glu Asp Asp Gly Thr Phe Gly Glu Tyr Ser Asp<br>                 1180                     1185                     1190 | 3605 |
| GCA GAG GAC CAT AAA CCT CTA AAA AAA GGA AGT CGG ACA CCG TCA GAC<br>Ala Glu Asp His Lys Pro Leu Lys Lys Gly Ser Arg Thr Pro Ser Asp<br>                 1195                     1200                     1205 | 3653 |
| AGA ACT GTG AAA AAA GAA GAC AGT GAT GAT AGT TTA GTT GAC TAT GGA<br>Arg Thr Val Lys Lys Glu Asp Ser Asp Asp Ser Leu Val Asp Tyr Gly<br>                 1210                     1215                     1220 | 3701 |
| GAA GGT GTA AAT GGC CAG TTC AAT GAG GAT GGC TCC TTT ATT GGA CAA<br>Glu Gly Val Asn Gly Gln Phe Asn Glu Asp Gly Ser Phe Ile Gly Gln<br>                 1225                     1230                     1235 | 3749 |
| TAC AGC GGT AAA AAA GAG AAA GAA CCT GCA GAA GGA AAT GAA AGT TCT<br>Tyr Ser Gly Lys Lys Glu Lys Glu Pro Ala Glu Gly Asn Glu Ser Ser<br>1240                          1245                     1250                     1255 | 3797 |
| GAG GCT CCT TCT CCT GTA AAT GCC ATG AAT TCA TTT GTG TAATCAAAGA<br>Glu Ala Pro Ser Pro Val Asn Ala Met Asn Ser Phe Val<br>                         1260                     1265 | 3846 |
| ACTTGATTCC CTTGTGTTTT CTGTTTGTTT GCACTTGTAC ATCCTCCTTC TCGTACGATG | 3906 |
| AACATGCAGG TTACAAAGCT CCTCACCTCA AAGTATT | 3943 |

(2) INFORMATION FOR SEQ ID NO:28:

(i) SEQUENCE CHARACTERISTICS:
        (A) LENGTH: 1268 amino acids
        (B) TYPE: amino acid
        (D) TOPOLOGY: linear (ii) MOLECULE TYPE: protein (xi) SEQUENCE DESCRIPTION: SEQ ID NO:28:

Met Met Lys Glu Lys Ser Ile Ser Ala Ser Lys Ala Ser Leu Val Phe
 1              5                10               15

Phe Leu Cys Gln Met Ile Ser Ala Leu Asp Val Pro Leu Asp Ser Lys
             20                25               30

Leu Leu Glu Glu Leu Ser Gln Pro Pro Thr Ile Thr Gln Gln Ser Pro
          35                 40               45

Lys Asp Tyr Ile Val Asp Pro Arg Glu Asn Ile Val Ile Gln Cys Glu
    50                55                60

Ala Lys Gly Lys Pro Pro Pro Ser Phe Ser Trp Thr Arg Asn Gly Thr
 65              70               75               80

-continued

```
His Phe Asp Ile Asp Lys Asp Ala Gln Val Thr Met Lys Pro Asn Ser
                85                  90                  95
Gly Thr Leu Val Val Asn Ile Met Asn Gly Val Lys Ala Glu Ala Tyr
            100                 105                 110
Glu Gly Val Tyr Gln Cys Thr Ala Arg Asn Glu Arg Gly Ala Ala Ile
            115                 120                 125
Ser Asn Asn Ile Val Ile Arg Pro Ser Arg Ser Pro Leu Trp Thr Lys
130                 135                 140
Glu Lys Leu Glu Pro Asn His Val Arg Glu Gly Asp Ser Leu Val Leu
145                 150                 155                 160
Asn Cys Arg Pro Pro Val Gly Leu Pro Pro Pro Ile Ile Phe Trp Met
                165                 170                 175
Asp Asn Ala Phe Gln Arg Leu Pro Gln Ser Glu Arg Val Ser Gln Gly
            180                 185                 190
Leu Asn Gly Asp Leu Tyr Phe Ser Asn Val Gln Pro Glu Asp Thr Arg
            195                 200                 205
Val Asp Tyr Ile Cys Tyr Ala Arg Phe Asn His Thr Gln Thr Ile Gln
            210                 215                 220
Gln Lys Gln Pro Ile Ser Val Lys Val Phe Ser Thr Lys Pro Val Thr
225                 230                 235                 240
Glu Arg Pro Pro Val Leu Leu Thr Pro Met Gly Ser Thr Ser Asn Lys
                245                 250                 255
Val Glu Leu Arg Gly Asn Val Leu Leu Leu Glu Cys Ile Ala Ala Gly
            260                 265                 270
Leu Pro Thr Pro Val Ile Arg Trp Ile Lys Glu Gly Gly Glu Leu Pro
            275                 280                 285
Ala Asn Arg Thr Phe Phe Glu Asn Phe Lys Lys Thr Leu Lys Ile Ile
290                 295                 300
Asp Val Ser Glu Ala Asp Ser Gly Asn Tyr Lys Cys Thr Ala Arg Asn
305                 310                 315                 320
Thr Leu Gly Ser Thr His His Val Ile Ser Val Thr Val Lys Ala Ala
                325                 330                 335
Pro Tyr Trp Ile Thr Ala Pro Arg Asn Leu Val Leu Ser Pro Gly Glu
            340                 345                 350
Asp Gly Thr Leu Ile Cys Arg Ala Asn Gly Asn Pro Lys Pro Ser Ile
            355                 360                 365
Ser Trp Leu Thr Asn Gly Val Pro Ile Ala Ile Ala Pro Glu Asp Pro
            370                 375                 380
Ser Arg Lys Val Asp Gly Asp Thr Ile Ile Phe Ser Ala Val Gln Glu
385                 390                 395                 400
Arg Ser Ser Ala Val Tyr Gln Cys Asn Ala Ser Asn Glu Tyr Gly Tyr
                405                 410                 415
Leu Leu Ala Asn Ala Phe Val Asn Val Leu Ala Glu Pro Pro Arg Ile
            420                 425                 430
Leu Thr Pro Ala Asn Lys Leu Tyr Gln Val Ile Ala Asp Ser Pro Ala
            435                 440                 445
Leu Ile Asp Cys Ala Tyr Phe Gly Ser Pro Lys Pro Glu Ile Glu Trp
            450                 455                 460
Phe Arg Gly Val Lys Gly Ser Ile Leu Arg Gly Asn Glu Tyr Val Phe
465                 470                 475                 480
His Asp Asn Gly Thr Leu Glu Ile Pro Val Ala Gln Lys Asp Ser Thr
                485                 490                 495
```

-continued

```
Gly Thr Tyr Thr Cys Val Ala Arg Asn Lys Leu Gly Lys Thr Gln Asn
            500                 505                 510

Glu Val Gln Leu Glu Val Lys Asp Pro Thr Met Ile Ile Lys Gln Pro
            515                 520                 525

Gln Tyr Lys Val Ile Gln Arg Ser Ala Gln Ala Ser Phe Glu Cys Val
            530                 535                 540

Ile Lys His Asp Pro Thr Leu Ile Pro Thr Val Ile Trp Leu Lys Asp
545                 550                 555                 560

Asn Asn Glu Leu Pro Asp Asp Glu Arg Phe Leu Val Gly Lys Asp Asn
                565                 570                 575

Leu Thr Ile Met Asn Val Thr Asp Lys Asp Asp Gly Thr Tyr Thr Cys
            580                 585                 590

Ile Val Asn Thr Thr Leu Asp Ser Val Ser Ala Ser Ala Val Leu Thr
            595                 600                 605

Val Val Ala Ala Pro Pro Thr Pro Ala Ile Ile Tyr Ala Arg Pro Asn
            610                 615                 620

Pro Pro Leu Asp Leu Glu Leu Thr Gly Gln Leu Glu Arg Ser Ile Glu
625                 630                 635                 640

Leu Ser Trp Val Pro Gly Glu Glu Asn Asn Ser Pro Ile Thr Asn Phe
                645                 650                 655

Val Ile Glu Tyr Glu Asp Gly Leu His Glu Pro Gly Val Trp His Tyr
            660                 665                 670

Gln Thr Glu Val Pro Gly Ser His Thr Thr Val Gln Leu Lys Leu Ser
            675                 680                 685

Pro Tyr Val Asn Tyr Ser Phe Arg Val Ile Ala Val Asn Glu Ile Gly
            690                 695                 700

Arg Ser Gln Pro Ser Glu Pro Ser Glu Gln Tyr Leu Thr Lys Ser Ala
705                 710                 715                 720

Asn Pro Asp Glu Asn Pro Ser Asn Val Gln Gly Ile Gly Ser Glu Pro
                725                 730                 735

Asp Asn Leu Val Ile Thr Trp Glu Ser Leu Lys Gly Phe Gln Ser Asn
            740                 745                 750

Gly Pro Gly Leu Gln Tyr Lys Val Ser Trp Arg Gln Lys Asp Val Asp
            755                 760                 765

Asp Glu Trp Thr Ser Val Val Ala Asn Val Ser Lys Tyr Ile Val
            770                 775                 780

Ser Gly Thr Pro Thr Phe Val Pro Tyr Glu Ile Lys Val Gln Ala Leu
785                 790                 795                 800

Asn Asp Leu Gly Tyr Ala Pro Glu Pro Ser Glu Val Ile Gly His Ser
                805                 810                 815

Gly Glu Asp Leu Pro Met Val Ala Pro Gly Asn Val Gln Val His Val
            820                 825                 830

Ile Asn Ser Thr Leu Ala Lys Val His Trp Asp Pro Val Pro Leu Lys
            835                 840                 845

Ser Val Arg Gly His Leu Gln Gly Tyr Lys Val Tyr Tyr Trp Lys Val
            850                 855                 860

Gln Ser Leu Ser Arg Arg Ser Lys Arg His Val Glu Lys Lys Ile Leu
865                 870                 875                 880

Thr Phe Arg Gly Asn Lys Thr Phe Gly Met Leu Pro Gly Leu Glu Pro
                885                 890                 895

Tyr Ser Ser Tyr Lys Leu Asn Val Arg Val Val Asn Gly Lys Gly Glu
            900                 905                 910

Gly Pro Ala Ser Pro Asp Lys Val Phe Lys Thr Pro Glu Gly Val Pro
```

```
                915                 920                 925
Ser Pro Pro Ser Phe Leu Lys Ile Thr Asn Pro Thr Leu Asp Ser Leu
        930                 935                 940

Thr Leu Glu Trp Gly Ser Pro Thr His Pro Asn Gly Val Leu Thr Ser
945                 950                 955                 960

Tyr Ile Leu Lys Phe Gln Pro Ile Asn Asn Thr His Glu Leu Gly Pro
                965                 970                 975

Leu Val Glu Ile Arg Ile Pro Ala Asn Glu Ser Ser Leu Ile Leu Lys
            980                 985                 990

Asn Leu Asn Tyr Ser Thr Arg Tyr Lys Phe Tyr Phe Asn Ala Gln Thr
        995                 1000                1005

Ser Val Gly Ser Gly Ser Gln Ile Thr Glu Glu Ala Val Thr Ile Met
    1010                1015                1020

Asp Glu Val Gln Pro Leu Tyr Pro Arg Ile Arg Asn Val Thr Thr Ala
1025                1030                1035                1040

Ala Ala Glu Thr Tyr Ala Asn Ile Ser Trp Glu Tyr Glu Gly Pro Asp
                1045                1050                1055

His Ala Asn Phe Tyr Val Glu Tyr Gly Val Ala Gly Ser Lys Glu Asp
            1060                1065                1070

Trp Lys Lys Glu Ile Val Asn Gly Ser Arg Ser Phe Phe Val Leu Lys
        1075                1080                1085

Gly Leu Thr Pro Gly Thr Ala Tyr Lys Val Arg Val Gly Ala Glu Gly
    1090                1095                1100

Leu Ser Gly Phe Arg Ser Ser Glu Asp Leu Phe Glu Thr Gly Pro Ala
1105                1110                1115                1120

Met Ala Ser Arg Gln Val Asp Ile Ala Thr Gln Gly Trp Phe Ile Gly
                1125                1130                1135

Leu Met Cys Ala Val Ala Leu Leu Ile Leu Ile Leu Leu Ile Val Cys
            1140                1145                1150

Phe Ile Arg Arg Asn Lys Gly Gly Lys Tyr Pro Val Lys Glu Lys Glu
        1155                1160                1165

Asp Ala His Ala Asp Pro Glu Ile Gln Pro Met Lys Glu Asp Asp Gly
    1170                1175                1180

Thr Phe Gly Glu Tyr Ser Asp Ala Glu Asp His Lys Pro Leu Lys Lys
1185                1190                1195                1200

Gly Ser Arg Thr Pro Ser Asp Arg Thr Val Lys Lys Glu Asp Ser Asp
                1205                1210                1215

Asp Ser Leu Val Asp Tyr Gly Glu Gly Val Asn Gly Gln Phe Asn Glu
            1220                1225                1230

Asp Gly Ser Phe Ile Gly Gln Tyr Ser Gly Lys Lys Glu Lys Glu Pro
        1235                1240                1245

Ala Glu Gly Asn Glu Ser Ser Glu Ala Pro Ser Pro Val Asn Ala Met
    1250                1255                1260

Asn Ser Phe Val
1265

(2) INFORMATION FOR SEQ ID NO:29:

(i) SEQUENCE CHARACTERISTICS:
        (A) LENGTH: 23 base pairs
        (B) TYPE: nucleic acid
        (C) STRANDEDNESS: single
        (D) TOPOLOGY: linear (ii) MOLECULE TYPE: cDNA
```

(iii) HYPOTHETICAL: NO (iv) ANTI-SENSE: NO (xi) SEQUENCE DESCRIPTION: SEQ ID NO:29:

CAACCATGGG CAATGTGCAG GTT                                              23

(2) INFORMATION FOR SEQ ID NO:30:

(i) SEQUENCE CHARACTERISTICS:
            (A) LENGTH: 23 base pairs
            (B) TYPE: nucleic acid
            (C) STRANDEDNESS: single
            (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO:30:

CAGCCATGGG CCCTAGCCCA CCC                                              23

(2) INFORMATION FOR SEQ ID NO:31:

(i) SEQUENCE CHARACTERISTICS:
            (A) LENGTH: 24 base pairs
            (B) TYPE: nucleic acid
            (C) STRANDEDNESS: single
            (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO:31:

AAAGGATCCC TACCATCCTT GAGT                                             24

(2) INFORMATION FOR SEQ ID NO:32:

(i) SEQUENCE CHARACTERISTICS:
            (A) LENGTH: 23 base pairs
            (B) TYPE: nucleic acid
            (C) STRANDEDNESS: single
            (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO:32:

CAACCATGGG CGTAGAAAAA AAG                                              23

(2) INFORMATION FOR SEQ ID NO:33:

(i) SEQUENCE CHARACTERISTICS:
            (A) LENGTH: 24 base pairs
            (B) TYPE: nucleic acid
            (C) STRANDEDNESS: single
            (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO:33:

AAAGGATCCC TATTACACAA ATGA                                                      24

(2) INFORMATION FOR SEQ ID NO:34:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO:34:

GCGGGATCCA ATGTGGGGGT GGAACTGCTG                                                30

(2) INFORMATION FOR SEQ ID NO:35:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO:35:

GCGGGATCCC CCGGCCCCCC CGAGGAGCTC                                                30

(2) INFORMATION FOR SEQ ID NO:36:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO:36:

GCGGAATTCC CACCCCTTGG TGCAAACCCC                                                30

(2) INFORMATION FOR SEQ ID NO:37:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO:37:

GCGGGATCCG CCCCCCCCGA CCCCCCCCAA                                    30

(2) INFORMATION FOR SEQ ID NO:38:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO:38:

GCGGAATTCT TAATCCAGGG GGGGCCCAGC                                    30

(2) INFORMATION FOR SEQ ID NO:39:

(i) SEQUENCE CHARACTERISTICS:
        (A) LENGTH: 27 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO:39:

GCGGGATCCC TGGAAGGCAT TGAAATC                                       27

(2) INFORMATION FOR SEQ ID NO:40:

(i) SEQUENCE CHARACTERISTICS:
        (A) LENGTH: 27 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO:40:

GCGGGATCCC CTGGCCACCC CGAGGCG                                       27

(2) INFORMATION FOR SEQ ID NO:41:

(i) SEQUENCE CHARACTERISTICS:
        (A) LENGTH: 27 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO:41:

GCGGAATTCC CAGCCCTCAG TGGCGAA                                       27

(2) INFORMATION FOR SEQ ID NO:42:

(i) SEQUENCE CHARACTERISTICS:
        (A) LENGTH: 27 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO:42:

GCGGGATCCC ATATCCACAA AGACCAT                            27

(2) INFORMATION FOR SEQ ID NO:43:

(i) SEQUENCE CHARACTERISTICS:
        (A) LENGTH: 27 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO:43:

GCGGAATTCC TATTCTAGGG CCACGGC                            27

(2) INFORMATION FOR SEQ ID NO:44:

(i) SEQUENCE CHARACTERISTICS:
        (A) LENGTH: 27 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO:44:

GCGGGATCCC TTGAAGACAT CACAATC                            27

(2) INFORMATION FOR SEQ ID NO:45:

(i) SEQUENCE CHARACTERISTICS:
        (A) LENGTH: 27 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO:45:

GCGGGATCCC CTGGCCACCC TGAGGCA                            27

(2) INFORMATION FOR SEQ ID NO:46:

(i) SEQUENCE CHARACTERISTICS:

(A) LENGTH: 27 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO:46:

GCGGAATTCC CAGCCCTCGG AGGCAAA                                27

(2) INFORMATION FOR SEQ ID NO:47:

(i) SEQUENCE CHARACTERISTICS:
        (A) LENGTH: 27 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO:47:

GCGGGATCCC ATATCCACAA AAGCCAC                                27

(2) INFORMATION FOR SEQ ID NO:48:

(i) SEQUENCE CHARACTERISTICS:
        (A) LENGTH: 27 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO:48:

GCGGAATTCC TATTGTAGGG CTACTGC                                27

(2) INFORMATION FOR SEQ ID NO:49:

(i) SEQUENCE CHARACTERISTICS:
        (A) LENGTH: 27 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO:49:

GCGGGATCCA ATGTGCAGGT TCATGTC                                27

(2) INFORMATION FOR SEQ ID NO:50:

(i) SEQUENCE CHARACTERISTICS:
        (A) LENGTH: 27 base pairs
        (B) TYPE: nucleic acid
        (C) STRANDEDNESS: single (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO:50:

GCGGGATCCC CTAGCCCACC CTCCTTT                                                    27

(2) INFORMATION FOR SEQ ID NO:51:

(i) SEQUENCE CHARACTERISTICS:
            (A) LENGTH: 27 base pairs
            (B) TYPE: nucleic acid
            (C) STRANDEDNESS: single
            (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO:51:

GCGGAATTCC CATCCTTGAG TAGCAAT                                                    27

(2) INFORMATION FOR SEQ ID NO:52:

(i) SEQUENCE CHARACTERISTICS:
            (A) LENGTH: 27 base pairs
            (B) TYPE: nucleic acid
            (C) STRANDEDNESS: single
            (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO:52:

GCGGGATCCG TAGAAAAAAA GATCTTG                                                    27

(2) INFORMATION FOR SEQ ID NO:53:

(i) SEQUENCE CHARACTERISTICS:
            (A) LENGTH: 27 base pairs
            (B) TYPE: nucleic acid
            (C) STRANDEDNESS: single
            (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO:53:

GCGGAATTCT TACACAAATG AATTCAT                                                    27

(2) INFORMATION FOR SEQ ID NO:54:

(i) SEQUENCE CHARACTERISTICS:
            (A) LENGTH: 321 amino acids
            (B) TYPE: amino acid
            (D) TOPOLOGY: linear (ii) MOLECULE TYPE: protein (v) FRAGMENT TYPE: internal (xi) SEQUENCE DESCRIPTION: SEQ ID NO:54:

Asn Val Gly Val Glu Leu Leu Asn Ser Ser Thr Val Arg Val Arg Trp
1               5                   10                  15

Thr Leu Gly Gly Gly Pro Lys Glu Leu Arg Gly Arg Leu Arg Gly Phe
            20                  25                  30

Arg Val Leu Tyr Trp Arg Leu Gly Trp Val Gly Glu Arg Ser Arg Arg
            35                  40                  45

Gln Ala Pro Pro Asp Pro Pro Gln Ile Pro Gln Ser Pro Ala Glu Asp
    50                  55                  60

Pro Pro Pro Phe Pro Pro Val Ala Leu Thr Val Gly Asp Ala Arg
65                  70                  75                  80

Gly Ala Leu Leu Gly Gly Leu Arg Pro Trp Ser Arg Tyr Gln Leu Arg
                85                  90                  95

Val Leu Val Phe Asn Gly Arg Gly Asp Gly Pro Pro Ser Glu Pro Ile
                100                 105                 110

Ala Phe Glu Thr Pro Glu Gly Val Pro Gly Pro Pro Glu Glu Leu Arg
            115                 120                 125

Val Glu Arg Leu Asp Asp Thr Ala Leu Ser Val Val Glu Arg Arg Thr
130                 135                 140

Phe Lys Arg Ser Ile Thr Gly Tyr Val Leu Arg Tyr Gln Gln Val Glu
145                 150                 155                 160

Pro Gly Ser Ala Leu Pro Gly Gly Ser Val Leu Arg Asp Pro Gln Cys
                165                 170                 175

Asp Leu Arg Gly Leu Asn Ala Arg Ser Arg Tyr Arg Leu Ala Leu Pro
            180                 185                 190

Ser Thr Pro Arg Glu Arg Pro Ala Leu Gln Thr Val Gly Ser Thr Lys
            195                 200                 205

Pro Glu Pro Pro Ser Pro Leu Trp Ser Arg Phe Gly Val Gly Gly Arg
            210                 215                 220

Gly Gly Phe His Gly Ala Ala Val Glu Phe Gly Ala Ala Gln Glu Asp
225                 230                 235                 240

Asp Val Glu Phe Glu Val Gln Phe Met Asn Lys Ser Thr Asp Glu Pro
            245                 250                 255

Trp Arg Thr Ser Gly Arg Ala Asn Ser Ser Leu Arg Arg Tyr Arg Leu
            260                 265                 270

Glu Gly Leu Arg Pro Gly Thr Ala Tyr Arg Val Gln Phe Val Gly Arg
            275                 280                 285

Asn Arg Ser Gly Glu Asn Val Ala Phe Trp Glu Ser Glu Val Gln Thr
            290                 295                 300

Asn Gly Thr Val Val Pro Gln Pro Gly Gly Gly Val Cys Thr Lys Gly
305                 310                 315                 320

Trp (2) INFORMATION FOR SEQ ID NO:55:

(i) SEQUENCE CHARACTERISTICS:
        (A) LENGTH: 201 amino acids
        (B) TYPE: amino acid
        (D) TOPOLOGY: linear (ii) MOLECULE TYPE: protein (v) FRAGMENT TYPE: internal (xi) SEQUENCE DESCRIPTION: SEQ ID NO:55:

```
Pro Gly Pro Pro Glu Glu Leu Arg Val Glu Arg Leu Asp Asp Thr Ala
 1               5                  10                  15
Leu Ser Val Val Glu Arg Arg Thr Phe Lys Arg Ser Ile Thr Gly Tyr
                20                  25                  30
Val Leu Arg Tyr Gln Gln Val Glu Pro Gly Ser Ala Leu Pro Gly Gly
                35                  40                  45
Ser Val Leu Arg Asp Pro Gln Cys Asp Leu Arg Gly Leu Asn Ala Arg
 50                  55                  60
Ser Arg Tyr Arg Leu Ala Leu Pro Ser Thr Pro Arg Glu Arg Pro Ala
 65                  70                  75                  80
Leu Gln Thr Val Gly Ser Thr Lys Pro Glu Pro Pro Ser Pro Leu Trp
                85                  90                  95
Ser Arg Phe Gly Val Gly Gly Arg Gly Gly Phe His Gly Ala Ala Val
                100                 105                 110
Glu Phe Gly Ala Ala Gln Glu Asp Asp Val Glu Phe Glu Val Gln Phe
                115                 120                 125
Met Asn Lys Ser Thr Asp Glu Pro Trp Arg Thr Ser Gly Arg Ala Asn
                130                 135                 140
Ser Ser Leu Arg Arg Tyr Arg Leu Glu Gly Leu Arg Pro Gly Thr Ala
145                 150                 155                 160
Tyr Arg Val Gln Phe Val Gly Arg Asn Arg Ser Gly Glu Asn Val Ala
                165                 170                 175
Phe Trp Glu Ser Glu Val Gln Thr Asn Gly Thr Val Val Pro Gln Pro
                180                 185                 190
Gly Gly Gly Val Cys Thr Lys Gly Trp
                195                 200

(2) INFORMATION FOR SEQ ID NO:56:

(i) SEQUENCE CHARACTERISTICS:
        (A) LENGTH: 427 amino acids
        (B) TYPE: amino acid
        (D) TOPOLOGY: linear (ii) MOLECULE TYPE: protein (v) FRAGMENT TYPE: C-terminal (xi) SEQUENCE DESCRIPTION: SEQ ID NO:56:

Ile His Lys Asp His Val Val Pro Ala Asn Thr Thr Ser Val Ile
 1               5                  10                  15
Leu Ser Gly Leu Arg Pro Tyr Ser Ser Tyr His Leu Glu Val Gln Ala
                20                  25                  30
Phe Asn Gly Arg Gly Ser Gly Pro Ala Ser Glu Phe Thr Phe Ser Thr
                35                  40                  45
Pro Glu Gly Val Pro Gly His Pro Glu Ala Leu His Leu Glu Cys Gln
 50                  55                  60
Ser Asn Thr Ser Leu Leu Leu Arg Trp Gln Pro Pro Leu Ser His Asn
 65                  70                  75                  80
Gly Val Leu Thr Gly Tyr Val Leu Ser Tyr His Pro Leu Asp Glu Gly
                85                  90                  95
Gly Lys Gly Gln Leu Ser Phe Asn Leu Arg Asp Pro Glu Leu Arg Thr
                100                 105                 110
His Asn Leu Thr Asp Leu Ser Pro His Leu Arg Tyr Arg Phe Gln Leu
                115                 120                 125
Gln Ala Thr Thr Lys Glu Gly Pro Gly Glu Ala Ile Val Arg Glu Gly
```

```
                    130                 135                 140
Gly Thr Met Ala Leu Ser Gly Ile Ser Asp Phe Gly Asn Ile Ser Ala
145                 150                 155                 160

Thr Ala Gly Glu Asn Tyr Ser Val Val Ser Trp Val Pro Lys Glu Gly
                165                 170                 175

Gln Cys Asn Phe Arg Phe His Ile Leu Phe Lys Ala Leu Gly Glu Glu
                180                 185                 190

Lys Gly Gly Ala Ser Leu Ser Pro Gln Tyr Val Ser Tyr Asn Gln Ser
                195                 200                 205

Ser Tyr Thr Gln Trp Asp Leu Gln Pro Asp Thr Asp Tyr Glu Ile His
                210                 215                 220

Leu Phe Lys Glu Arg Met Phe Arg His Gln Met Ala Val Lys Thr Asn
225                 230                 235                 240

Gly Thr Gly Arg Val Arg Leu Pro Pro Ala Gly Phe Ala Thr Glu Gly
                245                 250                 255

Trp Phe Ile Gly Phe Val Ser Ala Ile Ile Leu Leu Leu Val Leu
                260                 265                 270

Leu Ile Leu Cys Phe Ile Lys Arg Ser Lys Gly Lys Tyr Ser Val
    275                 280                 285

Lys Asp Lys Glu Asp Thr Gln Val Asp Ser Glu Ala Arg Pro Met Lys
290                 295                 300

Asp Glu Thr Phe Gly Glu Tyr Ser Asp Asn Glu Glu Lys Ala Phe Gly
305                 310                 315                 320

Ser Ser Gln Pro Ser Leu Asn Gly Asp Ile Lys Pro Leu Gly Ser Asp
                325                 330                 335

Asp Ser Leu Ala Asp Tyr Gly Gly Ser Val Asp Val Gln Phe Asn Glu
                340                 345                 350

Asp Gly Ser Phe Ile Gly Gln Tyr Ser Gly Lys Lys Glu Lys Glu Ala
                355                 360                 365

Ala Gly Gly Asn Asp Ser Ser Gly Ala Thr Ser Pro Ile Asn Pro Ala
                370                 375                 380

Val Ala Leu Glu Xaa Trp Ser Pro Gly Gln Glu Met Leu Cys Pro Trp
385                 390                 395                 400

Pro Trp Asp Pro Gly Pro Ser Leu Ser Ser Arg Pro Met Gly Gly Trp
                405                 410                 415

Ser Trp Gly Arg Gly Glu Leu Ala Ala Ser Asp
                420                 425

(2) INFORMATION FOR SEQ ID NO:57:

(i) SEQUENCE CHARACTERISTICS:
         (A) LENGTH: 304 amino acids
         (B) TYPE: amino acid
         (D) TOPOLOGY: linear (ii) MOLECULE TYPE: protein (v) FRAGMENT TYPE: internal (xi) SEQUENCE DESCRIPTION: SEQ ID NO:57:

Leu Glu Gly Ile Glu Ile Leu Asn Ser Ser Ala Val Leu Val Lys Trp
1               5                   10                  15

Arg Pro Val Asp Leu Ala Gln Val Lys Gly His Leu Arg Gly Tyr Asn
                20                  25                  30

Val Thr Tyr Trp Arg Glu Gly Ser Gln Arg Lys His Ser Lys Arg His
                35                  40                  45
```

```
Ile His Lys Asp His Val Val Pro Ala Asn Thr Thr Ser Val Ile
    50              55                  60
Leu Ser Gly Leu Arg Pro Tyr Ser Ser Tyr His Leu Glu Val Gln Ala
65              70              75                  80
Phe Asn Gly Arg Gly Ser Gly Pro Ala Ser Glu Phe Thr Phe Ser Thr
                85              90                  95
Pro Glu Gly Val Pro Gly His Pro Glu Ala Leu His Leu Glu Cys Gln
                100             105             110
Ser Asn Thr Ser Leu Leu Leu Arg Trp Gln Pro Pro Leu Ser His Asn
            115                 120             125
Gly Val Leu Thr Gly Tyr Val Leu Ser Tyr His Pro Leu Asp Glu Gly
    130             135                 140
Gly Lys Gly Gln Leu Ser Phe Asn Leu Arg Asp Pro Glu Leu Arg Thr
145             150                 155                 160
His Asn Leu Thr Asp Leu Ser Pro His Leu Arg Tyr Arg Phe Gln Leu
                165                 170                 175
Gln Ala Thr Thr Lys Glu Gly Pro Gly Glu Ala Ile Val Arg Glu Gly
                180             185                 190
Gly Thr Met Ala Leu Ser Gly Ile Ser Asp Phe Gly Asn Ile Ser Ala
    195                 200                 205
Thr Ala Gly Glu Asn Tyr Ser Val Val Ser Trp Val Pro Lys Glu Gly
    210                 215                 220
Gln Cys Asn Phe Arg Phe His Ile Leu Phe Lys Ala Leu Gly Glu Glu
225                 230                 235                 240
Lys Gly Gly Ala Ser Leu Ser Pro Gln Tyr Val Ser Tyr Asn Gln Ser
                245                 250                 255
Ser Tyr Thr Gln Trp Asp Leu Gln Pro Asp Thr Asp Tyr Glu Ile His
                260                 265                 270
Leu Phe Lys Glu Arg Met Phe Arg His Gln Met Ala Val Lys Thr Asn
                275                 280                 285
Gly Thr Gly Arg Val Arg Leu Pro Pro Ala Gly Phe Ala Thr Glu Gly
    290                 295                 300

(2) INFORMATION FOR SEQ ID NO:58:

(i) SEQUENCE CHARACTERISTICS:
        (A) LENGTH: 204 amino acids
        (B) TYPE: amino acid
        (D) TOPOLOGY: linear (ii) MOLECULE TYPE: protein (v) FRAGMENT TYPE: internal (xi) SEQUENCE DESCRIPTION: SEQ ID NO:58:

Pro Gly His Pro Glu Ala Leu His Leu Glu Cys Gln Ser Asn Thr Ser
1               5                   10                  15
Leu Leu Leu Arg Trp Gln Pro Pro Leu Ser His Asn Gly Val Leu Thr
                20                  25                  30
Gly Tyr Val Leu Ser Tyr His Pro Leu Asp Glu Gly Gly Lys Gly Gln
                35                  40                  45
Leu Ser Phe Asn Leu Arg Asp Pro Glu Leu Arg Thr His Asn Leu Thr
    50                  55                  60
Asp Leu Ser Pro His Leu Arg Tyr Arg Phe Gln Leu Gln Ala Thr Thr
65                  70                  75                  80
Lys Glu Gly Pro Gly Glu Ala Ile Val Arg Glu Gly Gly Thr Met Ala
                85                  90                  95
```

```
Leu Ser Gly Ile Ser Asp Phe Gly Asn Ile Ser Ala Thr Ala Gly Glu
            100                 105                 110

Asn Tyr Ser Val Val Ser Trp Val Pro Lys Glu Gly Gln Cys Asn Phe
            115                 120                 125

Arg Phe His Ile Leu Phe Lys Ala Leu Gly Glu Glu Lys Gly Gly Ala
            130                 135                 140

Ser Leu Ser Pro Gln Tyr Val Ser Tyr Asn Gln Ser Ser Tyr Thr Gln
145                 150                 155                 160

Trp Asp Leu Gln Pro Asp Thr Asp Tyr Glu Ile His Leu Phe Lys Glu
                165                 170                 175

Arg Met Phe Arg His Gln Met Ala Val Lys Thr Asn Gly Thr Gly Arg
            180                 185                 190

Val Arg Leu Pro Pro Ala Gly Phe Ala Thr Glu Gly
            195                 200
```

(2) INFORMATION FOR SEQ ID NO:59:

(i) SEQUENCE CHARACTERISTICS:
        (A) LENGTH: 397 amino acids
        (B) TYPE: amino acid
        (D) TOPOLOGY: linear (ii) MOLECULE TYPE: protein (v) FRAGMENT TYPE: C-terminal (xi) SEQUENCE DESCRIPTION: SEQ ID NO:59:

```
His Ile His Lys Ser His Ile Val Val Pro Ala Asn Thr Thr Ser Ala
1               5                   10                  15

Ile Leu Ser Gly Leu Arg Pro Tyr Ser Ser Tyr His Val Glu Val Gln
            20                  25                  30

Ala Phe Asn Gly Arg Gly Leu Gly Pro Ala Ser Glu Trp Thr Phe Ser
            35                  40                  45

Thr Pro Glu Gly Val Pro Gly His Pro Glu Ala Leu His Leu Glu Cys
            50                  55                  60

Gln Ser Asp Thr Ser Leu Leu Leu His Trp Gln Pro Pro Leu Ser His
65                  70                  75                  80

Asn Gly Val Leu Thr Gly Tyr Leu Leu Ser Tyr His Pro Val Glu Gly
            85                  90                  95

Glu Ser Lys Glu Gln Leu Phe Phe Asn Leu Ser Asp Pro Glu Leu Arg
            100                 105                 110

Thr His Asn Leu Thr Asn Leu Asn Pro Asp Leu Gln Tyr Arg Phe Gln
            115                 120                 125

Leu Gln Ala Thr Thr Gln Gln Gly Gly Pro Gly Gln Ala Ile Val Arg
            130                 135                 140

Glu Gly Gly Thr Met Ala Leu Phe Gly Lys Pro Asp Phe Gly Asn Ile
145                 150                 155                 160

Ser Ala Thr Ala Gly Glu Asn Tyr Ser Val Val Ser Trp Val Pro Arg
            165                 170                 175

Lys Gly Gln Cys Asn Phe Arg Phe His Ile Leu Phe Lys Ala Leu Pro
            180                 185                 190

Glu Gly Lys Val Ser Pro Asp His Gln Pro Gln Pro Gln Tyr Val Ser
            195                 200                 205

Tyr Asn Gln Ser Ser Tyr Thr Gln Trp Asn Leu Gln Pro Asp Thr Lys
            210                 215                 220

Tyr Glu Ile His Leu Ile Lys Glu Lys Val Leu Leu His His Leu Asp
```

```
225                 230                 235                 240
Val Lys Thr Asn Gly Thr Gly Pro Val Arg Val Ser Thr Thr Gly Ser
                245                 250                 255

Phe Ala Ser Glu Gly Trp Phe Ile Ala Phe Val Ser Ala Ile Ile Leu
                260                 265                 270

Leu Leu Leu Ile Leu Leu Ile Leu Cys Phe Ile Lys Arg Ser Lys Gly
                275                 280                 285

Gly Lys Tyr Ser Val Lys Asp Lys Glu Asp Thr Gln Val Asp Ser Glu
                290                 295                 300

Ala Arg Pro Met Lys Asp Glu Thr Phe Gly Glu Tyr Arg Ser Leu Glu
305                 310                 315                 320

Ser Asp Asn Glu Glu Lys Ala Phe Gly Ser Ser Gln Pro Ser Leu Asn
                325                 330                 335

Gly Asp Ile Lys Pro Leu Gly Ser Asp Asp Ser Leu Ala Asp Tyr Gly
                340                 345                 350

Gly Ser Val Asp Val Gln Phe Asn Glu Asp Gly Ser Phe Ile Gly Gln
                355                 360                 365

Tyr Ser Gly Lys Lys Glu Lys Glu Ala Ala Gly Gly Asn Asp Ser Ser
                370                 375                 380

Gly Ala Thr Ser Pro Ile Asn Pro Ala Val Ala Leu Glu
385                 390                 395

(2) INFORMATION FOR SEQ ID NO:60:

(i) SEQUENCE CHARACTERISTICS:
        (A) LENGTH: 309 amino acids
        (B) TYPE: amino acid
        (D) TOPOLOGY: linear (ii) MOLECULE TYPE: protein (v) FRAGMENT TYPE: internal (xi) SEQUENCE DESCRIPTION: SEQ ID NO:60:

Leu Glu Asp Ile Thr Ile Phe Asn Ser Ser Thr Val Leu Val Arg Trp
1               5                   10                  15

Arg Pro Val Asp Leu Ala Gln Val Lys Gly His Leu Lys Gly Tyr Asn
                20                  25                  30

Val Thr Tyr Trp Trp Lys Gly Ser Gln Arg Lys His Ser Lys Arg His
                35                  40                  45

Ile His Lys Ser His Ile Val Pro Ala Asn Thr Thr Ser Ala Ile
                50                  55                  60

Leu Ser Gly Leu Arg Pro Tyr Ser Ser Tyr His Val Glu Val Gln Ala
65                  70                  75                  80

Phe Asn Gly Arg Gly Leu Gly Pro Ala Ser Glu Trp Thr Phe Ser Thr
                85                  90                  95

Pro Glu Gly Val Pro Gly His Pro Glu Ala Leu His Leu Glu Cys Gln
                100                 105                 110

Ser Asp Thr Ser Leu Leu Leu His Trp Gln Pro Pro Leu Ser His Asn
                115                 120                 125

Gly Val Leu Thr Gly Tyr Leu Leu Ser Tyr His Pro Val Glu Gly Glu
                130                 135                 140

Ser Lys Glu Gln Leu Phe Phe Asn Leu Ser Asp Pro Glu Leu Arg Thr
145                 150                 155                 160

His Asn Leu Thr Asn Leu Asn Pro Asp Leu Gln Tyr Arg Phe Gln Leu
                165                 170                 175
```

```
Gln Ala Thr Thr Gln Gln Gly Gly Pro Gly Gln Ala Ile Val Arg Glu
                180                 185                 190

Gly Gly Thr Met Ala Leu Phe Gly Lys Pro Asp Phe Gly Asn Ile Ser
            195                 200                 205

Ala Thr Ala Gly Glu Asn Tyr Ser Val Val Ser Trp Val Pro Arg Lys
        210                 215                 220

Gly Gln Cys Asn Phe Arg Phe His Ile Leu Phe Lys Ala Leu Pro Glu
225                 230                 235                 240

Gly Lys Val Ser Pro Asp His Gln Pro Gln Pro Gln Tyr Val Ser Tyr
                245                 250                 255

Asn Gln Ser Ser Tyr Thr Gln Trp Asn Leu Gln Pro Asp Thr Lys Tyr
            260                 265                 270

Glu Ile His Leu Ile Lys Glu Lys Val Leu Leu His His Leu Asp Val
        275                 280                 285

Lys Thr Asn Gly Thr Gly Pro Val Arg Val Ser Thr Thr Gly Ser Phe
290                 295                 300

Ala Ser Glu Gly Trp
305

(2) INFORMATION FOR SEQ ID NO:61:

(i) SEQUENCE CHARACTERISTICS:
        (A) LENGTH: 209 amino acids
        (B) TYPE: amino acid
        (D) TOPOLOGY: linear (ii) MOLECULE TYPE: protein (v) FRAGMENT TYPE: internal (xi) SEQUENCE DESCRIPTION: SEQ ID NO:61:

Pro Gly His Pro Glu Ala Leu His Leu Glu Cys Gln Ser Asp Thr Ser
1               5                  10                  15

Leu Leu Leu His Trp Gln Pro Pro Leu Ser His Asn Gly Val Leu Thr
                20                  25                  30

Gly Tyr Leu Leu Ser Tyr His Pro Val Glu Gly Glu Ser Lys Glu Gln
            35                  40                  45

Leu Phe Phe Asn Leu Ser Asp Pro Glu Leu Arg Thr His Asn Leu Thr
50                  55                  60

Asn Leu Asn Pro Asp Leu Gln Tyr Arg Phe Gln Leu Gln Ala Thr Thr
65                  70                  75                  80

Gln Gln Gly Gly Pro Gly Gln Ala Ile Val Arg Glu Gly Gly Thr Met
                85                  90                  95

Ala Leu Phe Gly Lys Pro Asp Phe Gly Asn Ile Ser Ala Thr Ala Gly
            100                 105                 110

Glu Asn Tyr Ser Val Val Ser Trp Val Pro Arg Lys Gly Gln Cys Asn
        115                 120                 125

Phe Arg Phe His Ile Leu Phe Lys Ala Leu Pro Glu Gly Lys Val Ser
130                 135                 140

Pro Asp His Gln Pro Gln Pro Gln Tyr Val Ser Tyr Asn Gln Ser Ser
145                 150                 155                 160

Tyr Thr Gln Trp Asn Leu Gln Pro Asp Thr Lys Tyr Glu Ile His Leu
                165                 170                 175

Ile Lys Glu Lys Val Leu Leu His His Leu Asp Val Lys Thr Asn Gly
            180                 185                 190

Thr Gly Pro Val Arg Val Ser Thr Thr Gly Ser Phe Ala Ser Glu Gly
        195                 200                 205
```

Trp (2) INFORMATION FOR SEQ ID NO:62:

(i) SEQUENCE CHARACTERISTICS:
        (A) LENGTH: 394 amino acids
        (B) TYPE: amino acid
        (D) TOPOLOGY: linear (ii) MOLECULE TYPE: protein (v) FRAGMENT TYPE: C-terminal (xi) SEQUENCE DESCRIPTION: SEQ ID NO:62:

```
Val Glu Lys Lys Ile Leu Thr Phe Arg Gly Asn Lys Thr Phe Gly Met
  1               5                  10                  15

Leu Pro Gly Leu Glu Pro Tyr Ser Ser Tyr Lys Leu Asn Val Arg Val
             20                  25                  30

Val Asn Gly Lys Gly Glu Gly Pro Ala Ser Pro Asp Lys Val Phe Lys
         35                  40                  45

Thr Pro Glu Gly Val Pro Ser Pro Ser Phe Leu Lys Ile Thr Asn
 50                  55                  60

Pro Thr Leu Asp Ser Leu Thr Leu Glu Trp Gly Ser Pro Thr His Pro
 65                  70                  75                  80

Asn Gly Val Leu Thr Ser Tyr Ile Leu Lys Phe Gln Pro Ile Asn Asn
                 85                  90                  95

Thr His Glu Leu Gly Pro Leu Val Glu Ile Arg Ile Pro Ala Asn Glu
                100                 105                 110

Ser Ser Leu Ile Leu Lys Asn Leu Asn Tyr Ser Thr Arg Tyr Lys Phe
            115                 120                 125

Tyr Phe Asn Ala Gln Thr Ser Val Gly Ser Gly Ser Gln Ile Thr Glu
        130                 135                 140

Glu Ala Val Thr Ile Met Asp Glu Val Gln Pro Leu Tyr Pro Arg Ile
145                 150                 155                 160

Arg Asn Val Thr Thr Ala Ala Ala Glu Thr Tyr Ala Asn Ile Ser Trp
                165                 170                 175

Glu Tyr Glu Gly Pro Asp His Ala Asn Phe Tyr Val Glu Tyr Gly Val
            180                 185                 190

Ala Gly Ser Lys Glu Asp Trp Lys Lys Glu Ile Val Asn Gly Ser Arg
        195                 200                 205

Ser Phe Phe Val Leu Lys Gly Leu Thr Pro Gly Thr Ala Tyr Lys Val
210                 215                 220

Arg Val Gly Ala Glu Gly Leu Ser Gly Phe Arg Ser Ser Glu Asp Leu
225                 230                 235                 240

Phe Glu Thr Gly Pro Ala Met Ala Ser Arg Gln Val Asp Ile Ala Thr
                245                 250                 255

Gln Gly Trp Phe Ile Gly Leu Met Cys Ala Val Ala Leu Leu Ile Leu
            260                 265                 270

Ile Leu Leu Ile Val Cys Phe Ile Arg Arg Asn Lys Gly Gly Lys Tyr
        275                 280                 285

Pro Val Lys Glu Lys Glu Asp Ala His Ala Asp Pro Glu Ile Gln Pro
    290                 295                 300

Met Lys Glu Asp Asp Gly Thr Phe Gly Glu Tyr Ser Asp Ala Glu Asp
305                 310                 315                 320

His Lys Pro Leu Lys Lys Gly Ser Arg Thr Pro Ser Asp Arg Thr Val
                325                 330                 335
```

```
Lys Lys Glu Asp Ser Asp Asp Ser Leu Val Asp Tyr Gly Glu Gly Val
            340                 345                 350

Asn Gly Gln Phe Asn Glu Asp Gly Ser Phe Ile Gly Gln Tyr Ser Gly
            355                 360                 365

Lys Lys Glu Lys Glu Pro Ala Glu Gly Asn Glu Ser Ser Glu Ala Pro
            370                 375                 380

Ser Pro Val Asn Ala Met Asn Ser Phe Val
385                 390

(2) INFORMATION FOR SEQ ID NO:63:

(i) SEQUENCE CHARACTERISTICS:
        (A) LENGTH: 307 amino acids
        (B) TYPE: amino acid
        (D) TOPOLOGY: linear (ii) MOLECULE TYPE: protein (v) FRAGMENT TYPE: internal (xi) SEQUENCE DESCRIPTION: SEQ ID NO:63:

Asn Val Gln Val His Val Ile Asn Ser Thr Leu Ala Lys Val His Trp
1               5                   10                  15

Asp Pro Val Pro Leu Lys Ser Val Arg Gly His Leu Gln Gly Tyr Lys
            20                  25                  30

Val Tyr Tyr Trp Lys Val Gln Ser Leu Ser Arg Arg Ser Lys Arg His
            35                  40                  45

Val Glu Lys Lys Ile Leu Thr Phe Arg Gly Asn Lys Thr Phe Gly Met
50                  55                  60

Leu Pro Gly Leu Glu Pro Tyr Ser Ser Tyr Lys Leu Asn Val Arg Val
65                  70                  75                  80

Val Asn Gly Lys Gly Glu Gly Pro Ala Ser Pro Asp Lys Val Phe Lys
            85                  90                  95

Thr Pro Glu Gly Val Pro Ser Pro Ser Phe Leu Lys Ile Thr Asn
            100                 105                 110

Pro Thr Leu Asp Ser Leu Thr Leu Glu Trp Gly Ser Pro Thr His Pro
            115                 120                 125

Asn Gly Val Leu Thr Ser Tyr Ile Leu Lys Phe Gln Pro Ile Asn Asn
            130                 135                 140

Thr His Glu Leu Gly Pro Leu Val Glu Ile Arg Ile Pro Ala Asn Glu
145                 150                 155                 160

Ser Ser Leu Ile Leu Lys Asn Leu Asn Tyr Ser Thr Arg Tyr Lys Phe
            165                 170                 175

Tyr Phe Asn Ala Gln Thr Ser Val Gly Ser Gly Ser Gln Ile Thr Glu
            180                 185                 190

Glu Ala Val Thr Ile Met Asp Glu Val Gln Pro Leu Tyr Pro Arg Ile
            195                 200                 205

Arg Asn Val Thr Thr Ala Ala Ala Glu Thr Tyr Ala Asn Ile Ser Trp
            210                 215                 220

Glu Tyr Glu Gly Pro Asp His Ala Asn Phe Tyr Val Glu Tyr Gly Val
225                 230                 235                 240

Ala Gly Ser Lys Glu Asp Trp Lys Lys Glu Ile Val Asn Gly Ser Arg
            245                 250                 255

Ser Phe Phe Val Leu Lys Gly Leu Thr Pro Gly Thr Ala Tyr Lys Val
            260                 265                 270

Arg Val Gly Ala Glu Gly Leu Ser Gly Phe Arg Ser Ser Glu Asp Leu
```

```
                    275                 280                 285
Phe Glu Thr Gly Pro Ala Met Ala Ser Arg Gln Val Asp Ile Ala Thr
    290                 295                 300

Gln Gly Trp
305

(2) INFORMATION FOR SEQ ID NO:64:

(i) SEQUENCE CHARACTERISTICS:
        (A) LENGTH: 206 amino acids
        (B) TYPE: amino acid
        (D) TOPOLOGY: linear (ii) MOLECULE TYPE: protein (v) FRAGMENT TYPE: internal (xi) SEQUENCE DESCRIPTION: SEQ ID NO:64:

Pro Ser Pro Pro Ser Phe Leu Lys Ile Thr Asn Pro Thr Leu Asp Ser
1               5                   10                  15

Leu Thr Leu Glu Trp Gly Ser Pro Thr His Pro Asn Gly Val Leu Thr
            20                  25                  30

Ser Tyr Ile Leu Lys Phe Gln Pro Ile Asn Asn Thr His Glu Leu Gly
        35                  40                  45

Pro Leu Val Glu Ile Arg Ile Pro Ala Asn Glu Ser Ser Leu Ile Leu
    50                  55                  60

Lys Asn Leu Asn Tyr Ser Thr Arg Tyr Lys Phe Tyr Phe Asn Ala Gln
65                  70                  75                  80

Thr Ser Val Gly Ser Gly Ser Gln Ile Thr Glu Glu Ala Val Thr Ile
                85                  90                  95

Met Asp Glu Val Gln Pro Leu Tyr Pro Arg Ile Arg Asn Val Thr Thr
            100                 105                 110

Ala Ala Ala Glu Thr Tyr Ala Asn Ile Ser Trp Glu Tyr Glu Gly Pro
        115                 120                 125

Asp His Ala Asn Phe Tyr Val Glu Tyr Gly Val Ala Gly Ser Lys Glu
    130                 135                 140

Asp Trp Lys Lys Glu Ile Val Asn Gly Ser Arg Ser Phe Phe Val Leu
145                 150                 155                 160

Lys Gly Leu Thr Pro Gly Thr Ala Tyr Lys Val Arg Val Gly Ala Glu
                165                 170                 175

Gly Leu Ser Gly Phe Arg Ser Ser Glu Asp Leu Phe Glu Thr Gly Pro
            180                 185                 190

Ala Met Ala Ser Arg Gln Val Asp Ile Ala Thr Gln Gly Trp
        195                 200                 205

(2) INFORMATION FOR SEQ ID NO:65:

(i) SEQUENCE CHARACTERISTICS:
        (A) LENGTH: 644 amino acids
        (B) TYPE: amino acid
        (D) TOPOLOGY: linear (ii) MOLECULE TYPE: protein (v) FRAGMENT TYPE: C-terminal (xi) SEQUENCE DESCRIPTION: SEQ ID NO:65:

Met Ser Pro Ile Leu Gly Tyr Trp Lys Ile Lys Gly Leu Val Gln Pro
1               5                   10                  15

Thr Arg Leu Leu Leu Glu Tyr Leu Glu Glu Lys Tyr Glu Glu His Leu
```

```
                20                  25                  30
Tyr Glu Arg Asp Glu Gly Asp Lys Trp Arg Asn Lys Lys Phe Glu Leu
                35                  40                  45
Gly Leu Glu Phe Pro Asn Leu Pro Tyr Tyr Ile Asp Gly Asp Val Lys
 50                  55                  60
Leu Thr Gln Ser Met Ala Ile Ile Arg Tyr Ile Ala Asp Lys His Asn
 65                  70                  75                  80
Met Leu Gly Gly Cys Pro Lys Glu Arg Ala Glu Ile Ser Met Leu Glu
                85                  90                  95
Gly Ala Val Leu Asp Ile Arg Tyr Gly Val Ser Arg Ile Ala Tyr Ser
                100                 105                 110
Lys Asp Phe Glu Thr Leu Lys Val Asp Phe Leu Ser Lys Leu Pro Glu
                115                 120                 125
Met Leu Lys Met Phe Glu Asp Arg Leu Cys His Lys Thr Tyr Leu Asn
                130                 135                 140
Gly Asp His Val Thr His Pro Asp Phe Met Leu Tyr Asp Ala Leu Asp
145                 150                 155                 160
Val Val Leu Tyr Met Asp Pro Met Cys Leu Asp Ala Phe Pro Lys Leu
                165                 170                 175
Val Cys Phe Lys Lys Arg Ile Glu Ala Ile Pro Gln Ile Asp Lys Tyr
                180                 185                 190
Leu Lys Ser Ser Lys Tyr Ile Ala Trp Pro Leu Gln Gly Trp Gln Ala
                195                 200                 205
Thr Phe Gly Gly Gly Asp His Pro Pro Lys Ser Asp Leu Val Pro Arg
                210                 215                 220
Gly Ser Ala Pro Pro Asp Pro Pro Gln Ile Pro Gln Ser Pro Ala Glu
225                 230                 235                 240
Asp Pro Pro Pro Phe Pro Pro Val Ala Leu Thr Val Gly Gly Asp Ala
                245                 250                 255
Arg Gly Ala Leu Leu Gly Gly Leu Arg Pro Trp Ser Arg Tyr Gln Leu
                260                 265                 270
Arg Val Leu Val Phe Asn Gly Arg Gly Asp Gly Pro Pro Ser Glu Pro
                275                 280                 285
Ile Ala Phe Glu Thr Pro Glu Gly Val Pro Gly Pro Pro Glu Glu Leu
                290                 295                 300
Arg Val Glu Arg Leu Asp Asp Thr Ala Leu Ser Val Val Glu Arg Arg
305                 310                 315                 320
Thr Phe Lys Arg Ser Ile Thr Gly Tyr Val Leu Arg Tyr Gln Gln Val
                325                 330                 335
Glu Pro Gly Ser Ala Leu Pro Gly Gly Ser Val Leu Arg Asp Pro Gln
                340                 345                 350
Cys Asp Leu Arg Gly Leu Asn Ala Arg Ser Arg Tyr Arg Leu Ala Leu
                355                 360                 365
Pro Ser Thr Pro Arg Glu Arg Pro Ala Leu Gln Thr Val Gly Ser Thr
                370                 375                 380
Lys Pro Glu Pro Pro Ser Pro Leu Trp Ser Arg Phe Gly Val Gly Gly
385                 390                 395                 400
Arg Gly Gly Phe His Gly Ala Ala Val Glu Phe Gly Ala Ala Gln Glu
                405                 410                 415
Asp Asp Val Glu Phe Glu Val Gln Phe Met Asn Lys Ser Thr Asp Glu
                420                 425                 430
Pro Trp Arg Thr Ser Gly Arg Ala Asn Ser Ser Leu Arg Arg Tyr Arg
                435                 440                 445
```

```
Leu Glu Gly Leu Arg Pro Gly Thr Ala Tyr Arg Val Gln Phe Val Gly
    450                 455                 460

Arg Asn Arg Ser Gly Glu Asn Val Ala Phe Trp Glu Ser Glu Val Gln
465                 470                 475                 480

Thr Asn Gly Thr Val Val Pro Gln Pro Gly Gly Val Cys Thr Lys
                485                 490                 495

Gly Trp Phe Ile Gly Phe Val Ser Val Val Leu Leu Leu Ile
                500             505                 510

Leu Leu Ile Leu Cys Phe Ile Lys Arg Ser Lys Gly Gly Lys Tyr Ser
            515             520             525

Val Lys Asp Lys Glu Asp Thr Gln Val Asp Ser Glu Ala Arg Pro Met
    530                 535                 540

Lys Asp Glu Thr Phe Gly Glu Tyr Arg Ser Leu Glu Ser Glu Ala Glu
545                 550                 555                 560

Lys Gly Ser Ala Ser Gly Ser Gly Ala Gly Ser Gly Val Gly Ser Pro
                565                 570                 575

Gly Arg Gly Pro Cys Ala Ala Gly Ser Glu Asp Ser Leu Ala Gly Tyr
            580                 585                 590

Gly Gly Ser Gly Asp Val Gln Phe Asn Glu Asp Gly Ser Phe Ile Gly
            595                 600                 605

Gln Tyr Arg Gly Pro Gly Ala Gly Pro Gly Ser Ser Gly Pro Ala Ser
    610                 615                 620

Pro Cys Ala Gly Pro Pro Leu Asp Pro Arg Asn Ser Arg Val Asp Ser
625                 630                 635                 640

Ser Gly Arg Ile (2) INFORMATION FOR SEQ ID NO:66:

(i) SEQUENCE CHARACTERISTICS:
        (A) LENGTH: 559 amino acids
        (B) TYPE: amino acid
        (D) TOPOLOGY: linear (ii) MOLECULE TYPE: protein (v) FRAGMENT TYPE: internal (xi) SEQUENCE DESCRIPTION: SEQ ID NO:66:

Met Ser Pro Ile Leu Gly Tyr Trp Lys Ile Lys Gly Leu Val Gln Pro
1               5                   10                  15

Thr Arg Leu Leu Leu Glu Tyr Leu Glu Glu Lys Tyr Glu Glu His Leu
                20                  25                  30

Tyr Glu Arg Asp Glu Gly Asp Lys Trp Arg Asn Lys Lys Phe Glu Leu
            35                  40                  45

Gly Leu Glu Phe Pro Asn Leu Pro Tyr Tyr Ile Asp Gly Asp Val Lys
    50                  55                  60

Leu Thr Gln Ser Met Ala Ile Ile Arg Tyr Ile Ala Asp Lys His Asn
65                  70                  75                  80

Met Leu Gly Gly Cys Pro Lys Glu Arg Ala Glu Ile Ser Met Leu Glu
                85                  90                  95

Gly Ala Val Leu Asp Ile Arg Tyr Gly Val Ser Arg Ile Ala Tyr Ser
                100                 105                 110

Lys Asp Phe Glu Thr Leu Lys Val Asp Phe Leu Ser Lys Leu Pro Glu
            115                 120                 125

Met Leu Lys Met Phe Glu Asp Arg Leu Cys His Lys Thr Tyr Leu Asn
    130                 135                 140
```

-continued

```
Gly Asp His Val Thr His Pro Asp Phe Met Leu Tyr Asp Ala Leu Asp
145                 150                 155                 160

Val Val Leu Tyr Met Asp Pro Met Cys Leu Asp Ala Phe Pro Lys Leu
                165                 170                 175

Val Cys Phe Lys Lys Arg Ile Glu Ala Ile Pro Gln Ile Asp Lys Tyr
                180                 185                 190

Leu Lys Ser Ser Lys Tyr Ile Ala Trp Pro Leu Gln Gly Trp Gln Ala
                195                 200                 205

Thr Phe Gly Gly Gly Asp His Pro Pro Lys Ser Asp Leu Val Pro Arg
            210                 215                 220

Gly Ser Asn Val Gly Val Glu Leu Leu Asn Ser Ser Thr Val Arg Val
225                 230                 235                 240

Arg Trp Thr Leu Gly Gly Pro Lys Glu Leu Arg Gly Arg Leu Arg
                245                 250                 255

Gly Phe Arg Val Leu Tyr Trp Arg Leu Gly Trp Val Gly Glu Arg Ser
                260                 265                 270

Arg Arg Gln Ala Pro Pro Asp Pro Gln Ile Pro Gln Ser Pro Ala
                275                 280                 285

Glu Asp Pro Pro Phe Pro Pro Val Ala Leu Thr Val Gly Gly Asp
290                 295                 300

Ala Arg Gly Ala Leu Leu Gly Gly Leu Arg Pro Trp Ser Arg Tyr Gln
305                 310                 315                 320

Leu Arg Val Leu Val Phe Asn Gly Arg Gly Asp Gly Pro Pro Ser Glu
                325                 330                 335

Pro Ile Ala Phe Glu Thr Pro Glu Gly Val Pro Gly Pro Pro Glu Glu
                340                 345                 350

Leu Arg Val Glu Arg Leu Asp Asp Thr Ala Leu Ser Val Val Glu Arg
                355                 360                 365

Arg Thr Phe Lys Arg Ser Ile Thr Gly Tyr Val Leu Arg Tyr Gln Gln
                370                 375                 380

Val Glu Pro Gly Ser Ala Leu Pro Gly Gly Ser Val Leu Arg Asp Pro
385                 390                 395                 400

Gln Cys Asp Leu Arg Gly Leu Asn Ala Arg Ser Arg Tyr Arg Leu Ala
                405                 410                 415

Leu Pro Ser Thr Pro Arg Glu Arg Pro Ala Leu Gln Thr Val Gly Ser
                420                 425                 430

Thr Lys Pro Glu Pro Pro Ser Pro Leu Trp Ser Arg Phe Gly Val Gly
                435                 440                 445

Gly Arg Gly Gly Phe His Gly Ala Ala Val Glu Phe Gly Ala Ala Gln
450                 455                 460

Glu Asp Val Glu Phe Glu Val Gln Phe Met Asn Lys Ser Thr Asp
465                 470                 475                 480

Glu Pro Trp Arg Thr Ser Gly Arg Ala Asn Ser Ser Leu Arg Arg Tyr
                485                 490                 495

Arg Leu Glu Gly Leu Arg Pro Gly Thr Ala Tyr Arg Val Gln Phe Val
                500                 505                 510

Gly Arg Asn Arg Ser Gly Glu Asn Val Ala Phe Trp Glu Ser Glu Val
                515                 520                 525

Gln Thr Asn Gly Thr Val Val Pro Gln Pro Gly Gly Val Cys Thr
                530                 535                 540

Lys Gly Trp Pro Gly Ile Pro Gly Ser Thr Arg Ala Ala Ala Ser
545                 550                 555
```

(2) INFORMATION FOR SEQ ID NO:67:

(i) SEQUENCE CHARACTERISTICS:
        (A) LENGTH: 439 amino acids
        (B) TYPE: amino acid
        (D) TOPOLOGY: linear (ii) MOLECULE TYPE: protein (v) FRAGMENT TYPE: internal (xi) SEQUENCE DESCRIPTION: SEQ ID NO:67:

```
Met Ser Pro Ile Leu Gly Tyr Trp Lys Ile Lys Gly Leu Val Gln Pro
1               5                   10                  15

Thr Arg Leu Leu Leu Glu Tyr Leu Glu Glu Lys Tyr Glu Glu His Leu
            20                  25                  30

Tyr Glu Arg Asp Glu Gly Asp Lys Trp Arg Asn Lys Lys Phe Glu Leu
        35                  40                  45

Gly Leu Glu Phe Pro Asn Leu Pro Tyr Tyr Ile Asp Gly Asp Val Lys
    50                  55                  60

Leu Thr Gln Ser Met Ala Ile Ile Arg Tyr Ile Ala Asp Lys His Asn
65                  70                  75                  80

Met Leu Gly Gly Cys Pro Lys Glu Arg Ala Glu Ile Ser Met Leu Glu
                85                  90                  95

Gly Ala Val Leu Asp Ile Arg Tyr Gly Val Ser Arg Ile Ala Tyr Ser
            100                 105                 110

Lys Asp Phe Glu Thr Leu Lys Val Asp Phe Leu Ser Lys Leu Pro Glu
        115                 120                 125

Met Leu Lys Met Phe Glu Asp Arg Leu Cys His Lys Thr Tyr Leu Asn
    130                 135                 140

Gly Asp His Val Thr His Pro Asp Phe Met Leu Tyr Asp Ala Leu Asp
145                 150                 155                 160

Val Val Leu Tyr Met Asp Pro Met Cys Leu Asp Ala Phe Pro Lys Leu
                165                 170                 175

Val Cys Phe Lys Lys Arg Ile Glu Ala Ile Pro Gln Ile Asp Lys Tyr
            180                 185                 190

Leu Lys Ser Ser Lys Tyr Ile Ala Trp Pro Leu Gln Gly Trp Gln Ala
        195                 200                 205

Thr Phe Gly Gly Gly Asp His Pro Pro Lys Ser Asp Leu Val Pro Arg
    210                 215                 220

Gly Ser Pro Gly Pro Pro Glu Glu Leu Arg Val Glu Arg Leu Asp Asp
225                 230                 235                 240

Thr Ala Leu Ser Val Val Glu Arg Arg Thr Phe Lys Arg Ser Ile Thr
                245                 250                 255

Gly Tyr Val Leu Arg Tyr Gln Gln Val Glu Pro Gly Ser Ala Leu Pro
            260                 265                 270

Gly Gly Ser Val Leu Arg Asp Pro Gln Cys Asp Leu Arg Gly Leu Asn
        275                 280                 285

Ala Arg Ser Arg Tyr Arg Leu Ala Leu Pro Ser Thr Pro Arg Glu Arg
    290                 295                 300

Pro Ala Leu Gln Thr Val Gly Ser Thr Lys Pro Glu Pro Pro Ser Pro
305                 310                 315                 320

Leu Trp Ser Arg Phe Gly Val Gly Gly Arg Gly Gly Phe His Gly Ala
                325                 330                 335

Ala Val Glu Phe Gly Ala Ala Gln Glu Asp Asp Val Glu Phe Glu Val
            340                 345                 350
```

```
Gln Phe Met Asn Lys Ser Thr Asp Glu Pro Trp Arg Thr Ser Gly Arg
            355                 360                 365

Ala Asn Ser Ser Leu Arg Arg Tyr Arg Leu Glu Gly Leu Arg Pro Gly
        370                 375                 380

Thr Ala Tyr Arg Val Gln Phe Val Gly Arg Asn Arg Ser Gly Glu Asn
385                 390                 395                 400

Val Ala Phe Trp Glu Ser Glu Val Gln Thr Asn Gly Thr Val Val Pro
                405                 410                 415

Gln Pro Gly Gly Gly Val Cys Thr Lys Gly Trp Pro Gly Ile Pro Gly
            420                 425                 430

Ser Thr Arg Ala Ala Ala Ser
            435

(2) INFORMATION FOR SEQ ID NO:68:

(i) SEQUENCE CHARACTERISTICS:
        (A) LENGTH: 665 amino acids
        (B) TYPE: amino acid
        (D) TOPOLOGY: linear (ii) MOLECULE TYPE: protein (v) FRAGMENT TYPE: C-terminal (xi) SEQUENCE DESCRIPTION: SEQ ID NO:68:

Met Ser Pro Ile Leu Gly Tyr Trp Lys Ile Lys Gly Leu Val Gln Pro
1               5                   10                  15

Thr Arg Leu Leu Leu Glu Tyr Leu Glu Glu Lys Tyr Glu Glu His Leu
            20                  25                  30

Tyr Glu Arg Asp Glu Gly Asp Lys Trp Arg Asn Lys Lys Phe Glu Leu
            35                  40                  45

Gly Leu Glu Phe Pro Asn Leu Pro Tyr Tyr Ile Asp Gly Asp Val Lys
        50                  55                  60

Leu Thr Gln Ser Met Ala Ile Ile Arg Tyr Ile Ala Asp Lys His Asn
65                  70                  75                  80

Met Leu Gly Gly Cys Pro Lys Glu Arg Ala Glu Ile Ser Met Leu Glu
                85                  90                  95

Gly Ala Val Leu Asp Ile Arg Tyr Gly Val Ser Arg Ile Ala Tyr Ser
            100                 105                 110

Lys Asp Phe Glu Thr Leu Lys Val Asp Phe Leu Ser Lys Leu Pro Glu
        115                 120                 125

Met Leu Lys Met Phe Glu Asp Arg Leu Cys His Lys Thr Tyr Leu Asn
130                 135                 140

Gly Asp His Val Thr His Pro Asp Phe Met Leu Tyr Asp Ala Leu Asp
145                 150                 155                 160

Val Val Leu Tyr Met Asp Pro Met Cys Leu Asp Ala Phe Pro Lys Leu
                165                 170                 175

Val Cys Phe Lys Lys Arg Ile Glu Ala Ile Pro Gln Ile Asp Lys Tyr
            180                 185                 190

Leu Lys Ser Ser Lys Tyr Ile Ala Trp Pro Leu Gln Gly Trp Gln Ala
        195                 200                 205

Thr Phe Gly Gly Gly Asp His Pro Pro Lys Ser Asp Leu Val Pro Arg
        210                 215                 220

Gly Ser Ile His Lys Asp His Val Val Pro Ala Asn Thr Thr Ser
225                 230                 235                 240

Val Ile Leu Ser Gly Leu Arg Pro Tyr Ser Ser Tyr His Leu Glu Val
```

-continued

```
                245                 250                 255
Gln Ala Phe Asn Gly Arg Gly Ser Gly Pro Ala Ser Glu Phe Thr Phe
                260                 265                 270
Ser Thr Pro Glu Gly Val Pro Gly His Pro Glu Ala Leu His Leu Glu
                275                 280                 285
Cys Gln Ser Asn Thr Ser Leu Leu Leu Arg Trp Gln Pro Pro Leu Ser
                290                 295                 300
His Asn Gly Val Leu Thr Gly Tyr Val Leu Ser Tyr His Pro Leu Asp
305                 310                 315                 320
Glu Gly Gly Lys Gly Gln Leu Ser Phe Asn Leu Arg Asp Pro Glu Leu
                325                 330                 335
Arg Thr His Asn Leu Thr Asp Leu Ser Pro His Leu Arg Tyr Arg Phe
                340                 345                 350
Gln Leu Gln Ala Thr Thr Lys Glu Gly Pro Gly Glu Ala Ile Val Arg
                355                 360                 365
Glu Gly Gly Thr Met Ala Leu Ser Gly Ile Ser Asp Phe Gly Asn Ile
                370                 375                 380
Ser Ala Thr Ala Gly Glu Asn Tyr Ser Val Val Ser Trp Val Pro Lys
385                 390                 395                 400
Glu Gly Gln Cys Asn Phe Arg Phe His Ile Leu Phe Lys Ala Leu Gly
                405                 410                 415
Glu Glu Lys Gly Gly Ala Ser Leu Ser Pro Gln Tyr Val Ser Tyr Asn
                420                 425                 430
Gln Ser Ser Tyr Thr Gln Trp Asp Leu Gln Pro Asp Thr Asp Tyr Glu
                435                 440                 445
Ile His Leu Phe Lys Glu Arg Met Phe Arg His Gln Met Ala Val Lys
450                 455                 460
Thr Asn Gly Thr Gly Arg Val Arg Leu Pro Pro Ala Gly Phe Ala Thr
465                 470                 475                 480
Glu Gly Trp Phe Ile Gly Phe Val Ser Ala Ile Ile Leu Leu Leu Leu
                485                 490                 495
Val Leu Leu Ile Leu Cys Phe Ile Lys Arg Ser Lys Gly Gly Lys Tyr
                500                 505                 510
Ser Val Lys Asp Lys Glu Asp Thr Gln Val Asp Ser Glu Ala Arg Pro
                515                 520                 525
Met Lys Asp Glu Thr Phe Gly Glu Tyr Ser Asp Asn Glu Glu Lys Ala
                530                 535                 540
Phe Gly Ser Ser Gln Pro Ser Leu Asn Gly Asp Ile Lys Pro Leu Gly
545                 550                 555                 560
Ser Asp Asp Ser Leu Ala Asp Tyr Gly Gly Ser Val Asp Val Gln Phe
                565                 570                 575
Asn Glu Asp Gly Ser Phe Ile Gly Gln Tyr Ser Gly Lys Lys Glu Lys
                580                 585                 590
Glu Ala Ala Gly Gly Asn Asp Ser Ser Gly Ala Thr Ser Pro Ile Asn
                595                 600                 605
Pro Ala Val Ala Leu Glu Xaa Trp Ser Pro Gly Gln Glu Met Leu Cys
                610                 615                 620
Pro Trp Pro Trp Asp Pro Gly Pro Ser Leu Ser Ser Arg Pro Met Gly
625                 630                 635                 640
Gly Trp Ser Trp Gly Arg Gly Glu Leu Ala Ala Ser Asp Pro Arg Asn
                645                 650                 655
Ser Arg Val Asp Ser Ser Gly Arg Ile
                660                 665
```

(2) INFORMATION FOR SEQ ID NO:69:

(i) SEQUENCE CHARACTERISTICS:
        (A) LENGTH: 542 amino acids
        (B) TYPE: amino acid
        (D) TOPOLOGY: linear (ii) MOLECULE TYPE: protein (v) FRAGMENT TYPE: internal (xi) SEQUENCE DESCRIPTION: SEQ ID NO:69:

```
Met Ser Pro Ile Leu Gly Tyr Trp Lys Ile Lys Gly Leu Val Gln Pro
  1               5                  10                  15

Thr Arg Leu Leu Leu Glu Tyr Leu Glu Glu Lys Tyr Glu Glu His Leu
                 20                  25                  30

Tyr Glu Arg Asp Glu Gly Asp Lys Trp Arg Asn Lys Lys Phe Glu Leu
             35                  40                  45

Gly Leu Glu Phe Pro Asn Leu Pro Tyr Tyr Ile Asp Gly Asp Val Lys
 50                  55                  60

Leu Thr Gln Ser Met Ala Ile Ile Arg Tyr Ile Ala Asp Lys His Asn
 65                  70                  75                  80

Met Leu Gly Gly Cys Pro Lys Glu Arg Ala Glu Ile Ser Met Leu Glu
                 85                  90                  95

Gly Ala Val Leu Asp Ile Arg Tyr Gly Val Ser Arg Ile Ala Tyr Ser
                100                 105                 110

Lys Asp Phe Glu Thr Leu Lys Val Asp Phe Leu Ser Lys Leu Pro Glu
            115                 120                 125

Met Leu Lys Met Phe Glu Asp Arg Leu Cys His Lys Thr Tyr Leu Asn
130                 135                 140

Gly Asp His Val Thr His Pro Asp Phe Met Leu Tyr Asp Ala Leu Asp
145                 150                 155                 160

Val Val Leu Tyr Met Asp Pro Met Cys Leu Asp Ala Phe Pro Lys Leu
                165                 170                 175

Val Cys Phe Lys Lys Arg Ile Glu Ala Ile Pro Gln Ile Asp Lys Tyr
                180                 185                 190

Leu Lys Ser Ser Lys Tyr Ile Ala Trp Pro Leu Gln Gly Trp Gln Ala
            195                 200                 205

Thr Phe Gly Gly Gly Asp His Pro Pro Lys Ser Asp Leu Val Pro Arg
210                 215                 220

Gly Ser Leu Glu Gly Ile Glu Ile Leu Asn Ser Ser Ala Val Leu Val
225                 230                 235                 240

Lys Trp Arg Pro Val Asp Leu Ala Gln Val Lys Gly His Leu Arg Gly
                245                 250                 255

Tyr Asn Val Thr Tyr Trp Arg Glu Gly Ser Gln Arg Lys His Ser Lys
                260                 265                 270

Arg His Ile His Lys Asp His Val Val Pro Ala Asn Thr Thr Ser
            275                 280                 285

Val Ile Leu Ser Gly Leu Arg Pro Tyr Ser Ser Tyr His Leu Glu Val
            290                 295                 300

Gln Ala Phe Asn Gly Arg Gly Ser Gly Pro Ala Ser Glu Phe Thr Phe
305                 310                 315                 320

Ser Thr Pro Glu Gly Val Pro Gly His Pro Glu Ala Leu His Leu Glu
                325                 330                 335

Cys Gln Ser Asn Thr Ser Leu Leu Leu Arg Trp Gln Pro Pro Leu Ser
```

```
                340              345              350
His Asn Gly Val Leu Thr Gly Tyr Val Leu Ser Tyr His Pro Leu Asp
            355              360              365

Glu Gly Gly Lys Gly Gln Leu Ser Phe Asn Leu Arg Asp Pro Glu Leu
    370              375              380

Arg Thr His Asn Leu Thr Asp Leu Ser Pro His Leu Arg Tyr Arg Phe
385              390              395              400

Gln Leu Gln Ala Thr Thr Lys Glu Gly Pro Gly Glu Ala Ile Val Arg
                405              410              415

Glu Gly Gly Thr Met Ala Leu Ser Gly Ile Ser Asp Phe Gly Asn Ile
            420              425              430

Ser Ala Thr Ala Gly Glu Asn Tyr Ser Val Val Ser Trp Val Pro Lys
            435              440              445

Glu Gly Gln Cys Asn Phe Arg Phe His Ile Leu Phe Lys Ala Leu Gly
    450              455              460

Glu Glu Lys Gly Gly Ala Ser Leu Ser Pro Gln Tyr Val Ser Tyr Asn
465              470              475              480

Gln Ser Ser Tyr Thr Gln Trp Asp Leu Gln Pro Asp Thr Asp Tyr Glu
                485              490              495

Ile His Leu Phe Lys Glu Arg Met Phe Arg His Gln Met Ala Val Lys
            500              505              510

Thr Asn Gly Thr Gly Arg Val Arg Leu Pro Pro Ala Gly Phe Ala Thr
            515              520              525

Glu Gly Pro Gly Ile Pro Gly Ser Thr Arg Ala Ala Ala Ser
            530              535              540

(2) INFORMATION FOR SEQ ID NO:70:

(i) SEQUENCE CHARACTERISTICS:
        (A) LENGTH: 442 amino acids
        (B) TYPE: amino acid
        (D) TOPOLOGY: linear (ii) MOLECULE TYPE: protein (v) FRAGMENT TYPE: internal (xi) SEQUENCE DESCRIPTION: SEQ ID NO:70:

Met Ser Pro Ile Leu Gly Tyr Trp Lys Ile Lys Gly Leu Val Gln Pro
1               5                   10                  15

Thr Arg Leu Leu Leu Glu Tyr Leu Glu Glu Lys Tyr Glu Glu His Leu
            20                  25                  30

Tyr Glu Arg Asp Glu Gly Asp Lys Trp Arg Asn Lys Lys Phe Glu Leu
        35                  40                  45

Gly Leu Glu Phe Pro Asn Leu Pro Tyr Tyr Ile Asp Gly Asp Val Lys
    50                  55                  60

Leu Thr Gln Ser Met Ala Ile Ile Arg Tyr Ile Ala Asp Lys His Asn
65                  70                  75                  80

Met Leu Gly Gly Cys Pro Lys Glu Arg Ala Glu Ile Ser Met Leu Glu
                85                  90                  95

Gly Ala Val Leu Asp Ile Arg Tyr Gly Val Ser Arg Ile Ala Tyr Ser
            100                 105                 110

Lys Asp Phe Glu Thr Leu Lys Val Asp Phe Leu Ser Lys Leu Pro Glu
        115                 120                 125

Met Leu Lys Met Phe Glu Asp Arg Leu Cys His Lys Thr Tyr Leu Asn
    130                 135                 140
```

-continued

```
Gly Asp His Val Thr His Pro Asp Phe Met Leu Tyr Asp Ala Leu Asp
145                 150                 155                 160

Val Val Leu Tyr Met Asp Pro Met Cys Leu Asp Ala Phe Pro Lys Leu
                165                 170                 175

Val Cys Phe Lys Lys Arg Ile Glu Ala Ile Pro Gln Ile Asp Lys Tyr
            180                 185                 190

Leu Lys Ser Ser Lys Tyr Ile Ala Trp Pro Leu Gln Gly Trp Gln Ala
        195                 200                 205

Thr Phe Gly Gly Gly Asp His Pro Pro Lys Ser Asp Leu Val Pro Arg
    210                 215                 220

Gly Ser Pro Gly His Pro Glu Ala Leu His Leu Glu Cys Gln Ser Asn
225                 230                 235                 240

Thr Ser Leu Leu Leu Arg Trp Gln Pro Pro Leu Ser His Asn Gly Val
                245                 250                 255

Leu Thr Gly Tyr Val Leu Ser Tyr His Pro Leu Asp Glu Gly Gly Lys
            260                 265                 270

Gly Gln Leu Ser Phe Asn Leu Arg Asp Pro Glu Leu Arg Thr His Asn
        275                 280                 285

Leu Thr Asp Leu Ser Pro His Leu Arg Tyr Arg Phe Gln Leu Gln Ala
    290                 295                 300

Thr Thr Lys Glu Gly Pro Gly Glu Ala Ile Val Arg Glu Gly Gly Thr
305                 310                 315                 320

Met Ala Leu Ser Gly Ile Ser Asp Phe Gly Asn Ile Ser Ala Thr Ala
                325                 330                 335

Gly Glu Asn Tyr Ser Val Val Ser Trp Val Pro Lys Glu Gly Gln Cys
            340                 345                 350

Asn Phe Arg Phe His Ile Leu Phe Lys Ala Leu Gly Glu Glu Lys Gly
        355                 360                 365

Gly Ala Ser Leu Ser Pro Gln Tyr Val Ser Tyr Asn Gln Ser Ser Tyr
    370                 375                 380

Thr Gln Trp Asp Leu Gln Pro Asp Thr Asp Tyr Glu Ile His Leu Phe
385                 390                 395                 400

Lys Glu Arg Met Phe Arg His Gln Met Ala Val Lys Thr Asn Gly Thr
                405                 410                 415

Gly Arg Val Arg Leu Pro Pro Ala Gly Phe Ala Thr Glu Gly Pro Gly
            420                 425                 430

Ile Pro Gly Ser Thr Arg Ala Ala Ala Ser
        435                 440
```

(2) INFORMATION FOR SEQ ID NO:71:

(i) SEQUENCE CHARACTERISTICS:
        (A) LENGTH: 635 amino acids
        (B) TYPE: amino acid
        (D) TOPOLOGY: linear (ii) MOLECULE TYPE: protein (v) FRAGMENT TYPE: C-terminal (xi) SEQUENCE DESCRIPTION: SEQ ID NO:71:

```
Met Ser Pro Ile Leu Gly Tyr Trp Lys Ile Lys Gly Leu Val Gln Pro
1               5                   10                  15

Thr Arg Leu Leu Leu Glu Tyr Leu Glu Glu Lys Tyr Glu Glu His Leu
                20                  25                  30

Tyr Glu Arg Asp Glu Gly Asp Lys Trp Arg Asn Lys Lys Phe Glu Leu
            35                  40                  45
```

```
Gly Leu Glu Phe Pro Asn Leu Pro Tyr Tyr Ile Asp Gly Asp Val Lys
    50                  55                  60
Leu Thr Gln Ser Met Ala Ile Ile Arg Tyr Ile Ala Asp Lys His Asn
 65                  70                  75                  80
Met Leu Gly Gly Cys Pro Lys Glu Arg Ala Glu Ile Ser Met Leu Glu
                 85                  90                  95
Gly Ala Val Leu Asp Ile Arg Tyr Gly Val Ser Arg Ile Ala Tyr Ser
                100                 105                 110
Lys Asp Phe Glu Thr Leu Lys Val Asp Phe Leu Ser Lys Leu Pro Glu
            115                 120                 125
Met Leu Lys Met Phe Glu Asp Arg Leu Cys His Lys Thr Tyr Leu Asn
            130                 135                 140
Gly Asp His Val Thr His Pro Asp Phe Met Leu Tyr Asp Ala Leu Asp
145                 150                 155                 160
Val Val Leu Tyr Met Asp Pro Met Cys Leu Asp Ala Phe Pro Lys Leu
                165                 170                 175
Val Cys Phe Lys Lys Arg Ile Glu Ala Ile Pro Gln Ile Asp Lys Tyr
                180                 185                 190
Leu Lys Ser Ser Lys Tyr Ile Ala Trp Pro Leu Gln Gly Trp Gln Ala
            195                 200                 205
Thr Phe Gly Gly Asp His Pro Pro Lys Ser Asp Leu Val Pro Arg
            210                 215                 220
Gly Ser His Ile His Lys Ser His Ile Val Pro Ala Asn Thr Thr
225                 230                 235                 240
Ser Ala Ile Leu Ser Gly Leu Arg Pro Tyr Ser Ser Tyr His Val Glu
                245                 250                 255
Val Gln Ala Phe Asn Gly Arg Gly Leu Gly Pro Ala Ser Glu Trp Thr
            260                 265                 270
Phe Ser Thr Pro Glu Gly Val Pro Gly His Pro Glu Ala Leu His Leu
            275                 280                 285
Glu Cys Gln Ser Asp Thr Ser Leu Leu Leu His Trp Gln Pro Pro Leu
            290                 295                 300
Ser His Asn Gly Val Leu Thr Gly Tyr Leu Leu Ser Tyr His Pro Val
305                 310                 315                 320
Glu Gly Glu Ser Lys Glu Gln Leu Phe Phe Asn Leu Ser Asp Pro Glu
                325                 330                 335
Leu Arg Thr His Asn Leu Thr Asn Leu Asn Pro Asp Leu Gln Tyr Arg
            340                 345                 350
Phe Gln Leu Gln Ala Thr Thr Gln Gln Gly Pro Gly Gln Ala Ile
            355                 360                 365
Val Arg Glu Gly Gly Thr Met Ala Leu Phe Gly Lys Pro Asp Phe Gly
    370                 375                 380
Asn Ile Ser Ala Thr Ala Gly Glu Asn Tyr Ser Val Val Ser Trp Val
385                 390                 395                 400
Pro Arg Lys Gly Gln Cys Asn Phe Arg Phe His Ile Leu Phe Lys Ala
            405                 410                 415
Leu Pro Glu Gly Lys Val Ser Pro Asp His Gln Pro Gln Pro Gln Tyr
            420                 425                 430
Val Ser Tyr Asn Gln Ser Ser Tyr Thr Gln Trp Asn Leu Gln Pro Asp
            435                 440                 445
Thr Lys Tyr Glu Ile His Leu Ile Lys Glu Lys Val Leu Leu His His
    450                 455                 460
```

```
Leu Asp Val Lys Thr Asn Gly Thr Gly Pro Val Arg Val Ser Thr Thr
465                 470                 475                 480

Gly Ser Phe Ala Ser Glu Gly Trp Phe Ile Ala Phe Val Ser Ala Ile
                485                 490                 495

Ile Leu Leu Leu Leu Ile Leu Leu Ile Leu Cys Phe Ile Lys Arg Ser
                500                 505                 510

Lys Gly Gly Lys Tyr Ser Val Lys Asp Lys Glu Asp Thr Gln Val Asp
            515                 520                 525

Ser Glu Ala Arg Pro Met Lys Asp Glu Thr Phe Gly Glu Tyr Arg Ser
530                 535                 540

Leu Glu Ser Asp Asn Glu Glu Lys Ala Phe Gly Ser Ser Gln Pro Ser
545                 550                 555                 560

Leu Asn Gly Asp Ile Lys Pro Leu Gly Ser Asp Ser Leu Ala Asp
                565                 570                 575

Tyr Gly Gly Ser Val Asp Val Gln Phe Asn Glu Asp Gly Ser Phe Ile
                580                 585                 590

Gly Gln Tyr Ser Gly Lys Lys Glu Lys Glu Ala Ala Gly Gly Asn Asp
            595                 600                 605

Ser Ser Gly Ala Thr Ser Pro Ile Asn Pro Ala Val Ala Leu Glu Pro
610                 615                 620

Arg Asn Ser Arg Val Asp Ser Ser Gly Arg Ile
625                 630                 635

(2) INFORMATION FOR SEQ ID NO:72:

(i) SEQUENCE CHARACTERISTICS:
        (A) LENGTH: 547 amino acids
        (B) TYPE: amino acid
        (D) TOPOLOGY: linear (ii) MOLECULE TYPE: protein (v) FRAGMENT TYPE: internal (xi) SEQUENCE DESCRIPTION: SEQ ID NO:72:

Met Ser Pro Ile Leu Gly Tyr Trp Lys Ile Lys Gly Leu Val Gln Pro
1               5                   10                  15

Thr Arg Leu Leu Leu Glu Tyr Leu Glu Glu Lys Tyr Glu Glu His Leu
                20                  25                  30

Tyr Glu Arg Asp Glu Gly Asp Lys Trp Arg Asn Lys Lys Phe Glu Leu
                35                  40                  45

Gly Leu Glu Phe Pro Asn Leu Pro Tyr Tyr Ile Asp Gly Asp Val Lys
            50                  55                  60

Leu Thr Gln Ser Met Ala Ile Ile Arg Tyr Ile Ala Asp Lys His Asn
65                  70                  75                  80

Met Leu Gly Gly Cys Pro Lys Glu Arg Ala Glu Ile Ser Met Leu Glu
                85                  90                  95

Gly Ala Val Leu Asp Ile Arg Tyr Gly Val Ser Arg Ile Ala Tyr Ser
                100                 105                 110

Lys Asp Phe Glu Thr Leu Lys Val Asp Phe Leu Ser Lys Leu Pro Glu
            115                 120                 125

Met Leu Lys Met Phe Glu Asp Arg Leu Cys His Lys Thr Tyr Leu Asn
            130                 135                 140

Gly Asp His Val Thr His Pro Asp Phe Met Leu Tyr Asp Ala Leu Asp
145                 150                 155                 160

Val Val Leu Tyr Met Asp Pro Met Cys Leu Asp Ala Phe Pro Lys Leu
                165                 170                 175
```

```
Val Cys Phe Lys Lys Arg Ile Glu Ala Ile Pro Gln Ile Asp Lys Tyr
            180                 185                 190

Leu Lys Ser Ser Lys Tyr Ile Ala Trp Pro Leu Gln Gly Trp Gln Ala
            195                 200                 205

Thr Phe Gly Gly Gly Asp His Pro Pro Lys Ser Asp Leu Val Pro Arg
            210                 215                 220

Gly Ser Leu Glu Asp Ile Thr Ile Phe Asn Ser Ser Thr Val Leu Val
225                 230                 235                 240

Arg Trp Arg Pro Val Asp Leu Ala Gln Val Lys Gly His Leu Lys Gly
            245                 250                 255

Tyr Asn Val Thr Tyr Trp Trp Lys Gly Ser Gln Arg Lys His Ser Lys
            260                 265                 270

Arg His Ile His Lys Ser His Ile Val Val Pro Ala Asn Thr Thr Ser
            275                 280                 285

Ala Ile Leu Ser Gly Leu Arg Pro Tyr Ser Ser Tyr His Val Glu Val
            290                 295                 300

Gln Ala Phe Asn Gly Arg Gly Leu Gly Pro Ala Ser Glu Trp Thr Phe
305                 310                 315                 320

Ser Thr Pro Glu Gly Val Pro Gly His Pro Glu Ala Leu His Leu Glu
            325                 330                 335

Cys Gln Ser Asp Thr Ser Leu Leu His Trp Gln Pro Pro Leu Ser
            340                 345                 350

His Asn Gly Val Leu Thr Gly Tyr Leu Leu Ser Tyr His Pro Val Glu
            355                 360                 365

Gly Glu Ser Lys Glu Gln Leu Phe Phe Asn Leu Ser Asp Pro Glu Leu
            370                 375                 380

Arg Thr His Asn Leu Thr Asn Leu Asn Pro Asp Leu Gln Tyr Arg Phe
385                 390                 395                 400

Gln Leu Gln Ala Thr Thr Gln Gln Gly Gly Pro Gly Gln Ala Ile Val
            405                 410                 415

Arg Glu Gly Gly Thr Met Ala Leu Phe Gly Lys Pro Asp Phe Gly Asn
            420                 425                 430

Ile Ser Ala Thr Ala Gly Glu Asn Tyr Ser Val Val Ser Trp Val Pro
            435                 440                 445

Arg Lys Gly Gln Cys Asn Phe Arg Phe His Ile Leu Phe Lys Ala Leu
            450                 455                 460

Pro Glu Gly Lys Val Ser Pro Asp His Gln Pro Gln Pro Gln Tyr Val
465                 470                 475                 480

Ser Tyr Asn Gln Ser Ser Tyr Thr Gln Trp Asn Leu Gln Pro Asp Thr
            485                 490                 495

Lys Tyr Glu Ile His Leu Ile Lys Glu Lys Val Leu Leu His His Leu
            500                 505                 510

Asp Val Lys Thr Asn Gly Thr Gly Pro Val Arg Val Ser Thr Thr Gly
            515                 520                 525

Ser Phe Ala Ser Glu Gly Trp Pro Gly Ile Pro Gly Ser Thr Arg Ala
            530                 535                 540

Ala Ala Ser
545

(2) INFORMATION FOR SEQ ID NO:73:

(i) SEQUENCE CHARACTERISTICS:
        (A) LENGTH: 447 amino acids
        (B) TYPE: amino acid
```

-continued

```
       (D) TOPOLOGY: linear (ii) MOLECULE TYPE: protein (v) FRAGMENT TYPE: internal (xi) SEQUENCE DESCRIPTION: SEQ ID NO:73:

Met Ser Pro Ile Leu Gly Tyr Trp Lys Ile Lys Gly Leu Val Gln Pro
1               5                   10                  15

Thr Arg Leu Leu Leu Glu Tyr Leu Glu Glu Lys Tyr Glu Glu His Leu
            20                  25                  30

Tyr Glu Arg Asp Glu Gly Asp Lys Trp Arg Asn Lys Lys Phe Glu Leu
        35                  40                  45

Gly Leu Glu Phe Pro Asn Leu Pro Tyr Tyr Ile Asp Gly Asp Val Lys
50                  55                  60

Leu Thr Gln Ser Met Ala Ile Ile Arg Tyr Ile Ala Asp Lys His Asn
65                  70                  75                  80

Met Leu Gly Gly Cys Pro Lys Glu Arg Ala Glu Ile Ser Met Leu Glu
                85                  90                  95

Gly Ala Val Leu Asp Ile Arg Tyr Gly Val Ser Arg Ile Ala Tyr Ser
            100                 105                 110

Lys Asp Phe Glu Thr Leu Lys Val Asp Phe Leu Ser Lys Leu Pro Glu
        115                 120                 125

Met Leu Lys Met Phe Glu Asp Arg Leu Cys His Lys Thr Tyr Leu Asn
130                 135                 140

Gly Asp His Val Thr His Pro Asp Phe Met Leu Tyr Asp Ala Leu Asp
145                 150                 155                 160

Val Val Leu Tyr Met Asp Pro Met Cys Leu Asp Ala Phe Pro Lys Leu
                165                 170                 175

Val Cys Phe Lys Lys Arg Ile Glu Ala Ile Pro Gln Ile Asp Lys Tyr
            180                 185                 190

Leu Lys Ser Ser Lys Tyr Ile Ala Trp Pro Leu Gln Gly Trp Gln Ala
        195                 200                 205

Thr Phe Gly Gly Gly Asp His Pro Pro Lys Ser Asp Leu Val Pro Arg
210                 215                 220

Gly Ser Pro Gly His Pro Glu Ala Leu His Leu Glu Cys Gln Ser Asp
225                 230                 235                 240

Thr Ser Leu Leu Leu His Trp Gln Pro Pro Leu Ser His Asn Gly Val
                245                 250                 255

Leu Thr Gly Tyr Leu Leu Ser Tyr His Pro Val Glu Gly Glu Ser Lys
            260                 265                 270

Glu Gln Leu Phe Phe Asn Leu Ser Asp Pro Glu Leu Arg Thr His Asn
        275                 280                 285

Leu Thr Asn Leu Asn Pro Asp Leu Gln Tyr Arg Phe Gln Leu Gln Ala
290                 295                 300

Thr Thr Gln Gln Gly Gly Pro Gly Gln Ala Ile Val Arg Glu Gly Gly
305                 310                 315                 320

Thr Met Ala Leu Phe Gly Lys Pro Asp Phe Gly Asn Ile Ser Ala Thr
                325                 330                 335

Ala Gly Glu Asn Tyr Ser Val Val Ser Trp Val Pro Arg Lys Gly Gln
            340                 345                 350

Cys Asn Phe Arg Phe His Ile Leu Phe Lys Ala Leu Pro Glu Gly Lys
        355                 360                 365

Val Ser Pro Asp His Gln Pro Gln Pro Gln Tyr Val Ser Tyr Asn Gln
370                 375                 380
```

```
Ser Ser Tyr Thr Gln Trp Asn Leu Gln Pro Asp Thr Lys Tyr Glu Ile
385                 390                 395                 400

His Leu Ile Lys Glu Lys Val Leu Leu His His Leu Asp Val Lys Thr
            405                 410                 415

Asn Gly Thr Gly Pro Val Arg Val Ser Thr Thr Gly Ser Phe Ala Ser
            420                 425                 430

Glu Gly Trp Pro Gly Ile Pro Gly Ser Thr Arg Ala Ala Ala Ser
            435                 440                 445
```

(2) INFORMATION FOR SEQ ID NO:74:

(i) SEQUENCE CHARACTERISTICS:
        (A) LENGTH: 632 amino acids
        (B) TYPE: amino acid
        (D) TOPOLOGY: linear (ii) MOLECULE TYPE: protein (v) FRAGMENT TYPE: C-terminal (xi) SEQUENCE DESCRIPTION: SEQ ID NO:74:

```
Met Ser Pro Ile Leu Gly Tyr Trp Lys Ile Lys Gly Leu Val Gln Pro
1               5                   10                  15

Thr Arg Leu Leu Leu Glu Tyr Leu Glu Glu Lys Tyr Glu Glu His Leu
            20                  25                  30

Tyr Glu Arg Asp Glu Gly Asp Lys Trp Arg Asn Lys Lys Phe Glu Leu
            35                  40                  45

Gly Leu Glu Phe Pro Asn Leu Pro Tyr Tyr Ile Asp Gly Asp Val Lys
50                  55                  60

Leu Thr Gln Ser Met Ala Ile Ile Arg Tyr Ile Ala Asp Lys His Asn
65                  70                  75                  80

Met Leu Gly Gly Cys Pro Lys Glu Arg Ala Glu Ile Ser Met Leu Glu
            85                  90                  95

Gly Ala Val Leu Asp Ile Arg Tyr Gly Val Ser Arg Ile Ala Tyr Ser
            100                 105                 110

Lys Asp Phe Glu Thr Leu Lys Val Asp Phe Leu Ser Lys Leu Pro Glu
            115                 120                 125

Met Leu Lys Met Phe Glu Asp Arg Leu Cys His Lys Thr Tyr Leu Asn
            130                 135                 140

Gly Asp His Val Thr His Pro Asp Phe Met Leu Tyr Asp Ala Leu Asp
145                 150                 155                 160

Val Val Leu Tyr Met Asp Pro Met Cys Leu Asp Ala Phe Pro Lys Leu
                165                 170                 175

Val Cys Phe Lys Lys Arg Ile Glu Ala Ile Pro Gln Ile Asp Lys Tyr
            180                 185                 190

Leu Lys Ser Ser Lys Tyr Ile Ala Trp Pro Leu Gln Gly Trp Gln Ala
            195                 200                 205

Thr Phe Gly Gly Asp His Pro Pro Lys Ser Asp Leu Val Pro Arg
            210                 215                 220

Gly Ser Val Glu Lys Lys Ile Leu Thr Phe Arg Gly Asn Lys Thr Phe
225                 230                 235                 240

Gly Met Leu Pro Gly Leu Glu Pro Tyr Ser Ser Tyr Lys Leu Asn Val
            245                 250                 255

Arg Val Val Asn Gly Lys Gly Glu Gly Pro Ala Ser Pro Asp Lys Val
            260                 265                 270

Phe Lys Thr Pro Glu Gly Val Pro Ser Pro Pro Ser Phe Leu Lys Ile
```

```
                275                 280                 285
Thr Asn Pro Thr Leu Asp Ser Leu Thr Leu Glu Trp Gly Ser Pro Thr
290                 295                 300

His Pro Asn Gly Val Leu Thr Ser Tyr Ile Leu Lys Phe Gln Pro Ile
305                 310                 315                 320

Asn Asn Thr His Glu Leu Gly Pro Leu Val Glu Ile Arg Ile Pro Ala
                325                 330                 335

Asn Glu Ser Ser Leu Ile Leu Lys Asn Leu Asn Tyr Ser Thr Arg Tyr
                340                 345                 350

Lys Phe Tyr Phe Asn Ala Gln Thr Ser Val Gly Ser Gly Ser Gln Ile
                355                 360                 365

Thr Glu Glu Ala Val Thr Ile Met Asp Glu Val Gln Pro Leu Tyr Pro
370                 375                 380

Arg Ile Arg Asn Val Thr Thr Ala Ala Ala Glu Thr Tyr Ala Asn Ile
385                 390                 395                 400

Ser Trp Glu Tyr Glu Gly Pro Asp His Ala Asn Phe Tyr Val Glu Tyr
                405                 410                 415

Gly Val Ala Gly Ser Lys Glu Asp Trp Lys Lys Glu Ile Val Asn Gly
                420                 425                 430

Ser Arg Ser Phe Phe Val Leu Lys Gly Leu Thr Pro Gly Thr Ala Tyr
                435                 440                 445

Lys Val Arg Val Gly Ala Glu Gly Leu Ser Gly Phe Arg Ser Ser Glu
450                 455                 460

Asp Leu Phe Glu Thr Gly Pro Ala Met Ala Ser Arg Gln Val Asp Ile
465                 470                 475                 480

Ala Thr Gln Gly Trp Phe Ile Gly Leu Met Cys Ala Val Ala Leu Leu
                485                 490                 495

Ile Leu Ile Leu Leu Ile Val Cys Phe Ile Arg Arg Asn Lys Gly Gly
                500                 505                 510

Lys Tyr Pro Val Lys Glu Lys Glu Asp Ala His Ala Asp Pro Glu Ile
                515                 520                 525

Gln Pro Met Lys Glu Asp Asp Gly Thr Phe Gly Glu Tyr Ser Asp Ala
                530                 535                 540

Glu Asp His Lys Pro Leu Lys Lys Gly Ser Arg Thr Pro Ser Asp Arg
545                 550                 555                 560

Thr Val Lys Lys Glu Asp Ser Asp Ser Leu Val Asp Tyr Gly Glu
                565                 570                 575

Gly Val Asn Gly Gln Phe Asn Glu Asp Gly Ser Phe Ile Gly Gln Tyr
                580                 585                 590

Ser Gly Lys Lys Glu Lys Glu Pro Ala Glu Gly Asn Glu Ser Ser Glu
                595                 600                 605

Ala Pro Ser Pro Val Asn Ala Met Asn Ser Phe Val Pro Arg Asn Ser
                610                 615                 620

Arg Val Asp Ser Ser Gly Arg Ile
625                 630
```

(2) INFORMATION FOR SEQ ID NO:75:

(i) SEQUENCE CHARACTERISTICS:
        (A) LENGTH: 545 amino acids
        (B) TYPE: amino acid
        (D) TOPOLOGY: linear (ii) MOLECULE TYPE: protein (v) FRAGMENT TYPE: internal (xi) SEQUENCE DESCRIPTION: SEQ ID NO:75:

```
Met Ser Pro Ile Leu Gly Tyr Trp Lys Ile Lys Gly Leu Val Gln Pro
1               5                   10                  15

Thr Arg Leu Leu Leu Glu Tyr Leu Glu Glu Lys Tyr Glu Glu His Leu
            20                  25                  30

Tyr Glu Arg Asp Glu Gly Asp Lys Trp Arg Asn Lys Lys Phe Glu Leu
        35                  40                  45

Gly Leu Glu Phe Pro Asn Leu Pro Tyr Tyr Ile Asp Gly Asp Val Lys
    50                  55                  60

Leu Thr Gln Ser Met Ala Ile Ile Arg Tyr Ile Ala Asp Lys His Asn
65                  70                  75                  80

Met Leu Gly Gly Cys Pro Lys Glu Arg Ala Glu Ile Ser Met Leu Glu
                85                  90                  95

Gly Ala Val Leu Asp Ile Arg Tyr Gly Val Ser Arg Ile Ala Tyr Ser
            100                 105                 110

Lys Asp Phe Glu Thr Leu Lys Val Asp Phe Leu Ser Lys Leu Pro Glu
        115                 120                 125

Met Leu Lys Met Phe Glu Asp Arg Leu Cys His Lys Thr Tyr Leu Asn
    130                 135                 140

Gly Asp His Val Thr His Pro Asp Phe Met Leu Tyr Asp Ala Leu Asp
145                 150                 155                 160

Val Val Leu Tyr Met Asp Pro Met Cys Leu Asp Ala Phe Pro Lys Leu
                165                 170                 175

Val Cys Phe Lys Lys Arg Ile Glu Ala Ile Pro Gln Ile Asp Lys Tyr
            180                 185                 190

Leu Lys Ser Ser Lys Tyr Ile Ala Trp Pro Leu Gln Gly Trp Gln Ala
        195                 200                 205

Thr Phe Gly Gly Asp His Pro Pro Lys Ser Asp Leu Val Pro Arg
    210                 215                 220

Gly Ser Asn Val Gln Val His Val Ile Asn Ser Thr Leu Ala Lys Val
225                 230                 235                 240

His Trp Asp Pro Val Pro Leu Lys Ser Val Arg Gly His Leu Gln Gly
                245                 250                 255

Tyr Lys Val Tyr Tyr Trp Lys Val Gln Ser Leu Ser Arg Arg Ser Lys
            260                 265                 270

Arg His Val Glu Lys Lys Ile Leu Thr Phe Arg Gly Asn Lys Thr Phe
        275                 280                 285

Gly Met Leu Pro Gly Leu Glu Pro Tyr Ser Ser Tyr Lys Leu Asn Val
    290                 295                 300

Arg Val Val Asn Gly Lys Gly Glu Gly Pro Ala Ser Pro Asp Lys Val
305                 310                 315                 320

Phe Lys Thr Pro Glu Gly Val Pro Ser Pro Ser Phe Leu Lys Ile
                325                 330                 335

Thr Asn Pro Thr Leu Asp Ser Leu Thr Leu Glu Trp Gly Ser Pro Thr
            340                 345                 350

His Pro Asn Gly Val Leu Thr Ser Tyr Ile Leu Lys Phe Gln Pro Ile
        355                 360                 365

Asn Asn Thr His Glu Leu Gly Pro Leu Val Glu Ile Arg Ile Pro Ala
    370                 375                 380

Asn Glu Ser Ser Leu Ile Leu Lys Asn Leu Asn Tyr Ser Thr Arg Tyr
385                 390                 395                 400

Lys Phe Tyr Phe Asn Ala Gln Thr Ser Val Gly Ser Gly Ser Gln Ile
```

-continued

```
                        405                 410                 415
Thr Glu Glu Ala Val Thr Ile Met Asp Glu Val Gln Pro Leu Tyr Pro
                420                 425                 430
Arg Ile Arg Asn Val Thr Thr Ala Ala Glu Thr Tyr Ala Asn Ile
            435                 440                 445
Ser Trp Glu Tyr Glu Gly Pro Asp His Ala Asn Phe Tyr Val Glu Tyr
    450                 455                 460
Gly Val Ala Gly Ser Lys Glu Asp Trp Lys Lys Glu Ile Val Asn Gly
465                 470                 475                 480
Ser Arg Ser Phe Phe Val Leu Lys Gly Leu Thr Pro Gly Thr Ala Tyr
                485                 490                 495
Lys Val Arg Val Gly Ala Glu Gly Leu Ser Gly Phe Arg Ser Ser Glu
                500                 505                 510
Asp Leu Phe Glu Thr Gly Pro Ala Met Ala Ser Arg Gln Val Asp Ile
                515                 520                 525
Ala Thr Gln Gly Trp Pro Gly Ile Pro Gly Ser Thr Arg Ala Ala Ala
                530                 535                 540
Ser
545

(2) INFORMATION FOR SEQ ID NO:76:

(i) SEQUENCE CHARACTERISTICS:
        (A) LENGTH: 443 amino acids
        (B) TYPE: amino acid
        (D) TOPOLOGY: linear (ii) MOLECULE TYPE: protein (v) FRAGMENT TYPE: internal (xi) SEQUENCE DESCRIPTION: SEQ ID NO:76:

Met Ser Pro Ile Leu Gly Tyr Trp Lys Ile Lys Gly Leu Val Gln Pro
1               5                   10                  15
Thr Arg Leu Leu Leu Glu Tyr Leu Glu Glu Lys Tyr Glu Glu His Leu
                20                  25                  30
Tyr Glu Arg Asp Glu Gly Asp Lys Trp Arg Asn Lys Lys Phe Glu Leu
            35                  40                  45
Gly Leu Glu Phe Pro Asn Leu Pro Tyr Tyr Ile Asp Gly Asp Val Lys
    50                  55                  60
Leu Thr Gln Ser Met Ala Ile Ile Arg Tyr Ile Ala Asp Lys His Asn
65                  70                  75                  80
Met Leu Gly Gly Cys Pro Lys Glu Arg Ala Glu Ile Ser Met Leu Glu
                85                  90                  95
Gly Ala Val Leu Asp Ile Arg Tyr Gly Val Ser Arg Ile Ala Tyr Ser
                100                 105                 110
Lys Asp Phe Glu Thr Leu Lys Val Asp Phe Leu Ser Lys Leu Pro Glu
            115                 120                 125
Met Leu Lys Met Phe Glu Asp Arg Leu Cys His Lys Thr Tyr Leu Asn
            130                 135                 140
Gly Asp His Val Thr His Pro Asp Phe Met Leu Tyr Asp Ala Leu Asp
145                 150                 155                 160
Val Val Leu Tyr Met Asp Pro Met Cys Leu Asp Ala Phe Pro Lys Leu
                165                 170                 175
Val Cys Phe Lys Lys Arg Ile Glu Ala Ile Pro Gln Ile Asp Lys Tyr
                180                 185                 190
```

-continued

```
Leu Lys Ser Ser Lys Tyr Ile Ala Trp Pro Leu Gln Gly Trp Gln Ala
        195             200             205

Thr Phe Gly Gly Gly Asp His Pro Pro Lys Ser Asp Leu Val Pro Arg
    210             215             220

Gly Ser Pro Ser Pro Pro Ser Phe Leu Lys Ile Thr Asn Pro Thr Leu
225             230             235             240

Asp Ser Leu Thr Leu Glu Trp Gly Ser Pro Thr His Pro Asn Gly Val
                245             250             255

Leu Thr Ser Tyr Ile Leu Lys Phe Gln Pro Ile Asn Asn Thr His Glu
            260             265             270

Leu Gly Pro Leu Val Glu Ile Arg Ile Pro Ala Asn Glu Ser Ser Leu
        275             280             285

Ile Leu Lys Asn Leu Asn Tyr Ser Thr Arg Tyr Lys Phe Tyr Phe Asn
    290             295             300

Ala Gln Thr Ser Val Gly Ser Gly Ser Gln Ile Thr Glu Glu Ala Val
305             310             315             320

Thr Ile Met Asp Glu Val Gln Pro Leu Tyr Pro Arg Ile Arg Asn Val
                325             330             335

Thr Thr Ala Ala Ala Glu Thr Tyr Ala Asn Ile Ser Trp Glu Tyr Glu
            340             345             350

Gly Pro Asp His Ala Asn Phe Tyr Val Glu Tyr Gly Val Ala Gly Ser
        355             360             365

Lys Glu Asp Trp Lys Lys Glu Ile Val Asn Gly Ser Arg Ser Phe Phe
    370             375             380

Val Leu Lys Gly Leu Thr Pro Gly Thr Ala Tyr Lys Val Arg Val Gly
385             390             395             400

Ala Glu Gly Leu Ser Gly Phe Arg Ser Ser Glu Asp Leu Phe Glu Thr
                405             410             415

Gly Pro Ala Met Ala Ser Arg Gln Val Asp Ile Ala Thr Gln Gly Trp
            420             425             430

Pro Gly Ile Pro Gly Ser Thr Arg Ala Ala Ser
        435             440
```

(2) INFORMATION FOR SEQ ID NO:77:

(i) SEQUENCE CHARACTERISTICS:
       (A) LENGTH: 15 amino acids
       (B) TYPE: amino acid
       (D) TOPOLOGY: linear (ii) MOLECULE TYPE: peptide (v) FRAGMENT TYPE: internal (xi) SEQUENCE DESCRIPTION: SEQ ID NO:77:

```
Phe Asn Gly Arg Gly Asp Gly Pro Pro Ser Glu Pro Ile Ala Cys
1               5               10              15
```